(12) United States Patent
Du et al.

(10) Patent No.: US 8,173,621 B2
(45) Date of Patent: May 8, 2012

(54) NUCLEOSIDE CYCLICPHOSPHATES

(75) Inventors: Jinfa Du, New Hope, PA (US);
Dhanapalan Nagarathnam, Bethany, CT (US); Ganapati Reddy Pamulapati, Plainsboro, NJ (US); Bruce S. Ross, Plainsboro, NJ (US); Michael Joseph Sofia, Doylestown, PA (US)

(73) Assignee: Gilead Pharmasset LLC, Princeton, NJ (US)

( * ) Notice: Subject to any disclaimer, the term of this patent is extended or adjusted under 35 U.S.C. 154(b) by 222 days.

(21) Appl. No.: 12/479,075

(22) Filed: Jun. 5, 2009

(65) Prior Publication Data

US 2010/0081628 A1    Apr. 1, 2010

Related U.S. Application Data

(60) Provisional application No. 61/060,683, filed on Jun. 11, 2008, provisional application No. 61/140,369, filed on Dec. 23, 2008, provisional application No. 61/140,317, filed on Dec. 23, 2008.

(51) Int. Cl.
    A01N 43/04    (2006.01)
    A61K 31/70    (2006.01)
    C07H 19/00    (2006.01)
    C07H 19/04    (2006.01)
    C07H 19/20    (2006.01)

(52) U.S. Cl. ... 514/48; 536/26.1; 536/26.11; 536/26.12; 536/26.7; 536/26.71; 536/26.72; 514/45

(58) Field of Classification Search .......... None
See application file for complete search history.

(56) References Cited

U.S. PATENT DOCUMENTS

| | | |
|---|---|---|
| 3,798,209 A | 3/1974 | Witkowski |
| 3,852,267 A | 12/1974 | Meyer |
| 3,994,974 A | 11/1976 | Murakami |
| RE29,835 E | 11/1978 | Witkowski |
| 4,797,285 A | 1/1989 | Barenholz |
| 4,814,477 A | 3/1989 | Wijnberg |
| 4,957,924 A | 9/1990 | Beauchamp |
| 5,013,556 A | 5/1991 | Woodle |
| 5,026,687 A | 6/1991 | Yarchoan |
| 5,077,056 A | 12/1991 | Bally |
| 5,077,057 A | 12/1991 | Szoka |
| 5,091,188 A | 2/1992 | Haynes |
| 5,118,820 A | 6/1992 | Hertel |
| 5,145,684 A | 9/1992 | Liversidge |
| 5,149,794 A | 9/1992 | Yatvin |
| 5,154,930 A | 10/1992 | Popescu |
| 5,157,027 A | 10/1992 | Biller |
| 5,192,549 A | 3/1993 | Barenolz |
| 5,194,654 A | 3/1993 | Hostetler |
| 5,213,804 A | 5/1993 | Martin |
| 5,223,263 A | 6/1993 | Hostetler |
| 5,225,212 A | 7/1993 | Martin |
| 5,256,641 A | 10/1993 | Yatvin |
| 5,256,798 A | 10/1993 | Chou |
| 5,277,914 A | 1/1994 | Szoka |
| 5,316,771 A | 5/1994 | Barenholz |
| 5,372,808 A | 12/1994 | Blatt |
| 5,376,380 A | 12/1994 | Kikuchi |
| 5,405,598 A | 4/1995 | Schinazi |
| 5,411,947 A | 5/1995 | Hostetler |
| 5,420,266 A | 5/1995 | Britton |
| 5,426,183 A | 6/1995 | Kjell |
| 5,453,499 A | 9/1995 | Chou |
| 5,462,724 A | 10/1995 | Schinazi |
| 5,463,092 A | 10/1995 | Hostetler |
| 5,496,546 A | 3/1996 | Wang |
| 5,538,865 A | 7/1996 | Reyes |
| 5,543,389 A | 8/1996 | Yatvin |
| 5,543,390 A | 8/1996 | Yatvin |
| 5,543,391 A | 8/1996 | Yatvin |
| 5,549,910 A | 8/1996 | Szoka |
| 5,554,728 A | 9/1996 | Basava |
| 5,567,434 A | 10/1996 | Szoka |
| 5,610,054 A | 3/1997 | Draper |
| 5,633,358 A | 5/1997 | Gruetzke |
| 5,633,388 A | 5/1997 | Diana |
| 5,676,942 A | 10/1997 | Testa |
| 5,695,784 A | 12/1997 | Pollinger |

(Continued)

FOREIGN PATENT DOCUMENTS

CN    101108870    1/2008

(Continued)

OTHER PUBLICATIONS

Byrn et al. Solid-State Chemistry of Drugs, 2d, Chapter 11 Hydrates and Solvates, 233-247, 2003.* Morissette et al. Adv. Drug Delivery Rev. 2004, 56, 275-300.*
Beres et al. J. Med Chem., 1986, vol. 29(4) 494-499.*
Gromova et al., Biochem. Biophys. Acta, 1971, 240, 1-11.
Harris et al., Antiviral Chemistry & Chemotherapy, 2002, 12, 293-300.
Juodka et al., J. Carbohydrates, Nucleosides, Nucleotides, 1979, 6(4), 333-357.
Juodka et al., J. Carbohydrates, Nucleosides, Nucleotides, 1981, 8(1), 19-39.
Juodka et al., J. Carbohydrates, Nucleosides, Nucleotides, 1981, 8(6), 519-535.

(Continued)

*Primary Examiner* — Traviss C McIntosh, III
(74) *Attorney, Agent, or Firm* — Fitzpatrick, Cella, Harper & Scinto

(57) ABSTRACT

Cyclic phosphate of nucleoside derivatives for the treatment of viral infections in mammals, which is a compound, its stereoisomers, salts (acid or basic addition salts), hydrates, solvates, or crystalline forms thereof, represented by the following structure:

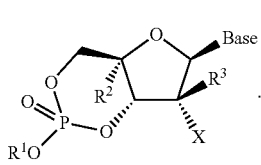

46 Claims, No Drawings

U.S. PATENT DOCUMENTS

| | | |
|---|---|---|
| 5,703,058 A | 12/1997 | Schinazi |
| 5,711,944 A | 1/1998 | Gilbert |
| 5,725,859 A | 3/1998 | Omer |
| 5,736,155 A | 4/1998 | Bally |
| 5,738,845 A | 4/1998 | Imakawa |
| 5,738,846 A | 4/1998 | Greenwald |
| 5,747,646 A | 5/1998 | Hakimi |
| 5,767,097 A | 6/1998 | Tam |
| 5,792,834 A | 8/1998 | Hakimi |
| 5,827,533 A | 10/1998 | Needham |
| 5,830,455 A | 11/1998 | Valtuena |
| 5,830,905 A | 11/1998 | Diana |
| 5,834,594 A | 11/1998 | Hakimi |
| 5,837,257 A | 11/1998 | Tsai |
| 5,846,964 A | 12/1998 | Ozeki |
| 5,849,696 A | 12/1998 | Chretien |
| 5,869,253 A | 2/1999 | Draper |
| 5,882,679 A | 3/1999 | Needham |
| 5,891,468 A | 4/1999 | Martin |
| 5,891,874 A | 4/1999 | Colacino |
| 5,905,070 A | 5/1999 | Schinazi |
| 5,908,621 A | 6/1999 | Glue |
| 5,922,757 A | 7/1999 | Chojkier |
| 5,928,636 A | 7/1999 | Alber |
| 5,942,223 A | 8/1999 | Bazer |
| 5,980,884 A | 11/1999 | Blatt |
| 5,990,276 A | 11/1999 | Zhang |
| 6,004,933 A | 12/1999 | Spruce |
| 6,034,134 A | 3/2000 | Gold |
| 6,043,077 A | 3/2000 | Barber |
| 6,056,961 A | 5/2000 | Lavie |
| 6,060,080 A | 5/2000 | Kikuchi |
| 6,090,932 A | 7/2000 | McGee |
| 6,130,326 A | 10/2000 | Ramasamy |
| 6,132,763 A | 10/2000 | Fisher |
| 6,143,321 A | 11/2000 | Needham |
| 6,156,501 A | 12/2000 | McGall |
| 6,180,134 B1 | 1/2001 | Zalipsky |
| 6,200,598 B1 | 3/2001 | Needham |
| 6,214,375 B1 | 4/2001 | Modi |
| 6,224,903 B1 | 5/2001 | Martin |
| 6,232,300 B1 | 5/2001 | Schinazi |
| 6,239,159 B1 | 5/2001 | Brown |
| 6,267,985 B1 | 7/2001 | Chen |
| 6,294,192 B1 | 9/2001 | Patel |
| 6,296,870 B1 | 10/2001 | Needham |
| 6,348,587 B1 | 2/2002 | Schinazi |
| 6,372,883 B1 | 4/2002 | Attwood |
| 6,383,471 B1 | 5/2002 | Chen |
| 6,391,859 B1 | 5/2002 | Schinazi |
| 6,395,300 B1 | 5/2002 | Straub |
| 6,410,531 B1 | 6/2002 | Llinas-Brunet |
| 6,420,380 B2 | 7/2002 | Llinas-Brunet |
| 6,455,513 B1 | 9/2002 | McGuigan |
| 6,455,690 B1 | 9/2002 | Tam |
| 6,475,985 B1 | 11/2002 | Wagner |
| 6,479,463 B1 | 11/2002 | Wang |
| 6,495,677 B1 | 12/2002 | Ramasamy |
| 6,509,320 B1 | 1/2003 | Wang |
| 6,534,523 B1 | 3/2003 | Llimas-Brunet et al. |
| 6,552,183 B1 | 4/2003 | Ramasamy |
| 6,555,677 B2 | 4/2003 | Petrillo |
| 6,569,463 B2 | 5/2003 | Patel |
| 6,573,248 B2 | 6/2003 | Ramasamy |
| 6,635,278 B1 | 10/2003 | Dahl |
| 6,642,206 B2 | 11/2003 | Ramasamy |
| 6,645,528 B1 | 11/2003 | Straub |
| 6,653,455 B1 | 11/2003 | Johdo |
| 6,660,721 B2 | 12/2003 | Devos |
| 6,677,314 B2 | 1/2004 | Klecker |
| 6,677,315 B2 | 1/2004 | Klecker |
| 6,680,068 B2 | 1/2004 | Campbell |
| 6,680,303 B2 | 1/2004 | Schinazi |
| 6,682,715 B2 | 1/2004 | Klecker |
| 6,683,045 B2 | 1/2004 | Klecker |
| 6,703,374 B1 | 3/2004 | Klecker |
| 6,726,925 B1 | 4/2004 | Needham |
| 6,753,309 B2 | 6/2004 | Klecker |
| 6,777,395 B2 | 8/2004 | Bhat |
| 6,784,166 B2 | 8/2004 | Devos |
| 6,787,305 B1 | 9/2004 | Li |
| 6,787,526 B1 | 9/2004 | Bryant |
| 6,815,542 B2 | 11/2004 | Hong |
| 6,846,810 B2 | 1/2005 | Martin |
| 6,897,201 B2 | 5/2005 | Boyer |
| 6,908,924 B2 | 6/2005 | Watanabe |
| 6,911,424 B2 | 6/2005 | Schinazi |
| 6,914,054 B2 | 7/2005 | Sommadossi |
| 6,923,988 B2 | 8/2005 | Patel |
| 6,932,983 B1 | 8/2005 | Straub |
| 6,962,991 B2 | 11/2005 | Dempcy |
| 6,977,257 B2 | 12/2005 | Parab |
| 7,018,985 B1 | 3/2006 | Boyer |
| 7,018,989 B2 | 3/2006 | McGuigan |
| 7,060,294 B2 | 6/2006 | Batra |
| 7,060,689 B2 | 6/2006 | Goins |
| 7,070,801 B2 | 7/2006 | Yamazaki |
| 7,081,449 B2 | 7/2006 | Pietrzkowski |
| 7,105,499 B2 | 9/2006 | Carroll |
| 7,148,206 B2 | 12/2006 | Sommadossi |
| 7,163,929 B2 | 1/2007 | Sommadossi |
| 7,217,523 B2 | 5/2007 | Wagner |
| 7,268,119 B2 | 9/2007 | Cook |
| 7,307,065 B2 | 12/2007 | Schinazi |
| 7,365,057 B2 | 4/2008 | LaColla |
| 7,429,572 B2 | 9/2008 | Clark |
| 7,462,608 B2 | 12/2008 | Chen |
| 7,601,820 B2 | 10/2009 | Wang |
| 7,754,699 B2 | 7/2010 | Chun |
| 2001/0034440 A1 | 10/2001 | Shepard |
| 2002/0058635 A1 | 5/2002 | Averett |
| 2002/0142050 A1 | 10/2002 | Straub |
| 2002/0198173 A1 | 12/2002 | Schinazi |
| 2003/0050229 A1 | 3/2003 | Sommadossi |
| 2003/0060400 A1 | 3/2003 | Dempcy |
| 2003/0120071 A1 | 6/2003 | McGuigan |
| 2003/0144502 A1 | 7/2003 | Pietrzkowski |
| 2003/0153744 A1 | 8/2003 | Mekouar |
| 2003/0187018 A1 | 10/2003 | Llinas-Brunet |
| 2004/0006007 A1 | 1/2004 | Gosselin |
| 2004/0014108 A1 | 1/2004 | Eldrup |
| 2004/0023240 A1 | 2/2004 | Marliere |
| 2004/0023901 A1 | 2/2004 | Cook |
| 2004/0059104 A1 | 3/2004 | Cook |
| 2004/0063622 A1 | 4/2004 | Sommadossi |
| 2004/0067901 A1 | 4/2004 | Bhat |
| 2004/0072788 A1 | 4/2004 | Bhat |
| 2004/0097461 A1 | 5/2004 | Sommadossi |
| 2004/0097462 A1 | 5/2004 | Sommadossi |
| 2004/0101535 A1 | 5/2004 | Sommadossi |
| 2004/0102414 A1 | 5/2004 | Sommadossi |
| 2004/0110717 A1 | 6/2004 | Carroll |
| 2004/0167140 A1 | 8/2004 | Schinazi |
| 2004/0191824 A1 | 9/2004 | Dempcy |
| 2004/0214844 A1 | 10/2004 | Otto |
| 2004/0224917 A1 | 11/2004 | Dahl |
| 2004/0229839 A1 | 11/2004 | Babu |
| 2004/0229840 A1 | 11/2004 | Bhat |
| 2004/0248892 A1 | 12/2004 | Wang |
| 2004/0254141 A1 | 12/2004 | Schinazi |
| 2004/0259934 A1 | 12/2004 | Olsen |
| 2004/0265969 A1 | 12/2004 | Li |
| 2004/0266996 A1 | 12/2004 | Rabi |
| 2005/0009737 A1 | 1/2005 | Clark |
| 2005/0020825 A1 | 1/2005 | Storer |
| 2005/0026853 A1 | 2/2005 | Mekouar |
| 2005/0031588 A1 | 2/2005 | Sommadossi |
| 2005/0048116 A1 | 3/2005 | Straub |
| 2005/0058710 A1 | 3/2005 | Straub |
| 2005/0075309 A1 | 4/2005 | Storer |
| 2005/0080034 A1 | 4/2005 | Standring |
| 2005/0090660 A1 | 4/2005 | Watanabe |
| 2005/0124532 A1 | 6/2005 | Sommadossi |
| 2005/0130931 A1 | 6/2005 | Boyer |
| 2005/0137161 A1 | 6/2005 | Sommadossi |
| 2005/0148534 A1 | 7/2005 | Castellino |
| 2005/0154056 A1 | 7/2005 | Yang |

| | | | | | | |
|---|---|---|---|---|---|---|
| 2005/0164960 | A1 | 7/2005 | Olsen | WO | WO96/32403 | 10/1996 |
| 2005/0215513 | A1 | 9/2005 | Boojamra | WO | WO 97/12033 | 4/1997 |
| 2005/0227947 | A1 | 10/2005 | Chan | WO | WO 9736554 | 10/1997 |
| 2005/0261237 | A1 | 11/2005 | Boojamra | WO | WO98/16184 | 4/1998 |
| 2005/0267018 | A1 | 12/2005 | Blatt | WO | WO 9817679 | 4/1998 |
| 2006/0003951 | A1 | 1/2006 | Mekouar | WO | WO 9822496 | 5/1998 |
| 2006/0014943 | A1 | 1/2006 | Dempcy | WO | WO 9907734 | 2/1999 |
| 2006/0034937 | A1 | 2/2006 | Patel | WO | WO 9915194 | 4/1999 |
| 2006/0035866 | A1 | 2/2006 | Cannizzaro | WO | WO 9932139 | 7/1999 |
| 2006/0040890 | A1 | 2/2006 | Martin | WO | WO 9932140 | 7/1999 |
| 2006/0040927 | A1 | 2/2006 | Blake | WO | WO99/43691 | 9/1999 |
| 2006/0040944 | A1 | 2/2006 | Gosselin | WO | WO 9959621 | 11/1999 |
| 2006/0057196 | A1 | 3/2006 | Hussain | WO | WO 9964016 | 12/1999 |
| 2006/0079478 | A1 | 4/2006 | Boojamra | WO | WO00/09531 | 2/2000 |
| 2006/0110727 | A9 | 5/2006 | McGall | WO | WO 0006529 | 2/2000 |
| 2006/0122146 | A1 | 6/2006 | Chun | WO | WO 0037110 | 6/2000 |
| 2006/0122154 | A1 | 6/2006 | Olsen | WO | WO 0109121 | 2/2001 |
| 2006/0142238 | A1 | 6/2006 | McGuigan | WO | WO 0132153 | 5/2001 |
| 2006/0166964 | A1 | 7/2006 | Hudyma | WO | WO01/60315 | 8/2001 |
| 2006/0188570 | A1 | 8/2006 | Batra | WO | WO01/79246 | 10/2001 |
| 2006/0194749 | A1 | 8/2006 | Keicher | WO | WO01/90121 | 11/2001 |
| 2006/0199783 | A1 | 9/2006 | Wang | WO | WO 0181359 | 11/2001 |
| 2006/0241064 | A1 | 10/2006 | Roberts | WO | WO01/91737 | 12/2001 |
| 2006/0252715 | A1 | 11/2006 | Keicher | WO | WO01/92282 | 12/2001 |
| 2006/0276511 | A1 | 12/2006 | Serrano-Wu | WO | WO01/96353 | 12/2001 |
| 2006/0293306 | A1 | 12/2006 | Beaulieu | WO | WO 0208187 | 1/2002 |
| 2007/0015905 | A1 | 1/2007 | LaColla | WO | WO 0208198 | 1/2002 |
| 2007/0026073 | A1 | 2/2007 | Doney | WO | WO 0208251 | 1/2002 |
| 2007/0037735 | A1 | 2/2007 | Gosselin | WO | WO 0208256 | 1/2002 |
| 2007/0037773 | A1 | 2/2007 | Sommadossi | WO | WO02/18404 | 3/2002 |
| 2007/0042939 | A1 | 2/2007 | LaColla | WO | WO02/32920 | 4/2002 |
| 2007/0042988 | A1 | 2/2007 | Klumpp | WO | WO 0232414 | 4/2002 |
| 2007/0042990 | A1 | 2/2007 | Gosselin | WO | WO02/48165 | 6/2002 |
| 2007/0049754 | A1 | 3/2007 | Boojamra | WO | WO 0248116 | 6/2002 |
| 2007/0059360 | A1 | 3/2007 | Jaiswal | WO | WO 0248157 | 6/2002 |
| 2007/0060498 | A1 | 3/2007 | Gosselin | WO | WO 0248172 | 6/2002 |
| 2007/0060541 | A1 | 3/2007 | Gosselin | WO | WO02/057287 | 7/2002 |
| 2007/0077295 | A1 | 4/2007 | Dahl | WO | WO02/057425 | 7/2002 |
| 2007/0087960 | A1 | 4/2007 | Storer | WO | WO 02060926 | 8/2002 |
| 2007/0099902 | A1 | 5/2007 | Dahl | WO | WO02/100415 | 12/2002 |
| 2007/0197463 | A1 | 8/2007 | Chun | WO | WO 03000713 | 1/2003 |
| 2007/0225249 | A1 | 9/2007 | Shi | WO | WO 03006490 | 1/2003 |
| 2007/0265222 | A1 | 11/2007 | MacCoss | WO | WO 03010141 | 2/2003 |
| 2007/0275912 | A1 | 11/2007 | Bhat | WO | WO 03011877 | 2/2003 |
| 2007/0275947 | A1 | 11/2007 | Bergstrom | WO | WO 03024461 | 3/2003 |
| 2008/0014228 | A1 | 1/2008 | Darmuzey | WO | WO03/026589 | 4/2003 |
| 2008/0139802 | A1 | 6/2008 | Axt | WO | WO 03037895 | 5/2003 |
| 2009/0137521 | A1 | 5/2009 | Hamilton | WO | WO 03051899 | 6/2003 |
| 2009/0176732 | A1 | 7/2009 | Beigelman | WO | WO03/053989 | 7/2003 |
| 2009/0233879 | A1 | 9/2009 | Reddy | WO | WO 03061576 | 7/2003 |
| 2009/0280084 | A1 | 11/2009 | Schinazi | WO | WO 03062256 | 7/2003 |
| 2009/0306007 | A1 | 12/2009 | Wagner | WO | WO03/068244 | 8/2003 |
| 2010/0029008 | A1 | 2/2010 | Rojas Stutz et al. | WO | WO 03084456 | 8/2003 |
| 2010/0035835 | A1 | 2/2010 | Narjes | WO | WO03/105770 | 12/2003 |
| 2010/0137576 | A1 | 6/2010 | Stec | WO | WO03/106477 | 12/2003 |
| 2010/0173863 | A1 | 7/2010 | Schinazi | WO | WO2004/000858 | 12/2003 |
| 2010/0227801 | A1 | 9/2010 | Hopkins | WO | WO 03101993 | 12/2003 |
| | | | | WO | WO 03104250 | 12/2003 |
| | FOREIGN PATENT DOCUMENTS | | | WO | WO 03105770 | 12/2003 |
| DE | 19914474 | | 10/1999 | WO | WO 04000858 | 12/2003 |
| EP | 180276 | | 5/1986 | WO | WO2004/003000 | 1/2004 |
| EP | 350287 | | 1/1990 | WO | WO2004/003138 | 1/2004 |
| EP | 0524579 | | 1/1993 | WO | WO2004/007512 | 1/2004 |
| EP | 1828217 | A2 | 9/2007 | WO | WO2004/009020 | 1/2004 |
| EP | 1881001 | | 1/2008 | WO | WO 2004002422 | 1/2004 |
| EP | 2097430 | A1 | 9/2009 | WO | WO 2004002940 | 1/2004 |
| EP | 2124555 | A2 | 12/2009 | WO | WO 2004002944 | 1/2004 |
| EP | 2207786 | | 7/2010 | WO | WO 2004002977 | 1/2004 |
| JP | 5238939 | | 9/1993 | WO | WO 2004002999 | 1/2004 |
| WO | WO 8902733 | | 4/1989 | WO | WO 2004009610 | 1/2004 |
| WO | WO90/00555 | | 1/1990 | WO | WO2004/011478 | 2/2004 |
| WO | WO 9116920 | | 11/1991 | WO | WO 2004014313 | 2/2004 |
| WO | WO91/19721 | | 12/1991 | WO | WO 2004014852 | 2/2004 |
| WO | WO 9118914 | | 12/1991 | WO | WO 2004035571 | 4/2004 |
| WO | WO 9300910 | | 1/1993 | WO | WO 2004041201 | 5/2004 |
| WO | WO 9426273 | | 11/1994 | WO | WO2004/046331 | 6/2004 |
| WO | WO 9513090 | | 5/1995 | WO | WO 2004065367 | 8/2004 |
| WO | WO95/24185 | | 9/1995 | WO | WO 2004080466 | 9/2004 |
| WO | WO 9615132 | | 5/1996 | WO | WO2004/096286 | 11/2004 |

| WO | WO 2004094452 | 11/2004 |
| WO | WO 2004096210 | 11/2004 |
| WO | WO 2004096234 | 11/2004 |
| WO | WO 2004096235 | 11/2004 |
| WO | WO2004/106356 | 12/2004 |
| WO | WO2005/002626 | 1/2005 |
| WO | WO2005/003147 | 1/2005 |
| WO | WO2005/007810 | 1/2005 |
| WO | WO2005/009418 | 2/2005 |
| WO | WO2005012327 | 2/2005 |
| WO | WO2005/020884 | 3/2005 |
| WO | WO2005/021568 | 3/2005 |
| WO | WO 2005021568 | 3/2005 |
| WO | WO 2005028502 | 3/2005 |
| WO | WO 2005037214 | 4/2005 |
| WO | WO 2005067900 | 7/2005 |
| WO | WO 2005072361 | 8/2005 |
| WO | WO 2005082144 | 9/2005 |
| WO | WO2005087788 | 9/2005 |
| WO | WO 2005095403 | 10/2005 |
| WO | WO 2005103045 | 11/2005 |
| WO | WO 2005123087 | 12/2005 |
| WO | WO2006/000922 | 1/2006 |
| WO | WO2006/012078 | 2/2006 |
| WO | WO2006/012440 | 2/2006 |
| WO | WO 2006012440 | 2/2006 |
| WO | WO 2006020082 | 2/2006 |
| WO | WO2006/029081 | 3/2006 |
| WO | WO2006/031725 | 3/2006 |
| WO | WO 2006031725 | 3/2006 |
| WO | WO2006/037028 | 4/2006 |
| WO | WO 2006035061 | 4/2006 |
| WO | WO2006/063149 | 6/2006 |
| WO | WO2006/065335 | 6/2006 |
| WO | WO2006063149 | 6/2006 |
| WO | WO 2006063717 A2 | 6/2006 |
| WO | WO 2006065590 | 6/2006 |
| WO | WO 2006093801 | 9/2006 |
| WO | WO 2006094347 | 9/2006 |
| WO | WO 2006100310 | 9/2006 |
| WO | WO 2006120251 | 11/2006 |
| WO | WO 2006120252 | 11/2006 |
| WO | WO2006121820 | 11/2006 |
| WO | WO 2007002602 | 1/2007 |
| WO | WO 2007014920 | 2/2007 |
| WO | WO 2007014921 | 2/2007 |
| WO | WO 2007014922 | 2/2007 |
| WO | WO 2007014925 | 2/2007 |
| WO | WO 2007014926 | 2/2007 |
| WO | WO 2007015824 | 2/2007 |
| WO | WO 2007020193 | 2/2007 |
| WO | WO 2007027248 | 3/2007 |
| WO | WO 2007039142 | 4/2007 |
| WO | WO 2007039145 | 4/2007 |
| WO | WO 2007065829 | 6/2007 |
| WO | WO 2007070556 | 6/2007 |
| WO | WO 2007076034 | 7/2007 |
| WO | WO 2007088148 | 8/2007 |
| WO | WO 2007092000 | 8/2007 |
| WO | WO 2007093901 | 8/2007 |
| WO | WO2007095269 | 8/2007 |
| WO | WO 2008010921 | 1/2008 |
| WO | WO 2008045419 | 4/2008 |
| WO | WO 2008048128 A1 | 4/2008 |
| WO | WO2008062206 | 5/2008 |
| WO | WO2008/082601 | 7/2008 |
| WO | WO2008079206 | 7/2008 |
| WO | WO 2008085508 | 7/2008 |
| WO | WO 2008121634 | 10/2008 |
| WO | WO2008142055 | 11/2008 |
| WO | WO 2009052287 A1 | 4/2009 |
| WO | WO 2009115893 A2 | 9/2009 |
| WO | WO 2009120878 A2 | 10/2009 |
| WO | WO 2009129120 A2 | 10/2009 |
| WO | WO 2010042834 A1 | 4/2010 |
| WO | WO 2010075554 | 7/2010 |
| WO | WO 2010080878 A1 | 7/2010 |

OTHER PUBLICATIONS

Lackey et al., Biochemical Pharmacology, 2001, 61, 179-189.
McIntee et al., Biorg. & Med. Chem. Lett., 2001, 11, 2803-2805.
Remy et al., J. Org. Chem., 1962, 27, 2491-2500.
Smirnov et al., FEBS Letters, 1975, 51(1), 211-214.
Yuodka et al., translated from Bioorganicheskaya Khimiya, 1976, 2(11), 1513-1519.
Sofia, "Discovery of PSI-352938 and PSI-353661: Purine Nucleotide Prodrugs for the treatment of HCV", First Disclosure Symposium, ACS 240th National Meeting, Boston, MA, Aug. 2010.
Abraham et al., J. Med. Chem., 1996, 4569-4575.
Aquaro et al., Antimicrobial Agents and Chemotherapy, 2000, 1, 173-177.
Chapman, et al., Nucleotides, Nucleosides and Nucleic Acids, 2001, 20(4-7), 1085-1090.
Chapman et al., Nuecleotides, Nucleosides and Nucleic Acids, 2001, 20(4-7), 621-628.
Eisenberg et al., Nucleosides, Nucleotides & Nucleic Acids, 2001, 20(4-7), 1091-1098.
Lee et al., Antimicrobial Agents and Chemotherapy, 2005, 49(5), 1898-1906.
McGuigan et al., Antiviral Chemistry and Chemotherapy 1998, 9, 473-479.
Murakami et al., Antimicrobial Agents and Chemotherapy (Feb. 2008), 52 (2), 458-464.
Murakami et al., Antiviral Chemistry & Chemotherapy, 2007, 51(2), 503-509.
Perrone et al., J. Med. Chem., 2007, 50:8, 1840-1849.
Ray et al., Antimicrobial Agents and Chemotherapy, 2008, 52(2), 648-654.
Sofia et al., "β-D2'-Deoxy-2'-C-methyluridine Phosphoramidates: Potent and Selective Inhibitors of HCV RNA Replication", Postser # P-259, presented at the 14th International Symposium on Hepatitis C Virus and Related Viruses, Glasgow, Scotland, UK, Sep. 9-13, 2007.
Sofia, "β-D-2'-Deoxy-2'-fluoro-2'-C-methyluridine Phosphoramidates: Potent and Selective Inhibitors of HCV RNA Replication", 2nd International Workshop on HCV—Resistance and New Compounds, Oct. 31, 2007.
Sofia et al, "β -D-2'-Deoxy-2'-fluoro-2'-C-methyluridine Phosphoramidates: Potent and Selective Inhibitors of HCV RNA Replication", 2nd International Workshop on HCV, Poster #7, 2007.
Stuyver et al., Antiviral Chemistry & Chemotherapy, 2004, 48(2), 651-654.
Office Action mailed mailed Mar. 30, 2007 in co-pending U.S. Appl. No. 10/828,753.
Office Action mailed Feb. 26, 2008 in co-pending U.S. Appl. No. 10/828,753.
Office Action mailed Nov. 13, 2008 in co-pending U.S. Appl. No. 11/225,425.
Office Action mailed Jul. 7, 2009 in co-pending U.S. Appl. No. 11/225,425.
U.S. Appl. No. 11/225,425 pending claims filed Oct. 2, 2009.
Office Action mailed Feb. 18, 2010 in co-pending U.S. Appl. No. 11/225,425.
Office Action mailed Oct. 2, 2007 in co-pending U.S. Appl. No. 11/353,597.
Office Action mailed Jul. 17, 2008 in co-pending U.S. Appl. No. 11/353,597.
Office Action mailed Dec. 2, 2008 in co-pending U.S. Appl. No. 11/353,597.
Office Action mailed Jul. 28, 2009 in co-pending U.S. Appl. No. 11/635,898.
U.S. Appl. No. 11/635,898 pending claims filed Dec. 24, 2009.
U.S. Appl. No. 11/854,218 pending claims filed Sep. 12, 2007.
Office Action mailed Oct. 1, 2009 in co-pending U.S. Appl. No. 11/854,218.
Office Action mailed Jul. 22, 2010 in co-pending U.S. Appl. No. 11/854,218.
U.S. Appl. No. 12/053,015 filed Mar. 31, 2008.
U.S. Appl. No. 12/053,015 pending claims filed Mar. 31, 2008.
Office Action mailed Oct. 2, 2009 in co-pending U.S. Appl. No. 12/142,536.
U.S. Appl. No. 12/142,536 pending claims filed Mar. 31, 2010.
Office Action mailed Jul. 8, 2010 in co-pending U.S. Appl. No. 12/142,536.

Office Action mailed Oct. 1, 2009 in co-pending U.S. Appl. No. 12/142,554.
U.S. Appl. No. 12/142,554 pending claims filed Dec. 17, 2009.
Office Action mailed Mar. 19, 2010 in co-pending U.S. Appl. No. 12/142,554.
Office Action mailed Oct. 1, 2009 in co-pending U.S. Appl. No. 12/240,342.
U.S. Appl. No. 12/240,342 pending claims filed Mar. 31, 2010.
Office Action mailed Dec. 17, 2009 in co-pending U.S. Appl. No. 12/553,483.
U.S. Appl. No. 12/553,483 pending claims filed Feb. 22, 2010.
U.S. Appl. No. 12/645,710, filed Dec. 23, 2009.
U.S. Appl. No. 12/645,765, filed Dec. 23, 2009.
U.S. Appl. No. 12/645,821, filed Dec. 23, 2009.
U.S. Appl. No. 12/783,680, filed May 20, 2010.
U.S. Appl. No. 60/392,350, filed Jun. 28, 2002, Storer.
U.S. Appl. No. 60/392,351, filed Jun. 28, 2002, Gosselin.
Asif, Pharmacokinetics of the Antiviral Agent B-D-2'-Deoxy-2'-Fluoro-2'-C-Methylcytidine in Rhesus Monkeys, Antimicrobial Agents and Chemotherapy, vol. 51, No. 8, 2877-2882, Aug. 2007.
Banker, G.S., "Modern Pharmaceutics, 3ed.", Marcel Dekker, New York, 1996, pp. 451 and 596.
Battaglia, A., "Combination Therapy with Interferon and Ribavirin in the Treatment of Chronic Hepatitis C Infection," The Annals of Pharmacotherapy, vol. 34, No. 4, pp. 487-494 (Apr. 2000).
Berenguer, M., "Hepatitis C virus in the transplant setting," Antiviral Therapy. Second International Conference on Therapies for Viral Hepatitis, vol. 3, Supplement 3, pp. 125-136 (1998).
Clark, J., "Design, Synthesis, and Antiviral Activity of 2'-Deoxy-2'-fluoro-2'-C-methylcytidine, a Potent Inhibitor of Hepatitis C Virus Replication," Journal of Medicinal Chemistry, vol. 48, No. 17, pp. 5504-5508 (2005).
Davis, G. L., "Current Therapy for Chronic Hepatitis C," Gastroenterology 118: S104-S114, 2000.
Eldrup, A., "Structure Activity Relationship of 2' Modified Nucleosides for Inhibition of Hepatitis C Virus," (Oral Session V: Hepatitis C Virus, Flavaviruses), 16th International Conference on Antiviral Research, Abstract No. 119, p. A75 (Apr. 27-May 1, 2003, Savannah, GA).
Eldrup, A., "Structure-Activity Relationship of Purine Ribonucleosides for Inhibition of Hepatitis C Virus RNA-Dependent RNA Polymerase," J. Med. Chem., vol. 47, No. 9, pp. 2283-2295 (2004).
Farquhar, D., "Synthesis and Biological Evaluation of Neutral Derivatives of 5-Fluoro-2'-deoxyuridine 5'-Phosphate," J. Med. Chem., vol. 26, No. 8, pp. 1153-1158 (Aug. 1983).
Farquhar, D., "Synthesis of Biological Evaluation of 9-[5'-(2-Oxo-1,3,2-oxazaphosphorinan-2-yl)-∂-D-arabinosyl]adenine and 9-[5'-(2-Oxo-1,3,2-dioxaphosphorinan-2-yl)-∂-D-arabinosyl]adenine: Potential Neutral Precursors of 9[∂-D-Arabinofuranosyl]adenine 5'-Monophosphate," J. Med. Chem., vol. 28, No. 9, pp. 1358-1361 (Sep. 1985).
Freed, J., "Evidence for acyloxymethyl esters of pyrimidine 5'-deoxyribonucleotides as extracellular sources of active 5'-deoxyribonucleotides in cultured cells," Biochemical Pharmacology, vol. 38, No. 19, pp. 3193-3198 (Oct. 1, 1989).
Hertel, "Synthesis of 2-Deoxy-2,2-difluoro-D-ribose and 2-Deoxy-2,2-difluoro-D-ribofuranosyl Nucleosides," J. Org. Chem. vol. 53, pp. 2406-2409, (1988).
Hostetler, K., "Synthesis and Antiretroviral Activity of Phospholipid Analogs of Azidothymidine and Other Antiviral Nucleosides," J. Biol. Chem., vol. 265, No. 11, pp. 6112-6117 (Apr. 15, 1990).
Hunston, R., "Synthesis and Biological Properties of Some Cyclic Phosphotriesters Derived from 2'-Deoxy-5-fluorouridine," J. Med. Chem., vol. 27, No. 4, pp. 440-444 (Apr. 1984).
International Search Report of International Application No. PCT/US05/25916 mailed Jun. 15, 2006.
Jones, R., "Minireview: Nucleotide Prodrugs," Antiviral Research, vol. 27, pp. 1-17 (1995).
Khamnei, S., "Neighboring Group Catalysis in the Design of Nucleotide Prodrugs," J. Med. Chem., vol. 39, No. 20, pp. 4109-4115 (1996).

Kotra, L.P., "Structure-Activity Relationships of 2'-Deoxy-2',2'-difluoro-L-erythro-pentofuranosyl Nucleosides," J. Med. Chem., vol. 40, pp. 3635-3644, (1997).
Kryuchkov, A., "Influence of Solvent on the Strength of Cyclic Oxygen-Containing Phosphorus Acids," Bulletin of the Academy of Sciences of the USSR. Division of Chemical Science, vol. 36, No. 6, Part 1, pp. 1145-1148 (1987).
Li, N.S. and Piccirilli, J., "Synthesis of the Phosphoramidite Derivative of 2'-Deoxy-2'-C-β-methylcytidine", J. Org. Chem., 2003, 68, 6799-6802.
Ma, "Characterization of the Metabolic Activation of Hepatitis C Virus Nucleoside Inhibitor B-D-2'-Deoxy-2-Fluro-2'-C-Methylcytidine (PSI-6130) and Identification of a Novel Active 5'-Triphosphate Species," The Journal of Biological Chemistry, vol. 282, No. 41, 29812-29820, Oct. 12, 2007.
Mitchell, A., "Bioreversible Protection for the Phospho Group: Bioactivation of the Di(4-acyloxybenzyl) and Mono(4-acyloxybenzyl) Phosphoesters of Methylphosphonate and Phosphonoacetate," Journal of the Chemical Society, Perkin Transactions 1, No. 18, pp. 2345-2353 (Sep. 21, 1992).
Olsen, D., "2'-Modified Nucleoside Analogs as Inhibitors of Hepatitis C RNA Replication," (Oral Session V: Hepatitis C Virus, Flaviviruses), 16th International Conference on Antiviral Research, Abstract No. 121, p. A76 (Apr. 27-May 1, 2003, Savannah, GA)).
Otto, "Evaluation of Nucleoside Analogs in the Hepatitis C Virus Replicon System," Framing the Knowledge of Therapeutics for Viral Hepatitis Ed. By RF Schinazi and ER Schiff., 247-261, 2006.
Piantadosi, C., "Synthesis and Evaluation of Novel Ether Lipid Nucleoside Conjugates for Anti-HIV-1 Activity,", J. Med. Chem., vol. 34, No. 4, pp. 1408-1414 (1991).
Pierra, C., "Synthesis and Pharmacokinetics of Valopicitabine (NM283), an Efficient Prodrug of the Potent Anti-HCV Agent 2'-C-Methylcytidine," J. Med. Chem. 2006 49(22):6614-6620.
Starrett, Jr., J., "Synthesis, Oral Bioavailability Determination, and in Vitro Evaluation of Prodrugs of the Antiviral Agent 9-[2-(Phosphonomethoxy)ethyl]adenine (PMEA)," J. Med. Chem., vol. 37, No. 12, pp. 1857-1864 (1994).
Stuyver, "Inhibition of hepatitis C replicon RNA synthesis by B-D-2'-deoxy-2'-fluoro-2'-C-methlcytidine: a specific inhibitor of hepatitis C virus replication," Antiviral Chemistry & Chemotherapy 2006, 17:79-87, 2006.
Stuyver, L., "Dynamics of Subgenomic Hepatitis C Virus Replicon RNA Levels in Huh-7 Cells after Exposure to Nucleoside Antimetabolites," Journal of Virology, vol. 77, No. 19, pp. 10689-10694 (Oct. 2003).
Stuyver, L., "Ribonucleoside Analogue that Blocks Replication of Bovine Viral Diarrhea and Hepatitis C Viruses in Culture," Antimicrob. Agents Chemother., vol. 47, No. 1, pp. 244-254 (Jan. 2003).
Wolff, Mandred E. "Burger's Medicinal Chemistry, 5ed, Part I", John Wiley & Sons, 1995, pp. 975-977.
Zon, G., "4 Cyclophosphoamide Analogues," Progress in Medicinal Chemistry, vol. 19, pp. 205-246 (1982).
Abraham et al., "Synthesis, Biological Activity and Decomposition Studies of Amino Acid Phosphomonoester Amidates of Acyclovir" Nucleosides, Nucleotides and Nucleic Acids, 1997, 16(10), 2079-2092.
Abraham et al., "Synthesis and Biological Activity of Aromatic Amino Acid Phosphoramidates of 5-Fluoro-2'deoxyuridine and 1β-Arabinofuranosylcytosine: Evidence of Phosphoramidase Activity" Journal of Medicinal Chemistry, 1996, 39, 4569-4575.
Balzarini et al., "Mechanism of anti-HIV action of masked alaninyl d4t-MP derivatives" PNAS, 1996, 93, 7295-7299.
Chang et al., "Amino Acid Phosphoramidate Monoesters of 3'-Azido-3'-deoxythymidine: Relationship between Antiviral Potency and Intracellular Metabolism" Journal of Medicinal Chemistry, 2001, 44, 223-231.
Chen et al., "In Vivo Pharmacokinetics and Metabolism of Anti-Human Immunodeficiency Virus Agent D4t-5'-[P-Bromophenyl Methoxyalaninyl Phosphate] (Sampidine) in Mice" Drug Metabolism and Disposition, 2001, 29(7), 1035-1041.

Chen et al., "Metabolism of Stavudine-5'-[P-Bromophenyl Methoxyalaninyl Phosphate], Stampidine, in Mice, Dogs, and Cats" Drug Metabolism and Disposition, 2002, 30(12) 1523-1531.

Chou et al., "Evidence that Human Histidine Triad Nucleotide Binding Protein 3 (Hint3) is a Distinct Branch of the Histidine Triad (HIT) Super family" Journal of Molecular Biology, 2007, 373, 978-989.

Chou et al., "Phosphoramidate Pronucleotides: A Comparison of the Phosphoramidase Substrate Specificity of Human and *Escherichia coli* Histidine Triad Nucleotide Binding Proteins" Molecular Pharmaceutics, 2007, 4(2), 208-217.

Cihlar et al., "Design and Profiling of GS-9148, a Novel Nucleotide Analog Active against Nucleoside-Resistant Variants of Human Immunodeficiency Virus Type 1, and Its Orally Bioavailable Phosphonoamidate Prodrug, GS-9131" Antimicrobial Agents and Chemotherapy, 2008, 52(2), 655-665.

Congiatu et al., "Molecular Modeling Studies on the Binding of Some Protides to the Putative Human Phosphoramidase HintI" Nucleosides, Nucleotides and Nucleic Acids, 2007, 26(8), 1121-1124.

Congiatu et al., "Naphthyl Phosphoramidate Derivatives of BVdU as Potential Anticancer Agents: Design, Synthesis and Biological Evaluation" Nucleosides, Nucleotides, and Nucleic Acids, 2005, 24(5-7), 485-489.

Curley et al., "Synthesis and anti-HIV evaluation of some phosphoramidate derivatives of AZT: studies on the effect of chain elongation on biological activity" Antiviral research, 1990, 14, 345-356.

D'Cruz et al., "Stampidine: a selective oculo-genital microbicide" Journal of Antimicrobial Chemotherapy, 2005, 56, 10-19.

Drontle et al., "Designing a Pronucleotide Stratagem: Lessons from Amino Acid Phosphoramidates of Anticancer and Antiviral Pyrimidines" MiniReviews in Medicinal Chemistry, 2004, 4, 409-419.

Egron et al., "S-Acyl-2-thioethyl Phosphoramidate Diester Derivatives as Mononucleotide Prodrugs" Journal of Medicinal Chemistry, 2003, 46, 4564-4571.

Howes et al., "The Regiospecific One-Pot Phosphorylation of Either the 5'—or 2'-Hydroxyl in 3'-Deoxycytidines Without Protection: Critical Role of the Base" Nucleosides, Nucleotides, and Nucleic Acids, 2003, 22 (5-8), 687-689.

Iyer et al., "Synthesis, in Vitro Anti-Breast Cancer Activity, and Intracellular Decomposition of Amino Acid Methyl Ester and Alkyl Amide Phosphoramidate Monoesters of 3'-Azido-3'-deoxythymidine (AZT)" Journal of Medicinal Chemistry 2000, 43, 2266-2274.

Kim et al., "Monitoring the Intracellular Metabolism of Nucleoside Phosphoramidate Pronucleotides by $^{31}$P NMR" Nucleosides, Nucleotides and Nucleic Acid, 2004, 23(1) 483-493.

Lehsten et al., "An Improved Procedure for the Synthesis of Nucleoside Phosphoramidates" Organic Process Research and Development, 2002, 6, 819-822.

McGuigan et al., "Aryl phosphate derivatives of AZT retain activity against HIV1 in cell lines which are resistant to the action of AZT" Antiviral Research,1992, 17, 311-321.

McGuigan et al., "Application of Phosphoramidate ProTide Technology Significantly Improves Antiviral Potency of Carbocyclic Adenosine Derivatives" Journal of Medicinal Chemistry, 2006, 49, 7215-7726.

McGuigan et al., "Application of Phosphoramidate Pronucleotides Technology to Abacavir Leads to a Significant Enhancement of Antiviral Potency" Journal of Medicinal Chemistry, 2005, 48, 3504-3515.

McGuigan et al., "Aryl Phosphoramidate Derivatives of d4T Have Improved Anti-HIV Efficacy in Tissue Culture and May Act by the Generation of a Novel Intracellular Metabolite" Journal of Medicinal Chemistry, 1996, 39, 1748-1753.

McGuigan et al., "Synthesis and anti-HIV activity of some novel chain-extended phosphoramidate derivatives of d4T (stavudine): esterase hydrolysis as a rapid predictive test for antiviral potency" Antiviral Chemistry and Chemotherapy, 1998, 9, 109-115.

McGuigan et al., "Synthesis and evaluation of some novel phosphoramidate derivatives of 3'-azido-3'-deoxythymidine (AZT) as anti-HIV compounds" Antiviral Chemistry and Chemotherapy, 1990, 1(2), 107-113.

McIntee et al., "Probing the Mechanism of Action and Decomposition of Amino Acid Phosphomonoester Amidates of Antiviral Nucleoside Prodrugs" Journal of Medicinal Chemistry, 1997, 40, 3323-3331.

Perrone et al., "First Example of Phosphoramidate Approach Applied to a 4'Substituted Purine Nucleoside (4'-Azidoadenosine): Conversion of an Inactive Nucleoside to a Submicromolar Compound versus Hepatitis C Virus" Journal of Medicinal Chemistry, 2007 50, 5463-5470.

Perrone et al., "Application of the Phosphoramidate ProTide Approach to 4'-Azidouridine Confers Sub-micromolar Potency versus Hepatitis C Virus on an Inactive Nucleoside" J. Med. Chem. 2007, 50(8), 1840-1849.

Saboulard et al., "Characterization of the Activation Pathway of Phosphoramidate Triester Prodrugs of Stavudine and Zidovudine" American Society for Pharmacology and Experimental Therapeutics, 1999, 56, 693-704.

Schultz et al., "Prodrugs of Biologically Active Phosphate Esters" Bioorganic and Medicinal Chemistry, 2003, 11, 885-898.

Siccardi et al., "Stereoselective and Concentration-Dependent Polarized Epithelial Permeability of a Series of Phosphoramidate Triester Prodrugs of d4T: An in Vitro Study in Caco-2 and Madin-Darby Canine Kidney Cell Monolayers" The Journal of Pharmacology and Experimental Therapeutics, 2003, 307(3), 1112-1119.

Siccardi et al., "Stereospecific chemical and enzymatic stability of phosphoramidate triester prodrugs of d4T in vitro" European Journal of Pharmaceutical Sciences, 2004, 22, 25-31.

Siddiqui et al., "Design and Synthesis of Lipophilic Phosphoramidate d4T-MP Prodrugs Expressing High Potency Against HIV in Cell Culture: Structural Determinants for in Vitro Activity and QSAR" Journal of Medicinal Chemistry, 1999, 42, 4122-4128.

Siddiqui et al., "Enhancing the Aqueous Solubility of d4T-based Phosphoramidate Prodrugs" Bioorganic and Medicinal Chemistry Letters, 2000, 10, 381-384.

Song et al., "Pharmacokinetics of Amino Acid Phosphoramidate Monoesters of Zidovudine in Rats" Antimicrobial Agents and Chemotherapy, 2002, 46(5), 1357-1363.

Uckun et al., "In Vivo Pharmacokinetics and Toxicity Profile of the Anti-HIV Agent Stampidine in Dogs and Feline Immunodeficiency Virus-infected Cats" Arzneim.-Forsch./Drug Research 2006, 56(2a), 176-192.

Valette et al., "Decomposition Pathways and in Vitro HIV Inhibitory Effects of IsoddA Pronucleotides: Toward a Rational Approach for Intracellular Delivery of Nucleoside 5'-Monophosphates" Journal of Medicinal Chemistry, 1996, 39, 1981-1990.

Venkatachalam et al., "Synthesis and metabolism of naphthyl substituted phosphoramidate derivatives of stavudine" Bioorganic and Medicinal Chemistry, 2006, 14, 5161-5177.

Venkatachalam et al., Rational Drug Design of Multifunctional Phosphoramidate Substituted Nucleoside Analogs Current Pharmaceutical Design, 2004, 10 (15), 1713-1726.

Wagner et al., "Antiviral Nucleoside Drug Delivery via Amino Acid Phosphoramidates', Nucleosides, Nucleotides and Nucleic Acids" Nucleosides, Nucleotides and nucleic Acids, 1999, 18(4), 913-918.

Wu et al., "Synthesis and Biological Activity of a Gemcitabine Phosphoramidate Prodrug" Journal of Medicinal Chemistry, 2007, 50, 3743-3746.

Bazan and Fletterick, Virology, 1989,171,637-639.

Beres et al., J. Med. Chem., 1986, 29, 1243-1249.

Gunic et al., Biorganic and Medicinal Chemistry Letters, 2007, vol. 17, 2452-2455.

Broeders et al., Journal of American Chemical Society, 1990, vol. 112, 7475-7482.

Broeders et al., Can J. Chem., 1993, 71, 855-863.

Gorbalenya et al., Nature, 1988, 333, 22.

Hooz et al., Can. J. Chem., 1968, 46, 86-87.

Ishii et al., Heptology, 1999, 29:1227-1235.

Lohmann et al., Virology, 1998, 249: 108-118.

Bartenschlager, J. Virol., 1993, 67, 3835-3844.

Bartenschlager, J. Virol., 1994, 68, 5045-5055.

Bazan and Fletterick ,Virology, 1989, 171, 637-639.

Beaulieu, Current Opinion in Investigational Drugs, 2004, 5, 838-850.
Behrens, EMBO, 1996, 15, 12-22.
Calisher, J. Gen. Virol, 1989, 70, 37-43.
Carrol, Infectious Disorders-Drug Targets, 2006, 6, 17-29.
Eckart, Biochem. Biophys. Res. Comm. 1993, 192, 399-406.
Failla, J. Virol., 1994, 68, 3753-3760.
Fields Virology, Editors: Fields, B. N., Knipe, D. M., and Howley, P. M., Lippincott—Raven Publishers, Philadelphia, PA, 1996, Chapter 31, 931-959.
Gorbalenya, Nature, 1988, 333, 22.
Gorbalenya, Nucleic Acid Res.,1989, 17, 3889-3897.
Grakoui, J. Virol. 1993, 67, 2832-2843.
Grakoui, Proc. Natl. Acad Sci. USA 1993, 90, 10583-10587.
Griffith, Annual Reports in Medicinal Chemistry, 2004, 39, 223-237.
Halstead, Rev. Infect. Dis., 1984, 6, 251-264.
Halstead, Science, 1988, 239, 476-481.
Hijikata, J. Virol. 1993, 67, 4665-4675.
Jin and Peterson, Arch. Biochem. Biophys., 1995, 323, 47-53.
Kim et al., Biochem. Biophys. Res. Comm., 1995, 215, 160-166.
Koonin et al., V.V., Crir. Rev. Biochem. Molec. Biol. 1993, 28, 375-430.
Lochmann, J. Virol., 1997, 71, 8416-8428.
Meyers et al., Advances in Virus Research, 1996, 47, 53-118.
Moennig, Adv. Vir. Res. 1992, 41, 53-98.
Monath, New Eng. J. Med, 1988, 319, 641-643.
Ni, Current Opinion in Drug Discovery and Development, 2004, 7, 446-459.
Tan, Nature Rev. Drug Discov., 2002, 1, 867-881.
Tome, J. Virol., 1993, 67, 4017-4026.
Walker, Exp. Opin. Investigational Drugs, 2003, 12, 1269-1280.
Warrener et al., J. Virol. 1995, 69, 1720-1726.
Wiskerchen et al.,, Virology, 1991, 184, 341-350.
Wu, Current Drug Targets—Infectious Disorders, 2003, 3, 207-219.
Xu et al., J. Virol., 1997, 71:5312-5322.
Yuan, Biochem. Biophys. Res. Comm. 1997, 232, 231-235.
Zhong, J. Virol., 1998, 72, 9365-9369.
Bhat, "Synthesis and Pharmacokinetic Properties of Nucleoside Analogues as Possible Inhibitors of HCV RNA Replication," (Oral Session V: Hepatitis C Virus, Flaviviruses), 16th International Conference on Antiviral Research, Abstract No. 120, p. A75 (Apr. 27-May 1, 2003, Savannah, GA).
Baschang et al., Angewandte Chemie, 85:1, 44-45, 1973.
Broders et al., J. Am. Chem. Soc., 112:21, 7475-7482, 1990.
Chu, Bioorganic & Medicinal Chemistry Letters, vol. 9, 1949-1952, 1999.
Chu, Tetrahedron Letters, vol. 37, No. 40, 7229-7232, 1996.
De Lombaert, J. Med. Chem., vol. 37, No. 4, 498-511, 1994.
Edmundson, J. Chem. Res. Synop., 1989, 5:122-123.
Engels et al., Chem. Ber., 110:6, 2019-2027, 1977.
Goekjian, Journal of Organic Chemistry, 1999, 64 (12) 4238-4246.
Gunic, Bioorg. & Med. Chem.Letters, vol. 17, No. 9, pp. 2456-2458, 2007.
Hernandez, Journal of Organic Chemistry, 2004, 69 (24), 8437-8444.
Hostetler, K., Antimicrob. Agents Chemother., vol. 36, No. 9, 2025-2029, 1992.
Kucera, AIDS Research and Human Retroviruses, vol. 6, No. 4, 491-501, 1990.
Lopez Aparicio et al., "Branched-Chain Sugars, Part VII, Synthesis of Saccharinic Acid Derivatives" Carbohydrate Research, 129, 99-109, 1984.
Meier, Bioorganic & Medicinal Chemistry Letters, vol. 7, No. 2, 99-104, 1997.
Neidlein, Heterocycles, vol. 35, No. 2, 1185-1203, 1993.
Nelson et al., J. Am. Chem. Soc., 109:13, 4058-4064, 1987.
Nifantyev, Phosphorus, Sulfur, and Silicon and the Related Elements, vol. 113, 1-13, 1996.
Novak, Collection of Czechoslovak Chemical Communications, vol. 39, 869-882, 1974.
Novak, Collection of Czechoslovak Chemical Communications, vol. 36, 3670-3677, 1971.
Oishi, Tetrahedron Letters, 1993, 34 (22), 3573-3576.
Pogam et al., "No Evidence of R7128 Drug Resistance After Up to 4 Weeks Treatment of GT1, 2 and 3 Hepatitis C Virus Infected Individuals", from 44th Annual Meeting of European Association for the Study of the Liver (EASL), Copenhagen, Denmark Apr. 22-Apr. 26, 2009.
Sofia et al., "R7128, A Potent and Selective Nucleoside Inhibitor of HCV NS5B Polymerase: An Overview of Clinical Efficacy and Progress Toward Second Generation Inhibitors", From HCV Drug Discovery 2008, Chicago, IL, Apr. 28, 2008.
Shih, Bull. Inst. Chem., Academia Sinica, 41:9-16, 1994.
Stella, "Prodrugs as Therapeutics", Expert Opinion Ther. Patents, 2004, 14:3, 277-280.
Sun Xiao-Ling and Wu Yu-Lin, "Study on the Chirality of Sulfur in Ethyl (2S, 3R,4R)-4,5- O-Isopropylidene-2,3-sulfinyl-2,3,4,5-tetrahydroxy-pentanoate", Acta Chimica Sinica, 1997, vol. 55, 600-604.
Sun Xiao-Ling and Wu Yu-Lin, "The Synthesis of (2s,3R)-Sphingosine from D-Mannitol", Acta Chimica Sinica, 1996, vol. 54, 826-832.
International Search Report of PCT/US2004/012472 (WO2005/003147) mailed Dec. 30, 2004.
Written Opinion of PCT/US2004/012472 mailed Dec. 30, 2004.
International Preliminary Examination Report of PCT/US2004/012472 issued Dec. 1, 2005.
Written Opinion of PCT/US2005/025916 mailed Jun. 15, 2006.
International Preliminary Examination Report of PCT/US2005/025916 issued Jan. 23, 2007.
Supplemental European Search Report of European patent appln No. EP 05775359.2 dated Sep. 15, 2010.
International Search Report of PCT/US2005/032406 (W02006/031725) mailed May 8, 2008.
Written Opinion of PCT/US2005/032406 mailed May 8, 2008.
International Preliminary Examination Report of PCT/US2005/032406 issued Mar. 10, 2009.
International Search Report of PCT/EP2006/069060 (WO2007/065829) mailed Jan. 30, 2007.
Written Opinion of PCT/EP2006/069060 mailed Jan. 30, 2007.
International Preliminary Examination Report of PCT/EP2006/069060 mailed Nov. 5, 2008.
International Search Report of PCT/US2008/058183 (WO2008/121634) mailed Mar. 31, 2010.
Written Opinion of PCT/US2008/058183 mailed Mar. 31, 2010.
International Preliminary Examination Report of PCT/US2008/058183 issued Apr. 7, 2010.
International Search Report of PCT/US2009/046619 (WO/2009/152095) mailed Sep. 23, 2010.
Partial International Search Report of PCT/US2009/069475 (WO/2010/075554) mailed Mar. 5, 2010.
Final International Report and Written Opinion of PCT/US2009/069475 mailed May 10, 2010.
Invitation to Pay Additional Fees & Partial International Search Report of PCT/US2010/035641 mailed Jul. 23, 2010.
International Search Report of PCT/US2010/035641 mailed Sep. 28, 2010.
Written Opinion of PCT/US2010/035641 mailed Sep. 28, 2010.
Response filed Oct. 25, 2010 at the EPO for European patent application No. EP08732818.3.
Selected Prosecution Documents for U.S. Appl. No. 12/142,536: (1) Jun. 19, 2008 Preliminary Amendment; (2) Oct. 2, 2009 Office Action; (3) Mar. 31, 2010 Amendment; (4) Jul. 8, 2010 Office Action; (5) Oct. 8, 2010 Amendment; (6) Oct. 8, 2010 Declaration; (7) Nov. 26, 2010 Advisory Action; (8) May 17, 2011 Response.
U.S. Appl. No. 12/645,821: Preliminary Amendment filed Dec. 13, 2011.
Selected Prosecution Documents for U.S. Appl. No. 12/131,868: (1) Jun. 2, 2008 Preliminary Amendment; (2) Nov. 15, 2010 Restriction/Election Requirement; (3) Dec. 14, 2010 Response; (4) Mar. 3, 2011 Office Action; (5) May 27, 2011 Amendment; (6) Aug. 8, 2011 Office Action; (7) Sep. 20, 2011.

* cited by examiner

NUCLEOSIDE CYCLICPHOSPHATES

PRIORITY CLAIM

Priority is claimed to U.S. Provisional Application Nos. 61/060,683, filed on Jun. 11, 2008; 61/140,369, filed on Dec. 23, 2008, and 61/140,317, filed on Dec. 23, 2008.

FIELD OF INVENTION

The present invention pertains to nucleoside cyclic phosphates and their use as agents for treating viral diseases. These compounds are inhibitors of RNA-dependent RNA viral replication and are useful as inhibitors of HCV NS5B polymerase, as inhibitors of HCV replication and for treatment of hepatitis C infection in mammals. The invention provides novel chemical compounds, and the use of these compounds alone or in combination with other antiviral agents for treating HCV infection.

BACKGROUND

Hepatitis C virus (HCV) infection is a major health problem that leads to chronic liver disease, such as cirrhosis and hepatocellular carcinoma, in a substantial number of infected individuals, estimated to be 2-15% of the world's population. There are an estimated 4.5 million infected people in the United States alone, according to the U.S. Center for Disease Control. According to the World Health Organization, there are more than 200 million infected individuals worldwide, with at least 3 to 4 million people being infected each year. Once infected, about 20% of people clear the virus, but the rest can harbor HCV the rest of their lives. Ten to twenty percent of chronically infected individuals eventually develop liver-destroying cirrhosis or cancer. The viral disease is transmitted parenterally by contaminated blood and blood products, contaminated needles, or sexually and vertically from infected mothers or carrier mothers to their offspring. Current treatments for HCV infection, which are restricted to immunotherapy with recombinant interferon-β alone or in combination with the nucleoside analog ribavirin, are of limited clinical benefit as resistance develops rapidly. Moreover, there is no established vaccine for HCV. Consequently, there is an urgent need for improved therapeutic agents that effectively combat chronic HCV infection.

The HCV virion is an enveloped positive-strand RNA virus with a single oligoribonucleotide genomic sequence of about 9600 bases which encodes a polyprotein of about 3,010 amino acids. The protein products of the HCV gene consist of the structural proteins C, E1, and E2, and the non-structural proteins NS2, NS3, NS4A and NS4B, and NS5A and NS5B. The nonstructural (NS) proteins are believed to provide the catalytic machinery for viral replication. The NS3 protease releases NS5B, the RNA-dependent RNA polymerase from the polyprotein chain. HCV NS5B polymerase is required for the synthesis of a double-stranded RNA from a single-stranded viral RNA that serves as a template in the replication cycle of HCV. Therefore, NS5B polymerase is considered to be an essential component in the HCV replication complex (K. Ishi, et al, *Heptology*, 1999, 29: 1227-1235; V. Lohmann, et al., *Virology*, 1998, 249: 108-118). Inhibition of HCV NS5B polymerase prevents formation of the double-stranded HCV RNA and therefore constitutes an attractive approach to the development of HCV-specific antiviral therapies.

HCV belongs to a much larger family of viruses that share many common features.

Flaviviridae Viruses

The Flaviviridae family of viruses comprises at least three distinct genera: pestiviruses, which cause disease in cattle and pigs; flavivruses, which are the primary cause of diseases such as dengue fever and yellow fever; and hepaciviruses, whose sole member is HCV. The flavivirus genus includes more than 68 members separated into groups on the basis of serological relatedness (Calisher et al., *J. Gen. Virol*, 1993, 70,37-43). Clinical symptoms vary and include fever, encephalitis and hemorrhagic fever (*Fields Virology*, Editors: Fields, B. N., Knipe, D. M., and Howley, P. M., Lippincott-Raven Publishers, Philadelphia, Pa., 1996, Chapter 31, 931-959). Flaviviruses of global concern that are associated with human disease include the Dengue Hemorrhagic Fever viruses (DHF), yellow fever virus, shock syndrome and Japanese encephalitis virus (Halstead, S. B., *Rev. Infect. Dis.*, 1984, 6, 251-264; Halstead, S. B., *Science*, 239:476-481, 1988; Monath, T. P., *New Eng. J. Med*, 1988, 319, 64 1-643).

The pestivirus genus includes bovine viral diarrhea virus (BVDV), classical swine fever virus (CSFV, also called hog cholera virus) and border disease virus (BDV) of sheep (Moennig, V. et al. *Adv. Vir. Res.* 1992, 41, 53-98). Pestivirus infections of domesticated livestock (cattle, pigs and sheep) cause significant economic losses worldwide. BVDV causes mucosal disease in cattle and is of significant economic importance to the livestock industry (Meyers, G. and Thiel, H. J., Advances in Virus Research, 1996, 47, 53-118; Moennig V., et al, Adv. Vir. Res. 1992, 41, 53-98). Human pestiviruses have not been as extensively characterized as the animal pestiviruses. However, serological surveys indicate considerable pestivirus exposure in humans.

Pestiviruses and hepaciviruses are closely related virus groups within the Flaviviridae family. Other closely related viruses in this family include the GB virus A, GB virus A-like agents, GB virus-B and GB virus-C (also called hepatitis G virus, HGV). The hepacivirus group (hepatitis C virus; HCV) consists of a number of closely related but genotypically distinguishable viruses that infect humans. There are at least 6 HCV genotypes and more than 50 subtypes. Due to the similarities between pestiviruses and hepaciviruses, combined with the poor ability of hepaciviruses to grow efficiently in cell culture, bovine viral diarrhea virus (BVDV) is often used as a surrogate to study the HCV virus.

The genetic organization of pestiviruses and hepaciviruses is very similar. These positive stranded RNA viruses possess a single large open reading frame (ORF) encoding all the viral proteins necessary for virus replication. These proteins are expressed as a polyprotein that is co- and post-translationally processed by both cellular and virus-encoded proteinases to yield the mature viral proteins. The viral proteins responsible for the replication of the viral genome RNA are located within approximately the carboxy-terminal. Two-thirds of the ORF are termed nonstructural (NS) proteins. The genetic organization and polyprotein processing of the nonstructural protein portion of the ORF for pestiviruses and hepaciviruses is very similar. For both the pestiviruses and hepaciviruses, the mature nonstructural (NS) proteins, in sequential order from the amino-terminus of the nonstructural protein coding region to the carboxy-terminus of the ORF, consist of p7, NS2, NS3, NS4A, NS4B, NS5A, and NS5B.

The NS proteins of pestiviruses and hepaciviruses share sequence domains that are characteristic of specific protein functions. For example, the NS3 proteins of viruses in both groups possess amino acid sequence motifs characteristic of serine proteinases and of helicases (Gorbalenya et al., *Nature*, 1988, 333, 22; Bazan and Fletterick *Virology*, 1989, 171,637-639; Gorbalenya et al., *Nucleic Acid Res.*,1989, 17, 3889-

3897). Similarly, the NS5B proteins of pestiviruses and hepaciviruses have the motifs characteristic of RNA-directed RNA polymerases (Koonin, E. V. and Dolja, V. V., *Crir. Rev. Biochem. Molec. Biol.* 1993, 28, 375-430).

The actual roles and functions of the NS proteins of pestiviruses and hepaciviruses in the lifecycle of the viruses are directly analogous. In both cases, the NS3 serine proteinase is responsible for all proteolytic processing of polyprotein precursors downstream of its position in the ORF (Wiskerchen and Collett, *Virology*, 1991, 184, 341-350; Bartenschlager et al., *J. Virol.* 1993, 67, 3835-3844; Eckart et al. *Biochem. Biophys. Res. Comm.* 1993, 192, 399-406; Grakoui et al., *J. Virol.* 1993, 67, 2832-2843; Grakoui et al., *Proc. Natl. Acad Sci. USA* 1993, 90, 10583-10587; Hijikata et al., *J. Virol.* 1993, 67, 4665-4675; Tome et al., *J. Virol.*, 1993, 67, 4017-4026). The NS4A protein, in both cases, acts as a cofactor with the NS3 serine protease (Bartenschlager et al., *J. Virol.* 1994, 68, 5045-5055; Failla et al., *J. Virol.* 1994, 68, 3753-3760; Xu et al., *J. Virol.*, 1997, 71:53 12-5322). The NS3 protein of both viruses also functions as a helicase (Kim et al., *Biochem. Biophys. Res. Comm.*, 1995, 215, 160-166; Jin and Peterson, *Arch. Biochem. Biophys.*, 1995, 323, 47-53; Warrener and Collett, *J. Virol.* 1995, 69,1720-1726). Finally, the NS5B proteins of pestiviruses and hepaciviruses have the predicted RNA-directed RNA polymerases activity (Behrens et al., EMBO, 1996, 15, 12-22; Lechmann et al., *J. Virol.*, 1997, 71, 8416-8428; Yuan et al., *Biochem. Biophys. Res. Comm.* 1997, 232, 231-235; Hagedorn, PCT WO 97/12033; Zhong et al, *J. Virol.*, 1998, 72, 9365-9369).

Currently, there are limited treatment options for individuals infected with hepatitis C virus. The current approved therapeutic option is the use of immunotherapy with recombinant interferon-α alone or in combination with the nucleoside analog ribavirin. This therapy is limited in its clinical effectiveness and only 50% of treated patients respond to therapy. Therefore, there is significant need for more effective and novel therapies to address the unmet medical need posed by HCV infection.

A number of potential molecular targets for drug development of direct acting antivirals as anti -HCV therapeutics have now been identified including, but not limited to, the NS2-NS3 autoprotease, the N3 protease, the N3 helicase and the NS5B polymerase. The RNA-dependent RNA polymerase is absolutely essential for replication of the single-stranded, positive sense, RNA genome and this enzyme has elicited significant interest among medicinal chemists.

Inhibitors of HCV NS5B as potential therapies for HCV infection have been reviewed: Tan, S.-L., et al., *Nature Rev. Drug Discov.*, 2002, 1, 867-881; Walker, M. P. et al., *Exp. Opin. Investigational Drugs*, 2003, 12, 1269-1280; Ni, Z-J., et al., *Current Opinion in Drug Discovery and Development*, 2004, 7, 446-459; Beaulieu, P. L., et al., Current Opinion in Investigational Drugs, 2004, 5, 838-850; Wu, J., et al., *Current Drug Targets-Infectious Disorders*, 2003, 3, 207-219; Griffith, R. C., et al, *Annual Reports in Medicinal Chemistry*, 2004, 39, 223-237; Carrol, S., et al., *Infectious Disorders-Drug Targets*, 2006, 6, 17-29. The potential for the emergence of resistant HCV strains and the need to identify agents with broad genotype coverage supports the need for continuing efforts to identify novel and more effective nucleosides as HCV NS5B inhibitors.

Nucleoside inhibitors of NS5B polymerase can act either as a non-natural substrate that results in chain termination or as a competitive inhibitor which competes with nucleotide binding to the polymerase. To function as a chain terminator the nucleoside analog must be taken up by the cell and converted in vivo to a triphosphate to compete for the polymerase nucleotide binding site. This conversion to the triphosphate is commonly mediated by cellular kinases which imparts additional structural requirements on a potential nucleoside polymerase inhibitor. Unfortunately, this limits the direct evaluation of nucleosides as inhibitors of HCV replication to cell-based assays capable of in situ phosphorylation.

In some cases, the biological activity of a nucleoside is hampered by its poor substrate characteristics for one or more of the kinases needed to convert it to the active triphosphate form. Formation of the monophosphate by a nucleoside kinase is generally viewed as the rate limiting step of the three phosphorylation events. To circumvent the need for the initial phosphorylation step in the metabolism of a nucleoside to the active triphosphate analog, the preparation of stable phosphate prodrugs has been reported. Nucleoside cyclic phosphate prodrugs have been shown to be precursors of the active nucleoside triphosphate and to inhibit viral replication when administered to viral infected whole cells (PCT Int. App. WO 2007/027248 A2; Bi-Organic and Medicinal Chemistry Letters, 2007, Vol 17, Page 2452-2455; Journal of American Chemical Society, 1990, Vol 112, Page 7475-7482.)

Also limiting the utility of nucleosides as viable therapeutic agents is their sometimes poor physicochemical and pharmacokinetic properties. These poor properties can limit the intestinal absorption of an agent and limit uptake into the target tissue or cell. To improve on their properties prodrugs of nucleosides have been employed.

SUMMARY OF THE INVENTION

The present invention is directed toward novel cyclic phosphate prodrugs of nucleoside derivatives for the treatment of viral infections in mammals, which is a compound, its stereoisomers, salts (acid or basic addition salts), hydrates, solvates, deuterated analogues, or crystalline forms thereof, represented by the following structure:

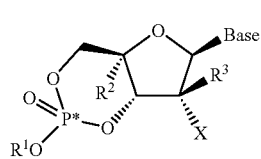

I wherein $R^1$ is hydrogen, n-alkyl, branched alkyl, cycloalkyl, alkaryl, or aryl, which includes, but is not limited to, phenyl or naphthyl, where phenyl or naphthyl are optionally substituted with at least one of H, F, Cl, Br, I, OH, OR', SH, SR', $NH_2$, NHR', $NR'_2$, $NHR'_2^+$, $NR'_3^+$, heterocycle, lower alkyl, halogenated (F, Cl, Br, I) lower alkyl, halogenated (F, Cl, Br, I) lower alkenyl of $C_2$-$C_6$, lower alkynyl of $C_2$-$C_6$, such as C≡CH, halogenated (F, Cl, Br, I) lower alkynyl of $C_2$-$C_6$, lower alkoxy of $C_1$-$C_6$, halogenated (F, Cl, Br, I) lower alkoxy of $C_1$-$C_6$, $CO_2H$, $CO_2R'$, $CONH_2$, CONHR', $CONR'_2$, CH=$CHCO_2H$, or CH=$CHCO_2R'$;

$R^2$ is H, an optionally substituted alkyl (including lower alkyl), cyano (CN), $CH_3$, vinyl, O-alkyl, O-(lower alkyl), including $OCH_3$, $OCH_2CH_3$, hydroxyl alkyl, i.e., —$(CH_2)_o$OH, wherein o is 1-10, hydroxyl lower alkyl, i.e., —$(CH_2)_p$OH, where p is 1-6, including hydroxyl methyl ($CH_2OH$), fluoromethyl ($CH_2F$), azido ($N_3$), $CH_2CN$, $CH_2N_3$, $CH_2NH_2$, $CH_2NHCH_3$, $CH_2N(CH_3)_2$, ethynyl alkyne (optionally substituted), or halogen, including F, Cl, Br, or I;

$R^3$ is H, $CH_3$, $CH_2F$, $CHF_2$, $CF_3$, F, or CN;

X is H, OH, F, OMe, halogen, $NH_2$, or $N_3$

Base is a naturally occurring or modified purine or pyrimidine base represented by the following structures:

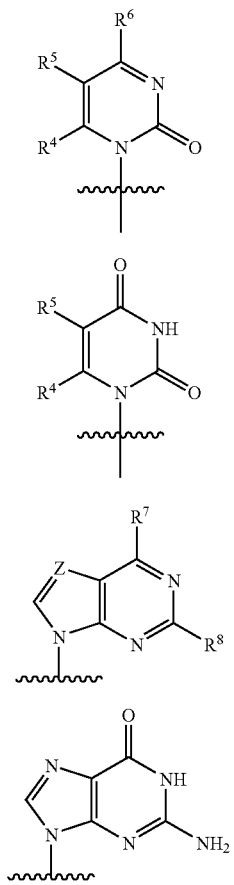

wherein

Z is N or $CR^9$;

$R^4$, $R^5$, $R^6$, $R^7$, and $R^8$ are independently H, F, Cl, Br, I, OH, OR', such as alkoxy, aryloxy, benzyloxy, substituted aryloxy, and substituted benzyloxy, SH, SR', $NH_2$, NHR', $NR'_2$, $NHR'_2{}^+$, $NR'_3{}^+$, heterocycle, lower alkyl, halogenated (F, Cl, Br, I) lower alkyl, lower alkenyl of $C_2$-$C_6$, halogenated (F, Cl, Br, I) lower alkenyl of $C_2$-$C_6$, lower alkynyl of $C_2$-$C_6$ such as C≡CH, halogenated (F, Cl, Br, I) lower alkynyl of $C_2$-$C_6$, lower alkoxy of $C_1$-$C_6$, halogenated (F, Cl, Br, I) lower alkoxy of $C_1$-$C_6$, $CO_2H$, $CO_2R'$, $CONH_2$, CONHR', $CONR'_2$, CH=CHCO$_2$H, or CH=CHCO$_2$R';

$R^9$ is an H, halogen (including F, Cl, Br, I), OH, OR', SH, SR', $NH_2$, NHR', $NR'_2$, $NHR'_2{}^+$, $NR'_3{}^+$, $NO_2$, lower alkyl, halogenated (F, Cl, Br, I) lower alkyl, lower alkenyl of $C_2$-$C_6$, halogenated (F, Cl, Br, I) lower alkenyl of $C_2$-$C_6$, lower alkynyl of $C_2$-$C_6$, halogenated (F, Cl, Br, I) lower alkynyl of $C_2$-$C_6$, lower alkoxy of $C_1$-$C_6$, halogenated (F, Cl, Br, I) lower alkoxy of $C_1$-$C_6$, $CO_2H$, $CO_2R'$, $CONH_2$, CONHR', $CONR'_2$, CH=CHCO$_2$H, or CH=CHCO$_2$R';

wherein R' is an optionally substituted alkyl, an optionally substituted cycloalkyl, an optionally substituted alkynyl, an optionally substituted alkenyl, or an optionally substituted acyl, an optionally substituted alkoxyalkyl, where for the instance of $NR'_2$ or $NHR'_2{}^+$ each R' comprise at least one C atom that is independent of one another or are joined to form a heterocycle comprising at least two carbon atoms, and where for the instance of $NR'_3{}^+$ each R' comprises at least one C atom which are independent of one another or each R' comprises at least one C atom in which at least two R' are joined to form a heterocycle comprising at least two carbon atoms.

Alternatively, the Base may be selected from a group of formula c'

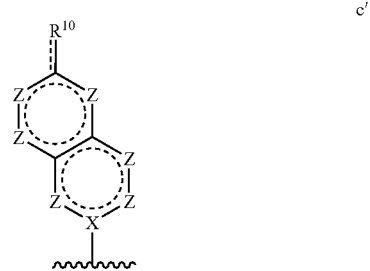

wherein for structure c', if Z is a participant in a pi bond (double bond), Z is independently selected from N or C-G; or, if Z is not a participant in a pi bond (double bond), Z is independently selected from O, S, Se, $NR^{11}$, $NOR^{11}$, $NNR^{11}{}_2$, CO, CS, $CNR^{11}$, SO, $S(O)_2$, SeO, $Se(O)_2$, or $C(G)_2$;

each G is independently selected from the group consisting of H, halogen, $OR^{11}$, $SR^{11}$, $NR^{11}{}_2$, $NR^{11}OR^{11}$, $N_3$, $COOR^{11}$, CN, $CONR^{11}{}_2$, $C(S)NR^{11}{}_2$, $C(=NR^{11})NR^{11}{}_2$, and $R^{11}$; and where any two adjacent Z are not both selected from O, S, and Se, or not both selected from CO, CS, $CNNR^{11}$, SO, $S(O)_2$, SeO and $Se(O)_2$;

wherein, if X is a participant in a pi bond (double bond), X is C; or if X is not a participant in a pi bond (double bond), X is $CR^{11}$ or N;

wherein, if $R^{10}$ is a participant in a pi bond (double bond), $R^{10}$ is O, S, Se, $NR^{11}$, $NOR^{11}$ or $NNR^{11}{}_2$; or if $R^{10}$ is not a participant in a pi bond (double bond), $R^{10}$ is $OR^{11}$, $SR^{11}$, F, Cl, $R^{10}$, or $SeR^{10}$; and dashed lines ( - - - ) indicate a possible pi or double bond;

each R is independently selected from the group consisting of H, $CF_3$, optionally substituted alkyl, optionally substituted alkenyl, optionally substituted alkynyl, optionally substituted aryl, optionally substituted acyl, optionally substituted cycloalkyl, optionally substituted cycloalkenyl, optionally substituted heteroaryl, optionally substituted heterocyclyl, and optionally substituted arylalkyl; or Base may be a structure selected from the group consisting of structures d'-n

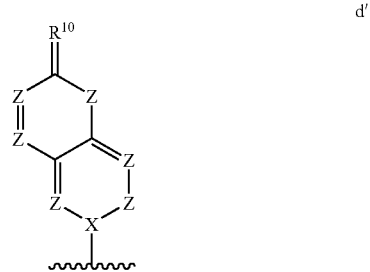

-continued
e
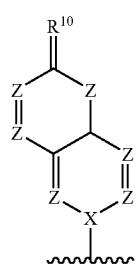
f
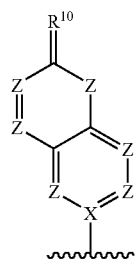
g
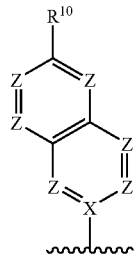
h
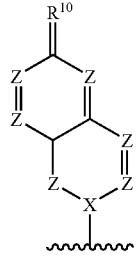
i
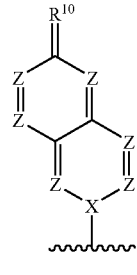
j
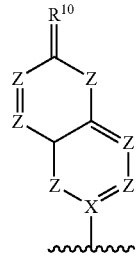
-continued
k
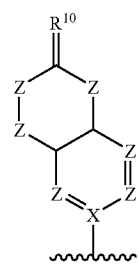
l
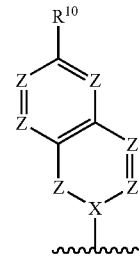
m
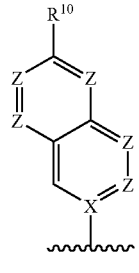
n
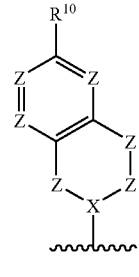
wherein Z, X, and $R^{10}$ are defined as in structure c';
Base may be a structure selected from the group consisting of structures o-ff
o
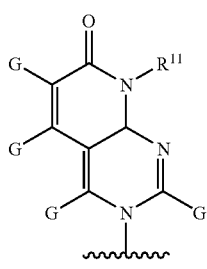

p
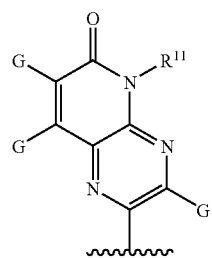
q
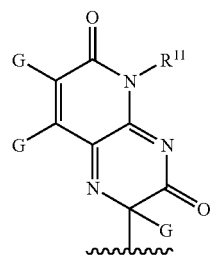
r
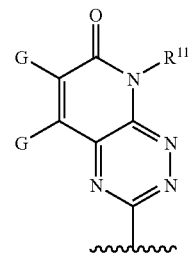
s
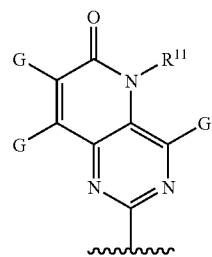
t
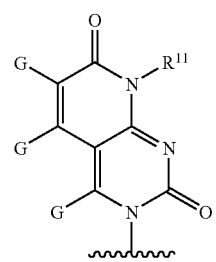
u
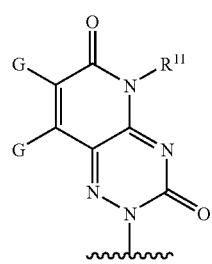
v
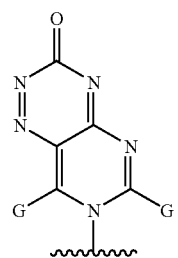
w
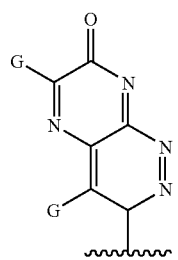
x
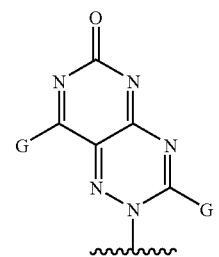
y
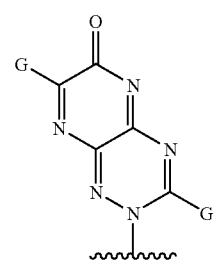
z
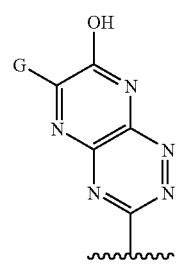
aa
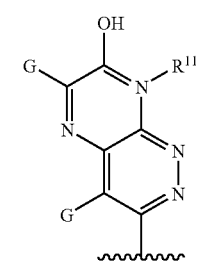

-continued bb
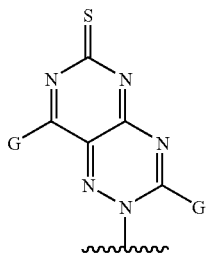

cc
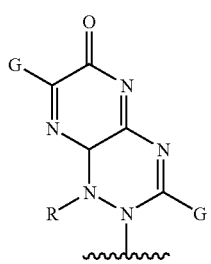

dd
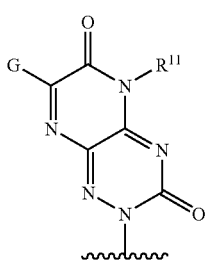

ee
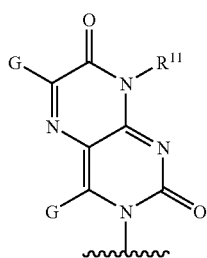

ff
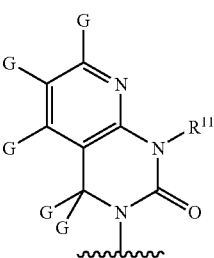

wherein G and R are defined as in structure c';

Base may be a structure gg gg
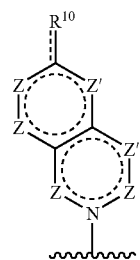

wherein each Z' is independently N (if a participant in a pi bond) or NR (if not a participant in a pi bond) and $R^{10}$, $R^{11}$, and Z are defined as in structure c';

Base may be a structure hh hh
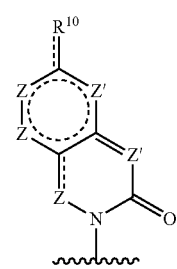

wherein each Z' is independently N (if a participant in a pi bond) or $NR^{11}$ (if not a participant in a pi bond), and each Z in independently CG (if a participant in a pi bond) or $>C(G)_2$ (if not a participant in a pi bond), wherein $R^{10}$ and G are defined as in structure c';

Base may be a structure ii ii
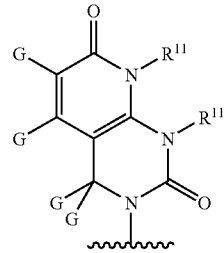

wherein $R^{11}$ and G are defined as in structure c';

Base may be a structure jj jj
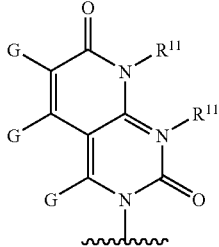

wherein R[11] and G are defined as in structure c'; or
Base may be a structure kk

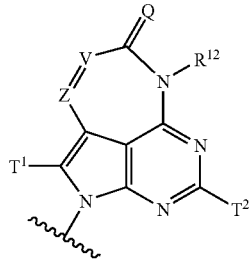

wherein for structure kk:
R[12] is selected from the group consisting of hydrogen and C$_1$-C$_3$ alkyl;
Q is absent or is selected from the group consisting of O, S, and NH, provided that when Q is absent, V and NH are both attached to a CH$_2$ group;
V is selected from the group consisting of N and C-G;
Z is selected from the group consisting of N and C-G';
G and G' are independently selected from the group consisting of hydrogen, amino, aminocarbonyl, methylamino, dimethylamino, acylamino, alkoxyamino, —SO$_3$H, —SO$_2$NH$_2$, aminocarbonylamino, oxycarbonylamino, HR[13]NCHR[14]C(O)NH—, azido, cyano, halo, hydroxyamino, and hydrazino, where R[13] is hydrogen and R[14] is a side-chain of an amino acid or where R[13] and R[14] together with the nitrogen and carbon bound to each group respectively form a pyrrolidinyl group;
with the proviso that V and Z are not identical and that when V is C—H, Z is N;
T[1] and T[2] are independently selected from the group consisting of hydrogen, hydroxyl, C$_1$-C$_4$-alkoxy, C$_1$-C$_4$-thioalkoxy, amino, substituted amino, and halo; and
each of W, W[1], and W[2] is independently selected from the group consisting of hydrogen, C$_1$-C$_4$ alkyl, and a prodrug group; or
Base may be a structure ll

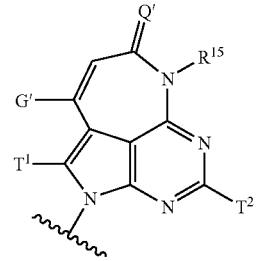

wherein for structure ll:
R[15] is hydrogen or C$_1$-C$_3$ alkyl;
Q' is selected from the group consisting of NH, O, and S;
G' is selected from the group consisting of amino, aminocarbonyl, methylamino, dimethylamino, acylamino, —SO$_3$H, —SO$_2$NH$_2$, alkoxyamino, aminocarbonylamino, oxycarbonylamino, HR[13]NCHR[14]C(O)NH—, azido, cyano, halo, hydroxyamino, and hydrazino, where R[13] is hydrogen and R[14] is a side-chain of an amino acid or where R[13] and R[14] together with the nitrogen and carbon bound to each group respectively form a pyrrolidinyl group; or Base may be a structure mm

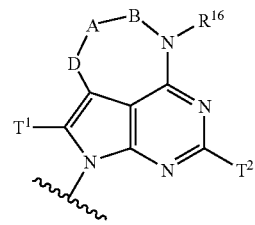

where in for structure mm A and B are independently selected from the group consisting of C=Q, NH, and methylene optionally substituted with 1 to 2 halo groups, provided that A and B are not both NH;
D is NH, or -D-A-B— together form a —N=CH—NH—, —(C=Q)-CH$_2$—(C=Q)-, —(C=Q)-NH—(C=Q)-, —(CX')=(CX')—(C=Q)-, or —CH=CH—NH— group where X' is halo;
each Q is independently selected from the group consisting of O, S, and NH;
R[16] is selected from the group consisting of hydrogen and C$_1$-C$_3$ alkyl;
T[1] and T[2] are independently selected from the group consisting of hydrogen, hydroxyl, C$_1$-C$_4$-alkoxy, C$_1$-C$_4$-thioalkoxy, amino, substituted amino, and halo; and
Y is selected from the group consisting of a bond, O, and CH$_2$; and each of W, W[1].
Alternatively, the Base can be selected from among structures ab, ac, ad, ae, af, ag, ah, ai, aj, ak, al, am, an, ao, ap, aq, ar, as, at, av, au, ax, ay, az, ba, bc, bd, be, bf, bg, bh, bi, bj, and bk, depicted below.

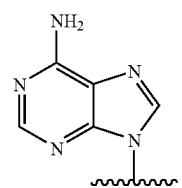

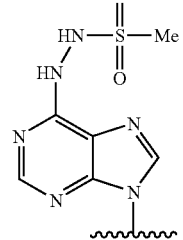

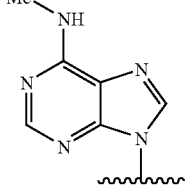

-continued
ae
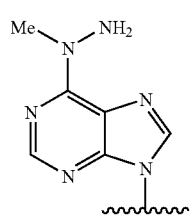
af
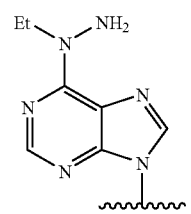
ag
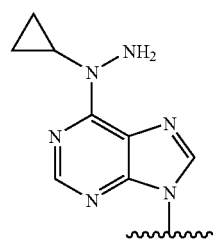
ah
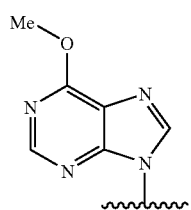
ai
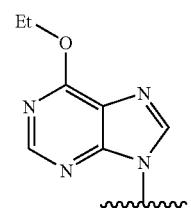
aj
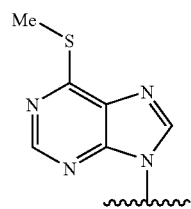
ak
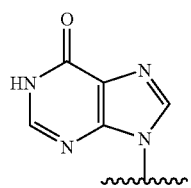
al
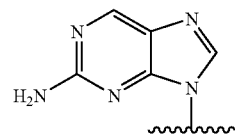
-continued
am
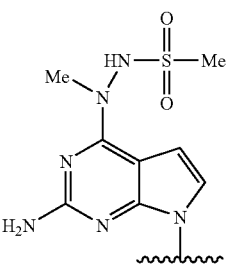
an
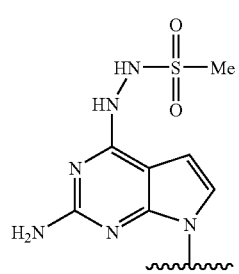
ao
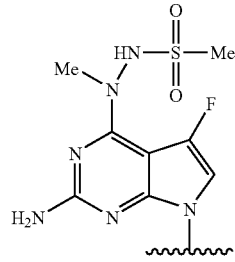
ap
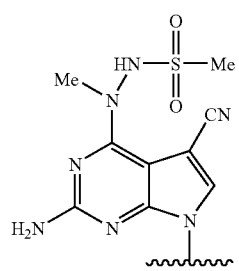
aq
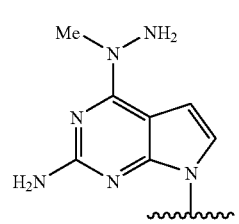
ar
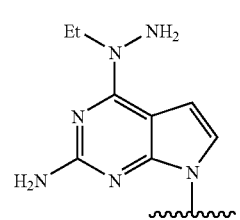

| | |
|---|---|
| 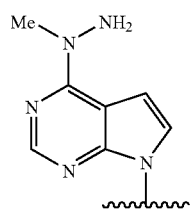 | as |
| 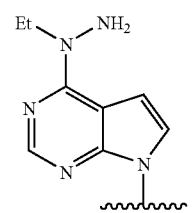 | at |
| 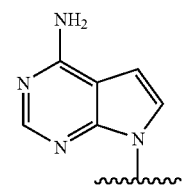 | au |
| 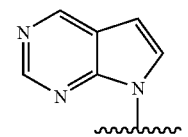 | av |
| 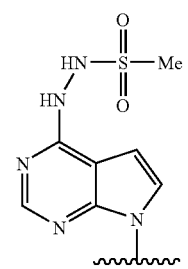 | ax |
| 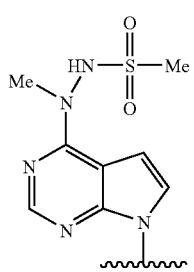 | ay |
| 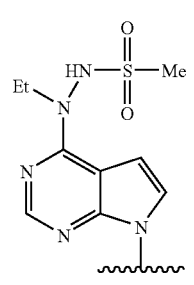 | az |
| | |
|---|---|
| 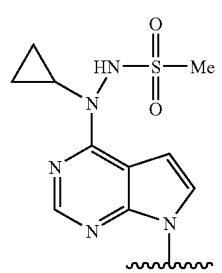 | ba |
| 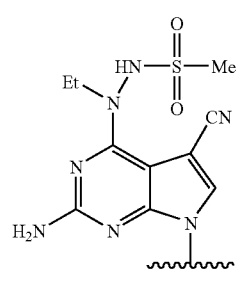 | bc |
| 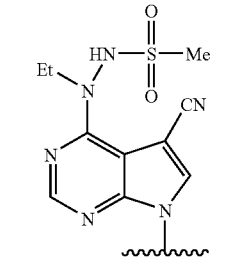 | bd |
| 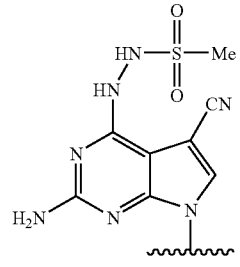 | be |
| 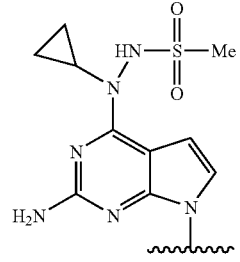 | bf |
| 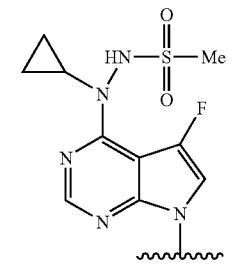 | bg |

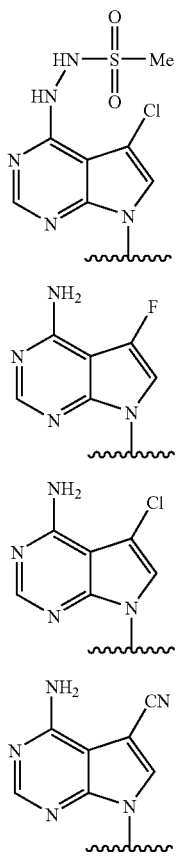

bh bi bj bk

DEFINITIONS

The phrase "a" or "an" entity as used herein refers to one or more of that entity; for example, a compound refers to one or more compounds or at least one compound. As such, the terms "a" (or "an"), "one or more", and "at least one" can be used interchangeably herein.

The terms "optional" or "optionally" as used herein means that a subsequently described event or circumstance may but need not occur, and that the description includes instances where the event or circumstance occurs and instances in which it does not. For example, "optional bond" means that the bond may or may not be present, and that the description includes single, double, or triple bonds. Moreover, "optionally substituted" means that the listed substituent is substituted or unsubstituted. In the instance where the substituent is substituted, unless otherwise specified, the substituent bears any one of the substituents defined below. For instance, an optionally substituted alkyl can mean that an alkyl is substituted or unsubstituted. In the case where the alkyl is substituted, i.e., by one or more substituents, the one or more substituents can include alkyl, halogenated alkyl, cycloalkyl, alkenyl, . . . aryl, and the like. For example, an alkyl can be substituted by an alkyl (i.e., methyl, ethyl, propyl, etc.), a cycloalkyl (c-propyl, c-butyl, c-pentyl, c-hexyl, etc.), or an aryl (phenyl, substituted phenyl, naphthyl, substituted naphtyl, etc.).

The term "independently" is used herein to indicate that a variable is applied in any one instance without regard to the presence or absence of a variable having that same or a different definition within the same compound. Thus, in a compound in which R appears twice and is defined as "independently carbon or nitrogen", both R's can be carbon, both R's can be nitrogen, or one R' can be carbon and the other nitrogen.

The term "alkyl" refers to an unbranched or branched chain, saturated, monovalent hydrocarbon residue containing 1 to 30 carbon atoms. The term "$C_{1-M}$ alkyl" refers to an alkyl comprising 2 to N carbon atoms, where M is an integer having the following values: 2, 3, 4, 5, 6, 7, 8, 9, 10, 11, 12, 13, 14, 15, 16, 17, 18, 19, 20, 21, 22, 23, 24, 25, 26, 27, 28, 29, or 30. The term "$C_{1-4}$ alkyl" refers to an alkyl containing 1 to 4 carbon atoms. The term "lower alkyl" denotes a straight or branched chain hydrocarbon residue comprising 1 to 6 carbon atoms. "$C_{1-20}$ alkyl" as used herein refers to an alkyl comprising 1 to 20 carbon atoms. "$C_{1-10}$ alkyl" as used herein refers to an alkyl comprising 1 to 10 carbons. Examples of alkyl groups include, but are not limited to, lower alkyl groups include methyl, ethyl, propyl, i-propyl, n-butyl, i-butyl, t-butyl or pentyl, isopentyl, neopentyl, hexyl, heptyl, and octyl. The term (ar)alkyl or (heteroaryl)alkyl indicate the alkyl group is optionally substituted by an aryl or a heteroaryl group respectively.

The term "halogenated alkyl" (or "haloalkyl") refers to an unbranched or branched chain alkyl comprising at least one of F, Cl, Br, and I. The term "$C_{1-3}$ haloalkyl" refers to a haloalkyl comprising 1 to 3 carbons and at least one of F, Cl, Br, and I. The term "halogenated lower alkyl" refers to a haloalkyl comprising 1 to 6 carbon atoms and at least one of F, Cl, Br, and I. Examples include, but are not limited to, fluoromethyl, chloromethyl, bromomethyl, iodomethyl, difluoromethyl, dichloromethyl, dibromomethyl, diiodomethyl, trifluoromethyl, trichloromethyl, tribromomethyl, triiodomethyl, 1-fluoroethyl, 1-chloroethyl, 1-bromoethyl, 1-iodoethyl, 2-fluoroethyl, 2-chloroethyl, 2-bromoethyl, 2-iodoethyl, 2,2-difluoroethyl, 2,2-dichloroethyl, 2,2-dibromomethyl, 2-2-diiodomethyl, 3-fluoropropyl, 3-chloropropyl, 3-bromopropyl, 2,2,2-trifluoroethyl or 1,1,2,2,2-pentafluoroethyl.

The term "cycloalkyl" refers to a saturated carbocyclic ring comprising 3 to 8 carbon atoms, i.e. cyclopropyl, cyclobutyl, cyclopentyl, cyclohexyl, cycloheptyl or cyclooctyl. The term "$C_{3-7}$ cycloalkyl" as used herein refers to a cycloalkyl comprising 3 to 7 carbons in the carbocyclic ring.

The term "alkenyl" refers to an unsubstituted hydrocarbon chain radical having from 2 to 10 carbon atoms having one or two olefinic double bonds, preferably one olefinic double bond. The term "$C_{2-N}$ alkenyl" refers to an alkenyl comprising 2 to N carbon atoms, where N is an integer having the following values: 3, 4, 5, 6, 7, 8, 9, or 10. The term "$C_{2-10}$ alkenyl" refers to an alkenyl comprising 2 to 10 carbon atoms. The term "$C_{2-4}$ alkenyl" refers to an alkenyl comprising 2 to 4 carbon atoms. Examples include, but are not limited to, vinyl, 1-propenyl, 2-propenyl (allyl) or 2-butenyl (crotyl).

The term "halogenated alkenyl" refers to an alkenyl comprising at least one of F, Cl, Br, and I.

The term "alkynyl" refers to an unbranched or branched hydrocarbon chain radical having from 2 to 10 carbon atoms, preferably 2 to 5 carbon atoms, and having one triple bond. The term "$C_{2-N}$ alkynyl" refers to an alkynyl comprising 2 to N carbon atoms, where N is an integer having the following values: 3, 4, 5, 6, 7, 8, 9, or 10. The term "C $C_{2-4}$ alkynyl" refers to an alkynyl comprising 2 to 4 carbon atoms. The term "$C_{2-10}$ alkynyl" refers to an alkynyl comprising 2 to 10 carbons. Examples include, but are not limited to, ethynyl, 1-propynyl, 2-propynyl, 1-butynyl, 2-butynyl or 3-butynyl.

The term "halogenated alkynyl" refers to an unbranched or branched hydrocarbon chain radical having from 2 to 10 carbon atoms, preferably 2 to 5 carbon atoms, and having one triple bond and at least one of F, Cl, Br, and I.

The term "alkoxy" refers to an —O-alkyl group, wherein alkyl is as defined above. Examples include, but are not limited to, methoxy, ethoxy, n-propyloxy, i-propyloxy, n-butyloxy, i-butyloxy, t-butyloxy. "Lower alkoxy" as used herein denotes an alkoxy group with a "lower alkyl" group as previously defined. "$C_{1-10}$ alkoxy" refers to an-O-alkyl wherein alkyl is $C_{1-10}$.

The term "alkoxyalkyl" refers to an alkyl-O-alkyl group, wherein alkyl is defined above. Examples include, but are not limited to, methoxymethyl, ethoxymethyl, n-propyloxymethyl, i-propyloxymethyl, n-butyloxymethyl, i-butyloxymethyl, t-butyloxymethyl, and the like, methoxyethyl, ethoxyethyl, n-propyloxyethyl, i-propyloxyethyl, n-butyloxyethyl, i-butyloxyethyl, t-butyloxyethyl, and the like, methoxypropyl, ethoxypropyl, n-propyloxypropyl, i-propyloxypropyl, n-butyloxypropyl, i-butyloxypropyl, t-butyloxypropyl, and the like, etc.

The term "halogenated alkoxy" refers to an —O-alkyl group in which the alkyl group comprises at least one of F, Cl, Br, and I.

The term "halogenated lower alkoxy" refers to an —O-(lower alkyl) group in which the lower alkyl group comprises at least one of F, Cl, Br, and I.

The terms "alkylamino" or "arylamino" refer to an amino group that has one or two alkyl or aryl substituents, respectively.

The term "protected," as used herein and unless otherwise defined, refers to a group that is added to an oxygen, nitrogen, or phosphorus atom to prevent its further reaction or for other purposes. A wide variety of oxygen and nitrogen protecting groups are known to those skilled in the art of organic synthesis. Non-limiting examples include: C(O)-alkyl, C(O)Ph, C(O)aryl, $CH_3$, $CH_2$-alkyl, $CH_2$-alkenyl, $CH_2$Ph, $CH_2$-aryl, $CH_2$O-alkyl, $CH_2$O-aryl, $SO_2$-alkyl, $SO_2$-aryl, tert-butyldimethylsilyl, tert-butyldiphenylsilyl, and 1,3-(1,1,3,3-tetraisopropyldisiloxanylidene).

The term "aryl," as used herein, and unless otherwise specified, refers to substituted or unsubstituted phenyl (Ph), biphenyl, or naphthyl, preferably the term aryl refers to substituted or unsubstituted phenyl. The aryl group can be substituted with one or more moieties selected from among hydroxyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in T.W. Greene and P.G.M. Wuts, "Protective Groups in Organic Synthesis," 3rd ed., John Wiley & Sons, 1999.

The terms "alkaryl" or "alkylaryl" refer to an alkyl group with an aryl substituent. It is understood that the aryl substituent of the "alkaryl" or "alkylaryl" can be substituted with at least one of a halogen (F, Cl, Br, or I), -hydroxyl, a lower alkoxy, such as —$OCH_3$, -amino, or an alkylamino, such as —$NHR$ or —$NR_2$, where R is a lower alkyl, such as —$NHCH_3$ or —$N(CH_3)_2$. Moreover, the term "lower alkylaryl" denotes a straight or branched chain hydrocarbon residue comprising 1 to 6 carbon atoms that is substituted with a substituted or unsubstituted aryl, such as, benzyl. The terms "aralkyl" or "arylalkyl" refer to an aryl group with an alkyl substituent.

The term "halo," as used herein, includes chloro, bromo, iodo and fluoro.

The term "acyl" refers to a substituent containing a carbonyl moiety and a non-carbonyl moiety. The carbonyl moiety contains a double-bond between the carbonyl carbon and a heteroatom, where the heteroatom is selected from among O, N and S. When the heteroatom is N, the N is substituted by a lower alkyl. The non-carbonyl moiety is selected from straight, branched, or cyclic alkyl, which includes, but is not limited to, a straight, branched, or cyclic $C_{1-20}$ alkyl, $C_{1-10}$ alkyl, or lower alkyl; alkoxyalkyl, including methoxymethyl; aralkyl, including benzyl; aryloxyalkyl, such as phenoxymethyl; or aryl, including phenyl optionally substituted with halogen (F, Cl, Br, I), hydroxyl, $C_1$ to $C_4$ alkyl, or $C_1$ to $C_4$ alkoxy, sulfonate esters, such as alkyl or aralkyl sulphonyl, including methanesulfonyl, the mono, di or triphosphate ester, trityl or monomethoxytrityl, substituted benzyl, trialkylsilyl (e.g. dimethyl-t-butylsilyl) or diphenylmethylsilyl. When at least one aryl group is present in the non-carbonyl moiety, it is preferred that the aryl group comprises a phenyl group.

The term "lower acyl" refers to an acyl group in which the non-carbonyl moiety is lower alkyl.

The term "purine" or "pyrimidine" base includes, but is not limited to, adenine, $N^6$-alkylpurines, $N^6$-acylpurines (wherein acyl is C(O)(alkyl, aryl, alkylaryl, or arylalkyl), $N^6$-benzylpurine, $N^6$-halopurine, $N^6$-vinylpurine, $N^6$-acetylenic purine, $N^6$-acyl purine, $N^6$-hydroxyalkyl purine, $N^6$-allylaminopurine, $N^6$-thioallyl purine, $N^2$-alkylpurines, $N^2$-alkyl-6-thiopurines, thymine, cytosine, 5-fluorocytosine, 5-methylcytosine, 6-azapyrimidine, including 6-azacytosine, 2- and/or 4-mercaptopyrmidine, uracil, 5-halouracil, including 5-fluorouracil, $C^5$-alkylpyrimidines, $C^5$-benzylpyrimidines, $C^5$-halopyrimidines, $C^5$-vinylpyrimidine, $C^5$-acetylenic pyrimidine, $C^5$-acyl pyrimidine, $C^5$-hydroxyalkyl purine, $C^5$-amidopyrimidine, $C^5$-cyanopyrimidine, $C^5$-iodopyrimidine, $C^6$-Iodo-pyrimidine, $C^5$-Br-vinyl pyrimidine, $C^6$-Br-vinyl pyrimidine, $C^5$-nitropyrimidine, $C^5$-amino-pyrimidine, $N^2$-alkylpurines, $N^2$-alkyl-6-thiopurines, 5-azacytidinyl, 5-azauracilyl, triazolopyridinyl, imidazolopyridinyl, pyrrolopyrimidinyl, and pyrazolopyrimidinyl. Purine bases include, but are not limited to, guanine, adenine, hypoxanthine, 2,6-diaminopurine, and 6-chloropurine. Functional oxygen and nitrogen groups on the base can be protected as necessary or desired. Suitable protecting groups are well known to those skilled in the art, and include trimethylsilyl, dimethylhexylsilyl, t-butyldimethylsilyl, and t-butyldiphenylsilyl, trityl, alkyl groups, and acyl groups such as acetyl and propionyl, methanesulfonyl, and p-toluenesulfonyl.

The term "heterocycle" or "heterocyclyl" as used herein refers to any 3-, 4-, 5-, 6-, 8-, 9-, 10-, or 11-membered saturated or unsaturated ring containing carbon atoms and from one to three heteroatoms independently selected from the group consisting of one, two, or three nitrogens, one oxygen and one nitrogen, and one sulfur and one nitrogen and including any bicyclic group in which any of the defined heterocyclic ring(s) is fused to a benzene ring; wherein the nitrogen and sulfur heteroatoms may be optionally oxidized, wherein the nitrogen heteroatoms may be optionally quaternized, and wherein one or more carbon or nitrogen atoms may be substituted with a lower alkyl. In a disclosed embodiment, heterocycles include, but are not limited to, aziridinyl, azetidinyl, pyrrolidinyl, piperidinyl, morpholinyl, piperazinyl, thiomorpholinyl, and the like. In an alternative embodiment, "heterocycle" or "heterocyclyl" include, but are not limited to the following: azepanyl, benzimidazolyl, benzodioxolyl, benzofuranyl, benzofurazanyl, benzopyranyl, benzopyrazolyl, benzotriazolyl, benzothiazolyl, benzothienyl, benzothiofuranyl, benzothiophenyl, benzothiopyranyl, benzoxazepinyl, benzoxazolyl, carbazolyl, carbolinyl, chromanyl, cinnolinyl, diazepanyl, diazapinonyl, dihydrobenzofuranyl, dihydrobenzofuryl, dihydrobenzoimidazolyl, dihydrobenzothienyl, dihydrobenzothiopyranyl, diydrobenzothiopyranyl sulfone, dihydrobenzothiophenyl, dihydrobenzoxazolyl, dihydrocyclopentapyridinyl, dihydrofuranyl, dihydroimidazolyl, dihydroindolyl, dihydroisooxazolyl, dihydroisoquinolinyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, dioxanyl, dioxidotetrahydrothienyl, dioxidothiomorpholinyl, furyl, furanyl, imidazolyl, imidazolinyl, imidazolidinyl, imidazothiazolyl, imidazopyridinyl, indazolyl, indolazinyl, indolinyl, indolyl, isobenzofuranyl, isochromanyl, isoindolyl, isoindolinyl, isoquinolinone, isoquinolyl, isothiazolyl, isothiazolidinyl, isoxazolinyl, isoxazolyl, methylenedioxybenzoyl, morpholinyl, naphthpyridinyl, oxadiazolyl, oxazolyl, oxazolinyl, oxetanyl, oxoazepinyl, oxadiazolyl, oxidothiomorpholinyl, oxodihydrophthalazinyl, oxodihydroindolyl, oxoimidazolidinyl, oxopiperazinyl, oxopiperdinyl, oxopyrrolidinyl, oxopyrimidinyl, oxopyrrolyl, oxotriazolyl, piperidyl, piperidinyl, piperazinyl, pyranyl, pyrazinyl, pyrazolyl, pyridazinyl, pyridinonyl, pyridopyridinyl, pyridazinyl, pyridyl, pyrimidinyl, pyrrolyl, pyrrolidinyl, quinazolinyl, quinolinyl, quinolyl, quinolinonyl, quinoxalinyl, tetrahydrocycloheptapyridinyl, tetrahydrofuranyl, tetrahydrofuryl, tetrahydroisoquinolinyl, tetrahydropyranyl, tetrahydroquinolinyl, tetrazolyl, tetrazolopyridyl, thiadiazolyl, thiazolyl, thiazolinyl, thienofuryl, thienyl, thiomorpholinyl, triazolyl, azetidinyl, 1,4-dioxanyl, hexahydroazepinyl, and the like.

The term "tautomerism" and "tautomers" have their accepted plain meanings

The term "deuterated analogues" refer to compounds in which at least one hydrogen atom of the compound of formula I is replaced with at least one deuterium atom.

The term "P*" means that the phosphorous atom is chiral and that it has a corresponding Cahn-Ingold-Prelog designation of "R" or "S" which have their accepted plain meanings.

DETAILED DESCRIPTION OF THE INVENTION

An aspect of the invention is directed to a compound, its stereoisomers, salts (acid or basic addition salts), hydrates, solvates, deuterated analogues, or crystalline forms thereof, and the like represented by formula I:

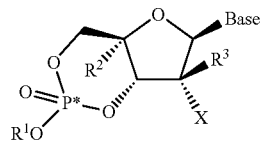

wherein (a) $R^1$ is hydrogen, n-alkyl, branched alkyl, cycloalkyl, alkaryl, or aryl, which includes, but is not limited to, phenyl or naphthyl, where phenyl or naphthyl are optionally substituted with at least one of H, F, Cl, Br, I, OH, OR', SH, SR', $NH_2$, NHR', $NR'_2$, $NHR'_2{}^+$, $NR'_3{}^+$, heterocycle, lower alkyl, halogenated (F, Cl, Br, I) lower alkyl, halogenated (F, Cl, Br, I) lower alkenyl of $C_2$-$C_6$, lower alkynyl of $C_2$-$C_6$ such as C≡CH, halogenated (F, Cl, Br, I) lower alkynyl of $C_2$-$C_6$, lower alkoxy of $C_1$-$C_6$, halogenated (F, Cl, Br, I) lower alkoxy of $C_1$-$C_6$, $CO_2H$, $CO_2R'$, $CONH_2$, CONHR', $CONR'_2$, CH=CHCO₂H, or CH=CHCO₂R';

(b) $R^2$ is H, an optionally substituted alkyl (including lower alkyl), cyano (CN), $CH_3$, vinyl, O-alkyl, O-(lower alkyl), including $OCH_3$, $OCH_2CH_3$, hydroxyl alkyl, i.e., —$(CH_2)_o$OH, wherein o is 1-10, hydroxyl lower alkyl, i.e., —$(CH_2)_p$OH, where p is 1-6, including hydroxyl methyl ($CH_2OH$), fluoromethyl ($CH_2F$), azido ($N_3$), $CH_2CN$, $CH_2N_3$, $CH_2NH_2$, $CH_2NHCH_3$, $CH_2N(CH_3)_2$, ethynyl alkyne (optionally substituted), or halogen, including F, Cl, Br, or I (c) $R^3$ is H, $CH_3$, $CH_2F$, $CHF_2$, $CF_3$, F, or CN;

(d) X is H, OH, F, OMe, halogen, $NH_2$, or $N_3$;

The base is a naturally occurring or modified purine or pyrimidine base represented by the following structures:

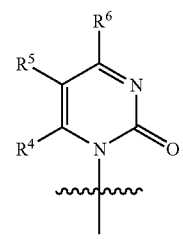

a

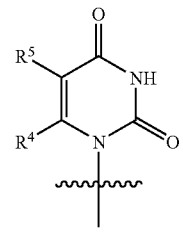

b

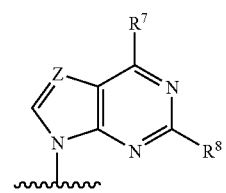

c

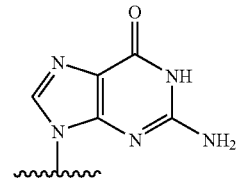

d wherein

Z is N or $CR^9$;

$R^4$, $R^5$, $R^6$, $R^7$, and $R^8$ are independently H, F, Cl, Br, I, OH, OR', such as alkoxy, aryloxy, benzyloxy, substituted aryloxy, and substituted benzyloxy, SH, SR', $NH_2$, NHR', $NR'_2$, $NHR'_2{}^+$, $NR'_3{}^+$, heterocycle, lower alkyl, halogenated (F, Cl, Br, I) lower alkyl, lower alkenyl of $C_2$-$C_6$, halogenated (F, Cl, Br, I) lower alkenyl of $C_2$-$C_6$, lower alkynyl of $C_2$-$C_6$ such as C≡CH, halogenated (F, Cl, Br, I) lower alkynyl of $C_2$-$C_6$, lower alkoxy of $C_1$-$C_6$, halogenated (F, Cl, Br, I) lower alkoxy of $C_1$-$C_6$, $CO_2H$, $CO_2R'$, $CONH_2$, CONHR', $CONR'_2$, CH=CHCO₂H, or CH=CHCO₂R';

$R^9$ is an H, halogen (including F, Cl, Br, I), OH, OR', SH, SR', $NH_2$, NHR', $NR'_2$, $NHR'_2{}^+$, $NR'_3{}^+$, $NO_2$, lower alkyl, halogenated (F, Cl, Br, I) lower alkyl, lower alkenyl of $C_2$-$C_6$, halogenated (F, Cl, Br, I) lower alkenyl of $C_2$-$C_6$, lower alkynyl of $C_2$-$C_6$, halogenated (F, Cl, Br, I) lower alkynyl of $C_2$-$C_6$, lower alkoxy of $C_1$-$C_6$, halogenated (F, Cl, Br, I) lower alkoxy of $C_1$-$C_6$, $CO_2H$, $CO_2R'$, $CONH_2$, CONHR', $CONR'_2$, CH=CHCO₂H, or CH=CHCO₂R';

wherein R' is an optionally substituted alkyl, an optionally substituted cycloalkyl, an optionally substituted alkynyl, an optionally substituted alkenyl, or an optionally substituted acyl, an optionally substituted alkoxyalkyl, where for the instance of NR'$_2$ or NHR'$_2$$^+$ each R' comprise at least one C atom that is independent of one another or are joined to form a heterocycle comprising at least two carbon atoms, and where for the instance of NR'$_3$$^+$ each R' comprises at least one C atom which are independent of one another or each R' comprises at least one C atom in which at least two R' are joined to form a heterocycle comprising at least two carbon atoms.

Alternatively, the Base may be selected from a group of formula c'

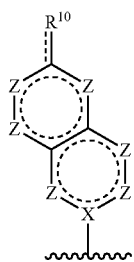

c' wherein for structure c', if Z is a participant in a pi bond (double bond), Z is independently selected from N or C-G; or, if Z is not a participant in a pi bond (double bond), Z is independently selected from O, S, Se, NR$^{11}$, NOR$^{11}$, NNR$^{11}$$_2$, CO, CS, CNR$^{11}$, SO, S(O)$_2$, SeO, Se(O)$_2$, or C(G)$_2$;

each G is independently selected from the group consisting of H, halogen, OR$^{11}$, SR$^{11}$, NR$^{11}$$_2$, NR$^{11}$OR$^{11}$, N$_3$, COOR$^{11}$, CN, CONR$^{11}$$_2$, C(S)NR$^{11}$$_2$, C(=NR$^{11}$)NR$^{22}$$_2$, and R$^{11}$; and where any two adjacent Z are not both selected from O, S, and Se, or not both selected from CO, CS, CNNR$^{11}$, SO, S(O)$_2$, SeO and Se(O)$_2$;

wherein, if X is a participant in a pi bond (double bond), X is C; or if X is not a participant in a pi bond (double bond), X is CR$^{11}$ or N;

wherein, if R$^{10}$ is a participant in a pi bond (double bond), R$^{10}$ is O, S, Se, NR$^{11}$, NOR$^{11}$ or NNR$^{11}$$_2$; or if R$^{10}$ is not a participant in a pi bond (double bond), R$^{10}$ is OR$^{11}$, SR$^{11}$, F, Cl, R$^{10}$, or SeR$^{10}$; and dashed lines ( - - - ) indicate a possible pi or double bond;

each R is independently selected from the group consisting of H, CF$_3$, optionally substituted alkyl, optionally substituted alkenyl, optionally substituted alkynyl, optionally substituted aryl, optionally substituted acyl, optionally substituted cycloalkyl, optionally substituted cycloalkenyl, optionally substituted heteroaryl, optionally substituted heterocyclyl, and optionally substituted arylalkyl; or Base may be a structure selected from the group consisting of structures d'-n

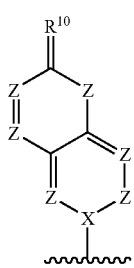

d'

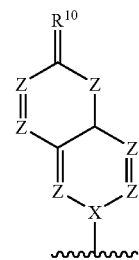

e

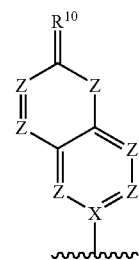

f

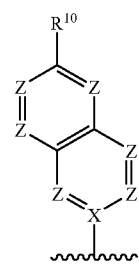

g

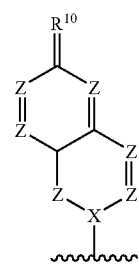

h

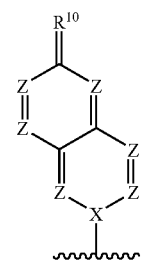

i

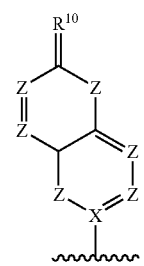

j k
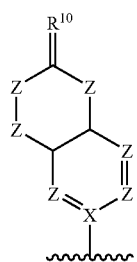
l
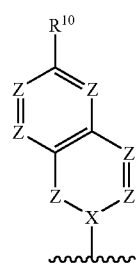
m
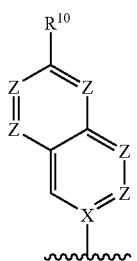
n
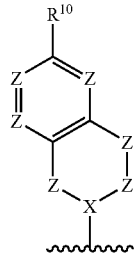
wherein Z, X, and R$^{10}$ are defined as in structure c';
Base may be a structure selected from the group consisting of structures o-ff
o
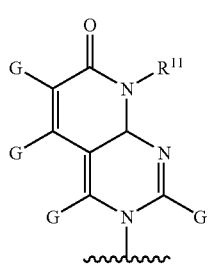
p
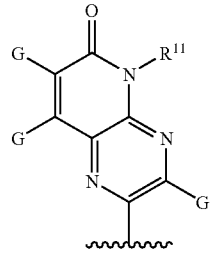
q
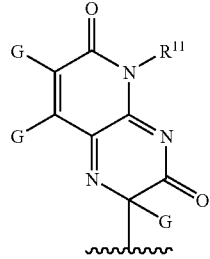
r
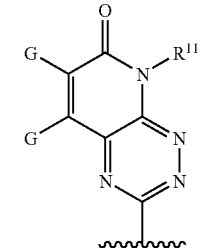
s
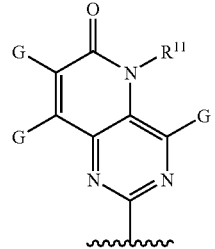
t
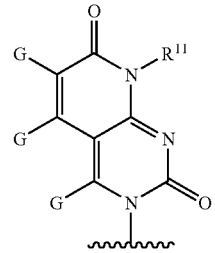
u
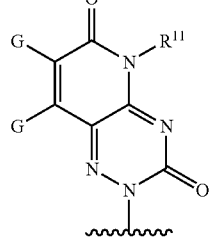

-continued
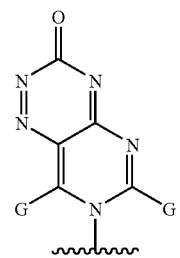
v
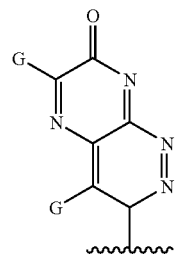
w
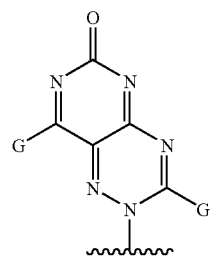
x
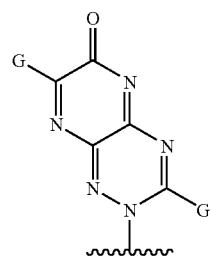
y
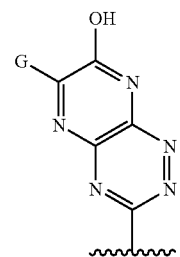
z
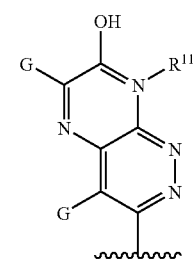
aa
-continued
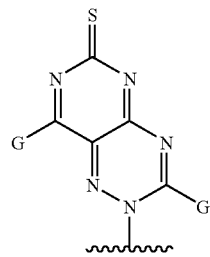
bb
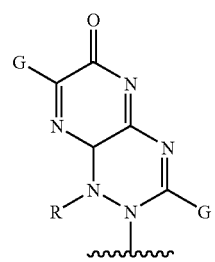
cc
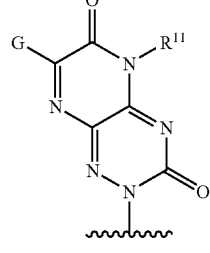
dd
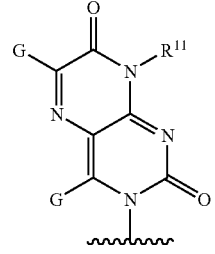
ee
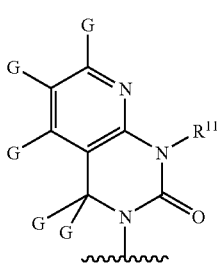
ff wherein G and R are defined as in structure c';
Base may be a structure gg

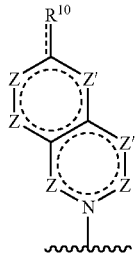

wherein each Z' is independently N (if a participant in a pi bond) or NR (if not a participant in a pi bond) and $R^{10}$, $R^{11}$, and Z are defined as in structure c';
Base may be a structure hh

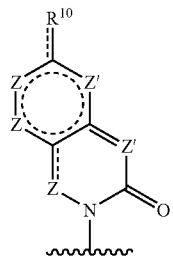

wherein each Z' is independently N (if a participant in a pi bond) or $NR^{11}$ (if not a participant in a pi bond), and each Z in independently CG (if a participant in a pi bond) or $>C(G)_2$ (if not a participant in a pi bond), wherein $R^{10}$ and G are defined as in structure c';
Base may be a structure ii

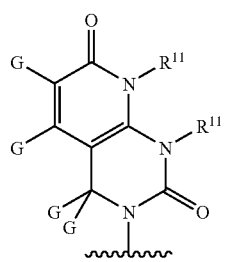

wherein $R^{11}$ and G are defined as in structure c';
Base may be a structure jj

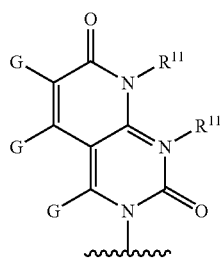

wherein $R^{11}$ and G are defined as in structure c'; or
Base may be a structure kk

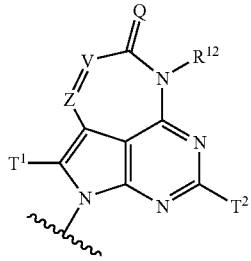

wherein for structure kk:
$R^{12}$ is selected from the group consisting of hydrogen and $C_1$-$C_3$ alkyl;
Q is absent or is selected from the group consisting of O, S, and NH, provided that when Q is absent, V and NH are both attached to a $CH_2$ group;
V is selected from the group consisting of N and C-G;
Z is selected from the group consisting of N and C-G';
G and G' are independently selected from the group consisting of hydrogen, amino, aminocarbonyl, methylamino, dimethylamino, acylamino, alkoxyamino, —$SO_3H$, —$SO_2NH_2$, aminocarbonylamino, oxycarbonylamino, $HR^{13}NCHR^{14}C(O)NH$—, azido, cyano, halo, hydroxyamino, and hydrazino, where $R^{13}$ is hydrogen and $R^{14}$ is a side-chain of an amino acid or where $R^{13}$ and $R^{14}$ together with the nitrogen and carbon bound to each group respectively form a pyrrolidinyl group;
with the proviso that V and Z are not identical and that when V is C—H, Z is N;
$T^1$ and $T^2$ are independently selected from the group consisting of hydrogen, hydroxyl, $C_1$-$C_4$-alkoxy, $C_1$-$C_4$-thioalkoxy, amino, substituted amino, and halo; and
each of W, $W^1$, and $W^2$ is independently selected from the group consisting of hydrogen, $C_1$-$C_4$ alkyl, and a prodrug group; or
Base may be a structure ll

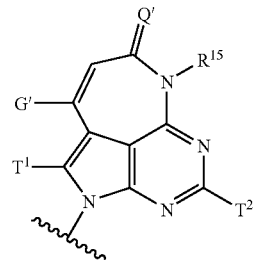

wherein for structure ll:
$R^{15}$ is hydrogen or $C_1$-$C_3$ alkyl;
Q' is selected from the group consisting of NH, O, and S;
G' is selected from the group consisting of amino, aminocarbonyl, methylamino, dimethylamino, acylamino, —$SO_3H$, —$SO_2NH_2$, alkoxyamino, aminocarbonylamino, oxycarbonylamino, $HR^{13}NCHR^{14}C(O)NH$—, azido, cyano, halo, hydroxyamino, and hydrazino, where $R^{13}$ is hydrogen and $R^{14}$ is a side-chain of an amino acid or where $R^{13}$ and $R^{14}$ together with the nitrogen and carbon bound to each group respectively form a pyrrolidinyl group; or Base may be a structure mm

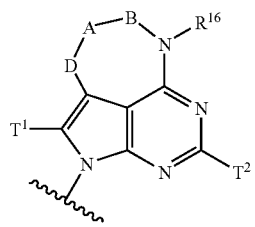

where in for structure mm

A and B are independently selected from the group consisting of C=Q, NH, and methylene optionally substituted with 1 to 2 halo groups, provided that A and B are not both NH;

D is NH, or -D-A-B— together form a —N=CH—NH—, —(C=Q)-CH$_2$—(C=Q)-, —(C=Q)-NH—(C=Q)-, —(CX')=(CX')—(C=Q)-, or —CH=CH—NH— group where X' is halo;

each Q is independently selected from the group consisting of O, S, and NH;

R$^{16}$ is selected from the group consisting of hydrogen and C$_1$-C$_3$ alkyl;

T$^1$ and T$^2$ are independently selected from the group consisting of hydrogen, hydroxyl, C$_1$-C$_4$-alkoxy, C$_1$-C$_4$-thio-alkoxy, amino, substituted amino, and halo; and Y is selected from the group consisting of a bond, O, and CH$_2$; and each of W, W$^1$.

Alternatively, the Base can be selected from among structures ab, ac, ad, ae, af, ag, ah, ai, aj, ak, al, am, an, ao, ap, aq, ar, as, at, av, au, ax, ay, az, ba, bc, bd, be, bf, bg, bh, bi, bj, and bk, depicted below.

ab
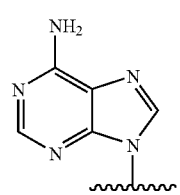

ac
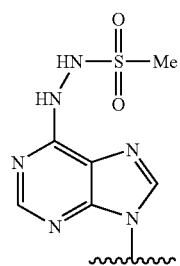

ad

ae
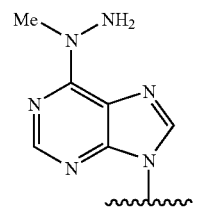

af
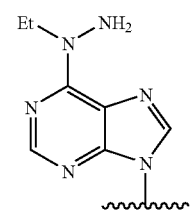

ag
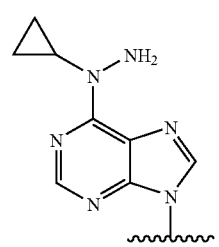

ah
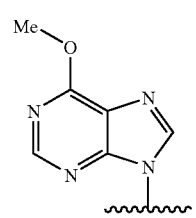

ai
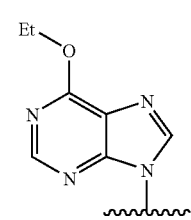

aj
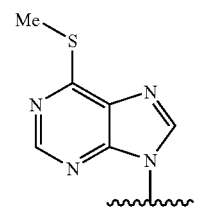

ak
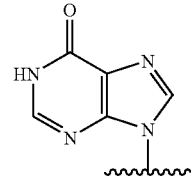

al
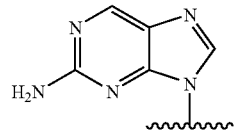

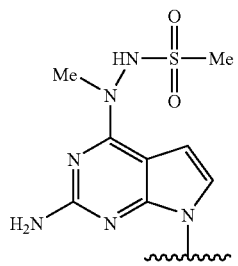
am
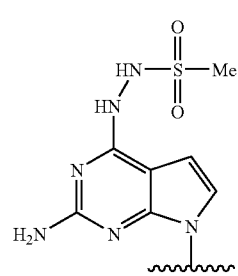
an
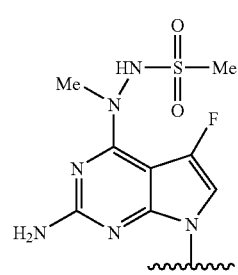
ao
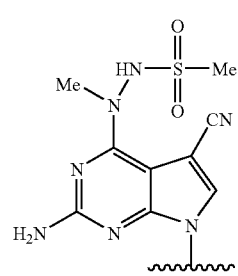
ap
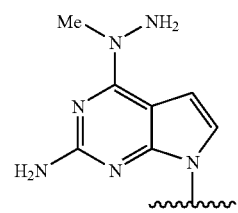
aq
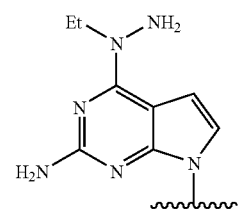
ar
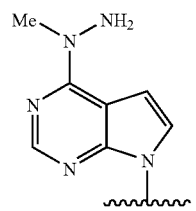
as
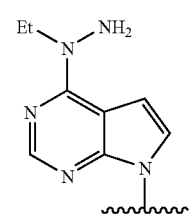
at
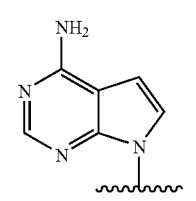
au
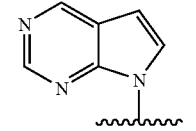
av
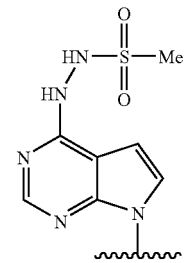
ax
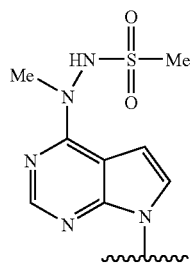
ay
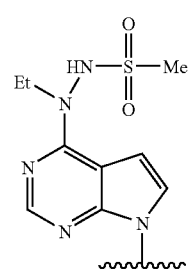
az ba 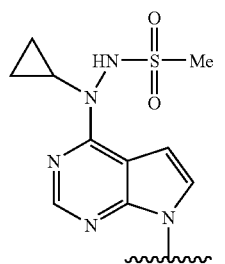

bc 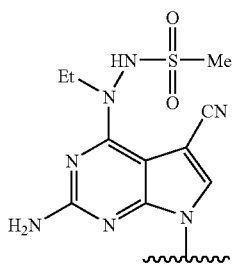

bd 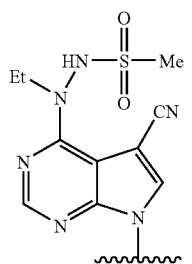

be 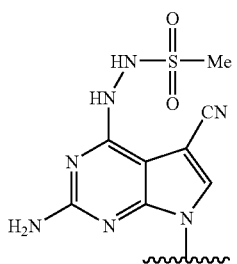

bf 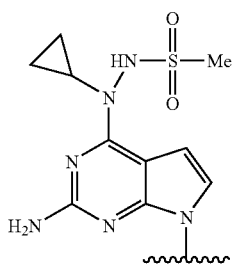

bg 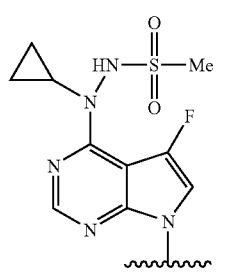

bh 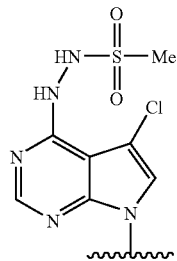

bi 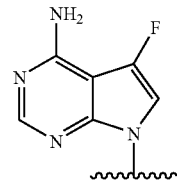

bj 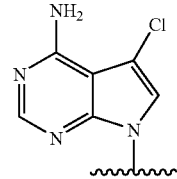

bk 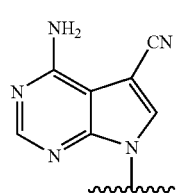

As can be appreciated from the structure represented by formula I above, there are myriad ways to express the several embodiments and aspects of each embodiment of the present invention. As seen below, the inventors have disclosed several embodiments, each having several aspects, based on the identity of the modified purine or pyrimidine base. This is not intended to be an explicit or implicit admission that the several embodiments are independent or distinct nor should it be interpreted as such. Rather, it is intended to convey information so that the full breadth of the present invention can be understood. Furthermore, the following embodiments, and aspects thereof, are not meant to be limiting on the full breadth of the invention as recited by the structure of formula I.

A first embodiment of the invention is directed to a compound represented by formula I-1:

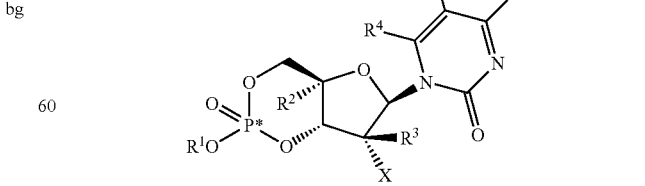

I-1 wherein
(a) $R^1$ is H, n-alkyl, branched alkyl, cycloalkyl, alkaryl, or aryl, which includes, but is not limited to, phenyl or naphthyl, where phenyl or naphthyl are optionally substituted with at least one of H, F, Cl, Br, I, OH, OR', SH, SR', $NH_2$, NHR', $NR'_2$, $NHR'_2{}^+$, $NR'_3{}^+$, heterocycle, lower alkyl, halogenated (F, Cl, Br, I), halogenated (F, Cl, Br, I) lower alkenyl of $C_2$-$C_6$, lower alkynyl of $C_2$-$C_6$ such as C≡CH, halogenated (F, Cl, Br, I) lower alkynyl of $C_2$-$C_6$, lower alkoxy of $C_1$-$C_6$, halogenated (F, Cl, Br, I) lower alkoxy of $C_1$-$C_6$, $CO_2H$, $CO_2R'$, $CONH_2$, CONHR', $CONR'_2$, CH=$CHCO_2H$, or CH=$CHCO_2R'$;

(b) $R^2$ is H, lower alkyl, cyano (CN), $CH_3$, vinyl, lower alkoxy, including $OCH_3$, $OCH_2CH_3$, hydroxyl lower alkyl, i.e., —$(CH_2)_pOH$, where p is 1-6, including hydroxyl methyl ($CH_2OH$), fluoromethyl ($CH_2F$), azido ($N_3$), $CH_2CN$, $CH_2N_3$, $CH_2NH_2$, $CH_2NHCH_3$, $CH_2N(CH_3)_2$, ethynyl alkyne (optionally substituted), or halogen, including F, Cl, Br, or I;

(c) $R^3$ is H, $CH_3$, $CH_2F$, $CHF_2$, $CF_3$, F, or CN;

(d) X is H, OH, F, OMe, halogen, $NH_2$, or $N_3$; and (e) $R^4$, $R^5$, $R^6$ are independently H, F, Cl, Br, I, OH, OR', such as alkoxy, aryloxy, benzyloxy, substituted aryloxy, and substituted benzyloxy, SH, SR', $NH_2$, NHR', $NR'_2$, $NHR'_2{}^+$, $NR'_3{}^+$, heterocycle, lower alkyl, halogenated (F, Cl, Br, I) lower alkyl, lower alkenyl of $C_2$-$C_6$, $CO_2H$, $CO_2R'$, $CONH_2$, CONHR', $CONR'_2$;

wherein R' is an optionally substituted alkyl, an optionally substituted cycloalkyl, an optionally substituted alkynyl, an optionally substituted alkenyl, or an optionally substituted acyl, an optionally substituted alkoxyalkyl, where for the instance of $NR'_2$ or $NHR'_2{}^+$ each R' comprise at least one C atom that is independent of one another or are joined to form a heterocycle comprising at least two carbon atoms, and where for the instance of $NR'_3{}^+$ each R' comprises at least one C atom which are independent of one another or each R' comprises at least one C atom in which at least two R' are joined to form a heterocycle comprising at least two carbon atoms.

A first aspect of the first embodiment is directed to a compound represented by formula I-1
wherein (a) $R^1$ is H, n-alkyl, branched alkyl, cycloalkyl, alkaryl, or aryl, which includes, but is not limited to, phenyl or naphthyl, where phenyl or naphthyl are optionally substituted with at least one of H, F, Cl, Br, I, OH, OR', SH, SR', $NH_2$, NHR', $NR'_2$, $NHR'_2{}^+$, $NR'_3{}^+$, heterocycle, lower alkyl, halogenated (F, Cl, Br, I), halogenated (F, Cl, Br, I) lower alkenyl of $C_2$-$C_6$, lower alkynyl of $C_2$-$C_6$ such as C≡CH, halogenated (F, Cl, Br, I) lower alkynyl of $C_2$-$C_6$, lower alkoxy of $C_1$-$C_6$, halogenated (F, Cl, Br, I) lower alkoxy of $C_1$-$C_6$, $CO_2H$, $CO_2R'$, $CONH_2$, CONHR', $CONR'_2$, CH=$CHCO_2H$, or CH=$CHCO_2R'$;

(b) $R^2$ is H, a lower alkyl, cyano (CN), vinyl, O-(lower alkyl), including $OCH_3$, $OCH_2CH_3$, hydroxyl lower alkyl, i.e., —$(CH_2)_pOH$, where p is 1-6, including hydroxyl methyl ($CH_2OH$), fluoromethyl ($CH_2F$), azido ($N_3$), $CH_2CN$, $CH_2N_3$, $CH_2NH_2$, $CH_2NHCH_3$, $CH_2N(CH_3)_2$, F, Cl, Br, or I;

(c) $R^3$ is H, $CH_3$, $CH_2F$, $CHF_2$, $CF_3$, or F;

(d) X is H, OH, F, OMe, $NH_2$, or $N_3$; and (e) $R^4$, $R^5$, $R^6$ are independently H, F, Cl, Br, I, OH, OR', such as alkoxy, aryloxy, benzyloxy, substituted aryloxy, and substituted benzyloxy, SH, SR', $NH_2$, NHR', $NR'_2$, $NHR'_2{}^+$, $NR'_3{}^+$, heterocycle, lower alkyl, halogenated (F, Cl, Br, I) lower alkyl, lower alkenyl of $C_2$-$C_6$, $CO_2H$, $CO_2R'$, $CONH_2$, CONHR', $CONR'_2$;

wherein R' is an optionally substituted alkyl, an optionally substituted cycloalkyl, an optionally substituted alkynyl, an optionally substituted alkenyl, or an optionally substituted acyl, an optionally substituted alkoxyalkyl, where for the instance of $NR'_2$ or $NHR'_2{}^+$ each R' comprise at least one C atom that is independent of one another or are joined to form a heterocycle comprising at least two carbon atoms, and where for the instance of $NR'_3{}^+$ each R' comprises at least one C atom which are independent of one another or each R' comprises at least one C atom in which at least two R' are joined to form a heterocycle comprising at least two carbon atoms.

A second aspect of the first embodiment is directed to a compound represented by formula I-1
wherein (a) $R^1$ is H, n-alkyl, branched alkyl, cycloalkyl, alkaryl, or aryl, which includes, but is not limited to, phenyl or naphthyl, where phenyl or naphthyl are optionally substituted with at least one of H, F, Cl, Br, I, OH, OR', SH, SR', $NH_2$, NHR', $NR'_2$, $NHR'_2{}^+$, $NR'_3{}^+$, heterocycle, lower alkyl, halogenated (F, Cl, Br, I), halogenated (F, Cl, Br, I) lower alkenyl of $C_2$-$C_6$, lower alkynyl of $C_2$-$C_6$ such as C≡CH, halogenated (F, Cl, Br, I) lower alkynyl of $C_2$-$C_6$, lower alkoxy of $C_1$-$C_6$, halogenated (F, Cl, Br, I) lower alkoxy of $C_1$-$C_6$, $CO_2H$, $CO_2R'$, $CONH_2$, CONHR', $CONR'_2$, CH=$CHCO_2H$, or CH=$CHCO_2R'$;

(b) $R^2$ is H, a lower alkyl, cyano (CN), vinyl, O-(lower alkyl), including $OCH_3$, $OCH_2CH_3$, hydroxyl lower alkyl, i.e., —$(CH_2)_pOH$, where p is 1-6, including hydroxyl methyl ($CH_2OH$), fluoromethyl ($CH_2F$), azido ($N_3$), $CH_2CN$, $CH_2N_3$, $CH_2NH_2$, $CH_2NHCH_3$, $CH_2N(CH_3)_2$, F, Cl, Br, or I;

(c) $R^3$ is H, $CH_3$, $CH_2F$, $CHF_2$, $CF_3$, or F;

(d) X is H, OH, F, OMe, $NH_2$, or $N_3$;

(e) $R^4$ and $R^5$ are independently H, F, Cl, OH, $OCH_3$, $CH_3$, $CH_{3-q}X_q$, where X is F, Cl, Br, or I and q is 1 to 3, vinyl, $CO_2H$, $CO_2CH_3$, $CONH_2$, $CONHCH_3$, or $CON(CH_3)_2$; and (f) $R^6$ is selected from among OH, $OCH_3$, $NH_2$, $NHCH_3$, $N(CH_3)_2$, $NHR'_2{}^+$, $NR'_3{}^+$, $OC(O)(C_{1-20}$ alkyl), which include but are not limited to $OC(O)(CH_2)_sCH_3$, $NHC(O)(C_{1-20}$ alkyl), which include but are not limited to $NHC(O)(CH_2)_sCH_3$, $N(C(O)(CH_2)_sCH_3)_2$, which include but is not limited to $N(C(O)(CH_2)_sCH_3)_2$, where s is an integer selected from 0, 1, 2, 3, 4, 5, 6, 7, 8, 9, 10, 11, 12, 13, 14, 15, 16, 17, 18, and 19;

wherein R' is an optionally substituted alkyl, an optionally substituted cycloalkyl, an optionally substituted alkynyl, an optionally substituted alkenyl, or an optionally substituted acyl, an optionally substituted alkoxyalkyl, where for the instance of $NR'_2$ or $NHR'_2{}^+$ each R' comprise at least one C atom that is independent of one another or are joined to form a heterocycle comprising at least two carbon atoms, and where for the instance of $NR'_3{}^+$ each R' comprises at least one C atom which are independent of one another or each R' comprises at least one C atom in which at least two R' are joined to form a heterocycle comprising at least two carbon atoms.

A third aspect of the first embodiment is directed to a compound represented by formula I-1
wherein (a) $R^1$ is H, n-alkyl, branched alkyl, cycloalkyl, alkaryl, or aryl, which includes, but is not limited to, phenyl or naphthyl, where phenyl or naphthyl are optionally substituted with at least one of H, F, Cl, Br, I, OH, OR', SH, SR', $NH_2$, NHR', $NR'_2$, $NHR'_2{}^+$, $NR'_3{}^+$, heterocycle, lower alkyl, halogenated (F, Cl, Br, I), halogenated (F, Cl, Br, I) lower alkenyl of $C_2$-$C_6$, lower alkynyl of $C_2$-$C_6$ such as C≡CH, halogenated (F, Cl, Br, I) lower alkynyl of $C_2$-$C_6$, lower alkoxy of $C_1$-$C_6$, halogenated (F, Cl, Br, I) lower alkoxy of $C_1$-$C_6$, $CO_2H$, $CO_2R'$, $CONH_2$, CONHR', $CONR'_2$, CH=$CHCO_2H$, or CH=$CHCO_2R'$;

(b) $R^2$ is H, a lower alkyl, cyano (CN), vinyl, O-(lower alkyl), including $OCH_3$, $OCH_2CH_3$, hydroxyl lower alkyl, i.e., —$(CH_2)_pOH$, where p is 1-6, including hydroxyl methyl ($CH_2OH$), fluoromethyl ($CH_2F$), azido ($N_3$), $CH_2CN$, $CH_2N_3$, $CH_2NH_2$, $CH_2NHCH_3$, $CH_2N(CH_3)_2$, F, Cl, Br, or I;

(c) $R^3$ is $CH_3$, $CH_2F$, $CHF_2$, $CF_3$;

(d) X is H, OH, F, OMe, $NH_2$, or $N_3$;

(e) $R^4$ and $R^5$ are independently H, F, Cl, OH, $OCH_3$, $CH_3$, $CH_{3-q}X_q$, where X is F, Cl, Br, or I and q is 1 to 3, vinyl, $CO_2H$, $CO_2CH_3$, $CONH_2$, $CONHCH_3$, or $CON(CH_3)_2$; and (f) $R^6$ is selected from among OH, $OCH_3$, $NH_2$, $NHCH_3$, $N(CH_3)_2$, $NHR'_2{}^+$, $NR'_3{}^+$, OC(O)(C1-20 alkyl), which include but are not limited to $OC(O)(CH_2)_sCH_3$, NHC(O) (C1-20 alkyl), which include but are not limited to $NHC(O)(CH_2)_sCH_3$, $N(C(O)(CH_2)_sCH_3)_2$, which include but is not limited to $N(C(O)(CH_2)_sCH_3)_2$ an integer selected from 0, 1, 2, 3, 4, 5, 6, 7, 8, 9, 10, 11, 12, 13, 14, 15, 16, 17, 18, and 19;

wherein R' is an optionally substituted alkyl, an optionally substituted cycloalkyl, an optionally substituted alkynyl, an optionally substituted alkenyl, or an optionally substituted acyl, an optionally substituted alkoxyalkyl, where for the instance of $NR'_2$ or $NHR'_2{}^+$ each R' comprise at least one C atom that is independent of one another or are joined to form a heterocycle comprising at least two carbon atoms, and where for the instance of $NR'_3{}^+$ each R' comprises at least one C atom which are independent of one another or each R' comprises at least one C atom in which at least two R' are joined to form a heterocycle comprising at least two carbon atoms.

A fourth aspect of the first embodiment is directed to a compound represented by formula I-1
wherein (a) $R^1$ is H, n-alkyl, branched alkyl, cycloalkyl, alkaryl, or aryl, which includes, but is not limited to, phenyl or naphthyl, where phenyl or naphthyl are optionally substituted with at least one of H, F, Cl, Br, I, OH, OR', SH, SR', $NH_2$, NHR', $NR'_2$, $NHR'_2{}^+$, $NR'_3{}^+$, heterocycle, lower alkyl, halogenated (F, Cl, Br, I), halogenated (F, Cl, Br, I) lower alkenyl of $C_2$-$C_6$, lower alkynyl of $C_2$-$C_6$ such as C≡CH, halogenated (F, Cl, Br, I) lower alkynyl of $C_2$-$C_6$, lower alkoxy of $C_1$-$C_6$, halogenated (F, Cl, Br, I) lower alkoxy of $C_1$-$C_6$, $CO_2H$, $CO_2R'$, $CONH_2$, CONHR', $CONR'_2$, CH═$CHCO_2H$, or CH═$CHCO_2R'$;

(b) $R^2$ is H, a lower alkyl, cyano (CN), vinyl, O-(lower alkyl), including $OCH_3$, $OCH_2CH_3$, hydroxyl lower alkyl, i.e., —$(CH_2)_pOH$, where p is 1-6, including hydroxyl methyl ($CH_2OH$), fluoromethyl ($CH_2F$), azido ($N_3$), $CH_2CN$, $CH_2N_3$, $CH_2NH_2$, $CH_2NHCH_3$, $CH_2N(CH_3)_2$, F, Cl, Br, or I;

(c) $R^3$ is $CH_3$, $CH_2F$, $CHF_2$, $CF_3$;

(d) X is F;

(e) $R^4$ and $R^5$ are independently H, F, Cl, OH, $OCH_3$, $CH_3$, $CH_{3-q}X_q$, where X is F, Cl, Br, or I and q is 1 to 3, vinyl, $CO_2H$, $CO_2CH_3$, $CONH_2$, $CONHCH_3$, or $CON(CH_3)_2$; and (f) $R^6$ is selected from among OH, $OCH_3$, $NH_2$, $NHCH_3$, $N(CH_3)_2$, $NR'_2$, OC(O)(C1-20 alkyl), which include but are not limited to $OC(O)(CH_2)_sCH_3$, NHC(O)(C1-20 alkyl), which include but are not limited to $NHC(O)(CH_2)_sCH_3$, $N(C(O)(CH_2)_sCH_3)_2$, which include but is not limited to $N(C(O)(CH_2)_sCH_3)_2$, where s is an integer selected from 0, 1, 2, 3, 4, 5, 6, 7, 8, 9, 10, 11, 12, 13, 14, 15, 16, 17, 18, and 19;

wherein R' is an optionally substituted alkyl, an optionally substituted cycloalkyl, an optionally substituted alkynyl, an optionally substituted alkenyl, or an optionally substituted acyl, an optionally substituted alkoxyalkyl, where for the instance of $NR'_2$ or $NHR'_2{}^+$ each R' comprise at least one C atom that is independent of one another or are joined to form a heterocycle comprising at least two carbon atoms, and where for the instance of $NR'_3{}^+$ each R' comprises at least one C atom which are independent of one another or each R' comprises at least one C atom in which at least two R' are joined to form a heterocycle comprising at least two carbon atoms.

A fifth aspect of the first embodiment is directed to a compound represented by formula I-1
wherein (a) $R^1$ is H, n-alkyl, branched alkyl, cycloalkyl, alkaryl, or aryl, which includes, but is not limited to, phenyl or naphthyl, where phenyl or naphthyl are optionally substituted with at least one of H, F, Cl, Br, I, OH, OR', SH, SR', $NH_2$, NHR', $NR'_2$, $NHR'_2{}^+$, $NR'_3{}^+$, heterocycle, lower alkyl, halogenated (F, Cl, Br, I), halogenated (F, Cl, Br, I) lower alkenyl of $C_2$-$C_6$, lower alkynyl of $C_2$-$C_6$ such as C≡CH, halogenated (F, Cl, Br, I) lower alkynyl of $C_2$-$C_6$, lower alkoxy of $C_1$-$C_6$, halogenated (F, Cl, Br, I) lower alkoxy of $C_1$-$C_6$, $CO_2H$, $CO_2R'$, $CONH_2$, CONHR', $CONR'_2$, CH═$CHCO_2H$, or CH═$CHCO_2R'$;

(b) $R^2$ is H, —$CH_3$, cyano (CN), vinyl, —$OCH_3$, —$CH_2OH$, -$CH_2F$, azido ($N_3$), $CH_2CN$, $CH_2N_3$, $CH_2NH_2$, $CH_2NHCH_3$, $CH_2N(CH_3)_2$, F, Cl, Br, or I (c) $R^3$ is $CH_3$;

(d) X is F;

(e) $R^4$ and $R^5$ are independently H, F, $CH_3$, $CH_{3-q}F_q$, and q is 1 to 3, vinyl, $CO_2CH_3$, $CONH_2$, $CONHCH_3$, or $CON(CH_3)_2$; and (f) $R^6$ is selected from among —OH, —$OCH_3$, —$NH_2$, —$NHCH_3$, —$N(CH_3)_2$, $NR'_2$, $NHR'_2{}^+$, $NR'_3{}^+$, —OC(O)$CH_3$, —NHC(O)$CH_3$, —N(C(O)$CH_3$)$_2$;

wherein R' is an optionally substituted alkyl, an optionally substituted cycloalkyl, an optionally substituted alkynyl, an optionally substituted alkenyl, or an optionally substituted acyl, an optionally substituted alkoxyalkyl, where for the instance of $NR'_2$ or $NHR'_2{}^+$ each R' comprise at least one C atom that is independent of one another or are joined to form a heterocycle comprising at least two carbon atoms, and where for the instance of $NR'_3{}^+$ each R' comprises at least one C atom which are independent of one another or each R' comprises at least one C atom in which at least two R' are joined to form a heterocycle comprising at least two carbon atoms.

A sixth aspect of the first embodiment is directed to a compound represented by formula I-1
wherein (a) $R^1$ is H, lower alkyl, lower alkylaryl, or aryl, which includes, but is not limited to, phenyl or naphthyl, where phenyl or naphthyl are optionally substituted with at least one of H, F, Cl, Br, I, OH, OR', SH, SR', $NH_2$, NHR', $NR'_2$, $NHR'_2{}^+$, $NR'_3{}^+$, lower alkyl, lower alkoxy of $C_1$-$C_6$, halogenated (F, Cl, Br, I) lower alkoxy of $C_1$-$C_6$;

(b) $R^2$ is H, —$CH_3$, cyano (CN), vinyl, —$OCH_3$, —$CH_2OH$, —$CH_2F$, azido ($N_3$), $CH_2CN$, $CH_2N_3$, $CH_2NH_2$, $CH_2NHCH_3$, $CH_2N(CH_3)_2$, F, Cl, Br, or I;

(c) $R^3$ is $CH_3$;

(d) X is F;

(e) $R^4$ and $R^5$ are independently H, F, $CH_3$, $CH_{3-q}F_q$, and q is 1 to 3, vinyl, $CO_2CH_3$, $CONH_2$, $CONHCH_3$, or $CON(CH_3)_2$; and (f) $R^6$ is selected from among —OH, —$OCH_3$, —$NH_2$, —$NHCH_3$, —$N(CH_3)_2$, $NR'_2$, $NHR'_2{}^+$, $NR'_3{}^+$, —OC(O)$CH_3$, —NHC(O)$CH_3$, —N(C(O)$CH_3$)$_2$, wherein R' is an optionally substituted alkyl, an optionally substituted cycloalkyl, an optionally substituted alkynyl, an optionally substituted alkenyl, or an optionally substituted acyl, an optionally substituted alkoxyalkyl, where for the instance of $NR'_2$ or $NHR'_2{}^+$ each R' comprise at least one C atom that is independent of one another or are joined to form a heterocycle comprising at least two carbon atoms, and where for the instance of $NR'_3{}^+$ each R' comprises at least one C atom which are independent of one another or each R' comprises at least one C atom in which at least two R' are joined to form a heterocycle comprising at least two carbon atoms.

A seventh aspect of the first embodiment is directed to a compound represented by formula I-1
wherein
(a) $R^1$ is H, lower alkyl, lower alkylaryl, or aryl, which includes, but is not limited to, phenyl or naphthyl, where phenyl or naphthyl are optionally substituted with at least one of H, F, Cl, Br, I, OH, OR', SH, SR', $NH_2$, NHR', $NR'_2$, $NHR'_2{}^+$, $NR'_3{}^+$, heterocycle, lower alkyl, lower alkoxy of $C_1$-$C_6$, halogenated (F, Cl, Br, I) lower alkoxy of $C_1$-$C_6$;
(b) $R^2$ is H;
(c) $R^3$ is $CH_3$;
(d) X is F;
(e) $R^4$ and $R^5$ are independently H, F, $CH_3$, $CH_{3-q}F_q$, and q is 1 to 3, vinyl, $CO_2CH_3$, $CONH_2$, $CONHCH_3$, or $CON(CH_3)_2$; and
(f) $R^6$ is selected from among —OH, —$OCH_3$, —$NH_2$, —$NHCH_3$, —$N(CH_3)_2$, $NR'_2$, $NHR'_2{}^+$, $NR'_3{}^+$, —$OC(O)CH_3$, —$NHC(O)CH_3$, —$N(C(O)CH_3)_2$;
wherein R' is an optionally substituted alkyl, an optionally substituted cycloalkyl, an optionally substituted alkynyl, an optionally substituted alkenyl, or an optionally substituted acyl, an optionally substituted alkoxyalkyl, where for the instance of $NR'_2$ or $NH'_2{}^+$ each R' comprise at least one C atom that is independent of one another or are joined to form a heterocycle comprising at least two carbon atoms, and where for the instance of $NR'_3{}^+$ each R' comprises at least one C atom which are independent of one another or each R' comprises at least one C atom in which at least two R' are joined to form a heterocycle comprising at least two carbon atoms.

A second embodiment of the invention is directed to a compound represented by formula I in which the base is a structure represented by formula b above, wherein $R^1$, $R^2$, $R^3$, X, Y, $R^4$, and $R^5$ are defined in the Summary of the Invention section above.

A first aspect of the second embodiment is directed to a compound represented by formula 1-2

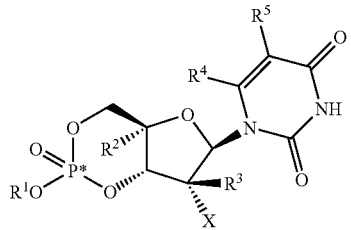

I-2 wherein
(a) $R^1$ is H, n-alkyl, branched alkyl, cycloalkyl, alkaryl, or aryl, which includes, but is not limited to, phenyl or naphthyl, where phenyl or naphthyl are optionally substituted with at least one of H, F, Cl, Br, I, OH, OR', SH, SR', $NH_2$, NHR', $NR'_2$, $NHR'_2{}^+$, $NR'_3{}^+$, heterocycle, lower alkyl, halogenated (F, Cl, Br, I), halogenated (F, Cl, Br, I) lower alkenyl of $C_2$-$C_6$, lower alkynyl of $C_2$-$C_6$ such as C≡CH, halogenated (F, Cl, Br, I) lower alkynyl of $C_2$-$C_6$, lower alkoxy of $C_1$-$C_6$, halogenated (F, Cl, Br, I) lower alkoxy of $C_1$-$C_6$, $CO_2H$, $CO_2R'$, $CONH_2$, CONHR', $CONR'_2$, CH=$CHCO_2H$, or CH=$CHCO_2R'$;

(b) $R^2$ is H, a lower alkyl, cyano (CN), vinyl, O-(lower alkyl), including $OCH_3$, $OCH_2CH_3$, hydroxyl lower alkyl, i.e., —$(CH_2)_pOH$, where p is 1-6, including hydroxyl methyl ($CH_2OH$), fluoromethyl ($CH_2F$), azido ($N_3$), $CH_2CN$, $CH_2N_3$, $CH_2NH_2$, $CH_2NHCH_3$, $CH_2N(CH_3)_2$, F, Cl, Br, or I;
(c) $R^3$ is H, $CH_3$, $CH_2F$, $CHF_2$, $CF_3$, or F;
(d) X is H, OH, F, OMe, $NH_2$, or $N_3$; and
(e) $R^4$ and $R^5$ are independently H, F, Cl, Br, I, OH, OR', SH, SR', $NH_2$, NHR', $NR'_2$, $NHR'_2{}^+$, $NR'_3{}^+$, heterocycle, lower alkyl, halogenated (F, Cl, Br, I) lower alkyl, lower alkenyl of $C_2$-$C_6$, $CO_2H$, $CO_2R'$, $CONH_2$, CONHR', $CONR'_2$;
wherein R' is an optionally substituted alkyl, an optionally substituted cycloalkyl, an optionally substituted alkynyl, an optionally substituted alkenyl, or an optionally substituted acyl, an optionally substituted alkoxyalkyl, where for the instance of $NR'_2$ or $NHR'_2{}^+$ each R' comprise at least one C atom that is independent of one another or are joined to form a heterocycle comprising at least two carbon atoms, and where for the instance of $NR'_3{}^+$ each R' comprises at least one C atom which are independent of one another or each R' comprises at least one C atom in which at least two R' are joined to form a heterocycle comprising at least two carbon atoms.

The second aspect of the second embodiment is directed to a compound represented by formula 1-2
wherein
(a) $R^1$ is H, n-alkyl, branched alkyl, cycloalkyl, alkaryl, or aryl, which includes, but is not limited to, phenyl or naphthyl, where phenyl or naphthyl are optionally substituted with at least one of H, F, Cl, Br, I, OH, OR', SH, SR', $NH_2$, NHR', $NR'_2$, $NHR'_2{}^+$, $NR'_3{}^+$, heterocycle, lower alkyl, halogenated (F, Cl, Br, I), halogenated (F, Cl, Br, I) lower alkenyl of $C_2$-$C_6$, lower alkynyl of $C_2$-$C_6$ such as C≡CH, halogenated (F, Cl, Br, I) lower alkynyl of $C_2$-$C_6$, lower alkoxy of $C_1$-$C_6$, halogenated (F, Cl, Br, I) lower alkoxy of $C_1$-$C_6$, $CO_2H$, $CO_2R'$, $CONH_2$, CONHR', $CONR'_2$, CH=$CHCO_2H$, or CH=$CHCO_2R'$;
(b) $R^2$ is H, a lower alkyl, cyano (CN), vinyl, O-(lower alkyl), including $OCH_3$, $OCH_2CH_3$, hydroxyl lower alkyl, i.e., —$(CH_2)_pOH$, where p is 1-6, including hydroxyl methyl ($CH_2OH$), fluoromethyl ($CH_2F$), azido ($N_3$), $CH_2CN$, $CH_2N_3$, $CH_2NH_2$, $CH_2NHCH_3$, $CH_2N(CH_3)_2$, F, Cl, Br, or I;
(c) $R^3$ is H, $CH_3$, $CH_2F$, $CHF_2$, $CF_3$, or F;
(d) X is H, OH, F, OMe, $NH_2$, or $N_3$; and
(e) $R^4$ and $R^5$ are independently H, F, Cl, OH, $OCH_3$, $CH_3$, $CH_{3-q}X_q$, where X is F, Cl, Br, or I and q is 1 to 3, vinyl, $CO_2H$, $CO_2CH_3$, $CONH_2$, $CONHCH_3$, or $CON(CH_3)_2$;
wherein R' is an optionally substituted alkyl, an optionally substituted cycloalkyl, an optionally substituted alkynyl, an optionally substituted alkenyl, or an optionally substituted acyl, an optionally substituted alkoxyalkyl, where for the instance of $NR'_2$ or $NHR'_2{}^+$ each R' comprise at least one C atom that is independent of one another or are joined to form a heterocycle comprising at least two carbon atoms, and where for the instance of $NR'_3{}^+$ each R' comprises at least one C atom which are independent of one another or each R' comprises at least one C atom in which at least two R' are joined to form a heterocycle comprising at least two carbon atoms.

The third aspect of the second embodiment is directed to a compound represented by formula 1-2
wherein
(a) $R^1$ is H, n-alkyl, branched alkyl, cycloalkyl, alkaryl, or aryl, which includes, but is not limited to, phenyl or naphthyl, where phenyl or naphthyl are optionally substituted with at least one of H, F, Cl, Br, I, OH, OR', SH, SR', $NH_2$, NHR', $NR'_2$, $NHR'^+_2$, $NR'^+_3$, heterocycle, lower alkyl, halogenated (F, Cl, Br, I), halogenated (F, Cl, Br, I) lower alkenyl of $C_2$-$C_6$, lower alkynyl of $C_2$-$C_6$ such as C≡CH, halogenated (F, Cl, Br, I) lower alkynyl of $C_2$-$C_6$, lower alkoxy of $C_1$-$C_6$, halogenated (F, Cl, Br, I) lower alkoxy of $C_1$-$C_6$, $CO_2H$, $CO_2R'$, $CONH_2$, CONHR', $CONR'_2$, CH=$CHCO_2H$, or CH=$CHCO_2R'$;

(b) $R^2$ is H, a lower alkyl, cyano (CN), vinyl, O-(lower alkyl), including $OCH_3$, $OCH_2CH_3$, hydroxyl lower alkyl, i.e., —$(CH_2)_p$OH, where p is 1-6, including hydroxyl methyl ($CH_2OH$), fluoromethyl ($CH_2F$), azido ($N_3$), $CH_2CN$, $CH_2N_3$, $CH_2NH_2$, $CH_2NHCH_3$, $CH_2N(CH_3)_2$, F, Cl, Br, or I;

(c) $R^3$ is $CH_3$, $CH_2F$, $CHF_2$, $CF_3$;

(d) X is H, OH, F, OMe, $NH_2$, or $N_3$; and (e) $R^4$ and $R^5$ are independently H, F, Cl, OH, $OCH_3$, $CH_3$, $CH_{3-q}X_q$, where X is F, Cl, Br, or I and q is 1 to 3, vinyl, $CO_2H$, $CO_2CH_3$, $CONH_2$, $CONHCH_3$, or $CON(CH_3)_2$;

wherein R' is an optionally substituted alkyl, an optionally substituted cycloalkyl, an optionally substituted alkynyl, an optionally substituted alkenyl, or an optionally substituted acyl, an optionally substituted alkoxyalkyl, where for the instance of $NR'_2$ or $NHR'^+_2$ each R' comprise at least one C atom that is independent of one another or are joined to form a heterocycle comprising at least two carbon atoms, and where for the instance of $NR'^+_3$ each R' comprises at least one C atom which are independent of one another or each R' comprises at least one C atom in which at least two R' are joined to form a heterocycle comprising at least two carbon atoms.

The fourth aspect of the second embodiment is directed to a compound represented by formula 1-2 wherein (a) $R^1$ is H, n-alkyl, branched alkyl, cycloalkyl, alkaryl, or aryl, which includes, but is not limited to, phenyl or naphthyl, where phenyl or naphthyl are optionally substituted with at least one of H, F, Cl, Br, I, OH, OR', SH, SR', $NH_2$, NHR', $NR'_2$, $NHR'^+_2$, $NR'^+_3$, heterocycle, lower alkyl, halogenated (F, Cl, Br, I), halogenated (F, Cl, Br, I) lower alkenyl of $C_2$-$C_6$, lower alkynyl of $C_2$-$C_6$ such as C≡CH, halogenated (F, Cl, Br, I) lower alkynyl of $C_2$-$C_6$, lower alkoxy of $C_1$-$C_6$, halogenated (F, Cl, Br, I) lower alkoxy of $C_1$-$C_6$, $CO_2H$, $CO_2R'$, $CONH_2$, CONHR', $CONR'_2$, CH=$CHCO_2H$, or CH=$CHCO_2R'$;

(b) $R^2$ is H, a lower alkyl, cyano (CN), vinyl, O-(lower alkyl), including $OCH_3$, $OCH_2CH_3$, hydroxyl lower alkyl, i.e., —$(CH_2)_p$OH, where p is 1-6, including hydroxyl methyl ($CH_2OH$), fluoromethyl ($CH_2F$), azido ($N_3$), $CH_2CN$, $CH_2N_3$, $CH_2NH_2$, $CH_2NHCH_3$, $CH_2N(CH_3)_2$, F, Cl, Br, or I;

(c) $R^3$ is $CH_3$, $CH_2F$, $CHF_2$, $CF_3$;

(d) X is F; and (e) $R^4$ and $R^5$ are independently H, F, Cl, OH, $OCH_3$, $CH_3$, $CH_{3-q}X_q$, where X is F, Cl, Br, or I and q is 1 to 3, vinyl, $CO_2H$, $CO_2CH_3$, $CONH_2$, $CONHCH_3$, or $CON(CH_3)_2$;

wherein R' is an optionally substituted alkyl, an optionally substituted cycloalkyl, an optionally substituted alkynyl, an optionally substituted alkenyl, or an optionally substituted acyl, an optionally substituted alkoxyalkyl, where for the instance of $NR'_2$ or $NHR'^+_2$ each R' comprise at least one C atom that is independent of one another or are joined to form a heterocycle comprising at least two carbon atoms, and where for the instance of $NR'^+_3$ each R' comprises at least one C atom which are independent of one another or each R' comprises at least one C atom in which at least two R' are joined to form a heterocycle comprising at least two carbon atoms.

The fifth aspect of the second embodiment is directed to a compound represented by formula I-2 wherein (a) $R^1$ is H, n-alkyl, branched alkyl, cycloalkyl, alkaryl, or aryl, which includes, but is not limited to, phenyl or naphthyl, where phenyl or naphthyl are optionally substituted with at least one of H, F, Cl, Br, I, OH, OR', SH, SR', $NH_2$, NHR', $NR'_2$, $NHR'^+_2$, $NR'^+_3$, heterocycle, lower alkyl, halogenated (F, Cl, Br, I), halogenated (F, Cl, Br, I) lower alkenyl of $C_2$-$C_6$, lower alkynyl of $C_2$-$C_6$ such as C≡CH, halogenated (F, Cl, Br, I) lower alkynyl of $C_2$-$C_6$, lower alkoxy of $C_1$-$C_6$, halogenated (F, Cl, Br, I) lower alkoxy of $C_1$-$C_6$, $CO_2H$, $CO_2R'$, $CONH_2$, CONHR', $CONR'_2$, CH=$CHCO_2H$, or CH=$CHCO_2R'$;

(b) $R^2$ is H, —$CH_3$, cyano (CN), vinyl, —$OCH_3$, —$CH_2OH$, —$CH_2F$, azido ($N_3$), $CH_2CN$, $CH_2N_3$, $CH_2NH_2$, $CH_2NHCH_3$, $CH_2N(CH_3)_2$, F, Cl, Br, or I;

(c) $R^3$ is $CH_3$;

(d) X is F; and (e) $R^4$ and $R^5$ are independently H, F, $CH_3$, $CH_{3-q}F_q$, and q is 1 to 3, vinyl, $CO_2CH_3$, $CONH_2$, $CONHCH_3$, or $CON(CH_3)_2$;

wherein R' is an optionally substituted alkyl, an optionally substituted cycloalkyl, an optionally substituted alkynyl, an optionally substituted alkenyl, or an optionally substituted acyl, an optionally substituted alkoxyalkyl, where for the instance of $NR'_2$ or $NHR'^+_2$ each R' comprise at least one C atom that is independent of one another or are joined to form a heterocycle comprising at least two carbon atoms, and where for the instance of $NR'^+_3$ each R' comprises at least one C atom which are independent of one another or each R' comprises at least one C atom in which at least two R' are joined to form a heterocycle comprising at least two carbon atoms.

The sixth aspect of the second embodiment is directed to a compound represented by formula I-2 wherein (a) $R^1$ is H, lower alkyl, lower alkylaryl, or aryl, which includes, but is not limited to, phenyl or naphthyl, where phenyl or naphthyl are optionally substituted with at least one of H, F, Cl, Br, I, OH, OR', SH, SR', $NH_2$, NHR', $NR'_2$, $NHR'^+_2$, $NR'^+_3$, heterocycle, lower alkyl, lower alkoxy of $C_1$-$C_6$, halogenated (F, Cl, Br, I) lower alkoxy of $C_1$-$C_6$;

(b) $R^2$ is H, —$CH_3$, cyano (CN), vinyl, —$OCH_3$, —$CH_2OH$, —$CH_2F$, azido ($N_3$), $CH_2CN$, $CH_2N_3$, $CH_2NH_2$, $CH_2NHCH_3$, $CH_2N(CH_3)_2$, F, Cl, Br, or I;

(c) $R^3$ is $CH_3$;

(d) X is F; and (e) $R^4$ and $R^5$ are independently H, F, $CH_3$, $CH_{3-q}F_q$, and q is 1 to 3, vinyl, $CO_2CH_3$, $CONH_2$, $CONHCH_3$, or $CON(CH_3)_2$;

wherein R' is an optionally substituted alkyl, an optionally substituted cycloalkyl, an optionally substituted alkynyl, an optionally substituted alkenyl, or an optionally substituted acyl, an optionally substituted alkoxyalkyl, where for the instance of $NR'_2$ or $NHR'^+_2$ each R' comprise at least one C atom that is independent of one another or are joined to form a heterocycle comprising at least two carbon atoms, and where for the instance of $NR'^+_3$ each R' comprises at least one C atom which are independent of one another or each R' comprises at least one C atom in which at least two R' are joined to form a heterocycle comprising at least two carbon atoms.

The seventh aspect of the second embodiment is directed to a compound represented by formula I-2 wherein (a) $R^1$ is H, lower alkyl, lower alkylaryl, or aryl, which includes, but is not limited to, phenyl or naphthyl, where phenyl or naphthyl are optionally substituted with at least one of H, F, Cl, Br, I, OH, OR', SH, SR', $NH_2$, NHR', $NR'_2$, $NHR'_2{}^+$, $NR'_3{}^+$, heterocycle, lower alkyl, lower alkoxy of $C_1$-$C_6$, halogenated (F, Cl, Br, I) lower alkoxy of $C_1$-$C_6$;

(b) $R^2$ is H;

(c) $R^3$ is $CH_3$;

(d) X is F; and (e) $R^4$ and $R^5$ are independently H, F, $CH_3$, $CH_{3-q}F_q$, and q is 1 to 3, vinyl, $CO_2CH_3$, $CONH_2$, $CONHCH_3$, or $CON(CH_3)_2$;

wherein R' is an optionally substituted alkyl, an optionally substituted cycloalkyl, an optionally substituted alkynyl, an optionally substituted alkenyl, or an optionally substituted acyl, an optionally substituted alkoxyalkyl, where for the instance of $NR'_2$ or $NHR'_2{}^+$ each R' comprise at least one C atom that is independent of one another or are joined to form a heterocycle comprising at least two carbon atoms, and where for the instance of $NR'_3{}^+$ each R' comprises at least one C atom which are independent of one another or each R' comprises at least one C atom in which at least two R' are joined to form a heterocycle comprising at least two carbon atoms.

A third embodiment of the invention is directed to a compound represented by formula I in which the base is a structure represented by formula c above.

The first aspect of the third embodiment is directed to a compound represented by formula I-3

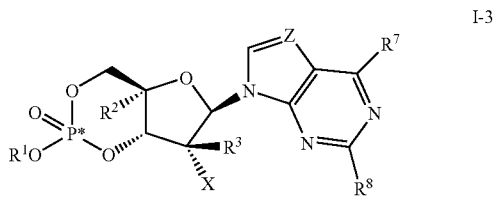

I-3 wherein (a) $R^1$ is H, n-alkyl, branched alkyl, cycloalkyl, alkaryl, or aryl, which includes, but is not limited to, phenyl or naphthyl, where phenyl or naphthyl are optionally substituted with at least one of H, F, Cl, Br, I, OH, OR', SH, SR', $NH_2$, NHR', $NR'_2$, $NHR'_2{}^+$, $NR'_3{}^+$, heterocycle, lower alkyl, halogenated (F, Cl, Br, I), halogenated (F, Cl, Br, I) lower alkenyl of $C_2$-$C_6$, lower alkynyl of $C_2$-$C_6$ such as C≡CH, halogenated (F, Cl, Br, I) lower alkynyl of $C_2$-$C_6$, lower alkoxy of $C_1$-$C_6$, halogenated (F, Cl, Br, I) lower alkoxy of $C_1$-$C_6$, $CO_2H$, $CO_2R'$, $CONH_2$, CONHR', $CONR'_2$, CH=$CHCO_2H$, or CH=$CHCO_2R'$;

(b) $R^2$ is H, a lower alkyl, cyano (CN), vinyl, O-(lower alkyl), including $OCH_3$, $OCH_2CH_3$, hydroxyl lower alkyl, i.e., —$(CH_2)_pOH$, where p is 1-6, including hydroxyl methyl ($CH_2OH$), fluoromethyl ($CH_2F$), azido ($N_3$), $CH_2CN$, $CH_2N_3$, $CH_2NH_2$, $CH_2NHCH_3$, $CH_2N(CH_3)_2$, F, Cl, Br, or I;

(c) $R^3$ is H, $CH_3$, $CH_2F$, $CHF_2$, $CF_3$, or F;

(d) X is H, OH, F, OMe, $NH_2$, or $N_3$;

(e) $R^7$ and $R^8$ are independently H, F, Cl, Br, I, OH, OR', such as alkoxy, aryloxy, benzyloxy, substituted aryloxy, and substituted benzyloxy, SH, SR', $NH_2$, NHR', $NR'_2$, $NR'_2$, $NHR'_2{}^+$, $NR'_3{}^+$, heterocycle, lower alkyl, halogenated (F, Cl, Br, I) lower alkyl, lower alkenyl of $C_2$-$C_6$, halogenated (F, Cl, Br, I) lower alkenyl of $C_2$-$C_6$, lower alkynyl of $C_2$-$C_6$ such as C≡CH, halogenated (F, Cl, Br, I) lower alkynyl of $C_2$-$C_6$, lower alkoxy of $C_1$-$C_6$, halogenated (F, Cl, Br, I) lower alkoxy of $C_1$-$C_6$, $CO_2H$, $CO_2R'$, $CONH_2$, CONHR', $CONR'_2$, CH=$CHCO_2H$, or CH=$CHCO_2R'$;

(f) Z is N or $CR^9$; and (g) $R^9$ is an H, halogen (including F, Cl, Br, I), OH, OR', SH, SR', $NH_2$, NHR', $NR'_2$, $NO_2$ lower alkyl, halogenated (F, Cl, Br, I) lower alkyl, lower alkenyl of $C_2{}^+C_6$, halogenated (F, Cl, Br, I) lower alkenyl of $C_2$-$C_6$, lower alkynyl of $C_2$-$C_6$, halogenated (F, Cl, Br, I) lower alkynyl of $C_2$-$C_6$, lower alkoxy of $C_1$-$C_6$, halogenated (F, Cl, Br, I) lower alkoxy of $C_1$-$C_6$, $CO_2H$, $CO_2R'$, $CONH_2$, CONHR', $CONR'_2$, CH=$CHCO_2H$, or CH=$CHCO_2R'$;

wherein R' is an optionally substituted alkyl, an optionally substituted cycloalkyl, an optionally substituted alkynyl, an optionally substituted alkenyl, or an optionally substituted acyl, an optionally substituted alkoxyalkyl, where for the instance of $NR'_2$ or $NHR'_2{}^+$ each R' comprise at least one C atom that is independent of one another or are joined to form a heterocycle comprising at least two carbon atoms, and where for the instance of $NR'_3{}^+$ each R' comprises at least one C atom which are independent of one another or each R' comprises at least one C atom in which at least two R' are joined to form a heterocycle comprising at least two carbon atoms.

A second aspect of the third embodiment is directed to a compound represented by formula I-3 wherein (a) $R^1$ is H, n-alkyl, branched alkyl, cycloalkyl, alkaryl, or aryl, which includes, but is not limited to, phenyl or naphthyl, where phenyl or naphthyl are optionally substituted with at least one of H, F, Cl, Br, I, OH, OR', SH, SR', $NH_2$, NHR', $NR'_2$, heterocycle, lower alkyl, halogenated (F, Cl, Br, I), halogenated (F, Cl, Br, I) lower alkenyl of $C_2$-$C_6$, lower alkynyl of $C_2$-$C_6$ such as C≡CH, halogenated (F, Cl, Br, I) lower alkynyl of $C_2$-$C_6$, lower alkoxy of $C_1$-$C_6$, halogenated (F, Cl, Br, I) lower alkoxy of $C_1$-$C_6$, $CO_2H$, $CO_2R'$, $CONH_2$, CONHR', $CONR'_2$, CH=$CHCO_2H$, or CH=$CHCO_2R'$;

(b) $R^2$ is H, a lower alkyl, cyano (CN), vinyl, O-(lower alkyl), including $OCH_3$, $OCH_2CH_3$, hydroxyl lower alkyl, i.e., —$(CH_2)_pOH$, where p is 1-6, including hydroxyl methyl ($CH_2OH$), fluoromethyl ($CH_2F$), azido ($N_3$), $CH_2CN$, $CH_2N_3$, $CH_2NH_2$, $CH_2NHCH_3$, $CH_2N(CH_3)_2$, F, Cl, Br, or I;

(c) $R^3$ is H, $CH_3$, $CH_2F$, $CHF_2$, $CF_3$, or F;

(d) X is H, OH, F, OMe, $NH_2$, or $N_3$;

(e) $R^7$ and $R^8$ are independently H, F, Cl, Br, I, OH, OR', such as alkoxy, aryloxy, benzyloxy, substituted aryloxy, and substituted benzyloxy, SH, SR', $NH_2$, NHR', $NR'_2$, $NHR'_2{}^+$, $NR'_3{}^+$, heterocycle, lower alkyl, halogenated (F, Cl, Br, I) lower alkyl, lower alkenyl of $C_2$-$C_6$, halogenated (F, Cl, Br, I) lower alkenyl of $C_2$-$C_6$, lower alkynyl of $C_2$-$C_6$ such as C≡CH, halogenated (F, Cl, Br, I) lower alkynyl of $C_2$-$C_6$, lower alkoxy of $C_1$-$C_6$, halogenated (F, Cl, Br, I) lower alkoxy of $C_1$-$C_6$, $CO_2H$, $CO_2R'$, $CONH_2$, CONHR', $CONR'_2$, CH=$CHCO_2H$, or CH=$CHCO_2R'$;

(f) Z is N or $CR^9$; and (g) $R^9$ is an H, F, OH, OR', $NH_2$, NHR', $NR'_2$, lower alkyl, halogenated (F, Cl, Br, I) lower alkyl;

wherein R' is an optionally substituted alkyl, an optionally substituted cycloalkyl, an optionally substituted alkynyl, an optionally substituted alkenyl, or an optionally substituted acyl, an optionally substituted alkoxyalkyl, where for the instance of $NR'_2$ or $NHR'_2{}^+$ each R' comprise at least one C atom that is independent of one another or are joined to form a heterocycle comprising at least two carbon atoms, and where for the instance of $NR'_3{}^+$ each R' comprises at least one C atom which are independent of one another or each R' comprises at least one C atom in which at least two R' are joined to form a heterocycle comprising at least two carbon atoms.

A third aspect of the third embodiment is directed to a compound represented by formula I-3
wherein
(1) $R^1$ is H, n-alkyl, branched alkyl, cycloalkyl, alkaryl, or aryl, which includes, but is not limited to, phenyl or naphthyl, where phenyl or naphthyl are optionally substituted with at least one of H, F, Cl, Br, I, OH, OR', SH, SR', $NH_2$, NHR', $NR'_2$, heterocycle, lower alkyl, halogenated (F, Cl, Br, I), halogenated (F, Cl, Br, I) lower alkenyl of $C_2$-$C_6$, lower alkynyl of $C_2$-$C_6$ such as C≡CH, halogenated (F, Cl, Br, I) lower alkynyl of $C_2$-$C_6$, lower alkoxy of $C_1$-$C_6$, halogenated (F, Cl, Br, I) lower alkoxy of $C_1$-$C_6$, $CO_2H$, $CO_2R'$, $CONH_2$, CONHR', $CONR'_2$, CH=$CHCO_2H$, or CH=$CHCO_2R$;

(b) $R^2$ is H, a lower alkyl, cyano (CN), vinyl, O-(lower alkyl), including $OCH_3$, $OCH_2CH_3$, hydroxyl lower alkyl, i.e., —$(CH_2)_pOH$, where p is 1-6, including hydroxyl methyl ($CH_2OH$), fluoromethyl ($CH_2F$), azido ($N_3$), $CH_2CN$, $CH_2N_3$, $CH_2NH_2$, $CH_2NHCH_3$, $CH_2N(CH_3)_2$, F, Cl, Br, or I;

(c) $R^3$ is $CH_3$, $CH_2F$, $CHF_2$, $CF_3$;

(d) X is H, OH, F, OMe, $NH_2$, or $N_3$;

(e) $R^7$ and $R^8$ are independently H, F, Cl, Br, I, OH, OR', such as alkoxy, aryloxy, benzyloxy, substituted aryloxy, and substituted benzyloxy, SH, SR', $NH_2$, NHR', $NR'_2$, $NHR'_2{}^+$, $NR'_3{}^+$, heterocycle, lower alkyl, halogenated (F, Cl, Br, I) lower alkyl, lower alkenyl of $C_2$-$C_6$, halogenated (F, Cl, Br, I) lower alkenyl of $C_2$-$C_6$, lower alkynyl of $C_2$-$C_6$ such as C≡CH, halogenated (F, Cl, Br, I) lower alkynyl of $C_2$-$C_6$, lower alkoxy of $C_1$-$C_6$, halogenated (F, Cl, Br, I) lower alkoxy of $C_1$-$C_6$, $CO_2H$, $CO_2R'$, $CONH_2$, CONHR', $CONR'_2$, CH=$CHCO_2H$, or CH=$CHCO_2R'$;

(f) Z is N or $CR^9$; and (g) $R^9$ is an H, F, OH, OR', $NH_2$, NHR', $NR'_2$, lower alkyl, halogenated (F, Cl, Br, I) lower alkyl;

wherein R' is an optionally substituted alkyl, an optionally substituted cycloalkyl, an optionally substituted alkynyl, an optionally substituted alkenyl, or an optionally substituted acyl, an optionally substituted alkoxyalkyl, where for the instance of $NR'_2$ or $NHR'_2{}^+$ each R' comprise at least one C atom that is independent of one another or are joined to form a heterocycle comprising at least two carbon atoms, and where for the instance of $NR'_3{}^+$ each R' comprises at least one C atom which are independent of one another or each R' comprises at least one C atom in which at least two R' are joined to form a heterocycle comprising at least two carbon atoms.

A fourth aspect of the third embodiment is directed to a compound represented by formula I-3
wherein
(a) $R^1$ is H, n-alkyl, branched alkyl, cycloalkyl, alkaryl, or aryl, which includes, but is not limited to, phenyl or naphthyl, where phenyl or naphthyl are optionally substituted with at least one of H, F, Cl, Br, I, OH, OR', SH, SR', $NH_2$, NHR', $NR'_2$, heterocycle, lower alkyl, halogenated (F, Cl, Br, I), halogenated (F, Cl, Br, I) lower alkenyl of $C_2$-$C_6$, lower alkynyl of $C_2$-$C_6$ such as C≡CH, halogenated (F, Cl, Br, I) lower alkynyl of $C_2$-$C_6$, lower alkoxy of $C_1$-$C_6$, halogenated (F, Cl, Br, I) lower alkoxy of $C_1$-$C_6$, $CO_2H$, $CO_2R'$, $CONH_2$, CONHR', $CONR'_2$, CH=$CHCO_2H$, or CH=$CHCO_2R'$ wherein R' is an optionally substituted alkyl, cycloalkyl, alkenyl, alkynyl, or alkoxyalkyl, which includes, but is not limited to, $C_{1-10}$ alkyl, $C_{3-7}$ cycloalkyl, $C_{2-10}$ alkenyl, $C_{2-10}$ alkynyl, or $C_{1-10}$ alkoxyalkyl;

(b) $R^2$ is H, a lower alkyl, cyano (CN), vinyl, O-(lower alkyl), including $OCH_3$, $OCH_2CH_3$, hydroxyl lower alkyl, i.e., —$(CH_2)_pOH$, where p is 1-6, including hydroxyl methyl ($CH_2OH$), fluoromethyl ($CH_2F$), azido ($N_3$), $CH_2CN$, $CH_2N_3$, $CH_2NH_2$, $CH_2NHCH_3$, $CH_2N(CH_3)_2$, F, Cl, Br, or I;

(c) $R^3$ is $CH_3$, $CH_2F$, $CHF_2$, $CF_3$;

(d) X is F;

(e) $R^7$ and $R^8$ are independently H, F, Cl, Br, I, OH, OR', such as alkoxy, aryloxy, benzyloxy, substituted aryloxy, and substituted benzyloxy, SH, SR', $NH_2$, NHR', $NR'_2$, $NHR'_2{}^+$, $NR'_3{}^+$, heterocycle, lower alkyl, halogenated (F, Cl, Br, I) lower alkyl, lower alkenyl of $C_2$-$C_6$, halogenated (F, Cl, Br, I) lower alkenyl of $C_2$-$C_6$, lower alkynyl of $C_2$-$C_6$ such as C≡CH, halogenated (F, Cl, Br, I) lower alkynyl of $C_2$-$C_6$, lower alkoxy of $C_1$-$C_6$, halogenated (F, Cl, Br, I) lower alkoxy of $C_1$-$C_6$, $CO_2H$, $CO_2R'$, $CONH_2$, CONHR', $CONR'_2$, CH=$CHCO_2H$, or CH=$CHCO_2R'$;

(f) Z is N or $CR^9$; and (g) $R^9$ is an H, F, OH, OR', $NH_2$, NHR', $NR'_2$, lower alkyl, halogenated (F, Cl, Br, I) lower alkyl;

wherein R' is an optionally substituted alkyl, an optionally substituted cycloalkyl, an optionally substituted alkynyl, an optionally substituted alkenyl, or an optionally substituted acyl, an optionally substituted alkoxyalkyl, where for the instance of $NR'_2$ or $NHR'_2{}^+$ each R' comprise at least one C atom that is independent of one another or are joined to form a heterocycle comprising at least two carbon atoms, and where for the instance of $NR'_3{}^+$ each R' comprises at least one C atom which are independent of one another or each R' comprises at least one C atom in which at least two R' are joined to form a heterocycle comprising at least two carbon atoms;

A fifth aspect of the third embodiment is directed to a compound represented by formula I-3
wherein
(a) $R^1$ is H, n-alkyl, branched alkyl, cycloalkyl, alkaryl, or aryl, which includes, but is not limited to, phenyl or naphthyl, where phenyl or naphthyl are optionally substituted with at least one of H, F, Cl, Br, I, OH, OR', SH, SR', $NH_2$, NHR', $NR'_2$, heterocycle, lower alkyl, halogenated (F, Cl, Br, I), halogenated (F, Cl, Br, I) lower alkenyl of $C_2$-$C_6$, lower alkynyl of $C_2$-$C_6$ such as C≡CH, halogenated (F, Cl, Br, I) lower alkynyl of $C_2$-$C_6$, lower alkoxy of $C_1$-$C_6$, halogenated (F, Cl, Br, I) lower alkoxy of $C_1$-$C_6$, $CO_2H$, $CO_2R'$, $CONH_2$, CONHR', $CONR'_2$, CH=$CHCO_2H$, or CH=$CHCO_2R'$ wherein R' is an optionally substituted alkyl, cycloalkyl, alkenyl, alkynyl, or alkoxyalkyl, which includes, but is not limited to, $C_{1-10}$ alkyl, $C_{3-7}$ cycloalkyl, $C_{2-10}$ alkenyl, $C_{2-10}$ alkynyl, or $C_{1-10}$ alkoxyalkyl;

(b) $R^2$ is H, —$CH_3$, cyano (CN), vinyl, —$OCH_3$, —$CH_2OH$, —$CH_2F$, azido ($N_3$), $CH_2CN$, $CH_2N_3$, $CH_2NH_2$, $CH_2NHCH_3$, $CH_2N(CH_3)_2$, F, Cl, Br, or I;

(c) $R^3$ is $CH_3$;

(d) X is F;

(e) $R^7$ and $R^8$ are independently H, F, Cl, Br, I, OH, OR', such as alkoxy, aryloxy, benzyloxy, substituted aryloxy, and substituted benzyloxy, SH, SR', $NH_2$, NHR', $NR'_2$, $NHR'_2{}^+$, $NR'_3{}^+$, heterocycle, lower alkyl, halogenated (F, Cl, Br, I) lower alkyl, lower alkenyl of $C_2$-$C_6$, halogenated (F, Cl, Br, I) lower alkenyl of $C_2$-$C_6$, lower alkynyl of $C_2$-$C_6$ such as C≡CH, halogenated (F, Cl, Br, I) lower alkynyl of $C_2$-$C_6$, lower alkoxy of $C_1$-$C_6$, halogenated (F, Cl, Br, I) lower alkoxy of $C_1$-$C_6$, $CO_2H$, $CO_2R'$, $CONH_2$, CONHR', $CONR'_2$, CH=$CHCO_2H$, or CH=$CHCO_2R'$;

(f) Z is N or $CR^9$; and (g) $R^9$ is an H, F, OH, OR', $NH_2$, NHR', $NR'_2$, lower alkyl, halogenated (F, Cl, Br, I) lower alkyl;

wherein R' is an optionally substituted alkyl, an optionally substituted cycloalkyl, an optionally substituted alkynyl, an optionally substituted alkenyl, or an optionally substituted acyl, an optionally substituted alkoxyalkyl, where for the instance of $NR'_2$ or $NHR'_2{}^+$ each R' comprise at least one C atom that is independent of one another or are joined to form a heterocycle comprising at least two carbon atoms, and where for the instance of $NR'_3{}^+$ each R' comprises at least one C atom which are independent of one another or each R' comprises at least one C atom in which at least two R' are joined to form a heterocycle comprising at least two carbon atoms.

A sixth aspect of the third embodiment is directed to a compound represented by formula I-3
wherein
(a) $R^1$ is H, heterocycle, lower alkyl, lower alkylaryl, or aryl, which includes, but is not limited to, phenyl or naphthyl, where phenyl or naphthyl are optionally substituted with at least one of H, F, Cl, Br, I, OH, OR', SH, SR', $NH_2$, NHR', $NR'_2$, lower alkoxy of $C_1$-$C_6$, halogenated (F, Cl, Br, I) lower alkoxy of $C_1$-$C_6$, wherein R' is an optionally substituted alkyl, cycloalkyl, alkenyl, alkynyl, or alkoxyalkyl, which includes, but is not limited to, $C_{1-10}$ alkyl, $C_{3-7}$ cycloalkyl, $C_{2-10}$ alkenyl, $C_{2-10}$ alkynyl, or $C_{1-10}$ alkoxyalkyl;
(b) $R^2$ is H, —$CH_3$, cyano (CN), vinyl, —$OCH_3$, —$CH_2OH$, —$CH_2F$, azido ($N_3$), $CH_2CN$, $CH_2N_3$, $CH_2NH_2$, $CH_2NHCH_3$, $CH_2N(CH_3)_2$, F, Cl, Br, or I;
(c) $R^3$ is $CH_3$;
(d) X is F;
(e) $R^7$ and $R^8$ are independently H, F, Cl, Br, I, OH, OR', such as alkoxy, aryloxy, benzyloxy, substituted aryloxy, and substituted benzyloxy, SH, SR', $NH_2$, NHR', $NR'_2$, $NHR'_2{}^+$, $NR'_3{}^+$, heterocycle, lower alkyl, halogenated (F, Cl, Br, I) lower alkyl, lower alkenyl of $C_2$-$C_6$, halogenated (F, Cl, Br, I) lower alkenyl of $C_2$-$C_6$, lower alkynyl of $C_2$-$C_6$ such as C≡CH, halogenated (F, Cl, Br, I) lower alkynyl of $C_2$-$C_6$, lower alkoxy of $C_1$-$C_6$, halogenated (F, Cl, Br, I) lower alkoxy of $C_1$-$C_6$, $CO_2H$, $CO_2R'$, $CONH_2$, CONHR', $CONR'_2$, CH=$CHCO_2H$, or CH=$CHCO_2R'$;
(f) Z is N or $CR^9$; and
(g) $R^9$ is an H, F, OH, OR', $NH_2$, NHR', $NR'_2$, lower alkyl, halogenated (F, Cl, Br, I) lower alkyl;
wherein R' is an optionally substituted alkyl, an optionally substituted cycloalkyl, an optionally substituted alkynyl, an optionally substituted alkenyl, or an optionally substituted acyl, an optionally substituted alkoxyalkyl, where for the instance of $NR'_2$ or $NHR'_2{}^+$ each R' comprise at least one C atom that is independent of one another or are joined to form a heterocycle comprising at least two carbon atoms, and where for the instance of $NR'_3{}^+$ each R' comprises at least one C atom which are independent of one another or each R' comprises at least one C atom in which at least two R' are joined to form a heterocycle comprising at least two carbon atoms.

A seventh aspect of the third embodiment is directed to a compound represented by formula I-3
wherein
(a) $R^1$ is H, lower alkyl, lower alkylaryl, or aryl, which includes, but is not limited to, phenyl or naphthyl, where phenyl or naphthyl are optionally substituted with at least one of H, F, Cl, Br, I, OH, OR', SH, SR', $NH_2$, NHR', $NR'_2$, lower alkoxy of $C_1$-$C_6$, halogenated (F, Cl, Br, I) lower alkoxy of $C_1$-$C_6$, wherein R' is an optionally substituted alkyl, cycloalkyl, alkenyl, alkynyl, or alkoxyalkyl, which includes, but is not limited to, $C_{1-10}$ alkyl, $C_{3-7}$ cycloalkyl, $C_{2-10}$ alkenyl, $C_{2-10}$ alkynyl, or $C_{1-10}$ alkoxyalkyl;
(b) $R^2$ is H;
(c) $R^3$ is $CH_3$;
(d) X is F;
(e) $R^7$ and $R^8$ are independently H, F, Cl, Br, I, OH, OR', such as alkoxy, aryloxy, benzyloxy, substituted aryloxy, and substituted benzyloxy, SH, SR', $NH_2$, NHR', $NR'_2$, $NHR'_2{}^+$, $NR'_3{}^+$, heterocycle, lower alkyl, halogenated (F, Cl, Br, I) lower alkyl, lower alkenyl of $C_2$-$C_6$, halogenated (F, Cl, Br, I) lower alkenyl of $C_2$-$C_6$, lower alkynyl of $C_2$-$C_6$ such as C≡CH, halogenated (F, Cl, Br, I) lower alkynyl of $C_2$-$C_6$, lower alkoxy of $C_1$-$C_6$, halogenated (F, Cl, Br, I) lower alkoxy of $C_1$-$C_6$, $CO_2H$, $CO_2R'$, $CONH_2$, CONHR', $CONR'_2$, CH=$CHCO_2H$, or CH=$CHCO_2R'$;
(f) Z is N or $CR^9$; and
(g) $R^9$ is an H, F, OH, OR', $NH_2$, NHR', $NR'_2$, lower alkyl, halogenated (F, Cl, Br, I) lower alkyl;
wherein R' is an optionally substituted alkyl, an optionally substituted cycloalkyl, an optionally substituted alkynyl, an optionally substituted alkenyl, or an optionally substituted acyl, an optionally substituted alkoxyalkyl, where for the instance of $NR'_2$ or $NHR'_2{}^+$ each R' comprise at least one C atom that is independent of one another or are joined to form a heterocycle comprising at least two carbon atoms, and where for the instance of $NR'_3{}^+$ each R' comprises at least one C atom which are independent of one another or each R' comprises at least one C atom in which at least two R' are joined to form a heterocycle comprising at least two carbon atoms.

An eighth aspect of the third embodiment is directed to a compound represented by formula I-3
wherein
(a) $R^1$ is H, lower alkyl, lower alkylaryl, or aryl, which includes, but is not limited to, phenyl or naphthyl, where phenyl or naphthyl are optionally substituted with at least one of H, F, Cl, Br, I, OH, OR', SH, SR', $NH_2$, NHR', $NR'_2$, lower alkoxy of $C_1$-$C_6$, halogenated (F, Cl, Br, I) lower alkoxy of $C_1$-$C_6$, wherein R' is an optionally substituted alkyl, cycloalkyl, alkenyl, alkynyl, or alkoxyalkyl, which includes, but is not limited to, $C_{1-10}$ alkyl, $C_{3-7}$ cycloalkyl, $C_{2-10}$ alkenyl, $C_{2-10}$ alkynyl, or $C_{1-10}$ alkoxyalkyl;
(b) $R^2$ is H;
(c) $R^3$ is $CH_3$;
(d) X is F;
(e) $R^7$ is OR', such as alkoxy, aryloxy, benzyloxy, substituted aryloxy, and substituted benzyloxy and $R^8$ is $NH_2$;
(f) Z is N; and
wherein R' is an optionally substituted alkyl, an optionally substituted cycloalkyl, an optionally substituted alkynyl, an optionally substituted alkenyl, or an optionally substituted acyl, an optionally substituted alkoxyalkyl, where for the instance of $NR'_2$ or $NHR'_2{}^+$ each R' comprise at least one C atom that is independent of one another or are joined to form a heterocycle comprising at least two carbon atoms, and where for the instance of $NR'_3{}^+$ each R' comprises at least one C atom which are independent of one another or each R' comprises at least one C atom in which at least two R' are joined to form a heterocycle comprising at least two carbon atoms.

A ninth aspect of the third embodiment is directed to a compound represented by formula I-3
wherein
(a) $R^1$ is H or lower alkyl;
(b) $R^2$ is H;
(c) $R^3$ is $CH_3$;
(d) X is F;
(e) $R^7$ is OR', such as alkoxy, aryloxy, benzyloxy, substituted aryloxy, and substituted benzyloxy and $R^8$ is $NH_2$;
(f) Z is N; and
wherein R' is an optionally substituted alkyl, an optionally substituted cycloalkyl, an optionally substituted alkynyl, an optionally substituted alkenyl, or an optionally substituted acyl, an optionally substituted alkoxyalkyl, where for the instance of $NR'_2$ or $NHR'_2{}^+$ each R' comprise at least one C atom that is independent of one another or are joined to form a heterocycle comprising at least two carbon atoms, and where for the instance of NR'$_3^+$ each R' comprises at least one C atom which are independent of one another or each R' comprises at least one C atom in which at least two R' are joined to form a heterocycle comprising at least two carbon atoms.

A tenth aspect of the third embodiment is directed to a compound represented by formula I-3
wherein
(a) R$^1$ is H, lower alkyl, lower alkylaryl, or aryl, which includes, but is not limited to, phenyl or naphthyl, where phenyl or naphthyl are optionally substituted with at least one of H, F, Cl, Br, I, OH, OR', SH, SR', NH$_2$, NHR', NR'$_2$, lower alkoxy of C$_1$-C$_6$, halogenated (F, Cl, Br, I) lower alkoxy of C$_1$-C$_6$, wherein R' is an optionally substituted alkyl, cycloalkyl, alkenyl, alkynyl, or alkoxyalkyl, which includes, but is not limited to, C$_{1-10}$ alkyl, C$_{3-7}$ cycloalkyl, C$_{2-10}$ alkenyl, C$_{2-10}$ alkynyl, or C$_{1-10}$ alkoxyalkyl;
(b) R$^2$ is H;
(c) R$^3$ is CH$_3$;
(d) X is F;
(e) R$^7$ is NHR', NR'$_2$, NHR'$_2^+$, or NR'$_3^+$ and R$^8$ is NH$_2$;
(f) Z is N; and
wherein R' is an optionally substituted alkyl, an optionally substituted cycloalkyl, an optionally substituted alkynyl, an optionally substituted alkenyl, or an optionally substituted acyl, an optionally substituted alkoxyalkyl, where for the instance of NR'$_2$ or NHR'$_2^+$ each R' comprise at least one C atom that is independent of one another or are joined to form a heterocycle comprising at least two carbon atoms, and where for the instance of NR'$_3^+$ each R' comprises at least one C atom which are independent of one another or each R' comprises at least one C atom in which at least two R' are joined to form a heterocycle comprising at least two carbon atoms.

An eleventh aspect of the third embodiment is directed to a compound represented by formula I-3 wherein (a) R$^1$ is CH$_3$ or $^i$Pr; (b) R$^2$ is H; (c) R$^3$ is CH$_3$; (d) X is F; (e) R$^7$ and R$^8$ are independently H, F, OH, OCH$_3$, SH, SCH$_3$, NH$_2$, NHCH$_3$, N(CH$_3$)$_2$, NR'$_2$, CH$_3$, CH$_{3-q}$X$_q$, where X is F, Cl, Br, or I and q is 1 to 3, vinyl, CO$_2$H, CO$_2$CH$_3$, CONH$_2$, CONHCH$_3$, CON(CH$_3$)$_2$, or OR', such as OMe, OEt, OBn, and (f) Z is N; wherein R' is an optionally substituted alkyl, an optionally substituted cycloalkyl, an optionally substituted alkynyl, an optionally substituted alkenyl, or an optionally substituted acyl, an optionally substituted alkoxyalkyl, where for the instance of NR'$_2$, each R' comprise at least one C atom that is independent of one another or are joined to form a heterocycle comprising at least two carbon atoms, and where for the instance of NR'$_3^+$ each R' comprises at least one C atom which are independent of one another or each R' comprises at least one C atom in which at least two R' are joined to form a heterocycle comprising at least two carbon atoms.

A twelvth aspect of the third embodiment is directed to a compound represented by formula I-3 wherein (a) R$^1$ is CH$_3$ or $^i$Pr; (b) R$^2$ is H; (c) R$^3$ is CH$_3$; (d) X is F; (e) R$^7$ is —N(—CH$_2$CH$_2$CH$_2$—) (azetidin-1-yl); and R$^8$ is NH$_2$; and (f) Z is N.

A thirteenth aspect of the third embodiment is directed to a compound represented by formula I wherein (a) R$^1$ is CH$_3$ or $^i$Pr; (b) R$^2$ is H; (c) R$^3$ is CH$_3$; (d) X is F; (e) R$^7$ is OEt and R$^8$ is NH$_2$; and (f) Z is N.

A fourteenth aspect of the third embodiment is directed to a compound represented by formula I-3 wherein (a) R$^1$ is CH$_3$ or $^i$Pr; (b) R$^2$ is H; (c) R$^3$ is CH$_3$; (e) R$^7$ is F; (e) R$^7$ is OEt and R$^8$ is NH$_2$; and (f) Z is N.

A fifteenth aspect of the third embodiment is directed to a compound represented by formula I-3 wherein (a) R$^1$ is CH$_3$; (b) R$^2$ is H; (c) R$^3$ is CH$_3$; (d) X is F; (e) R$^7$ is —N(—CH$_2$CH$_2$CH$_2$—) (azetidin-1-yl); and R$^8$ is NH$_2$; and (f) Z is N.

A sixteenth aspect of the third embodiment is directed to a compound represented by formula I-3 wherein (a) R$^1$ is CH$_3$; (b) R$^2$ is H; (c) R$^3$ is CH$_3$; (d) X is F; (e) R$^7$ is and R$^8$ is NH$_2$; and (f) Z is N.

A seventeenth aspect of the third embodiment is directed to a compound represented by formula I-3 wherein (a) R$^1$ is $^i$Pr; (b) R$^2$ is H; (c) R$^3$ is CH$_3$; (d) X is F; (e) R$^7$ is OEt and R$^8$ is NH$_2$; and (f) Z is N.

An N$^{th}$ aspect of the third embodiment is directed to a compound as exemplified below.

A fourth embodiment of the invention is directed to a compound represented by formula I in which the base is a structure represented by formula d above, wherein R$^1$, R$^2$, R$^3$, X, and Y are defined in the Summary of the Invention section above.

The first aspect of the fourth embodiment is directed to a compound represented by formula I-4

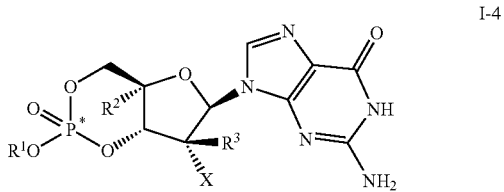

I-4 wherein
(a) R$^1$ is H, n-alkyl, branched alkyl, cycloalkyl, alkaryl, or aryl, which includes, but is not limited to, phenyl or naphthyl, where phenyl or naphthyl are optionally substituted with at least one of H, F, Cl, Br, I, OH, OR', SH, SR', NH$_2$, NHR', NR'$_2$, NHR'$_2^+$, NR'$_3^+$, heterocycle, lower alkyl, halogenated (F, Cl, Br, I), halogenated (F, Cl, Br, I) lower alkenyl of C$_2$-C$_6$, lower alkynyl of C$_2$-C$_6$ such as C≡CH, halogenated (F, Cl, Br, I) lower alkynyl of C$_2$-C$_6$, lower alkoxy of C$_1$-C$_6$, halogenated (F, Cl, Br, I) lower alkoxy of C$_1$-C$_6$, CO$_2$H, CO$_2$R', CONH$_2$, CONHR', CONR'$_2$, CH═CHCO$_2$H, or CH═CHCO$_2$R';
(b) R$^2$ is H, a lower alkyl, cyano (CN), vinyl, O-(lower alkyl), including OCH$_3$, OCH$_2$CH$_3$, hydroxyl lower alkyl, i.e., —(CH$_2$)$_p$OH, where p is 1-6, including hydroxyl methyl (CH$_2$OH), fluoromethyl (CH$_2$F), azido (N$_3$), CH$_2$CN, CH$_2$N$_3$, CH$_2$NH$_2$, CH$_2$NHCH$_3$, CH$_2$N(CH$_3$)$_2$, F, Cl, Br, or I;
(c) R$^3$ is H, CH$_3$, CH$_2$F, CHF$_2$, CF$_3$, or F; and
(d) X is H, OH, F, OMe, NH$_2$, or N$_3$;
wherein R' is an optionally substituted alkyl, an optionally substituted cycloalkyl, an optionally substituted alkynyl, an optionally substituted alkenyl, or an optionally substituted acyl, an optionally substituted alkoxyalkyl, where for the instance of NR'$_2$ or NHR'$_2^+$ each R' comprise at least one C atom that is independent of one another or are joined to form a heterocycle comprising at least two carbon atoms, and where for the instance of NR'$_3^+$ each R' comprises at least one C atom which are independent of one another or each R' comprises at least one C atom in which at least two R' are joined to form a heterocycle comprising at least two carbon atoms.

The second aspect of the fourth embodiment is directed to a compound represented by formula I-4
wherein
(a) $R^1$ is H, n-alkyl, branched alkyl, cycloalkyl, alkaryl, or aryl, which includes, but is not limited to, phenyl or naphthyl, where phenyl or naphthyl are optionally substituted with at least one of H, F, Cl, Br, I, OH, OR', SH, SR', $NH_2$, NHR', $NR'_2$, $NHR'_2{}^+$, $NR'_3{}^+$, heterocycle, lower alkyl, halogenated (F, Cl, Br, I), halogenated (F, Cl, Br, I) lower alkenyl of $C_2$-$C_6$, lower alkynyl of $C_2$-$C_6$ such as C≡CH, halogenated (F, Cl, Br, I) lower alkynyl of $C_2$-$C_6$, lower alkoxy of $C_1$-$C_6$, halogenated (F, Cl, Br, I) lower alkoxy of $C_1$-$C_6$, $CO_2H$, $CO_2R'$, $CONH_2$, CONHR', $CONR'_2$, CH═$CHCO_2H$, or CH═$CHCO_2R'$;
(b) $R^2$ is H, a lower alkyl, cyano (CN), vinyl, O-(lower alkyl), including $OCH_3$, $OCH_2CH_3$, hydroxyl lower alkyl, i.e., —$(CH_2)_p$OH, where p is 1-6, including hydroxyl methyl ($CH_2OH$), fluoromethyl ($CH_2F$), azido ($N_3$), $CH_2CN$, $CH_2N_3$, $CH_2NH_2$, $CH_2NHCH_3$, $CH_2N(CH_3)_2$, F, Cl, Br, or I;
(c) $R^3$ is H, $CH_3$, $CH_2F$, $CHF_2$, $CF_3$, or F; and
(d) X is H, OH, F, OMe, $NH_2$, or $N_3$;
wherein R' is an optionally substituted alkyl, an optionally substituted cycloalkyl, an optionally substituted alkynyl, an optionally substituted alkenyl, or an optionally substituted acyl, an optionally substituted alkoxyalkyl, where for the instance of $NR'_2$ or $NHR'_2{}^+$ each R' comprise at least one C atom that is independent of one another or are joined to form a heterocycle comprising at least two carbon atoms, and where for the instance of $NR'_3{}^+$ each R' comprises at least one C atom which are independent of one another or each R' comprises at least one C atom in which at least two R' are joined to form a heterocycle comprising at least two carbon atoms.

The third aspect of the fourth embodiment is directed to a compound represented by formula I-4
wherein
(a) $R^1$ is H, n-alkyl, branched alkyl, cycloalkyl, alkaryl, or aryl, which includes, but is not limited to, phenyl or naphthyl, where phenyl or naphthyl are optionally substituted with at least one of H, F, Cl, Br, I, OH, OR', SH, SR', $NH_2$, NHR', $NR'_2$, $NHR'_2{}^+$, $NR'_3{}^+$, heterocycle, lower alkyl, halogenated (F, Cl, Br, I), halogenated (F, Cl, Br, I) lower alkenyl of $C_2$-$C_6$, lower alkynyl of $C_2$-$C_6$ such as C≡CH, halogenated (F, Cl, Br, I) lower alkynyl of $C_2$-$C_6$, lower alkoxy of $C_1$-$C_6$, halogenated (F, Cl, Br, I) lower alkoxy of $C_1$-$C_6$, $CO_2H$, $CO_2R'$, $CONH_2$, CONHR', $CONR'_2$, CH═$CHCO_2H$, or CH═$CHCO_2R'$;
(b) $R^2$ is H, a lower alkyl, cyano (CN), vinyl, O-(lower alkyl), including $OCH_3$, $OCH_2CH_3$, hydroxyl lower alkyl, i.e., —$(CH_2)_p$OH, where p is 1-6, including hydroxyl methyl ($CH_2OH$), fluoromethyl ($CH_2F$), azido ($N_3$), $CH_2CN$, $CH_2N_3$, $CH_2NH_2$, $CH_2NHCH_3$, $CH_2N(CH_3)_2$, F, Cl, Br, or I;
(c) $R^3$ is $CH_3$, $CH_2F$, $CHF_2$, $CF_3$; and
(d) X is H, OH, F, OMe, $NH_2$, or $N_3$;
wherein R' is an optionally substituted alkyl, an optionally substituted cycloalkyl, an optionally substituted alkynyl, an optionally substituted alkenyl, or an optionally substituted acyl, an optionally substituted alkoxyalkyl, where for the instance of $NR'_2$ or $NHR'_2{}^+$ each R' comprise at least one C atom that is independent of one another or are joined to form a heterocycle comprising at least two carbon atoms, and where for the instance of $NR'_3{}^+$ each R' comprises at least one C atom which are independent of one another or each R' comprises at least one C atom in which at least two R' are joined to form a heterocycle comprising at least two carbon atoms.

The fourth aspect of the fourth embodiment is directed to a compound represented by formula I-4
wherein
(a) $R^1$ is H, n-alkyl, branched alkyl, cycloalkyl, alkaryl, or aryl, which includes, but is not limited to, phenyl or naphthyl, where phenyl or naphthyl are optionally substituted with at least one of H, F, Cl, Br, I, OH, OR', SH, SR', $NH_2$, NHR', $NR'_2$, $NHR'_2{}^+$, $NR'_3{}^+$, heterocycle, lower alkyl, halogenated (F, Cl, Br, I), halogenated (F, Cl, Br, I) lower alkenyl of $C_2$-$C_6$, lower alkynyl of $C_2$-$C_6$ such as C≡CH, halogenated (F, Cl, Br, I) lower alkynyl of $C_2$-$C_6$, lower alkoxy of $C_1$-$C_6$, halogenated (F, Cl, Br, I) lower alkoxy of $C_1$-$C_6$, $CO_2H$, $CO_2R'$, $CONH_2$, CONHR', $CONR'_2$, CH═$CHCO_2H$, or CH═$CHCO_2R'$;
(b) $R^2$ is H, a lower alkyl, cyano (CN), vinyl, O-(lower alkyl), including $OCH_3$, $OCH_2CH_3$, hydroxyl lower alkyl, i.e., —$(CH_2)_p$OH, where p is 1-6, including hydroxyl methyl ($CH_2OH$), fluoromethyl ($CH_2F$), azido ($N_3$), $CH_2CN$, $CH_2N_3$, $CH_2NH_2$, $CH_2NHCH_3$, $CH_2N(CH_3)_2$, F, Cl, Br, or I;
(c) $R^3$ is $CH_3$, $CH_2F$, $CHF_2$, $CF_3$; and
(d) X is F;
wherein R' is an optionally substituted alkyl, an optionally substituted cycloalkyl, an optionally substituted alkynyl, an optionally substituted alkenyl, or an optionally substituted acyl, an optionally substituted alkoxyalkyl, where for the instance of $NR'_2$ or $NHR'_2{}^+$ each R' comprise at least one C atom that is independent of one another or are joined to form a heterocycle comprising at least two carbon atoms, and where for the instance of $NR'_3{}^+$ each R' comprises at least one C atom which are independent of one another or each R' comprises at least one C atom in which at least two R' are joined to form a heterocycle comprising at least two carbon atoms.

The fifth aspect of the fourth embodiment is directed to a compound represented by formula I-4
wherein
(a) $R^1$ is H, n-alkyl, branched alkyl, cycloalkyl, alkaryl, or aryl, which includes, but is not limited to, phenyl or naphthyl, where phenyl or naphthyl are optionally substituted with at least one of H, F, Cl, Br, I, OH, OR', SH, SR', $NH_2$, NHR', $NR'_2$, $NHR'_2{}^+$, $NR'_3{}^+$, heterocycle, lower alkyl, halogenated (F, Cl, Br, I), halogenated (F, Cl, Br, I) lower alkenyl of $C_2$-$C_6$, lower alkynyl of $C_2$-$C_6$ such as C≡CH, halogenated (F, Cl, Br, I) lower alkynyl of $C_2$-$C_6$, lower alkoxy of $C_1$-$C_6$, halogenated (F, Cl, Br, I) lower alkoxy of $C_1$-$C_6$, $CO_2H$, $CO_2R'$, $CONH_2$, CONHR', $CONR'_2$, CH═$CHCO_2H$, or CH═$CHCO_2R'$;
(b) $R^2$ is H, —$CH_3$, cyano (CN), vinyl, —$OCH_3$, —$CH_2OH$, —$CH_2F$, azido ($N_3$), $CH_2CN$, $CH_2N_3$, $CH_2NH_2$, $CH_2NHCH_3$, $CH_2N(CH_3)_2$, F, Cl, Br, or I;
(c) $R^3$ is $CH_3$; and
(d) X is F;
wherein R' is an optionally substituted alkyl, an optionally substituted cycloalkyl, an optionally substituted alkynyl, an optionally substituted alkenyl, or an optionally substituted acyl, an optionally substituted alkoxyalkyl, where for the instance of $NR'_2$ or $NHR'_2{}^+$ each R' comprise at least one C atom that is independent of one another or are joined to form a heterocycle comprising at least two carbon atoms, and where for the instance of $NR'_3{}^+$ each R' comprises at least one C atom which are independent of one another or each R' comprises at least one C atom in which at least two R' are joined to form a heterocycle comprising at least two carbon atoms.

The sixth aspect of the fourth embodiment is directed to a compound represented by formula I-4
wherein
(a) $R^1$ is H, lower alkyl, lower alkylaryl, or aryl, which includes, but is not limited to, phenyl or naphthyl, where phenyl or naphthyl are optionally substituted with at least one of H, F, Cl, Br, I, OH, OR', SH, SR', $NH_2$, NHR', $NR'_2$, $NHR'_2{}^+$, $NR'_3{}^+$, heterocycle, lower alkoxy of $C_1$-$C_6$, halogenated (F, Cl, Br, I) lower alkoxy of $C_1$-$C_6$, wherein R' is an optionally substituted alkyl, cycloalkyl, alkenyl, alkynyl, or alkoxyalkyl, which includes, but is not limited to, $C_{1-10}$ alkyl, $C_{3-7}$ cycloalkyl, $C_{2-10}$ alkenyl, $C_{2-10}$ alkynyl, or $C_{1-10}$ alkoxyalkyl;
(b) $R^2$ is H, —$CH_3$, cyano (CN), vinyl, —$OCH_3$, —$CH_2OH$, —$CH_2F$, azido ($N_3$), $CH_2CN$, $CH_2N_3$, $CH_2NH_2$, $CH_2NHCH_3$, $CH_2N(CH_3)_2$, F, Cl, Br, or I;
(c) $R^3$ is $CH_3$; and
(d) X is F;
wherein R' is an optionally substituted alkyl, an optionally substituted cycloalkyl, an optionally substituted alkynyl, an optionally substituted alkenyl, or an optionally substituted acyl, an optionally substituted alkoxyalkyl, where for the instance of $NR'_2$ or $NHR'_2{}^+$ each R' comprise at least one C atom that is independent of one another or are joined to form a heterocycle comprising at least two carbon atoms, and where for the instance of $NR'_3{}^+$ each R' comprises at least one C atom which are independent of one another or each R' comprises at least one C atom in which at least two R' are joined to form a heterocycle comprising at least two carbon atoms.

The seventh aspect of the fourth embodiment is directed to a compound represented by formula I-4
wherein
(a) $R^1$ is H, lower alkyl, lower alkylaryl, or aryl, which includes, but is not limited to, phenyl or naphthyl, where phenyl or naphthyl are optionally substituted with at least one of H, F, Cl, Br, I, OH, OR', SH, SR', $NH_2$, NHR', $NR'_2$, $NHR'_2{}^+$, $NR'_3{}^+$, heterocycle, lower alkoxy of $C_1$-$C_6$, halogenated (F, Cl, Br, I) lower alkoxy of $C_1$-$C_6$, wherein R' is an optionally substituted alkyl, cycloalkyl, alkenyl, alkynyl, or alkoxyalkyl, which includes, but is not limited to, $C_{1-10}$ alkyl, $C_{3-7}$ cycloalkyl, $C_{2-10}$ alkenyl, $C_{2-10}$ alkynyl, or $C_{1-10}$ alkoxyalkyl;
(b) $R^2$ is H;
(c) $R^3$ is $CH_3$; and
(d) X is F;
wherein R' is an optionally substituted alkyl, an optionally substituted cycloalkyl, an optionally substituted alkynyl, an optionally substituted alkenyl, or an optionally substituted acyl, an optionally substituted alkoxyalkyl, where for the instance of $NR'_2$ or $NHR'_2{}^+$ each R' comprise at least one C atom that is independent of one another or are joined to form a heterocycle comprising at least two carbon atoms, and where for the instance of $NR'_3{}^+$ each R' comprises at least one C atom which are independent of one another or each R' comprises at least one C atom in which at least two R' are joined to form a heterocycle comprising at least two carbon atoms.

A fifth embodiment of the invention is directed to a compound represented by formula I in which the Base is a structure selected from among the structures c', d', e, f, g, h, i, j, k, l, m, n, o, p, q, r, s, t, u, v, w, x, y, z, aa, bb, cc, dd, ee, ff, gg, hh, ii, jj, kk, ll, and mm above, wherein $R^1$, $R^2$, $R^3$, X, and Y are defined in the Summary of the Invention section above.

The first aspect of the fifth embodiment is directed to a compound represented by formula I in which the Base is a structure selected from among the structures c', d', e, f, g, h, i, j, k, l, m, n, o, p, q, r, s, t, u, v, w, x, y, z, aa, bb, cc, dd, ee, ff, gg, hh, ii, jj, kk, ll, and mm above,
wherein
(a) $R^1$ is H, n-alkyl, branched alkyl, cycloalkyl, alkaryl, or aryl, which includes, but is not limited to, phenyl or naphthyl, where phenyl or naphthyl are optionally substituted with at least one of H, F, Cl, Br, I, OH, OR', SH, SR', $NH_2$, NHR', $NR'_2$, $NHR'_2{}^+$, $NR'_3{}^+$, heterocycle, lower alkyl, halogenated (F, Cl, Br, I), halogenated (F, Cl, Br, I) lower alkenyl of $C_2$-$C_6$, lower alkynyl of $C_2$-$C_6$ such as C≡CH, halogenated (F, Cl, Br, I) lower alkynyl of $C_2$-$C_6$, lower alkoxy of $C_1$-$C_6$, halogenated (F, Cl, Br, I) lower alkoxy of $C_1$-$C_6$, $CO_2H$, $CO_2R'$, $CONH_2$, CONHR', $CONR'_2$, CH═$CHCO_2H$, or CH═$CHCO_2R'$;
(b) $R^2$ is H, a lower alkyl, cyano (CN), vinyl, O-(lower alkyl), including $OCH_3$, $OCH_2CH_3$, hydroxyl lower alkyl, i.e., —$(CH_2)_pOH$, where p is 1-6, including hydroxyl methyl ($CH_2OH$), fluoromethyl ($CH_2F$), azido ($N_3$), $CH_2CN$, $CH_2N_3$, $CH_2NH_2$, $CH_2NHCH_3$, $CH_2N(CH_3)_2$, F, Cl, Br, or I;
(c) $R^3$ is H, $CH_3$, $CH_2F$, $CHF_2$, $CF_3$, or F; and
(d) X is H, OH, F, OMe, $NH_2$, or $N_3$;
wherein R' is an optionally substituted alkyl, an optionally substituted cycloalkyl, an optionally substituted alkynyl, an optionally substituted alkenyl, or an optionally substituted acyl, an optionally substituted alkoxyalkyl, where for the instance of $NR'_2$ or $NHR'_2{}^+$ each R' comprise at least one C atom that is independent of one another or are joined to form a heterocycle comprising at least two carbon atoms, and where for the instance of $NR'_3{}^+$ each R' comprises at least one C atom which are independent of one another or each R' comprises at least one C atom in which at least two R' are joined to form a heterocycle comprising at least two carbon atoms.

The second aspect of the fifth embodiment is directed to a compound represented by formula I in which the Base is a structure selected from among the structures c', d', e, f, g, h, i, j, k, l, m, n, o, p, q, r, s, t, u, v, w, x, y, z, aa, bb, cc, dd, ee, ff, gg, hh, ii, jj, kk, ll, and mm above,
wherein
(a) $R^1$ is H, n-alkyl, branched alkyl, cycloalkyl, alkaryl, or aryl, which includes, but is not limited to, phenyl or naphthyl, where phenyl or naphthyl are optionally substituted with at least one of H, F, Cl, Br, I, OH, OR', SH, SR', $NH_2$, NHR', $NR'_2$, $NHR'_2{}^+$, $NR'_3{}^+$, heterocycle, lower alkyl, halogenated (F, Cl, Br, I), halogenated (F, Cl, Br, I) lower alkenyl of $C_2$-$C_6$, lower alkynyl of $C_2$-$C_6$ such as C≡CH, halogenated (F, Cl, Br, I) lower alkynyl of $C_2$-$C_6$, lower alkoxy of $C_1$-$C_6$, halogenated (F, Cl, Br, I) lower alkoxy of $C_1$-$C_6$, $CO_2H$, $CO_2R'$, $CONH_2$, CONHR', $CONR'_2$, CH═$CHCO_2H$, or CH═$CHCO_2R'$;
(b) $R^2$ is H, a lower alkyl, cyano (CN), vinyl, O-(lower alkyl), including $OCH_3$, $OCH_2CH_3$, hydroxyl lower alkyl, i.e., —$(CH_2)_pOH$, where p is 1-6, including hydroxyl methyl ($CH_2OH$), fluoromethyl ($CH_2F$), azido ($N_3$), $CH_2CN$, $CH_2N_3$, $CH_2NH_2$, $CH_2NHCH_3$, $CH_2N(CH_3)_2$, F, Cl, Br, or I
(c) $R^3$ is H, $CH_3$, $CH_2F$, $CHF_2$, $CF_3$, or F; and
(d) X is H, OH, F, OMe, $NH_2$, or $N_3$;
wherein R' is an optionally substituted alkyl, an optionally substituted cycloalkyl, an optionally substituted alkynyl, an optionally substituted alkenyl, or an optionally substituted acyl, an optionally substituted alkoxyalkyl, where for the instance of $NR'_2$ or $NHR'_2{}^+$ each R' comprise at least one C atom that is independent of one another or are joined to form a heterocycle comprising at least two carbon atoms, and where for the instance of $NR'_3{}^+$ each R' comprises at least one C atom which are independent of one another or each R' comprises at least one C atom in which at least two R' are joined to form a heterocycle comprising at least two carbon atoms.

The third aspect of fifth embodiment is directed to a compound represented by formula I in which the Base is a structure selected from among the structures c', d', e, f, g, h, i, j, k, l, m, n, o, p, q, r, s, t, u, v, w, x, y, z, aa, bb, cc, dd, ee, ff, gg, hh, ii, jj, kk, ll, and mm above, wherein (a) $R^1$ is H, n-alkyl, branched alkyl, cycloalkyl, alkaryl, or aryl, which includes, but is not limited to, phenyl or naphthyl, where phenyl or naphthyl are optionally substituted with at least one of H, F, Cl, Br, I, OH, OR', SH, SR', $NH_2$, NHR', $NR'_2$, $NHR'_2{}^+$, $NR'_3{}^+$, heterocycle, lower alkyl, halogenated (F, Cl, Br, I), halogenated (F, Cl, Br, I) lower alkenyl of $C_2$-$C_6$, lower alkynyl of $C_2$-$C_6$ such as C≡CH, halogenated (F, Cl, Br, I) lower alkynyl of $C_2$-$C_6$, lower alkoxy of $C_1$-$C_6$, halogenated (F, Cl, Br, I) lower alkoxy of $C_1$-$C_6$, $CO_2H$, $CO_2R'$, $CONH_2$, CONHR', $CONR'_2$, CH=$CHCO_2H$, or CH=$CHCO_2R'$;

(b) $R^2$ is H, a lower alkyl, cyano (CN), vinyl, O-(lower alkyl), including $OCH_3$, $OCH_2CH_3$, hydroxyl lower alkyl, i.e., —$(CH_2)_pOH$, where p is 1-6, including hydroxyl methyl ($CH_2OH$), fluoromethyl ($CH_2F$), azido ($N_3$), $CH_2CN$, $CH_2N_3$, $CH_2NH_2$, $CH_2NHCH_3$, $CH_2N(CH_3)_2$, F, Cl, Br, or I (c) $R^3$ is $CH_3$, $CH_2F$, $CHF_2$, $CF_3$; and (d) X is H, OH, F, OMe, $NH_2$, or $N_3$;

wherein R' is an optionally substituted alkyl, an optionally substituted cycloalkyl, an optionally substituted alkynyl, an optionally substituted alkenyl, or an optionally substituted acyl, an optionally substituted alkoxyalkyl, where for the instance of $NR'_2$ or $NHR'_2{}^+$ each R' comprise at least one C atom that is independent of one another or are joined to form a heterocycle comprising at least two carbon atoms, and where for the instance of $NR'_3{}^+$ each R' comprises at least one C atom which are independent of one another or each R' comprises at least one C atom in which at least two R' are joined to form a heterocycle comprising at least two carbon atoms.

The fourth aspect of fifth embodiment is directed to a compound represented by formula I in which the Base is a structure selected from among the structures c', d', e, f, g, h, i, j, k, l, m, n, o, p, q, r, s, t, u, v, w, x, y, z, aa, bb, cc, dd, ee, ff, gg, hh, ii, jj, kk, ll, and mm above, wherein (a) $R^1$ is H, n-alkyl, branched alkyl, cycloalkyl, alkaryl, or aryl, which includes, but is not limited to, phenyl or naphthyl, where phenyl or naphthyl are optionally substituted with at least one of H, F, Cl, Br, I, OH, OR', SH, SR', $NH_2$, NHR', $NR'_2$, $NHR'_2{}^+$, $NR'_3{}^+$, heterocycle, lower alkyl, halogenated (F, Cl, Br, I), halogenated (F, Cl, Br, I) lower alkenyl of $C_2$-$C_6$, lower alkynyl of $C_2$-$C_6$ such as C≡CH, halogenated (F, Cl, Br, I) lower alkynyl of $C_2$-$C_6$, lower alkoxy of $C_1$-$C_6$, halogenated (F, Cl, Br, I) lower alkoxy of $C_1$-$C_6$, $CO_2H$, $CO_2R'$, $CONH_2$, CONHR', $CONR'_2$, CH=$CHCO_2H$, or CH=$CHCO_2R$;

(b) $R^2$ is H, a lower alkyl, cyano (CN), vinyl, O-(lower alkyl), including $OCH_3$, $OCH_2CH_3$, hydroxyl lower alkyl, i.e., —$(CH_2)_pOH$, where p is 1-6, including hydroxyl methyl ($CH_2OH$), fluoromethyl ($CH_2F$), azido ($N_3$), $CH_2CN$, $CH_2N_3$, $CH_2NH_2$, $CH_2NHCH_3$, $CH_2N(CH_3)_2$, F, Cl, Br, or I;

(c) $R^3$ is $CH_3$, $CH_2F$, $CHF_2$, $CF_3$; and (d) X is F;

wherein R' is an optionally substituted alkyl, an optionally substituted cycloalkyl, an optionally substituted alkynyl, an optionally substituted alkenyl, or an optionally substituted acyl, an optionally substituted alkoxyalkyl, where for the instance of $NR'_2$ or $NHR'_2{}^+$ each R' comprise at least one C atom that is independent of one another or are joined to form a heterocycle comprising at least two carbon atoms, and where for the instance of $NR'_3{}^+$ each R' comprises at least one C atom which are independent of one another or each R' comprises at least one C atom in which at least two R' are joined to form a heterocycle comprising at least two carbon atoms.

The fifth aspect of the fifth embodiment is directed to a compound represented by formula I in which the Base is a structure selected from among the structures c', d', e, f, g, h, i, j, k, l, m, n, o, p, q, r, s, t, u, v, w, x, y, z, aa, bb, cc, dd, ee, ff, gg, hh, ii, jj, kk, ll, and mm above, wherein (a) $R^1$ is H, n-alkyl, branched alkyl, cycloalkyl, alkaryl, or aryl, which includes, but is not limited to, phenyl or naphthyl, where phenyl or naphthyl are optionally substituted with at least one of H, F, Cl, Br, I, OH, OR', SH, SR', $NH_2$, NHR', $NR'_2$, $NHR'_2{}^+$, $NR'_3{}^+$, heterocycle, lower alkyl, halogenated (F, Cl, Br, I), halogenated (F, Cl, Br, I) lower alkenyl of $C_2$-$C_6$, lower alkynyl of $C_2$-$C_6$ such as C≡CH, halogenated (F, Cl, Br, I) lower alkynyl of $C_2$-$C_6$, lower alkoxy of $C_1$-$C_6$, halogenated (F, Cl, Br, I) lower alkoxy of $C_1$-$C_6$, $CO_2H$, $CO_2R'$, $CONH_2$, CONHR', $CONR'_2$, CH=$CHCO_2H$, or CH=$CHCO_2R'$;

(b) $R^2$ is H, —$CH_3$, cyano (CN), vinyl, —$OCH_3$, —$CH_2OH$, —$CH_2F$, azido ($N_3$), $CH_2CN$, $CH_2N_3$, $CH_2NH_2$, $CH_2NHCH_3$, $CH_2N(CH_3)_2$, F, Cl, Br, or I;

(c) $R^3$ is $CH_3$; and (d) X is F;

wherein R' is an optionally substituted alkyl, an optionally substituted cycloalkyl, an optionally substituted alkynyl, an optionally substituted alkenyl, or an optionally substituted acyl, an optionally substituted alkoxyalkyl, where for the instance of $NR'_2$ or $NHR'_2{}^+$ each R' comprise at least one C atom that is independent of one another or are joined to form a heterocycle comprising at least two carbon atoms, and where for the instance of $NR'_3{}^+$ each R' comprises at least one C atom which are independent of one another or each R' comprises at least one C atom in which at least two R' are joined to form a heterocycle comprising at least two carbon atoms.

The sixth aspect of the fifth embodiment is directed to a compound represented by formula I in which the Base is a structure selected from among the structures c', d', e, f, g, h, i, j, k, l, m, n, o, p, q, r, s, t, u, v, w, x, y, z, aa, bb, cc, dd, ee, ff, gg, hh, ii, jj, kk, ll, and mm above, wherein (a) $R^1$ is H, lower alkyl, lower alkylaryl, or aryl, which includes, but is not limited to, phenyl or naphthyl, where phenyl or naphthyl are optionally substituted with at least one of H, F, Cl, Br, I, OH, OR', SH, SR', $NH_2$, NHR', $NR'_2$, $NHR'_2{}^+$, $NR'_3{}^+$, heterocycle, lower alkoxy of $C_1$-$C_6$, halogenated (F, Cl, Br, I) lower alkoxy of $C_1$-$C_6$;

(b) $R^2$ is H, —$CH_3$, cyano (CN), vinyl, —$OCH_3$, —$CH_2OH$, —$CH_2F$, azido ($N_3$), $CH_2CN$, $CH_2N_3$, $CH_2NH_2$, $CH_2NHCH_3$, $CH_2N(CH_3)_2$, F, Cl, Br, or I;

(c) $R^3$ is $CH_3$; and (d) X is F;

wherein R' is an optionally substituted alkyl, an optionally substituted cycloalkyl, an optionally substituted alkynyl, an optionally substituted alkenyl, or an optionally substituted acyl, an optionally substituted alkoxyalkyl, where for the instance of $NR'_2$ or $NHR'_2{}^+$ each R' comprise at least one C atom that is independent of one another or are joined to form a heterocycle comprising at least two carbon atoms, and where for the instance of $NR'_3{}^+$ each R' comprises at least one C atom which are independent of one another or each R' comprises at least one C atom in which at least two R' are joined to form a heterocycle comprising at least two carbon atoms.

The seventh aspect of the fifth embodiment is directed to a compound represented by formula I in which the Base is a structure selected from among the structures c', d', e, f, g, h, i, j, k, l, m, n, o, p, q, r, s, t, u, v, w, x, y, z, aa, bb, cc, dd, ee, ff, gg, hh, ii, jj, kk, ll, and mm above,
wherein
(a) $R^1$ is H, lower alkyl, lower alkylaryl, or aryl, which includes, but is not limited to, phenyl or naphthyl, where phenyl or naphthyl are optionally substituted with at least one of H, F, Cl, Br, I, OH, OR', SH, SR', $NH_2$, NHR', $NR'_2$, $NHR'_2{}^+$, $NR'_3{}^+$, heterocycle, lower alkoxy of $C_1$-$C_6$, halogenated (F, Cl, Br, I) lower alkoxy of $C_1$-$C_6$;
(b) $R^2$ is H;
(c) $R^3$ is $CH_3$; and
(d) X is F;
wherein R' is an optionally substituted alkyl, an optionally substituted cycloalkyl, an optionally substituted alkynyl, an optionally substituted alkenyl, or an optionally substituted acyl, an optionally substituted alkoxyalkyl, where for the instance of $NR'_2$ or $NHR'_2{}^+$ each R' comprise at least one C atom that is independent of one another or are joined to form a heterocycle comprising at least two carbon atoms, and where for the instance of $NR'_3{}^+$ each R' comprises at least one C atom which are independent of one another or each R' comprises at least one C atom in which at least two R' are joined to form a heterocycle comprising at least two carbon atoms.

A sixth embodiment of the invention is directed to a compound represented by formula I in which the Base is a structure selected from among the structures ab, ac, ad, ae, af, ag, ah, ai, aj, ak, al, am, an, ao, ap, aq, ar, as, at, av, au, ax, ay, az, ba, bc, bd, be, bf, bg, bh, bi, bj, and bk, depicted above, wherein $R^1$, $R^2$, $R^3$, X, and Y are defined in the Summary of the Invention section above.

The first aspect of the sixth embodiment is directed to a compound represented by formula I in which the Base is a structure selected from among the structures ab, ac, ad, ae, af, ag, ah, ai, aj, ak, al, am, an, ao, ap, aq, ar, as, at, av, au, ax, ay, az, ba, bc, bd, be, bf, bg, bh, bi, bj, and bk, depicted above,
wherein
(a) $R^1$ is H, n-alkyl, branched alkyl, cycloalkyl, alkaryl, or aryl, which includes, but is not limited to, phenyl or naphthyl, where phenyl or naphthyl are optionally substituted with at least one of H, F, Cl, Br, I, OH, OR', SH, SR', $NH_2$, NHR', $NR'_2$, $NHR'_2{}^+$, $NR'_3{}^+$, heterocycle, lower alkyl, halogenated (F, Cl, Br, I), halogenated (F, Cl, Br, I) lower alkenyl of $C_2$-$C_6$, lower alkynyl of $C_2$-$C_6$ such as C≡CH, halogenated (F, Cl, Br, I) lower alkynyl of $C_2$-$C_6$, lower alkoxy of $C_1$-$C_6$, halogenated (F, Cl, Br, I) lower alkoxy of $C_1$-$C_6$, $CO_2H$, $CO_2R'$, $CONH_2$, CONHR', $CONR'_2$, CH=$CHCO_2H$, or CH=$CHCO_2R'$;
(b) $R^2$ is H, a lower alkyl, cyano (CN), vinyl, O-(lower alkyl), including $OCH_3$, $OCH_2CH_3$, hydroxyl lower alkyl, i.e., —$(CH_2)_pOH$, where p is 1-6, including hydroxyl methyl ($CH_2OH$), fluoromethyl ($CH_2F$), azido ($N_3$), $CH_2CN$, $CH_2N_3$, $CH_2NH_2$, $CH_2NHCH_3$, $CH_2N(CH_3)_2$, F, Cl, Br, or I;
(c) $R^3$ is H, $CH_3$, $CH_2F$, $CHF_2$, $CF_3$, or F; and
(d) X is H, OH, F, OMe, $NH_2$, or $N_3$;
wherein R' is an optionally substituted alkyl, an optionally substituted cycloalkyl, an optionally substituted alkynyl, an optionally substituted alkenyl, or an optionally substituted acyl, an optionally substituted alkoxyalkyl, where for the instance of $NR'_2$ or $NHR'_2{}^+$ each R' comprise at least one C atom that is independent of one another or are joined to form a heterocycle comprising at least two carbon atoms, and where for the instance of $NR'_3{}^+$ each R' comprises at least one C atom which are independent of one another or each R' comprises at least one C atom in which at least two R' are joined to form a heterocycle comprising at least two carbon atoms.

The second aspect of the sixth embodiment is directed to a compound represented by formula I in which the Base is a structure selected from among the structures ab, ac, ad, ae, af, ag, ah, ai, aj, ak, al, am, an, ao, ap, aq, ar, as, at, av, au, ax, ay, az, ba, bc, bd, be, bf, bg, bh, bi, bj, and bk, depicted above,
wherein
(a) $R^1$ is H, n-alkyl, branched alkyl, cycloalkyl, alkaryl, or aryl, which includes, but is not limited to, phenyl or naphthyl, where phenyl or naphthyl are optionally substituted with at least one of H, F, Cl, Br, I, OH, OR', SH, SR', $NH_2$, NHR', $NR'_2$, $NHR'_2{}^+$, $NR'_3{}^+$, heterocycle, lower alkyl, halogenated (F, Cl, Br, I), halogenated (F, Cl, Br, I) lower alkenyl of $C_2$-$C_6$, lower alkynyl of $C_2$-$C_6$ such as C≡CH, halogenated (F, Cl, Br, I) lower alkynyl of $C_2$-$C_6$, lower alkoxy of $C_1$-$C_6$, halogenated (F, Cl, Br, I) lower alkoxy of $C_1$-$C_6$, $CO_2H$, $CO_2R'$, $CONH_2$, CONHR', $CONR'_2$, CH=$CHCO_2H$, or CH=$CHCO_2R'$;
(b) $R^2$ is H, a lower alkyl, cyano (CN), vinyl, O-(lower alkyl), including $OCH_3$, $OCH_2CH_3$, hydroxyl lower alkyl, i.e., —$(CH_2)_pOH$, where p is 1-6, including hydroxyl methyl ($CH_2OH$), fluoromethyl ($CH_2F$), azido ($N_3$), $CH_2CN$, $CH_2N_3$, $CH_2NH_2$, $CH_2NHCH_3$, $CH_2N(CH_3)_2$, F, Cl, Br, or I;
(c) $R^3$ is H, $CH_3$, $CH_2F$, $CHF_2$, $CF_3$, or F; and
(d) X is H, OH, F, OMe, $NH_2$, or $N_3$;
wherein R' is an optionally substituted alkyl, an optionally substituted cycloalkyl, an optionally substituted alkynyl, an optionally substituted alkenyl, or an optionally substituted acyl, an optionally substituted alkoxyalkyl, where for the instance of $NR'_2$ or $NHR'_2{}^+$ each R' comprise at least one C atom that is independent of one another or are joined to form a heterocycle comprising at least two carbon atoms, and where for the instance of $NR'_3{}^+$ each R' comprises at least one C atom which are independent of one another or each R' comprises at least one C atom in which at least two R' are joined to form a heterocycle comprising at least two carbon atoms.

The third aspect of sixth embodiment is directed to a compound represented by formula I in which the Base is a structure selected from among the structures ab, ac, ad, ae, af, ag, ah, ai, aj, ak, al, am, an, ao, ap, aq, ar, as, at, av, au, ax, ay, az, ba, bc, bd, be, bf, bg, bh, bi, bj, and bk, depicted above,
wherein
(a) $R^1$ is H, n-alkyl, branched alkyl, cycloalkyl, alkaryl, or aryl, which includes, but is not limited to, phenyl or naphthyl, where phenyl or naphthyl are optionally substituted with at least one of H, F, Cl, Br, I, OH, OR', SH, SR', $NH_2$, NHR', $NR'_2$, $NHR'_2{}^+$, $NR'_3{}^+$, heterocycle, lower alkyl, halogenated (F, Cl, Br, I), halogenated (F, Cl, Br, I) lower alkenyl of $C_2$-$C_6$, lower alkynyl of $C_2$-$C_6$ such as C≡CH, halogenated (F, Cl, Br, I) lower alkynyl of $C_2$-$C_6$, lower alkoxy of $C_1$-$C_6$, halogenated (F, Cl, Br, I) lower alkoxy of $C_1$-$C_6$, $CO_2H$, $CO_2R'$, $CONH_2$, CONHR', $CONR'_2$, CH=$CHCO_2H$, or CH=$CHCO_2R'$;
(b) $R^2$ is H, a lower alkyl, cyano (CN), vinyl, O-(lower alkyl), including $OCH_3$, $OCH_2CH_3$, hydroxyl lower alkyl, i.e., —$(CH_2)_pOH$, where p is 1-6, including hydroxyl methyl ($CH_2OH$), fluoromethyl ($CH_2F$), azido ($N_3$), $CH_2CN$, $CH_2N_3$, $CH_2NH_2$, $CH_2NHCH_3$, $CH_2N(CH_3)_2$, F, Cl, Br, or I;
(c) $R^3$ is $CH_3$, $CH_2F$, $CHF_2$, $CF_3$; and
(d) X is H, OH, F, OMe, $NH_2$, or $N_3$;

wherein R' is an optionally substituted alkyl, an optionally substituted cycloalkyl, an optionally substituted alkynyl, an optionally substituted alkenyl, or an optionally substituted acyl, an optionally substituted alkoxyalkyl, where for the instance of NR'$_2$ or NHR'$_2^+$ each R' comprise at least one C atom that is independent of one another or are joined to form a heterocycle comprising at least two carbon atoms, and where for the instance of NR'$_3^+$ each R' comprises at least one C atom which are independent of one another or each R' comprises at least one C atom in which at least two R' are joined to form a heterocycle comprising at least two carbon atoms.

The fourth aspect of sixth embodiment is directed to a compound represented by formula I in which the Base is a structure selected from among the structures ab, ac, ad, ae, af, ag, ah, ai, aj, ak, al, am, an, ao, ap, aq, ar, as, at, av, au, ax, ay, az, ba, bc, bd, be, bf, bg, bh, bi, bj, and bk, depicted above, wherein (a) R$^1$ is H, n-alkyl, branched alkyl, cycloalkyl, alkaryl, or aryl, which includes, but is not limited to, phenyl or naphthyl, where phenyl or naphthyl are optionally substituted with at least one of H, F, Cl, Br, I, OH, OR', SH, SR', NH$_2$, NHR', NR'$_2$, NHR'$_2^+$, NR'$_3^+$, heterocycle, lower alkyl, halogenated (F, Cl, Br, I), halogenated (F, Cl, Br, I) lower alkenyl of C$_2$-C$_6$, lower alkynyl of C$_2$-C$_6$ such as C≡CH, halogenated (F, Cl, Br, I) lower alkynyl of C$_2$-C$_6$, lower alkoxy of C$_1$-C$_6$, halogenated (F, Cl, Br, I) lower alkoxy of C$_1$-C$_6$, CO$_2$H, CO$_2$R', CONH$_2$, CONHR', CONR'$_2$, CH=CHCO$_2$H, or CH=CHCO$_2$R';

(b) R$^2$ is H, a lower alkyl, cyano (CN), vinyl, O-(lower alkyl), including OCH$_3$, OCH$_2$CH$_3$, hydroxyl lower alkyl, i.e., —(CH$_2$)$_p$OH, where p is 1-6, including hydroxyl methyl (CH$_2$OH), fluoromethyl (CH$_2$F), azido (N$_3$), CH$_2$CN, CH$_2$N$_3$, CH$_2$NH$_2$, CH$_2$NHCH$_3$, CH$_2$N(CH$_3$)$_2$, F, Cl, Br, or I;

(c) R$^3$ is CH$_3$, CH$_2$F, CHF$_2$, CF$_3$; and (d) X is F;

wherein R' is an optionally substituted alkyl, an optionally substituted cycloalkyl, an optionally substituted alkynyl, an optionally substituted alkenyl, or an optionally substituted acyl, an optionally substituted alkoxyalkyl, where for the instance of NR'$_2$ or NHR'$_2^+$ each R' comprise at least one C atom that is independent of one another or are joined to form a heterocycle comprising at least two carbon atoms, and where for the instance of NR'$_3^+$ each R' comprises at least one C atom which are independent of one another or each R' comprises at least one C atom in which at least two R' are joined to form a heterocycle comprising at least two carbon atoms.

The fifth aspect of the sixth embodiment is directed to a compound represented by formula I in which the Base is a structure selected from among the structures ab, ac, ad, ae, af, ag, ah, ai, aj, ak, al, am, an, ao, ap, aq, ar, as, at, av, au, ax, ay, az, ba, bc, bd, be, bf, bg, bh, bi, bj, and bk, depicted above, wherein (a) R$^1$ is H, n-alkyl, branched alkyl, cycloalkyl, alkaryl, or aryl, which includes, but is not limited to, phenyl or naphthyl, where phenyl or naphthyl are optionally substituted with at least one of H, F, Cl, Br, I, OH, OR', SH, SR', NH$_2$, NHR', NR'$_2$, NHR'$_2^+$, NR'$_3^+$, heterocycle, lower alkyl, halogenated (F, Cl, Br, I), halogenated (F, Cl, Br, I) lower alkenyl of C$_2$-C$_6$, lower alkynyl of C$_2$-C$_6$ such as C≡CH, halogenated (F, Cl, Br, I) lower alkynyl of C$_2$-C$_6$, lower alkoxy of C$_1$-C$_6$, halogenated (F, Cl, Br, I) lower alkoxy of C$_1$-C$_6$, CO$_2$H, CO$_2$R', CONH$_2$, CONHR', CONR'$_2$, CH=CHCO$_2$H, or CH=CHCO$_2$R';

(b) R$^2$ is H, —CH$_3$, cyano (CN), vinyl, —OCH$_3$, —CH$_2$OH, —CH$_2$F, azido (N$_3$), CH$_2$CN, CH$_2$N$_3$, CH$_2$NH$_2$, CH$_2$NHCH$_3$, CH$_2$N(CH$_3$)$_2$, F, Cl, Br, or I;

(c) R$^3$ is CH$_3$; and (d) X is F;

wherein R' is an optionally substituted alkyl, an optionally substituted cycloalkyl, an optionally substituted alkynyl, an optionally substituted alkenyl, or an optionally substituted acyl, an optionally substituted alkoxyalkyl, where for the instance of NR'$_2$ or NHR'$_2^+$ each R' comprise at least one C atom that is independent of one another or are joined to form a heterocycle comprising at least two carbon atoms, and where for the instance of NR'$_3^+$ each R' comprises at least one C atom which are independent of one another or each R' comprises at least one C atom in which at least two R' are joined to form a heterocycle comprising at least two carbon atoms.

The sixth aspect of the sixth embodiment is directed to a compound represented by formula I in which the Base is a structure selected from among the structures ab, ac, ad, ae, af, ag, ah, ai, aj, ak, al, am, an, ao, ap, aq, ar, as, at, av, au, ax, ay, az, ba, bc, bd, be, bf, bg, bh, bi, bj, and bk, depicted above, wherein (a) R$^1$ is H, lower alkyl, lower alkylaryl, or aryl, which includes, but is not limited to, phenyl or naphthyl, where phenyl or naphthyl are optionally substituted with at least one of H, F, Cl, Br, I, OH, OR', SH, SR', NH$_2$, NHR', NR'$_2$, NHR'$_2^+$, NR'$_3^+$, heterocycle, lower alkoxy of C$_1$-C$_6$, halogenated (F, Cl, Br, I) lower alkoxy of C$_1$-C$_6$;

(b) R$^2$ is H, —CH$_3$, cyano (CN), vinyl, —OCH$_3$, —CH$_2$OH, —CHF, azido (N$_3$), CH$_2$CN, CH$_2$N$_3$, CH$_2$NH$_2$, CH$_2$NHCH$_3$, CH$_2$N(CH$_3$)$_2$, F, Cl, Br, or I (c) R$^3$ is CH$_3$; and (d) X is F;

wherein R' is an optionally substituted alkyl, an optionally substituted cycloalkyl, an optionally substituted alkynyl, an optionally substituted alkenyl, or an optionally substituted acyl, an optionally substituted alkoxyalkyl, where for the instance of NR'$_2$ or NHR'$_2^+$ each R' comprise at least one C atom that is independent of one another or are joined to form a heterocycle comprising at least two carbon atoms, and where for the instance of NR'$_3^+$ each R' comprises at least one C atom which are independent of one another or each R' comprises at least one C atom in which at least two R' are joined to form a heterocycle comprising at least two carbon atoms.

The seventh aspect of the sixth embodiment is directed to a compound represented by formula I in which the Base is a structure selected from among the structures ab, ac, ad, ae, af, ag, ah, ai, aj, ak, al, am, an, ao, ap, aq, ar, as, at, av, au, ax, ay, az, ba, bc, bd, be, bf, bg, bh, bi, bj, and bk, depicted above, wherein (a) R$^1$ is H, lower alkyl, lower alkylaryl, or aryl, which includes, but is not limited to, phenyl or naphthyl, where phenyl or naphthyl are optionally substituted with at least one of H, F, Cl, Br, I, OH, OR', SH, SR', NH$_2$, NHR', NR'$_2$, NHR'$_2^+$, NR'$_3^+$, heterocycle, lower alkoxy of C$_1$-C$_6$, halogenated (F, Cl, Br, I) lower alkoxy of C$_1$-C$_6$;

(b) R$^2$ is H;

(c) R$^3$ is CH$_3$; and (d) X is F;

wherein R' is an optionally substituted alkyl, an optionally substituted cycloalkyl, an optionally substituted alkynyl, an optionally substituted alkenyl, or an optionally substituted acyl, an optionally substituted alkoxyalkyl, where for the instance of NR'$_2$ or NHR'$_2^+$ each R' comprise at least one C atom that is independent of one another or are joined to form a heterocycle comprising at least two carbon atoms, and where for the instance of $NR'_3{}^+$ each R' comprises at least one C atom which are independent of one another or each R' comprises at least one C atom in which at least two R' are joined to form a heterocycle comprising at least two carbon atoms.

A seventh embodiment of the present invention is directed to a compound represented by formula I' its stereoisomers, salts, pharmaceutically acceptable salts, hydrates, solvates, crystalline, or metabolite forms thereof obtained by hydrolysis of the compound represented by formula I, followed by subsequent phosphorylation of the resultant hydrolysis product of the compound of formula I':

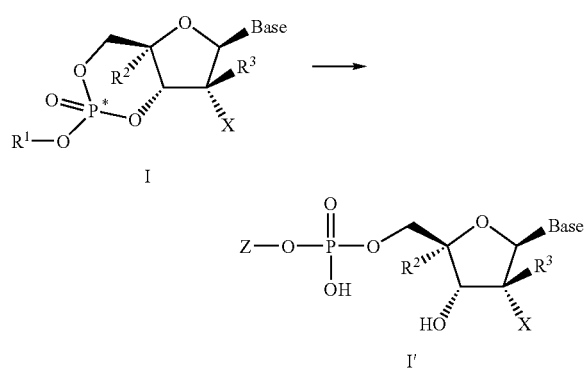

wherein

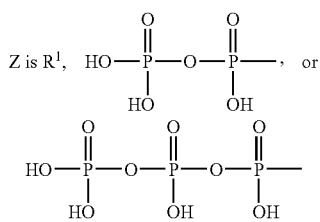

where $R^7$ is as defined herein above.

DOSAGE, ADMINISTRATION, AND USE

An eighth embodiment of the present invention is directed to a composition for the treatment of any of the viral agents disclosed herein said composition comprising a pharmaceutically acceptable medium selected from among an excipient, carrier, diluent, or equivalent medium and a compound, that is intended to include its salts (acid or basic addition salts), hydrates, solvates, and crystalline forms can be obtained, represented by formula I.

It is contemplated that the formulation of the eighth embodiment can contain any of the compounds contemplated in any of the aspects of the first, second, third, fourth, fifth, sixth, and seventh embodiments either alone or in combination with another compound of the present invention.

The compounds of the present invention may be formulated in a wide variety of oral administration dosage forms and carriers. Oral administration can be in the form of tablets, coated tablets, hard and soft gelatin capsules, solutions, emulsions, syrups, or suspensions. Compounds of the present invention are efficacious when administered by suppository administration, among other routes of administration. The most convenient manner of administration is generally oral using a convenient daily dosing regimen which can be adjusted according to the severity of the disease and the patient's response to the antiviral medication.

A compound or compounds of the present invention, as well as their pharmaceutically acceptable salts, together with one or more conventional excipients, carriers, or diluents, may be placed into the form of pharmaceutical compositions and unit dosages. The pharmaceutical compositions and unit dosage forms may be comprised of conventional ingredients in conventional proportions, with or without additional active compounds and the unit dosage forms may contain any suitable effective amount of the active ingredient commensurate with the intended daily dosage range to be employed. The pharmaceutical compositions may be employed as solids, such as tablets or filled capsules, semisolids, powders, sustained release formulations, or liquids such as suspensions, emulsions, or filled capsules for oral use; or in the form of suppositories for rectal or vaginal administration. A typical preparation will contain from about 5% to about 95% active compound or compounds (w/w). The term "preparation" or "dosage form" is intended to include both solid and liquid formulations of the active compound and one skilled in the art will appreciate that an active ingredient can exist in different preparations depending on the desired dose and pharmacokinetic parameters.

The term "excipient" as used herein refers to a compound that is used to prepare a pharmaceutical composition, and is generally safe, non-toxic and neither biologically nor otherwise undesirable, and includes excipients that are acceptable for veterinary use as well as human pharmaceutical use. The compounds of this invention can be administered alone but will generally be administered in admixture with one or more suitable pharmaceutical excipients, diluents or carriers selected with regard to the intended route of administration and standard pharmaceutical practice.

A "pharmaceutically acceptable salt" form of an active ingredient may also initially confer a desirable pharmacokinetic property on the active ingredient which were absent in the non-salt form, and may even positively affect the pharmacodynamics of the active ingredient with respect to its therapeutic activity in the body. The phrase "pharmaceutically acceptable salt" of a compound as used herein means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as glycolic acid, pyruvic acid, lactic acid, malonic acid, malic acid, maleic acid, fumaric acid, tartaric acid, citric acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, lauryl sulfuric acid, gluconic acid, glutamic acid, salicylic acid, muconic acid, and the like or (2) basic addition salts formed with the conjugate bases of any of the inorganic acids listed above, wherein the conjugate bases comprise a cationic component selected from among $Na^+$, $K^+$, $Mg^{2+}$, $Ca^{2+}$, $NH_g R'''_{4-g}{}^+$, in which R''' is a $C_{1-3}$ alkyl and g is a number selected from among 0, 1, 2, 3, or 4. It should be understood that all references to pharmaceutically acceptable salts include solvent addition forms (solvates) or crystal forms (polymorphs) as defined herein, of the same acid addition salt.

Solid form preparations include, for example, powders, tablets, pills, capsules, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Solid form preparations may contain, in addition to the active component, colorants, flavors, stabilizers, buffers, artificial and natural sweeteners, dispersants, thickeners, solubilizing agents, and the like. Examples of solid formulations are exemplified in EP 0524579; U.S. Pat. No. 6,635,278; US 2007/0099902; U.S. Pat. No. 7,060,294; US 2006/0188570; US 2007/0077295; US 2004/0224917; U.S. Pat. No. 7,462,608; US 2006/0057196; U.S. Pat. Nos. 6,267,985; 6,294,192; 6,569,463; 6,923,988; US 2006/0034937; U.S. Pat. Nos. 6,383,471; 6,395,300; 6,645,528; 6,932,983; US 2002/0142050; US 2005/0048116; US 2005/0058710; US 2007/0026073; US 2007/0059360; and US 2008/0014228, each of which is incorporated by reference.

Liquid formulations also are suitable for oral administration include liquid formulation including emulsions, syrups, elixirs and aqueous suspensions. These include solid form preparations which are intended to be converted to liquid form preparations shortly before use. Examples of liquid formulation are exemplified in U.S. Pat. Nos. 3,994,974; 5,695,784; and 6,977,257. Emulsions may be prepared in solutions, for example, in aqueous propylene glycol solutions or may contain emulsifying agents such as lecithin, sorbitan monooleate, or acacia. Aqueous suspensions can be prepared by dispersing the finely divided active component in water with viscous material, such as natural or synthetic gums, resins, methylcellulose, sodium carboxymethylcellulose, and other well known suspending agents.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

Suitable formulations along with pharmaceutical carriers, diluents and expcipients are described in *Remington: The Science and Practice of Pharmacy* 1995, edited by E. W. Martin, Mack Publishing Company, 19th edition, Easton, Pa., which is hereby incorporated by reference. A skilled formulation scientist may modify the formulations within the teachings of the specification to provide numerous formulations for a particular route of administration without rendering the compositions of the present invention unstable or compromising their therapeutic activity.

The modification of the present compounds to render them more soluble in water or other vehicle, for example, may be easily accomplished by minor modifications (e.g., salt formulation), which are well within the ordinary skill in the art. It is also well within the ordinary skill of the art to modify the route of administration and dosage regimen of a particular compound in order to manage the pharmacokinetics of the present compounds for maximum beneficial effect in patients.

Additionally, the compound of formula I may be independently formulated in conjunction with liposomes or micelles. As to liposomes, it is contemplated that the purified compounds can be formulated in a manner as disclosed in U.S. Pat. Nos. 5,013,556; 5,213,804; 5,225,212; 5,891,468; 6,224,903; 6,180,134; 5,192,549; 5,316,771; 4,797,285; 5,376,380; 6,060,080; 6,132,763; 6,653,455; 6,680,068; 7,060,689; 7,070,801; 5,077,057; 5,277,914; 5,549,910; 5,567,434; 5,077,056; 5,154,930; 5,736,155; 5,827,533; 5,882,679; 6,143,321; 6,200,598; 6,296,870; 6,726,925; and 6,214,375, each of which is incorporated by reference. As to micelles, it is contemplated that the purified compounds can be formulated in a manner as disclosed in U.S. Pat. Nos. 5,145,684 and 5,091,188, both of which are incorporated by reference.

A ninth embodiment of the present invention is directed to a use of the compound represented by formula I in the manufacture of a medicament for the treatment of any condition the result of an infection by any one of the following viral agents: hepatitis C virus, West Nile virus, yellow fever virus, degue virus, rhinovirus, polio virus, hepatitis A virus, bovine viral diarrhea virus and Japanese encephalitis virus.

The term "medicament" means a substance used in a method of treatment and/or prophylaxis of a subject in need thereof, wherein the substance includes, but is not limited to, a composition, a formulation, a dosage form, and the like, comprising the compound of formula I. It is contemplated that the compound of the use of the compound represented by formula I in the manufacture of a medicament for the treatment of any of the antiviral conditions disclosed herein of the night embodiment can be any of the compounds contemplated in any of the aspects of the first, second, third, fourth, fifth, sixth, and seventh embodiments or those specifically exemplified, either alone or in combination with another compound of the present invention. A medicament includes, but is not limited to, any one of the compositions contemplated by the eighth embodiment of the present invention.

A tenth embodiment of the present invention is directed to a method of treatment and/or prophylaxis in a subject in need thereof said method comprises administering a therapeutically effective amount of the compound represented by formula I to the subject.

A first aspect of the tenth embodiment is directed to a method of treatment and/or prophylaxis in a subject in need thereof said method comprises administering a therapeutically effective of at least two compounds falling within the scope of the compound represented by formula I to the subject.

A second aspect of the tenth embodiment is directed to a method of treatment and/or prophylaxis in a subject in need thereof said method comprises alternatively or concurrently administering a therapeutically effective of at least two compounds falling within the scope of the compound represented by formula I to the subject.

It is intended that a subject in need thereof is one that has any condition the result of an infection by any of the viral agents disclosed herein, which includes, but is not limited to, hepatitis C virus, West Nile virus, yellow fever virus, degue virus, rhinovirus, polio virus, hepatitis A virus, bovine viral diarrhea virus or Japanese encephalitis virus, flaviviridae viruses or pestiviruses or hepaciviruses or a viral agent causing symptoms equivalent or comparable to any of the above-listed viruses.

The term "subject" means a mammal, which includes, but is not limited to, cattle, pigs, sheep, chicken, turkey, buffalo, llama, ostrich, dogs, cats, and humans, preferably the subject is a human. It is contemplated that in the method of treating a subject thereof of the tenth embodiment can be any of the compounds contemplated in any of the aspects of the first, second, third, fourth, fifth, sixth, and seventh embodiments or those specifically recited in the tables above, either alone or in combination with another compound of the present invention.

The term "therapeutically effective amount" as used herein means an amount required to reduce symptoms of the disease in an individual. The dose will be adjusted to the individual requirements in each particular case. That dosage can vary within wide limits depending upon numerous factors such as the severity of the disease to be treated, the age and general health condition of the patient, other medicaments with which the patient is being treated, the route and form of administration and the preferences and experience of the medical practitioner involved. For oral administration, a daily dosage of between about 0.001 and about 10 g, including all values in between, such as 0.001, 0.0025, 0.005, 0.0075, 0.01, 0.025, 0.050, 0.075, 0.1, 0.125, 0.150, 0.175, 0.2, 0.25, 0.5, 0.75, 1, 1.5, 2, 2.5, 3, 3.5, 4, 4.5, 5, 5.5, 6, 6.5, 7, 7.5, 8, 8.5, 9, and 9.5, per day should be appropriate in monotherapy and/or in combination therapy. A particular daily dosage is between about 0.01 and about 1 g per day, including all incremental values of 0.01 g (i.e., 10 mg) in between, a preferred daily dosage about 0.01 and about 0.8 g per day, more preferably about 0.01 and about 0.6 g per day, and most preferably about 0.01 and about 0.25 g per day, each of which including all incremental values of 0.01 g in between. Generally, treatment is initiated with a large initial "loading dose" to rapidly reduce or eliminate the virus following by a decreasing the dose to a level sufficient to prevent resurgence of the infection. One of ordinary skill in treating diseases described herein will be able, without undue experimentation and in reliance on personal knowledge, experience and the disclosures of this application, to ascertain a therapeutically effective amount of the compounds of the present invention for a given disease and patient.

Therapeutic efficacy can be ascertained from tests of liver function including, but not limited to protein levels such as serum proteins (e.g., albumin, clotting factors, alkaline phosphatase, aminotransferases (e.g., alanine transaminase, aspartate transaminase), 5'-nucleosidase, γ-glutaminyl-transpeptidase, etc.), synthesis of bilirubin, synthesis of cholesterol, and synthesis of bile acids; a liver metabolic function, including, but not limited to, carbohydrate metabolism, amino acid and ammonia metabolism. Alternatively the therapeutic effectiveness may be monitored by measuring HCV-RNA. The results of these tests will allow the dose to be optimized.

A third aspect of the tenth embodiment, to a method of treatment and/or prophylaxis in a subject in need thereof said method comprises administering to the subject a therapeutically effective of a compound represented by formula I and a therapeutically effective amount of another antiviral agent; wherein the administration is concurrent or alternative. It is understood that the time between alternative administration can range between 1-24 hours, which includes any sub-range in between including, 2, 3, 4, 5, 6, 7, 8, 9, 10, 11, 12, 13, 14, 15, 16, 17, 18, 19, 20, 21, 22, and 23 hours. Examples of "another antiviral agent" include, but are not limited to: HCV NS3 protease inhibitors (see WO 2008010921, WO 2008010921, EP 1881001, WO 2007015824, WO 2007014925, WO 2007014926, WO 2007014921, WO 2007014920, WO 2007014922, US 2005267018, WO 2005095403, WO 2005037214, WO 2004094452, US 2003187018, WO 200364456, WO 2005028502, and WO 2003006490); HCV NS5B Inhibitors (see US 2007275947, US20072759300, WO2007095269, WO 2007092000, WO 2007076034, WO 200702602, US 2005-98125, WO 2006093801, US 2006166964, WO 2006065590, WO 2006065335, US 2006040927, US 2006040890, WO 2006020082, WO 2006012078, WO 2005123087, US 2005154056, US 2004229840, WO 2004065367, WO 2004003138, WO 2004002977, WO 2004002944, WO 2004002940, WO 2004000858, WO 2003105770, WO 2003010141, WO 2002057425, WO 2002057287, WO 2005021568, WO 2004041201, US 20060293306, US 20060194749, US 20060241064, U.S. Pat. No. 6,784,166, WO 2007088148, WO 2007039142, WO 2005103045, WO 2007039145, WO 2004096210, and WO 2003037895); HCV NS4 Inhibitors (see WO 2007070556 and WO 2005067900); HCV NS5a Inhibitors (see US 2006276511, WO 2006120252, WO 2006120251, WO 2006100310, WO 2006035061); Toll-like receptor agonists (see WO 2007093901); and other inhibitors (see WO 2004035571, WO 2004014852, WO 2004014313, WO 2004009020, WO 2003101993, WO 2000006529).

A fourth aspect of the tenth embodiment, to a method of treatment and/or prophylaxis in a subject in need thereof said method comprises alternatively or concurrently administering a therapeutically effective of a compound represented by formula I and another antiviral agent to the subject. It is understood that the time between alternative administration can range between 1-24 hours, which includes any sub-range in between including, 2, 3, 4, 5, 6, 7, 8, 9, 10, 11, 12, 13, 14, 15, 16, 17, 18, 19, 20, 21, 22, and 23 hours.

It is contemplated that the another antiviral agent such as interferon-α, interferon-β, pegylated interferon-α, ribavirin, levovirin, viramidine, another nucleoside HCV polymerase inhibitor, a HCV non-nucleoside polymerase inhibitor, a HCV protease inhibitor, a HCV helicase inhibitor or a HCV fusion inhibitor. When the active compound or its derivative or salt are administered in combination with another antiviral agent the activity may be increased over the parent compound. When the treatment is combination therapy, such administration may be concurrent or sequential with respect to that of the nucleoside derivatives. "Concurrent administration" as used herein thus includes administration of the agents at the same time or at different times. Administration of two or more agents at the same time can be achieved by a single formulation containing two or more active ingredients or by substantially simultaneous administration of two or more dosage forms with a single active agent.

It will be understood that references herein to treatment extend to prophylaxis as well as to the treatment of existing conditions. Furthermore, the term "treatment" of a HCV infection, as used herein, also includes treatment or prophylaxis of a disease or a condition associated with or mediated by HCV infection, or the clinical symptoms thereof.

An eleventh embodiment of the present invention is directed to a process for preparing the compound of formula I, which comprises reacting III with $R^1OP(NR_2)_2$, and then oxidizing II to form I according to the following scheme

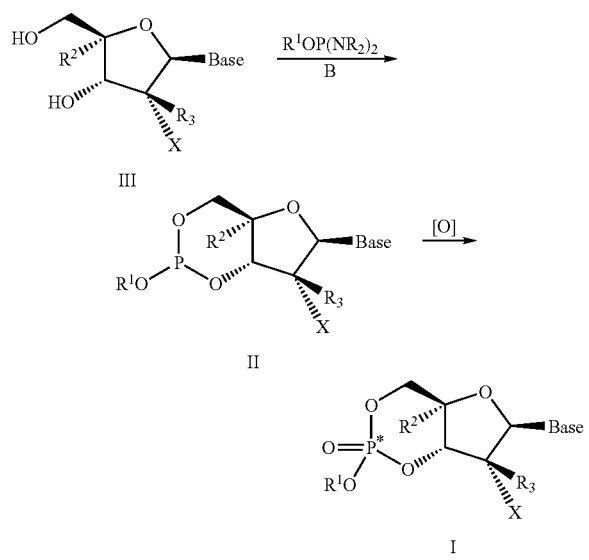

wherein $R^1$, $R^2$, $R^3$, X, and Base are defined above;
wherein $R^1OP(NR_2)_2$ is a dialkylamino-$R^1$phosphite, B is a Brönsted base, and [O] is an oxidant, such as, for example, m-chloroperbenzoic acid (MCPBA), hydrogen peroxide, $NO_2/N_2O_4$, etc.

A twelfth embodiment of the present invention is directed to a product, I, prepared by a process which comprises reacting III with $R^1OP(NR_2)_2$, and then oxidizing II according to the following scheme

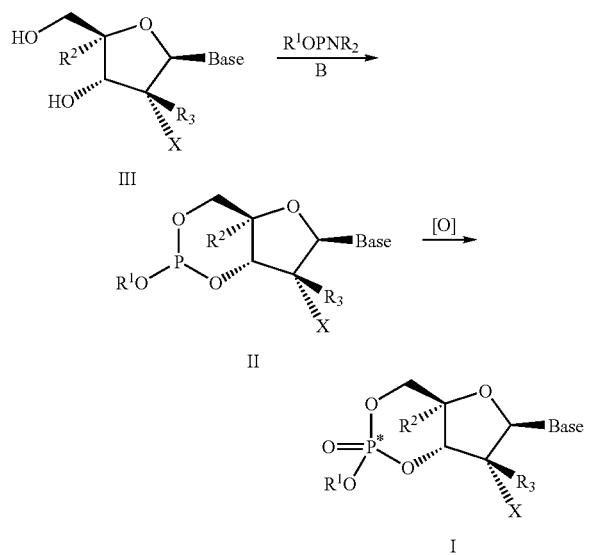

wherein $R^1$, $R^2$, $R^3$, X, and Base are defined above;
wherein $R^1OP(NR_2)_2$ is a dialkylamino-alkylphosphite, B is a Brönsted base, and [O] is an oxidant, such as, for example, m-chloroperbenzoic acid (MCPBA), hydrogen peroxide, $NO_2/N_2O_4$, etc.

Compounds and Preparation

The nucleoside analog is made by conventional procedures disclosed in any one of U.S. Published Application Nos. 2005/0009737, 2006/0199783, 2006/0122146, and 2007/0197463, each of which is incorporated by reference in its entirety. Bases represented by the structures c', d', e, f, g, h, i, j, k, l, m, n, o, p, q, r, s, t, u, v, w, x, y, z, aa, bb, cc, dd, ee, ff, gg, hh, ii, jj, kk, ll, and mm are prepared and coupled to a given sugar using methods known in the art, such as, for example, as disclosed in WO 2006/094347, WO 2005/021568, US 2006/0252715, and US 2006/0194749, each of which is incorporated by reference in its entirety. Bases represented by the structures formula I in which the Base is a structure selected from among the structures ab, ac, ad, ae, af, ag, ah, ai, aj, ak, al, am, an, ao, ap, aq, ar, as, at, av, au, ax, ay, az, ba, bc, bd, be, bf, bg, bh, bi, bj, and bk, depicted above, are prepared and coupled to a given sugar using methods known in the art, such as, for example, as disclosed in WO 2007/027248 which is incorporated by reference in its entirety.

Disclosed $^1$H-NMR values were recorded on a Varian AS-400 instrument. Mass spectral data were obtained using either a Micromass-Quattromicro API or a Waters Acquity.

General Experimental Procedure for the Preparation of bis(N,N'-diisopropylamino)alkylphosphite

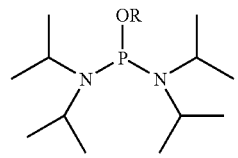

The alcohol (1.0 equiv) was added drop-wise to phosphorous trichloride (1.0 equiv) very slowly, while stirring. The inner temperature of the reaction flask was kept between 20 and 30° C., and the produced hydrochloric acid was absorbed in a gas trap containing aqueous sodium bicarbonate. The residue was distilled under reduced pressure to give pure alkoxydichlorophosphine. This compound was added to a stirred solution of N,N-diisopropylamine (6.0 equiv) in dry ether (5 mL/mmol) drop-wise, very slowly at 0° C. After completion of the addition the mixture was allowed to warm to room temperature at which temperature it was stirred overnight. The ammonium salt was removed by filtration, and the filtrate was concentrated. The residue was distilled under reduced pressure to give bis(N,N-diisopropylamino)alkylphosphite as a colorless liquid (10-40%). (See, e.g., N. L. H. L. Breeders et. al. *J. Am. Chem. Soc.* 1990, 112, 1415-1482)

General Method for the Preparation of 3',5'-Cyclic Phosphates

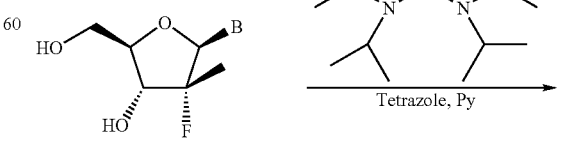

a

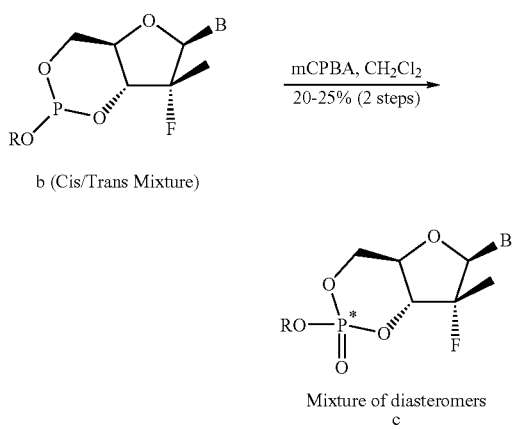

b (Cis/Trans Mixture)

mCPBA, CH₂Cl₂
──────────────→
20-25% (2 steps)

Mixture of diasteromers
c steps). ¹H NMR indicates that the product c is a mixture of two diastereomers.

These cyclic phosphates can also be prepared via an alternate route described below. Nucleoside III can be reacted with POCl₃ to produce the nucleoside mono phosphate, which upon cyclization and dehydration would give cyclic phosphate. Thus, upon alkylation with appropriate alkyl halide in the presence of bases such as TEA, DIEA in solvents such as DMF, acetonitrile etc or coupling with alcohols in the presence of reagents like DCC or EDC or MSNT would give desired products, using the procedures disclosed in, for example, Beres et al. *J. Med. Chem.* 1986, 29, 1243-1249 and WO 2007/027248 both of which are incorporated by reference, and as depicted in the following scheme.

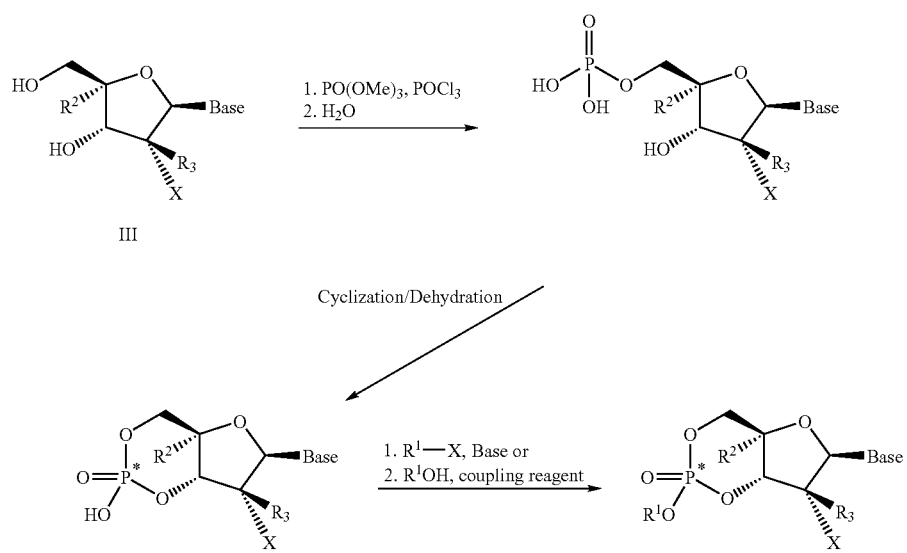

General Experimental Procedure: To a stirred solution of 3',5'-dihydroxy nucleoside a (1.0 equiv) in dry pyridine (5 mL/mmol) is added a 0.45M solution of tetrazole in acetonitrile (2.5 equiv) followed by bis(N,N-diisopropylamino)alkylphosphite (1.0 equiv) at room temperature. After stirring the mixture at room temperature for 2 h, TLC indicates the disappearance of starting material A and formation of two non-polar products. The reaction mixture is concentrated under reduced pressure at room temperature and the residue is triturated with EtOAc (10 mL/mmol). The precipitated tetrazole salts are removed by filtration and the filtrate is concentrated under reduced pressure. The residue is chromatographed to give cis and trans cyclicphosphites b in about 1:1 ratio.

To a stirred solution of the phosphate b (1 equiv) in dichloromethane (10 mL/mmol) is added a 77% m-CPBA (1.2 equiv) at room temperature. After 5 min, the TLC indicates the completion of the reaction. Solvent is evaporated and the residue is chromatographed using a short silica gel column to give pure product as a white solid (20-25% overall yield, 2

Preparation of 1-((2S,4aR,6R,7R,7aR)-7-Fluoro-2-methoxy-7-methyl-2-oxo-tetrahydro-2λ⁵-furo[3,2-d][1,3,2]dioxaphosphinin-6-yl)-1H-pyrimidine-2,4-dione (1)

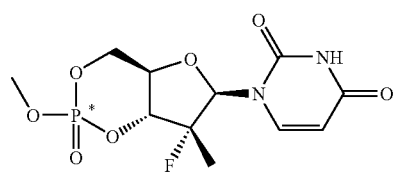

To a stirred solution of 1-((2R,3R,4R,5R)-3-fluoro-4-hydroxy-5-(hydroxymethyl)-3-methyltetrahydrofuran-2-yl)pyrimidine-2,4(1H,3H)-dione (730 mg, 2.8 mmol) in dry pyridine (15 mL) was added a 0.45M solution of tetrazole in acetonitrile (15 mL) followed by bis(N,N-diisopropylamino) methylphosphite (0.971 mL, 3.3 mmol) at room temperature. After 2 h, TLC indicated disappearance of the starting material and two non-polar products. The reaction mixture was concentrated under reduced pressure at room temperature and the residue was triturated with EtOAc (30 mL). Tetrazole salts precipitated were filtered off and the filtrate was concentrated under reduced pressure. The residue was chromatographed using 0-40% EtOAc/hexanes gradient to give pure product 2 (92 mg) and mixture of product 1&2 (102 mg). $^1$H NMR confirmed that the product 2 is a single isomer of the required compound. Stereochemistry is not determined.

To a stirred solution of phosphite (30 g, 0.09 mmol) in dichloromethane (1 mL) was added a 77% m-CPBA (26 mg, 0.113 mmol) at room temperature. After 5 min, the TLC indicated the completion of the reaction. The solvent was evaporated and the residue was chromatographed using a short silica gel (2 g) column with 70-100% EtOAc/hexanes gradient to give pure product as a white solid (21 mg). $^1$H NMR indicated that the product (1) is a mixture of isomers designated as 1a and 1b.

Data for 1a: $^{31}$P NMR (162 MHz, CD$_3$OD): δ –1.54 (minor diasteromer), –2.30 (major diasteromer).; $^1$H NMR (400 MHz, CD$_3$OD): δ 7.60-7.58 (m, 1H), 6.36 (d, J=20.8 Hz, 1H), 5.76 (d, J=8.0 Hz, 1H), 4.787-4.484 (m, 4H), 3.85 (d, J=12 Hz, 3H), 1.44 (d, J=22.0 Hz, 3H); MS (ESI) m/z 337 (M+H)$^+$.

Data for 1b: $^{31}$P NMR (162 MHz, CDCl$_3$+DMSO): δ –3.82 (minor), –4.54 (major); $^1$H NMR (400 MHz, CDCl$_3$+ DMSO): δ 11.41 and 11.25 (two s, 1H), 7.32 (bs, 1H), 6.38 (d, J=21.2 Hz, 1H), 5.75-5.70 (m, 1H), 5.45-5.20 (, 1H), 4.64-4.01 (m, 4H), 1.59 and 1.45 (two d, J=22.4 Hz, 3H); MS (ESI) m/z 337 (M+H)$^+$.

Preparation of 1-((2S,4aR,6R,7R,7aR)-2-Benzyloxy-7-fluoro-7-methyl-2-oxo-tetrahydro-2λ$^5$-furo[3,2-d][1,3,2]dioxaphosphinin-6-yl)-1H-pyrimidine-2,4-dione (2)

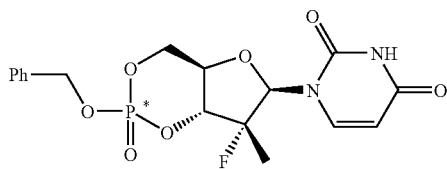

2

To a stirred solution of 1-((2R,3R,4R,5R)-3-fluoro-4-hydroxy-5-(hydroxymethyl)-3-methyltetrahydrofuran-2-yl)pyrimidine-2,4(1H,3H)-dione (1.04 g, 4 mmol, 1.0 equiv) in dry pyridine (22 mL) was added a 0.45M solution of tetrazole in acetonitrile (22.2 mL, 10 mmol, 2.5 equiv) followed by bis(N,N-diisopropylamino)benzylphosphite (1.35 mL, 4.6 mmol, 1.0 equiv) at room temperature. After stirring the mixture at room temperature for 2 h, TLC indicated disappearance of starting material and a non polar product. The reaction mixture was concentrated under reduced pressure at room temperature and the residue was chromatographed (Analogix, SF25-40 g, 35-100% EOAc/Hexanes gradient, 1 h) gave pure product as a white powder (640 mg, 40.4% yield).

To a stirred solution of phosphite (640 mg, 1.6 mmol) in dichloromethane (5 mL) was added a 77% m-CPBA (430 mg, 1.92 mmol, 1.2 equiv) at room temperature. After 5 min, TLC indicated the completion of the reaction and two well separated polar products. The solvent was evaporated and the residue was chromatographed (Analogix, 30-85% EtOAc/hexanes gradient, 60 min) to give pure product 1 (340 mg, 51.1% yield) and product 2 (194 mg, 29.1% yield) as a white solids. $^1$H-NMR indicated that the product 2 is a single diastereomer of the required compound (2a) which assigned as trans isomer based on the literature. The cis product (2a) is a mixture of diastereomers.

Data for 2a: $^{31}$P NMR (162 MHz, CDCl$_3$) δ –2.79; $^1$H NMR (400 MHz, CDCl$_3$): δ 9.34 (bs, 1H), 7.39 (s, 5H), 7.33 (d, J=7.2 Hz, 1H), 6.38 (d, J=19.2 Hz, 1H), 5.79 (d, J=8.4 Hz, 1H), 5.24-5.15 (m, 2H), 4.60 (bs, 2H), 4.38-4.35 (m, 2H), 1.46 (d, J=22 Hz, 3H); MS (ESI) m/z 413 (M+H)$^+$.

Data for 2b: $^{31}$P NMR (162 MHz, CDCl$_3$): δ 4.76 (minor), –5.64 (major); $^1$H NMR (400 MHz, CDCl$_3$): δ 9.64 (bs, 1H), 7.45-7.39 (m, 5H), 7.17 and 6.90 (two bs, 1H), 6.29 (d, J=18.8 Hz, 1H), 5.78 (d, J=7.6 Hz, 1H), 5.20-5.14 (m, 3H), 4.54-4.48 (m, 1H)4.27 (bs, 2H), 3.53 (bd, J=12.0 Hz, 1H), 1.37 and 1.16 (two d, J=20.8 Hz, 3H); MS (ESI) m/z 413 (M+H)$^+$.

Preparation of 6-Azetidin-1-yl-9-((4aR,6R,7R,7aR)-7-fluoro-2-methoxy-7-methyl-2-oxo-tetrahydro-2λ$^5$-furo[3,2-d][1,3,2]dioxaphosphinin-6-yl)-9H-purin-2-ylamine (3)

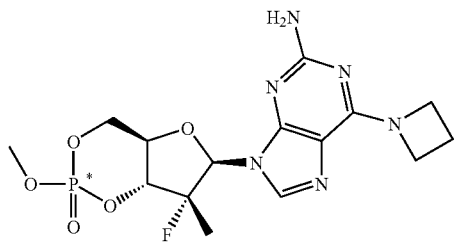

3

To a stirred solution of (2R,3R,4R,5R)-5-(2-amino-6-(azetidin-1-yl)-9H-purin-9-yl)-4-fluoro-2-(hydroxymethyl)-4-methyltetrahydrofuran-3-ol (100 mg, 0.3 mmol) in dry pyridine (1.5 mL) was added a 0.45M solution of tetrazole in acetonitrile (1.64 mL, 0.74 mmol) followed by bis(N,N-diisopropylamino)methylphosphoramidite (101 μL, 0.35 mmol) at room temperature. After stirring the mixture at room temperature for 2 h, TLC indicated disappearance of starting material. The reaction mixture was concentrated under reduced pressure at room temperature and the residue was triturated with EtOAc (30 mL). Tetrazole salts precipitated were filtered off and the filtrate was concentrated under reduced pressure. The crude compound (120 mg) was used in the next step without further purification.

To a stirred solution of cyclic-phosphite (119 mg, crude from the previous experiment, 0.3 mmol) in dichloromethane (3 mL) was added a 77% m-CPBA (78 mg, 0.35 mmol) at room temperature. After 5 min, the solvent was evaporated and the residue was chromatographed (Analogix, SF10-8 g column) using 0-2.5% MeOH/CH$_2$Cl$_2$ gradient to give pure product as a white solid (23 mg, 18.6% two steps).

Data for 3: $^{31}$P NMR (162 MHz, CDCl$_3$): δ –1.26, –3.58; $^1$H NMR (400 MHz, CDCl$_3$): δ 7.45 and 7.44 (two s, 1H), 5.45 (d, J=20 Hz, 1H), 4.89-4.41 (m, 10H), 3.93 (app. t, J=13.0 Hz, 3H), 2.49 (bs, 2H), 1.39 (overlapping d, J=22.4 Hz, 3H); MS (ESI) m/z 415 (M+H)+.

Preparation of 2-Amino-9-((4aR,6R,7R,7aR)-7-fluoro-2-methoxy-7-methyl-2-oxo-tetrahydro-2λ5-furo[3,2d][1,3,2]dioxaphosphinin-6-yl)-9H-purin-6-ol (4)

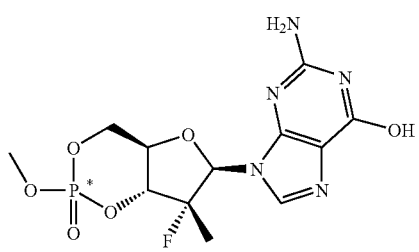

4

To a stirred solution of 2-amino-9-((2R,3R,4R,5R)-3-fluoro-4-hydroxy-5-(hydroxymethyl)-3-methyltetrahydrofuran-2-yl)-9H-purin-6-ol (116 mg, 0.33 mmol, 1.0 equiv) in dry pyridine (1.65 mL) was added a 0.45M solution of tetrazole in acetonitrile (1.8 mL, 0.85 mmol, 2.5 equiv) followed by bis(N,N-diisopropylamino)methylphosphite (114 µL, 0.396 mmol, 1.2 equiv) at room temperature. After stirring the mixture at room temperature for 2 h, TLC indicated the disappearance of starting material and a non-polar product. The reaction mixture was concentrated under reduced pressure at room temperature and the residue was triturated with EtOAc (5 mL). Tetrazole salts precipitated were filtered off and the filtrate was concentrated under reduced pressure.

The above residue was redissolved in dichloromethane in dichloromethane (3 mL) and was added a 77% m-CPBA (21 mg, 0.395 mmol, 1.2 equiv) at room temperature. After 5 min, TLC indicated the completion of the reaction. The solvent was evaporated and the residue was chromatographed using a short silica gel column to give pure product as a white solid (3.4 mg, 9% overall yield, 2 steps).

Data for 4: 31P NMR (162 MHz, CD3OD): δ −3.33; 1H NMR (400 MHz, CD3OD): δ 9.03 (s, 2H), 7.81 (s, 1H), 6.17 (d, J=20.4 Hz, 1H), 4.66 (dd, J=9.3, 5.1 Hz, 1H), 4.62-4.54 (m, 2H), 4.29-4.23 (m, 1H), 3.82 (d, J=11.2 Hz, 3H), 3.37 (quintet, J=6.4 Hz, 2H), 1.22 (d, J=6.4 Hz, 3H); MS (ESI) m/z 376 (M+H)+.

Preparation of 4-Amino-1-((2R,4aR,6R,7R,7aR)-7-fluoro-2-methoxy-7-methyl-2-oxo-tetrahydro-2λ5-furo[3,2-d][1,3,2]dioxaphosphinin-6-yl)-1H-pyrimidin-2-one (5)

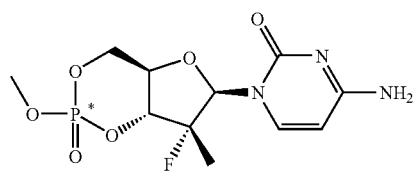

5

To a stirred solution of 4-amino-1-((2R,3R,4R,5R)-3-fluoro-4-hydroxy-5-(hydroxymethyl)-3-methyltetrahydrofuran-2-yl)pyrimidin-2(1H)-one (1.0 g, 3.86 mmol, 1.0 equiv) in dry pyridine (21 mL) was added a 0.45 M solution of tetrazole in acetonitrile (21 mL, 9.5 mmol, 2.5 equiv) followed by bis(N,N-diisopropylamino)methylphosphite (1.3 mL, 4.6 mmol, 1.2 equiv) at room temperature. After stirring the mixture at room temperature for 2 h, TLC indicated no starting material and a non polar product. The reaction mixture was concentrated under reduced pressure at room temperature and the residue was triturated with EtOAc (25 mL). Tetrazole salts precipitated were filtered off and the filtrate was concentrated under reduced pressure. Column chromatography of the crude compound (SF25-40 g, Analogix 0-20% MeOH/CH2Cl2 gradient, 1 h) gave pure product as a white powder (334 mg, 27% yield).

To a stirred solution of phosphite (334 mg, 1.05 mmol) in dichloromethane (3 mL) was added a 77% m-CPBA (309 mg, 1.26 mmol, 1.2 equiv) at room temperature. After 5 min, TLC indicated the completion of the reaction. The solvent was evaporated and the residue was chromatographed using a short silica gel column to give pure product as a white solid (80 mg, 23% yield). 1H NMR indicated that the product is a mixture of cis and trans isomers and their diastereomers.

Data for 5: 31P NMR (162 MHz, CD3OD): δ −0.70, −2.22, −2.77 (minor), −3.46 (major); 1H NMR (400 MHz, CD3OD): δ 7.62 (d, J=7.6 Hz, 1H), 6.41 (d, J=21.2 Hz, 1H), 5.97 (d, J=7.2 Hz, 1H), 4.77-4.57 (m, 2H), 4.48-4.18 (m, 4H), 3.88 (d, J=11.2 Hz) and 3.87 (d, J=12.0 Hz, total 3H), 1.55 and 1.39 (two d, J=22.4 Hz, 3H); MS (ESI) m/z 336 (M+H)+.

N6-Cyclobutyl-9-((4aR,6R,7R,7aR)-7-fluoro-2-methoxy-7-methyl-2-oxo-tetrahydro-2λ5-furo[3,2-d][1,3,2]dioxaphosphinin-6-yl)-9H-purine-2,6-diamine (6)

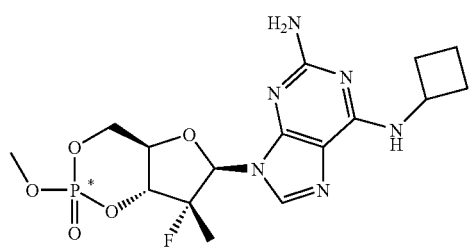

6

Compound 6 was prepared using a similar procedure described for the preparation of compound 4. Except that the N6-cyclobutyl-amino-purine derivative was employed rather than the 6-hydroxy-purine derivative.

Data for 6: 31P NMR (162 MHz, CDCl3): δ −1.26, −3.64; 1H NMR (400 MHz, CDCl3): δ 7.49 and 7.48 (two s, 1H), 6.02 (bs, 2H), 5.97 (d, J=19.2 Hz, 1H), 4.88 (bs, 1H), 4.73 (bs, 1H), 4.65-4.58 (m, 2H), 4.53-4.37 (m, 2H) 3.95 and 3.91 (two d, J=11.6 Hz, 3H-, 2.42 (bs, 2H), 2.00-1.95 (m, 2H), 1.79-1.73 (m, 2H), 1.38 (overlapping d, J=22.4 Hz, 3H); MS (ESI) m/z 429 (M+H)+.

Methods for prepeparing a compound having the structure:

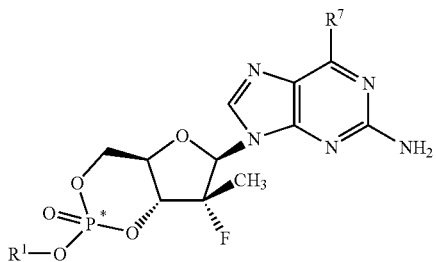

are included below. Inspection of the scheme below shows that compounds 17 and 3 are the same.

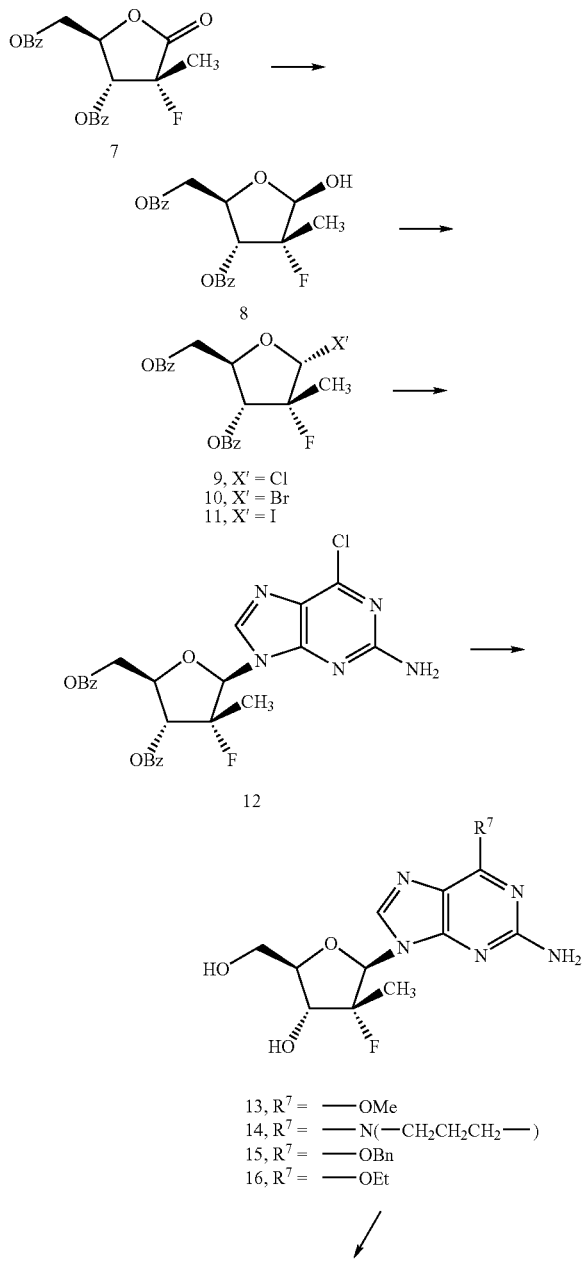

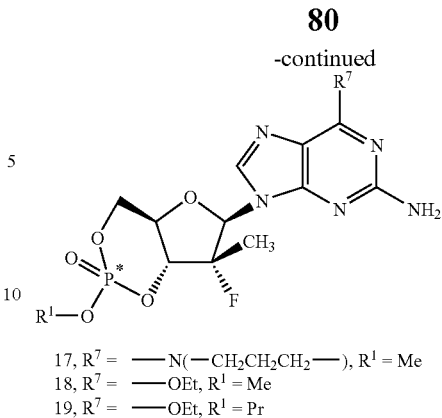

17, $R^7$ = —N(—CH$_2$CH$_2$CH$_2$—), $R^1$ = Me
18, $R^7$ = —OEt, $R^1$ = Me
19, $R^7$ = —OEt, $R^1$ = Pr

Compound (7) can be obtained by a process disclosed at page 5 in U.S. Published Application No. 2008/0139802 (which corresponds to WO 2008/045419), at pages 11-13 in WO 2006/012440, and at pages 20-22 and 30-31 in WO 2006/031725, each of which is hereby incorporated by reference.

The use of the convergent glycosylation route to prepare 2'-deoxy-2'-fluoro -2'-C-methyl purine nucleosides and their corresponding nucleotide phosphoramidates came about with the development of the synthesis of 3,5-di-O-benzoyl-2-deoxy-2-fluoro-2-C-methylribonolactone (Chun, K.; Wang, P. Intl. Pat. Appl. WO 2006/031725).

After several attempts using Vorbrueggen-type Lewis acid mediated coupling and the ribonolactol 1-O-acetate of 3,5-di-O-benzoyl-2-deoxy-2-fluoro-2-C-methylribonolactone, we observed very low coupling yields and the undesired α-anomer was the major product. Mitsunobu coupling with the ribonolactol (8) did give the desired product but with no stereoselectivity and very difficult chromatographic separation resulting in isolated yields of 6-10% for this step alone and the method was not scaleable.

The preferred approach became the $S_N2$ type reaction using a halo-sugar and a salt of the purine base. Again, the challenge of this approach was how to obtain an α halo-sugar stereospecifically in high yield to take advantage the inversion of configuration expected with $S_N2$ type reactions. A typical method treats an anomeric mixture of the 1-O-acetate of a sugar with HCl or HBr in acetic acid. However, this method resulted in production of unfavorable anomeric mixtures. Reducing the lactone (e.g., with LiAlH(t-BuO)$_3$ or Red-Al) initially generates at 2:1 ratio of β/α anomers but after initial purification through a silica gel filtration column, the resulting oil slowly anomerizes to form pure crystalline β-anomer of the lactol (8). This can be accelerated from several days at ambient temperature to 5-17 h at 50° C. with seeding β-crystals. We observed that once the lactol is in solution, it slowly anomerizes back towards the 2:1 equilibrium in solvents such as dichloromethane or chloroform at ambient temperature. This process can be slowed considerable by chilling the solution (eg –20° C.).

Chlorination through an $S_N2$ mechanism with N-chlorosuccinimide (NCS) produced an α-chlorosugar (9) in a stereospecific manner in almost quantitative yield.

To obtain an α-bromosugar (10), many bromination conditions were tried including N-bromosuccinimide (NBS) and HBr in acetic acid. Among them, we followed a general bromination reaction using a combination of triphenylphosphine (PPh$_3$) and carbon tetrabromide (CBr$_4$) (eg. Hooz et al, Can. J. Chem., 1968, 46, 86-87). Under the conditions of using methylene chloride as the solvent and maintaining a low temperature (–10 to –20° C.) we obtained the best result where the desired α/β isomer ratio was greater than 10:1, in a yield of greater than 80%. Applicants believe that there are no literature precedents describing this level of stereoselectivity for this reaction type. Another practical observation was that by conducting the bromination under sub-ambient temperature conditions, such as, most preferably about −20° C.) and exposing the cold reaction solution to silica gel as soon as possible after the completion of the reaction minimizes anomerization of the bromosugar. The bromosugar can be purified through a silica gel filtration column. Once treated with silica gel, the bromosugar it is practically stable even at elevated temperatures.

The iodosugar (11) was prepared in a similar manner, which can be coupled with the purine to produce the key intermediate (12).

Following the general purine coupling method of Bauta et al (Intl. Pat. Appl. WO 2003/011877), we coupled the α-bromosugar (10) with the potassium salt of 6-chloro-2-aminopurine in t-butanol in acetonitrile. The reaction took over a week at ambient temperatures. The reaction was optimized to go to completion in 24 h at 50° C. After partial purification through a silica gel filtration column, the anomeric mixture was isolated in 63% yield in a ratio of 14:1 β/α. The β-anomer (12) could be selectively crystallized out from a methanolic solution to give the pure desired β-anomer (6) in 55% yield from the bromosugar (10).

With the key intermediate 12 in hand, conversion to unprotected 2-amino-6-substituted purines (e.g., 13-16) was accomplished. Cyclic phosphate derivatives (e.g., 17-19) were prepared as described in *Can J. Chem.*, 1993, 71, 855 or as disclosed in U.S. Provisional Patent Application No. 61/060,683, filed Jun. 11, 2008, pp. 79-89.

Synthesis of ((2R,3R,4R,5R)-3-(benzoyloxy)-4-fluoro-5-hydroxy-4-methyltetrahydrofuran-2-yl)methyl benzoate (8)

To a 5 L of dry three-neck round-bottomed flask fit with a mechanical stirrer, addition funnel and thermometer was charged the lactone ((2R,3R,4R)-3-(benzoyloxy)-4-fluoro-4-methyl-5-oxotetrahydrofuran-2-yl)methyl benzoate) (7.379 g, 1.018 mol). The solid was dissolved in anhydrous THF (1.75 L) and cooled to −30° C. under a nitrogen atmosphere. A solution of lithium tri-tert-butoxyaluminohydride (1.0 M in THF, 1.527 L) was added to the lactone solution while stirring over 1 h and maintaining the −30° C. temperature. After finishing the addition, the temperature was slowly increased and the reaction was followed by TLC (lactol $R_f$ 0.4, 30% EtOAc in hexanes). The reaction was complete after 1 h 15 min (temperature reached −10° C.). The reaction was quenched by addition of Ethyl acetate (900 mL) via addition funnel. Sat. $NH_4Cl$ (40 mL) was added at 0° C. The cloudy mixture was decanted into a 10 L round-bottomed flask. The solid residue left behind was filtered and washed with ethyl acetate (2×200 mL). The filtrate was combined with the decanted solution and the combined solution was concentrated under reduced pressure. The oily residue was dissolved in ethyl acetate (2 L) and washed with 3 N HCl (600 mL). The aqueous layer was back-extracted with ethyl acetate (3×400 mL). The combined organic layer was washed with water (3×800 mL), sat. $NaHCO_3$ (400 mL) and brine (400 mL). The organic solution was dried over $MgSO_4$, filtered and concentrated under reduced pressure to afford a light brown oily residue. The residue was purified by plug column (2.2 kg of 40-63 micron silica gel, packed in a 6 L sintered glass funnel, 22 cm length of silica gel, diameter 15 cm) using suction and a step-gradient of 5%, 10%, 20%, and 30% ethyl acetate in hexanes—ca 5 L of each). The product containing fractions were combined and concentrated under reduced pressure to a colorless, very thick liquid (310.4 g).

The liquid slowly solidified after adding crystalline beta product as seeds (ca 100 mg spread out) under vacuum (0.2 mmHg) at 50° C. The process of solidification was complete in 20 hours at 50° C. with or without vacuum. The white solid thus collected (293.8 g, 77%) has amp of 79-80° C. and ratio of β/α is 20:1 based on NMR.

$^1$H-NMR (DMSO-$d_6$) β-isomer, δ=5.20 (dd, 1H, OH); α-isomer, δ=5.40 (dd, 1H, OH). (β-lactol). (DMSO-$d_6$): δ 7.99 (m, 2H, arom.), 7.93 (m, 2H, arom.), 7.70 (m, 1H, arom.), 7.61 (m, 1H, arom.), 7.55 (m, 2H, arom.), 7.42 (m, 2H, arom.), 7.32 (dd, 1H, C1-H), 5.54 (dd, 1H, C3-H), 5.20 (dd, 1H, OH), 4.55-4.50 (m, 1H, C5-Ha), 4.46-4.40 (m, 2H, C5-Hb and C4-H), 1.42 (d, 3H, $CH_3$).

Synthesis of ((2R,3R,4R,5R)-3-(benzoyloxy)-5-chloro-4-fluoro-4-methyltetrahydrofuran-2-yl)methyl benzoate (9)

To a solution of mixture of compound 8 (1.0 g, 2.67 mmol) and $PPh_3$ (1.4 g, 5.34 mmol) in $CH_2Cl_2$ (15 mL) was added NCS (1.07 g, 8.01 mmol) portionwise at 0° C. Then the resulting mixture was stirred at rt for 1 h and poured into a silica gel column and eluted with EtOAc-hexanes (1:4) using pressure. The collected right fractions were combined, concentrated, and co-evaporated with $CH_2Cl_2$ several times and used next step (1.0 g, 95%).

$^1$H-NMR (CDCl$_3$) δ=8.13-8.02 (m, 4H, aromatic), 7.78-7.50 (m, aromatic, 2H), 7.53-7.43 (m, 4H, aromatic), 6.01 (s, 1H, H-1), 5.28 (dd, 1H, J=3.2, 5.6 Hz, H-3), 4.88 (m, 1H, H—H-4), 4.77 (dd, 1H, J=3.2, 12.4 Hz, H-5), 4.61 (dd, 1H, J=4.0, 12.4 Hz, H-5'), 1.73 (d, 3H, J=21.6 Hz, $CH_3$).

Synthesis of ((2R,3R,4R,5R)-3-(benzoyloxy)-5-bromo-4-fluoro-4-methyltetrahydrofuran-2-yl)methyl benzoate (10)

Anhydrous dichloromethane (5.6 L) was charged into a reactor and cooled to −22° C. or below. Triphenylphosphine (205.4 g, 0.783 mol) was added to the cold solvent and the suspension was stirred to form a solution. The lactol (8, 209.4 g, 0.559 mol) in solid form was added to the cold solution and stirred for 15 mins. Carbon tetrabromide (278.2 g, 0.839 mol) was added portion-wise while maintaining the temperature of the solution between −22° C. to −20° C. under a flow of nitrogen gas (approx. 30 min). After finishing the addition of $CBr_4$, the temperature was slowly raised to −17° C. over 20 mins. The reaction was judged to be >95% complete by TLC ($R_f$s 0.61 (α), 0.72 (β), 0.36 lactol; 20% EtOAc in hexanes). The reaction solution was immediately transferred to a vessel containing 230 g of flash chromatography grade silica gel (40-63 microns). The stirred mixture was immediately passed through a pad of silica gel (680 g) in a 2.5 L sintered glass Buchner funnel. The filtrate was concentrated under reduced pressure to about 800 mL and the ratio of α/β isomers of the crude product was 10:1 as determined by $^1$H-NMR. (CDCl$_3$) δ=6.35, (s, α C1-H), 6.43, (d, β C1-H). The residue was purified by plug column chromatography using 2.1 kg of silica gel in a 6 L sintered glass Buchner funnel and eluted (via suction) with a stepwise gradient elution of 1%, 5%, 8% 12% EtOAc in hexane (ca 4 L each) to remove non-polar impurities followed by 12%, 25% EtOAc in hexane (6 L total) to elute the product. The product containing fractions were combined into two fractions, concentrated under reduced pressure, dried under vacuum (0.1 mmHg, ambient temp., 20 h) to colorless oils. Main fraction (197 g, 89% α/β=20:1). The alpha isomer crystallized from a small portion of the oil upon standing at 0° C. for several weeks to give large, thin plates, mp 59-61° C. The pure beta isomer crystallized from a mixture of alpha and beta product oil from an earlier less selective run to give needles, mp 77-79° C.

$^1$H-NMR (β-bromide) (CDCl$_3$): δ=8.08 (m, 2H, arom.), 8.04 (m, 2H, arom.), 7.62 (m, 1H, arom.), 7.54-7.45 (m, 3H, arom.), 7.35 (m, 2H, arom.), 6.43 (d, 1H, C1-H), 6.04 (dd, 1H, C3-H), 4.78-4.73 (m, 2H, C4-H and C5-Ha), 4.63-4.58 (m, 1H, C5-Hb), 1.76 (d, 3H, CH$_3$). α-bromide, α/β=20:1) (CDCl$_3$): δ 8.13 (m, 2H, arom.), 8.02 (m, 2H, arom.), 7.63-7.56 (m, 2H, arom.), 7.50-7.42 (m, 4H, arom.), 6.34 (s, 1H, C1-H), 5.29 (dd, 1H, C3-H), 4.88 (m, 1H, C4-H), 4.78 (dd, 1H, C5-Ha), 4.63 (dd, 1H, C5-Hb), 1.72 (d, 3H, CH$_3$).

Synthesis of ((2R,3R,4R,5R)-3-(benzoyloxy)-4-fluoro-5-iodo-4-methyltetrahydrofuran-2-yl)methyl benzoate (11)

To a solution of compound 8 (1 g, 2.67 mmol), triphenylphosphine (700 mg, 2.67 mmol), and imidazole (180 mg, 2.67 mmol) in anhydrous CH$_2$Cl$_2$ (10 mL) iodine (680 mg, 2.68 mmol) was added. The resulting mixture was stirred for 30 min and poured into a silica gel column and eluted with EtOAc-hexanes (1:4) to give a syrupy product (1.3 g, quantitative) and used in next reaction without further characterization.

Synthesis of (2R,3R,4R,5R)-5-(2-amino-6-chloro-9H-purin-9-yl)-2-(benzoyloxymethyl)-4-fluoro-4-methyltetrahydrofuran-3-yl benzoate (12)

To a 12 L of three-neck round-bottomed flask was charged 6-chloro-2-aminopurine (225.4 g, 1.329 mol). Anhydrous tert-BuOH (4.5 L) was added and the solution was stirred with a mechanical stirrer at ambient temperature. Potassium tert-butoxide (solid, 151.6 g, 1.35 mol) was added portion-wise under a flow of nitrogen gas while stirring. The mixture was stirred at RT for an additional 30 min. To a 5 L round-bottomed flask was loaded the α-bromide (10, 197 g, 0.451 mol) and 3 L of anhydrous acetonitrile at ambient temperature. The bromide solution was added to the purine base suspension over 1 min at ambient temperature. The 5 L flask was rinsed with acetonitrile (2×1 L) to transfer bromide completely to the reaction mixture. The mixture was heated gradually to 50° C. over 2 h with a heating mantle and controller, and stirred for 20 h. The reaction was almost complete as shown by TLC beta (R$_f$ 0.28, 30% EtOAc in hexanes). The reaction was quenched by the addition of sat. NH$_4$Cl (200 mL) to form a suspension. The suspended solid[1] was removed by filtration through a 3 cm pad of Celite in a 2.5 L porcelain Buchner funnel. The solid was washed with toluene (3×100 mL). The combined filtrate was neutralized by adding 6 N HCl solution until pH 7 (approx 220 mL). The mixture was concentrated under reduced pressure. When the volume of mixture was reduced to about one-third volume, additional precipitated solid was removed by filtration in a similar manner. The filtrate was further concentrated to a volume of about 800 mL. The residue was loaded onto a plug column (1.6 kg flash grade silica gel in a 6 L sintered glass Buchner funnel) and eluted (via suction) with a gradient of 10% ethyl acetate in hexanes (6 L) to remove non-polar impurities, 30% ethyl acetate in hexanes to afford a small amount of lactol (6 L), and then 40%~45% ethyl acetate in hexanes (4 L) to elute the main amount of product. The product containing fractions were combined, concentrated under reduced pressure and dried under vacuum (0.2 mmHg, 24 h, ambient temp.) to a white foam solid (150.7 g, β/α=14:1 by NMR.

$^1$H-NMR. (CDCl$_3$) beta: δ=1.33 (d, 22.4 Hz, 2'-C—CH$_3$), alpha: 1.55 (d, 22 Hz, 2'-C—CH$_3$).

The product mixture foam was dissolved in methanol (700 mL) at ambient temperature. Upon standing, a solid slowly formed over 2 h. The suspension was cooled in a freezer to −5° C. for 17 h. The resulting white solid was collected by filtration and washed with cold MeOH (−5° C., 3×60 mL) and ethyl ether (3×100 mL). The solid was dried under vacuum (0.2 mmHg, 24 h, ambient temp.) to afford 110.5 g of β-product with excellent de (β/α 99.8:1 by HPLC). The filtrate was partially concentrated (ca. 400 mL) and then diluted with more MeOH (400 mL) while heating to 60° C. The solution was cooled down to ambient temperature, seeded and the cooled to −5° C. The second crop was collected, washed and dried in a similar manner to give more product as a white solid (12.26 g) with similar diastereomeric purity. The mother liquor was concentrated to dryness under reduced pressure (ca. 25 g). The residue was a mixture of β and α-isomers. It was subjected to automated silica gel column chromatography (Analogix, 240 g cartridge, 40% to 50% ethyl acetate in hexanes) to afford 14.52 g of product foam which was recrystallized from MeOH, washed and dried in a similar manner to afford an additional 8.46 g of product in high purity.

The three solids were judged to be of similar purity and they were combined to give 131.2 g of white crystalline product 12, (55% from bromosugar, 49% from lactol). Mp 160.5-162.0° C. HPLC purity 99.5% including 0.20% alpha.

$^1$H-NMR (pure β-anomer, CDCl$_3$): δ=8.03 (m, 2H, arom.), 7.93 (m, 2H, arom.), 7.88 (s, 1H, C8-H), 7.60 (m, 1H, arom.), 7.50 (m, 1H, arom.), 7.44 (m, 2H, arom.), 7.33 (m, 2H, arom.), 6.44 (dd, 1H, C1'-H), 6.12 (d, 1H, C3'-H), 5.35 (s, 2H, NH$_2$), 5.00 (dd, 1H, C5'-Ha), 4.76 (m, 1H, C4'-H), 4.59 (dd, 1H, C5'-Hb), 1.33 (d, 3H, CH$_3$).

$^1$H-NMR (α-isomer, CDCl$_3$): δ=8.11-8.09 (m, 3H, arom. and C8-H), 8.01 (m, 2H, arom.), 7.63 (m, 1H, arom.), 7.55 (m, 1H, arom.), 7.48 (m, 2H, arom.), 7.39 (m, 2H, arom.), 6.35 (d, 1H, C1'-H), 5.76 (dd, 1H, C3'-H), 5.18 (s, 2H, NH$_2$), 4.93-4.89 (m, 1H, C4'-H), 4.75-4.71 (m, 1H, C5'-Ha), 4.58-4.54 (m, 1H, C5'-Hb), 1.55 (d, 3H, CH$_3$).

Synthesis of (2R,3R,4R,5R)-5-(2-amino-6-chloro-9H-purin-9-yl)-2-(benzoyloxymethyl)-4-fluoro-4-methyltetrahydrofuran-3-yl benzoate (12) from Compound 9

To a solution of compound 9 (450 mg, 2.68 mmol) in chlorobenzene (1.5 mL) were added potassium salt of the base (1.37 g, 8.05 mmol) in t-butanol (5 mL) and subsequently anhydrous acetonitrile (5 mL) at rt. The resulting mixture was stirred at 80-140° C. in a sealed tube for 7 days and concentrated in vacuo after neutralization with HCl. The residue was purified by silica gel column chromatography (hexanes:EtOAc=2:1) to give compound 12 (90 mg, 15%) as a white foam.

Synthesis of (2R,3R,4R,5R)-5-(2-amino-6-chloro-9H-purin-9-yl)-2-(benzoyloxymethyl)-4-fluoro-4-methyltetrahydrofuran-3-yl benzoate (12) from Compound 11

To a solution of compound 11 (1.3 g, 2.68 mmol) in t-butanol (10 mL) was added sodium salt of the base (1.37 g, 8.05 mmol) in DMF (10 mL) at ambient temperature. The resulting mixture was stirred for 15 h and concentrated in vacuo.

The residue was purified by silica gel column chromatography (hexanes:EtOAc=2:1) to give compound 12 (220 mg, 16%) as a white foam.

Synthesis of (2R,3R,4R,5R)-5-(2-amino-6-methoxy-9H-purin-9-yl)-4-fluoro-2-(hydroxymethyl)-4-methyltetrahydrofuran-3-ol (13)

To a 250 mL dry round-bottomed flask was charged (2R,3R,4R,5R)-5-(2-amino-6-chloro-9H-purin-9-yl)-2-(benzoyloxymethyl)-4-fluoro-4-methyltetrahydrofuran-3-yl benzoate (12, 7.50 g, 14.26 mmol) Anhydrous methanol (30 mL) was added and a white suspension was formed. At 50° C., a solution of sodium methoxide in methanol (25%, 19.7 mL, 64.17 mmol) was added via a dry syringe under a nitrogen atmosphere. A white cloudy reaction mixture was formed. After 3.5 h at 50° C., the reaction was complete with no starting material left as shown by TLC test. The mixture was cooled down to room temperature and neutralized by addition of glacial acetic acid (3 mL). A white solid was filtered out and washed with methanol (3×5 mL). The filtrate was mixed with 20 g of silica gel and concentrated to dryness. The mixture was loaded in line with a silica gel cartridge and separated via column chromatography using a gradient of methanol in dichloromethane 0 to 15% MeOH. The product eluted out at 12% methanol in dichloromethane. The product containing fractions were combined, concentrated under reduced pressure and dried under vacuum (0.2 mmHg, 50° C., 24 h) to a white powder solid (4.45 g, 98% yield), mp 199-202° C.

$^1$H-NMR (DMSO-d$_6$): δ=8.18 (1H, s, C8-H), 6.61 (2H, s, NH$_2$), 6.05 (1H, d, C1'-H), 5.68 (1H, d, 3'-OH), 5.26 (1H, m, 5'-OH), 4.23-4.13 (1H, m, C3'-H), 3.96 (3H, s, OCH$_3$), 3.92-3.83 (2H, m, C4'-H and C5'-H$_a$), 3.70-3.67 (1H, m, C5'-H$_b$), 1.06 (3H, d, C2'-CH$_3$).

Synthesis of (2R,3R,4R,5R)-5-(2-amino-6-(azetidin-1-yl)-9H-purin-9-yl)-4-fluoro-2-(hydroxymethyl)-4-methyltetrahydrofuran-3-ol (14)

To a 350 mL of dry seal pressure flask (Chemglass) were added (2R,3R,4R,5R)-5-(2-amino-6-chloro-9H-purin-9-yl)-2-(benzoyloxymethyl)-4-fluoro-4-methyltetrahydrofuran-3-yl benzoate (12, 3.6 g, 6.85 mmol) and 150 mL of absolute ethanol. Azetidine hydrochloride (2.56 g, 27.4 mmol) was added and then followed by triethylamine (4.16 g, 41.1 mmol). The supension was stirred and heated to 70° C. while sealed for 5 hours. All the starting material was consumed but the benzoyl groups remained as shown by TLC. Sodium methoxide (7.8 mL, 34.3 mmol, 25% solution in methanol) was added to the mixture and heated at 50° C. The reaction was complete after 3.5 h. The reaction mixture was allowed to cool to room temperature and neutralized by addition of glacial acetic acid (0.41 g, 6.85 mmol). The mixture was concentrated under reduced pressure and then the residue was triturated with ethyl acetate. The resulting solid was removed by filtration and the solid was washed with EtOAc (2×15 mL). The filtrate was concentrated under reduced pressure and the residue was purified via column chromatography (Analogix, 120 g cartridge, gradient of 0 to 15% MeOH in DCM). The pure product containing fractions were combined, concentrated under reduced pressure and dried (50° C., 0.2 mmHg, 17 h) to a light pink colored foam solid (2.15 g, 6.35 mmol, 93%).

$^1$H-NMR (DMSO-d$_6$) δ=8.00 (s, 1H, C8-H), 6.03 (s, 2H, NH$_2$), 6.00 (d, 1H, C1'-H), 5.64 (d, 1H, 3'-OH), 5.24 (t, 1H, 5'-OH), 4.24-4.10 (m, 5H, N—CH$_2$ of azetidine, C3'-H), 3.90-3.81 (m, 2H, C4'-H and C5'-H$_a$), 3.69-3.64 (m, 1H, C5'-H$_b$), 2.37 (penta, 2 H, center CH$_2$ of azetidine), 1.05 (d, 3H, C2'-CH$_3$).

Synthesis of (2R,3R,4R,5R)-5-(2-amino-6-(benzyloxy)-9H-purin-9-yl)-4-fluoro-2-(hydroxymethyl)-4-methyltetrahydrofuran-3-ol (15)

To a 500 mL of dry round-bottomed flask were added (2R,3R,4R,5R)-5-(2-amino-6-chloro-9H-purin-9-yl)-2-(benzoyloxymethyl)-4-fluoro-4-methyltetrahydrofuran-3-yl benzoate (12, 8.0 g, 15.2 mmol) and anhydrous benzyl alcohol (128 mL). To another 250 mL of dry round-bottomed flask were charged NaH (60% in mineral oil, 2.44 g, 60.8 mmol) and anhydrous DMF (40 mL). The suspension was stirred at 0° C. in an ice-water bath. Benzyl alcohol (27 mL) was added drop-wise via a syringe. A solution was slowly formed and it was transferred to the nucleoside suspension quickly under a nitrogen atmosphere at room temperature. The mixture was heated to 50° C. and stirred. The reaction was complete after 3 h and cooled to ambient temperature. It was neutralized by the addition of 4 N HCl to ca. pH=7 (12 mL). The solution was concentrated under reduced pressure (4 mbar, 90° C. bath). The cloudy residue was diluted with dichloromethane (100 mL) and washed with water (3×30 mL), brine (30 mL) and dried over Na$_2$SO$_4$. The suspension was filtered and the filtrate was concentrated under reduced pressure to an oily residue. This was purified by column chromatography (Analogix, 0 to 8% gradient of MeOH in DCM). The product eluted at 4% MeOH in DCM. The product containing fractions were combined, concentrated under reduced pressure and dried (50° C., 0.2 mmHg, 17 h) to a white foam solid (4.57 g, 11.7 mmol, 77.2%).

$^1$H-NMR (DMSO-d$_6$) δ=8.18 (s, 1H, 8-H), 7.53-7.51 (m, 2H, arom-H), 7.43-7.34 (m, 3H, arom-H), 6.66 (s, 2H, NH$_2$), 6.05 (d, 1H, C1'-H), 5.67 (d, 1H, 3'-OH), 5.48 (dd, 2H, CH$_2$ of Benzyl), 5.25 (t, 1H, 5'-OH), 4.18 (dt, 1H, C3'-H), 3.92-3.82 (m, 2H, C4'-H and C5'-H$_a$), 3.71-3.66 (m, 1H, C5'-H$_b$), 1.07 (d, 3H, C2'-CH$_3$).

Synthesis of (2R,3R,4R,5R)-5-(2-amino-6-ethoxy-9H-purin-9-yl)-4-fluoro-2-(hydroxymethyl)-4-methyltetrahydrofuran-3-ol (16)

To a 500 mL of dry round-bottomed flask was loaded (12, 11 g, 20.92 mmol). Anhydrous absolute ethanol (210 mL) was added and followed by anhydrous K$_2$CO$_3$ (28.91 g, 209.2 mmol). The suspension was stirred and heated at 75° C. under nitrogen for 5.5 h. All the starting material was consumed at that time by TLC test. The mixture was cooled to room temperature and solid was filtered out. The filtrate was neutralized by addition of glacial acetic acid (2.52 g) to pH~7 and concentrated under reduced pressure. The residue was dissolved in methanol and mixed with silica gel (15 g). The dried mixture of crude product and silica gel was transferred to an empty cartridge and separated through column chromatography (Analogix 220 g, gradient of 0 to 15% MeOH in DCM) to afford product (5% MeOH in DCM) as a white foam solid (3.73 g, 54.5%). A second white solid was isolated from column (10% MeOH in DCM, 1.44 g) and it is a mixture of two dimers of nucleoside. A more polar, third white solid was collected from column (15% MeOH in DCM, 0.47 g) and it is a mixture of trimers of nucleoside. HPLC purity of product 99.94%.

$^1$H-NMR (DMSO-d$_6$): δ 8.16 (s, 1H, 8-H), 6.55 (s, 2H, NH$_2$), 6.04 (d, 1H, C1'-H), 5.66 (d, 1H, 3'-OH), 5.24 (m, 1H, 5'-OH), 4.44 (q, 2H, 6-OCH$_2$), 4.23-4.08 (m, 1H, C3'-H), 3.91-3.82 (m, 2H, C4'-H and C5'-H$_a$), 3.71-3.66 (m, 1H, C5'-H$_b$), 1.36 (t, 3H, CH$_3$ of ethyl), 1.06 (d, 3H, C2'-CH$_3$).

Synthesis of 6-Azetidin-1-yl-9-((4aR,6R,7R,7aR)-7-fluoro-2-methoxy-7-methyl-tetrahydro-furo[3,2-d][1,3,2]dioxaphosphinin-6-yl)-9H-purin-2-ylamine phosphite precursor to 17

(2R,3R,4R,5R)-5-(2-Amino-6-azetidin-1-yl -purin-9-yl)-4-fluoro-2-hydroxymethyl-4-methyl-tetrahydro-furan-3-ol (14, 340 mg, 1.0 mmol) was dissolved in anhydrous pyridine (6 ml) at ambient temperature. A solution of 0.45 M 1H-tetrazole in acetonitrile (5.5 mL, 2.5 mmol) was added followed by bis (N,N-diisopropylamino)methylphosphoramidite (317 µL, 1.1 mmol). The mixture was stirred at ambient temperature for 17 h. The solvent was concentrated under reduced pressure and the residue was triturated with ethyl acetate (20 mL). The resulting precipitant of salts was removed by filtration and the filtrate was concentrated under reduced pressure. The residue was purified by silica gel column chromatography using a gradient of ethyl acetate in hexanes (40-80%). The product containing fractions were combined and concentrated to a white solid, 47 mg (12% yield).

Synthesis of 6-Azetidin-1-yl-9-((4aR,6R,7R,7aR)-7-fluoro-2-methoxy-7-methyl-2-oxo-tetrahydrofuro[3,2-d][1,3,2]dioxaphosphinin-6-yl)-9H-purin-2-ylamine (17, cf. 3)

To a stirred solution of the cyclic phosphite (47 mg, 0.12 mmol) in dichloromethane (2 mL) was added 77% mCPBA (32 mg, 0.14 mmol) at ambient temperature. After 5 min, the solution was concentrated under reduced pressure the residue was purified by silica gel column chromatography (4 g) using a gradient of ethyl acetate in hexanes (80-100%). The pure product fractions were combined and concentrated under reduced pressure to a white solid, 21 mg (43%).

$^1$H-NMR (400 MHz, CDCl$_3$): δ=7.45 and 7.44 (two s, 1H), 5.45 (d, J=20 Hz, 1H), 4.89-4.41 (m, 10H), 3.93 (app. t, J=13.0 Hz, 3H), 2.49 (bs, 2H), 1.39 (overlapping d, J=22.4 Hz, 3H); MS (ESI) m/z 415 (M+H)$^+$.

$^{31}$P-NMR (162 MHz, CDCl$_3$): δ=−1.26, −3.58;

Synthesis of 6-Ethoxy-9-((4aR,6R,7R,7aR)-7-fluoro-2-methoxy-7-methyl-2-oxo-tetrahydro-2,5-furo[3,2-d][1,3,2]dioxaphosphinin-6-yl)-9H-purin-2-ylamine (18)

(2R,3R,4R,5R)-5-(2-Amino-6-ethoxy-purin-9-yl) -4-fluoro-2-hydroxymethyl-4-methyl-tetrahydro-furan-3-ol (16, 150 mg, 0.46 mmol) was dissolved in anhydrous pyridine (2 ml) at 0° C. A solution of 0.45 M 1H-tetrazole in acetonitrile (2.55 mL) was added followed by bis (N,N-diisopropylamino)methylphosphoramidite (0.16 mL, 0.55 mmol). The mixture was allowed to slowly warm to ambient temperature over 5 h. TLC indicated a complete reaction. The reaction was quenched upon the addition of water (0.1 mL). The reaction solution was concentrated under reduced pressure and then the residue was triturated with ethyl acetate (5 mL). The resulting white precipitate was removed by filtration and the filtrate was concentrated under reduced pressure. The resulting intermediate cyclic phosphite residue was dissolved in acetonitrile (2 mL) and then treated with t-butyl hydroperoxide (70% in water, 0.25 mL) for 17 at ambient temperature. TLC indicated a complete reaction. The reaction solution was concentrated under reduced pressure and the residue was purified by column chromatography (Analogix using a gradient of 0 to 10% IPA in DCM). The product containing fractions were combined and concentrated under reduced pressure to a white solid, 80 mg (34% yield) as a mixture of two diastereomers ~2:1.

$^1$H-NMR (400 MHz, DMSO-d$_6$): δ=8.16 (s, 1.5H), 6.65 (s, 2H), 6.55 (bs, 1H), 6.28 (d, J=20.8 Hz, 1.5H), 4.78-4.60 (m, 4.5H), 4.45 (q, J=6.8 Hz, 1H), 4.44 (q, J=6.8 Hz, 2H), 4.28-4.22 (m, 1.5H), 3.83 (d, J=11.6 Hz, 1.5H), 3.76 (d, J=11.6 Hz, 3H), 1.36 (t, J=7.2 Hz, 1.5H), 1.36 (t, J=7.2 Hz, 3H), 2.46 (d, J=22.4 Hz, 1.5H), 2.44 (d, J=22.8 Hz, 3H).

$^{31}$P-NMR (162 MHz, DMSO-d$_6$): δ=−3.25, −4.16.

LRMS (ESI): [M+H]$^+$ calculated for C$_{14}$H$_{20}$FN$_5$O$_6$P 404.3, found 404.3.

Synthesis of 6-Ethoxy-9-((4aR,6R,7R,7aR)-7-fluoro-2-isopropoxy-7-methyl-2-oxo-tetrahydro-2,5-furo[3,2-d][1,3,2]dioxaphosphinin-6-yl)-9H-purin-2-yl amine (19)

(2R,3R,4R,5R)-5-(2-Amino-6-ethoxy-purin-9-yl) -4-fluoro-2-hydroxymethyl-4-methyl-tetrahydro-furan-3-ol (16, 150 mg, 0.46 mmol) was dissolved in anhydrous pyridine (2 ml) at 0° C. A solution of 0.45 M 1H-tetrazole in acetonitrile (2.55 mL) was added followed by bis (N,N-diisopropylamino)ispropylphosphoramidite (0.16 mL, 0.55 mmol, 1.2 eq). The mixture was allowed to slowly warm to ambient temperature over 3 h. TLC indicated a complete reaction. The reaction was quenched upon the addition of water (0.1 mL). The reaction solution was concentrated under reduced pressure and then the residue was triturated with ethyl acetate (5 mL). The resulting white precipitate was removed by filtration and the filtrate was concentrated under reduced pressure. The resulting intermediate cyclic phosphite residue was dissolved in acetonitrile (2 mL) and then treated with t-butyl hydroperoxide (70% in water, 0.19 mL) for 5 h at ambient temperature. TLC indicated a complete reaction. The reaction solution was concentrated under reduced pressure and the residue was purified by column chromatography (Analogix using a gradient of 0 to 5% IPA in DCM). The two diastereomers (19a and 19b) were separable. Fractions containing each diastereomer were separately combined and concentrated under reduced pressure to white solids to give 20 mg of each diastereomer (combined yield 20%).

19a $^{31}$P-NMR (162 MHz, DMSO): δ=−6.49;

$^1$H-NMR (400 MHz, DMSO): δ=8.17 (s, 1H), 6.47 (bs, 2H), 6.27 (d, J=21.2 Hz, 1H), 4.73-4.62 (m, 4H), 4.45 (q, J=7.0 Hz, 2H), 4.27-4.21 (m, 1H), 1.39-1.34 (m, 9H), 1.20 (d, J=22.8 Hz, 3H).

MS (ESI): m/z 432.4 [M+H]$^+$.

19b $^{31}$P-NMR (162 MHz, DMSO): δ=−4.68;

$^1$H-NMR (400 MHz, DMSO): δ 8.15 (s, 1H), 6.63 (s, 2H), 6.27 (d, J=21.2 Hz, 1H), 4.74-4.58 (m, 4H), 4.45 (q, J=6.4 Hz, 2H), 4.42-4.37 (m, 1H), 1.36 (t, J=7.2 Hz, 3H), 1.32 (d, J=3.6 Hz, 3H), 1.30 (d, J=3.6 Hz, 3H), 1.22 (d, J=22.8 Hz, 3H).

MS (ESI): m/z 432.4 [M+H]$^+$.

The structures for 19a and 19b are represented below.

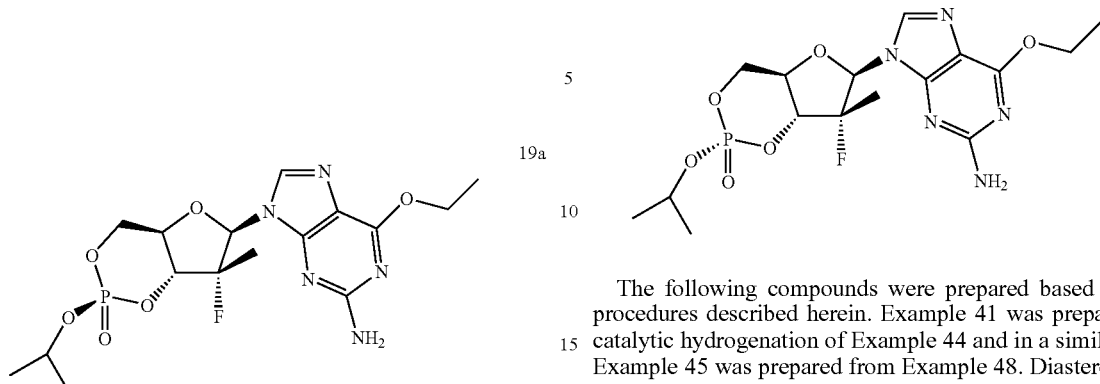

The following compounds were prepared based on the procedures described herein. Example 41 was prepared by catalytic hydrogenation of Example 44 and in a similar way Example 45 was prepared from Example 48. Diastereomers of some of the compounds have been resolved, but where the absolute stereochemistry is not known, the same structures are provided.

| Ex No | Structure | Chemical Name | Analytical Data |
|---|---|---|---|
| 20 | 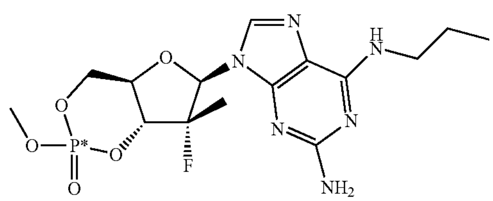 | 9-((4aR,6R,7R,7aR)-7-Fluoro-2-methoxy-7-methyl-2-oxo-tetrahydro-2λ$^5$-furo[3,2-d][1,3,2]dioxaphosphinin-6-yl)-N$^6$-propyl-9H-purine-2,6-diamine | $^{31}$P NMR (162 MHz, CDCl$_3$): δ −1.22, −3.64; MS (ESI) m/z 417 (M + H)$^+$. |
| 21 | 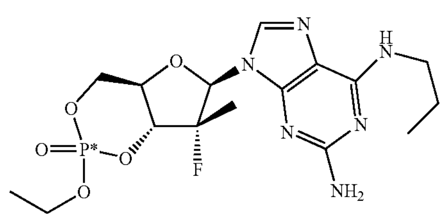 | 9-((4aR,6R,7R,7aR)-2-Ethoxy-7-fluoro-7-methyl-2-oxo-tetrahydro-2λ5-furo[3,2-d][1,3,2]dioxaphosphinin-6-yl)-N$^6$-propyl-9H-purine-2,6-diamine | $^{31}$P NMR (162 MHz, CDCl$_3$): δ −4.78; MS (ESI) m/z 431.3 (M + H)$^+$. |
| 22 | 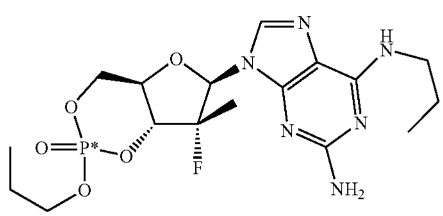 | 9-((4aR,6R,7R,7aR)-7-Fluoro-7-methyl-2-oxo-2-propoxy-tetrahydro-2λ$^5$-furo[3,2-d][1,3,2]dioxaphosphinin-6-yl)-N$^6$-propyl-9H-purine-2,6-diamine | $^{31}$P NMR (162 MHz, CDCl$_3$): δ −4.75; MS (ESI) m/z 445.3 (M + H)$^+$. |
| 23 | 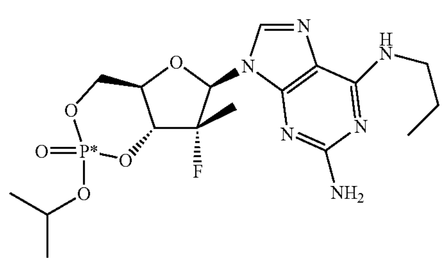 | 9-((4aR,6R,7R,7aR)-7-Fluoro-2-isopropoxy-7-methyl-2-oxo-tetrahydro-2λ$^5$-furo[3,2-d][1,3,2]dioxaphosphinin-6-yl)-N$^6$-propyl-9H-purine-2,6-diamine | $^{31}$P NMR (162 MHz, CDCl$_3$): δ −5.77; MS (ESI) m/z 445.3 (M + H)$^+$. |

-continued

| Ex No | Structure | Chemical Name | Analytical Data |
|---|---|---|---|
| 24 | 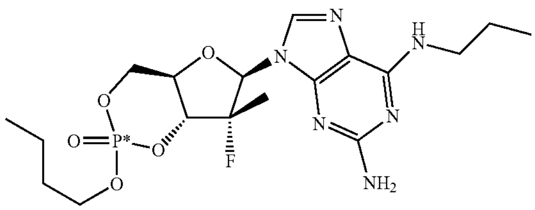 | 9-((4aR,6R,7R,7aR)-2-Butoxy-7-fluoro-7-methyl-2-oxo-tetrahydro-2λ$^5$-furo[3,2-d][1,3,2]dioxaphosphinin-6-yl)-N$^6$-propyl-9H-purine-2,6-diamine | $^{31}$P NMR (162 MHz, CDCl$_3$): δ −4.74; MS (ESI) m/z 459.4 (M + H)$^+$. |
| 25 | 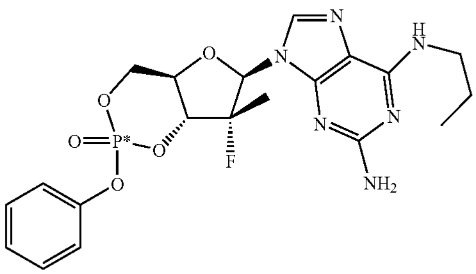 | 9-((4aR,6R,7R,7aR)-7-Fluoro-7-methyl-2-oxo-2-phenoxy-tetrahydro-2λ$^5$-furo[3,2-d][1,3,2]dioxaphosphinin-6-yl)-N$^6$-propyl-9H-purine-2,6-diamine | $^{31}$P NMR (162 MHz, CDCl$_3$): δ −10.84; MS (ESI) m/z 479.3 (M + H)$^+$. |
| 26 | 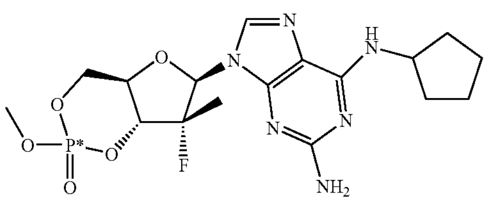 | N$^6$-Cyclopentyl-9-((4aR,6R,7R,7aR)-7-fluoro-2-methoxy-7-methyl-2-oxo-tetrahydro-2λ$^5$-furo[3,2-d][1,3,2]dioxaphosphinin-6-yl)-9H-purine-2,6-diamine | $^{31}$P NMR (162 MHz, CDCl$_3$): δ −1.20, −3.64; MS (ESI) m/z 443 (M + H)$^+$. |
| 27 | 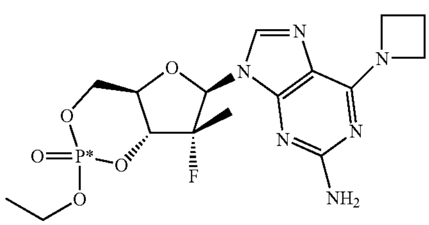 | 6-Azetidin-1-yl-9-((4aR,6R,7R,7aR)-2-ethoxy-7-fluoro-7-methyl-2-oxo-tetrahydro-2λ$^5$-furo[3,2-d][1,3,2]dioxaphosphinin-6-yl)-9H-purin-2-ylamine | $^{31}$P NMR (162 MHz, CDCl$_3$): δ −4.78; MS (ESI) m/z 429.3 (M + H)$^+$. |
| 28a | 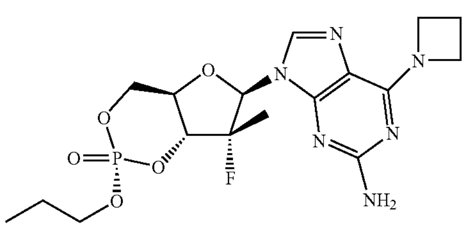 | 6-Azetidin-1-yl-9-((4aR,6R,7R,7aR)-7-fluoro-7-methyl-2-oxo-2-propoxy-tetrahydro-2λ$^5$-furo[3,2-d][1,3,2]dioxaphosphinin-6-yl)-9H-purin-2-ylamine | $^1$H NMR (400 MHz, DMSO): δ 7.95 (s, 1H), 6.22 (d, J = 20.8 Hz, 1H), 6.07 (s, 2H), 4.65-4.75 (m, 1H), 4.50-4.65 (m, 1H), 4.15-4.45 (m, 5H), 3.95-4.10 (m, 3H), 2.30-2.40 (m, 2H), 1.60-1.70 (m, 2H), 1.20 (d, J = 22.8 Hz, 3H), 0.90 (t, J = 7.2 Hz, 3H). MS(ESI), m/z 443.14 (M + 1)$^+$. |
| 28b | 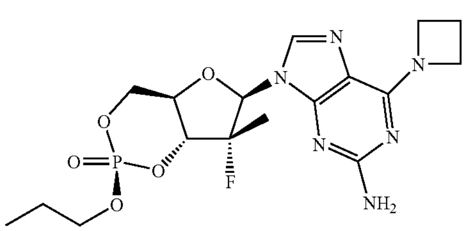 | 6-Azetidin-1-yl-9-((4aR,6R,7R,7aR)-7-fluoro-7-methyl-2-oxo-2-propoxy-tetrahydro-2λ$^5$-furo[3,2-d][1,3,2]dioxaphosphinin-6-yl)-9H-purin-2-ylamine | $^{31}$P NMR (162 MHz, CDCl$_3$): δ −4.75; MS (ESI) m/z 443.3 (M + H)$^+$. |

| Ex No | Structure | Chemical Name | Analytical Data |
|---|---|---|---|
| 29 | 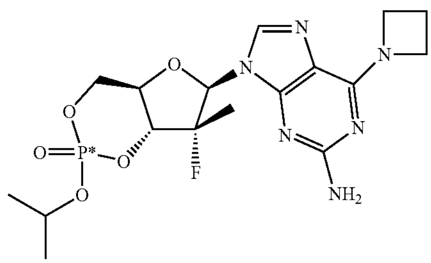 | 6-Azetidin-1-yl-9-((4aR,6R,7R,7aR)-7-fluoro-2-isopropoxy-7-methyl-2-oxo-tetrahydro-2λ⁵-furo[3,2-d][1,3,2]dioxaphosphinin-6-yl)-9H-purin-2-ylamine | $^{31}$P NMR (162 MHz, CDCl$_3$): δ −5.77; MS (ESI) m/z 443.3 (M + H)⁺. |
| 30 | 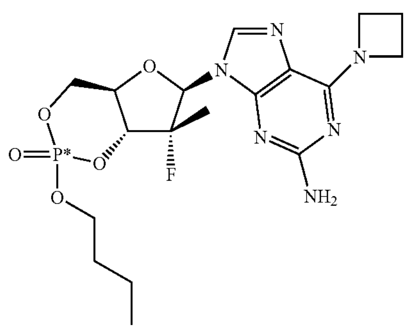 | 6-Azetidin-1-yl-9-((4aR,6R,7R,7aR)-2-butoxy-7-fluoro-7-methyl-2-oxo-tetrahydro-2λ⁵-furo[3,2-d][1,3,2]dioxaphosphinin-6-yl)-9H-purin-2-ylamine | $^{1}$H NMR (400 MHz, DMSO): δ 7.91 (s, 1H), 6.21 (d, J = 20.8 Hz, 1H), 5.85 (s, 2H), 4.50-4.75 (m, 3H), 3.90-4.40 (m, 7H), 2.30-2.40 (m, 2H), 1.60-1.70 (m, 2H), 1.30-1.40 (m, 2H), 1.15 (d, J = 22.8 Hz, 3H), 0.85 (t, J = 7.2 Hz, 3H). MS(ESI), m/z 457.17 (M + 1)⁺. |
| 31 | 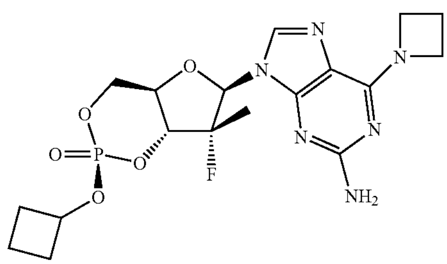 | 6-Azetidin-1-yl-9-((4aR,6R,7R,7aR)-2-cyclobutoxy-7-fluoro-7-methyl-2-oxo-tetrahydro-2λ⁵-furo[3,2-d][1,3,2]dioxaphosphinin-6-yl)-9H-purin-2-ylamine | $^{1}$H NMR (400 MHz, DMSO): δ 7.95 (s, 1H), 6.25 (d, J = 22.2 Hz, 1H), 4.74-4.83 (m, 1H), 4.60-4.69 (m, 2H), 4.19-4.31 (m, 6H), 2.30-2.39 (m, 2H), 2.22-2.27 (m, 4H), 1.67-1.75 (m, 1H), 1.46-1.58 (m, 1H), 1.19 (d, J = 22.4 Hz, 3H), MS(ESI), m/z 455.2 (M + 1)⁺. |
| 32a | 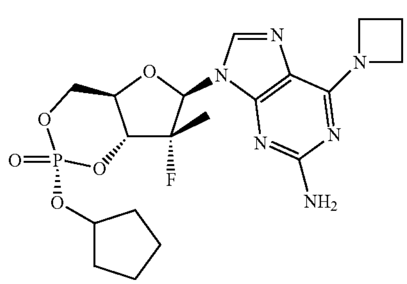 | 6-Azetidin-1-yl-9-((4aR,6R,7R,7aR)-2-cyclopentyloxy-7-fluoro-7-methyl-2-oxo-tetrahydro-2λ⁵-furo[3,2-d][1,3,2]dioxaphosphinin-6-yl)-9H-purin-2-ylamine | $^{1}$H NMR (400 MHz, DMSO): δ 7.96 (s, 1H), 6.21 (d, J = 21.2 Hz, 1H), 6.07 (s, 2H), 4.85-4.95 (m, 1H), 4.55-4.70 (m, 2H), 4.00-4.45 (m, 6H), 2.30-2.40 (m, 2H), 1.75-1.85 (m, 3H), 1.50-1.70 (m, 5H), 1.20 (d, J = 22.4 Hz, 6H). MS(ESI), m/z 469.11 (M + 1)⁺. |

| Ex No | Structure | Chemical Name | Analytical Data |
|---|---|---|---|
| 32b | 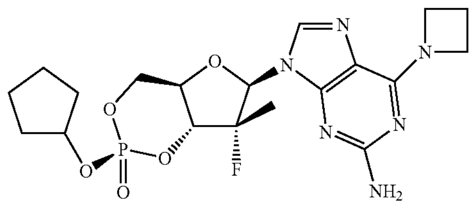 | 6-Azetidin-1-yl-9-((4aR,6R,7R,7aR)-2-cyclopentyloxy-7-fluoro-7-methyl-2-oxo-tetrahydro-2$\lambda^5$-furo[3,2-d][1,3,2]dioxaphosphinin-6-yl)-9H-purin-2-ylamine | $^1$H NMR (400 MHz, DMSO): δ 7.94 (s, 1H), 6.24 (d, J = 20.8 Hz, 1H), 5.85 (s, 2H), 4.85-4.95 (m, 1H), 4.60-4.75 (m, 2H), 4.00-4.60 (m, 6H), 2.30-2.40 (m, 2H), 1.80-1.90 (m, 3H), 1.70-1.80 (m, 3H), 1.50-1.60 (m, 2H), 1.14 (d, J = 22.4 Hz, 6H). MS(ESI), m/z 469.10 (M + 1)$^+$. |
| 33a | 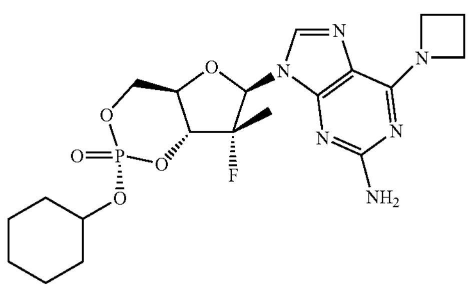 | 6-Azetidin-1-yl-9-((4aR,6R,7R,7aR)-2-cyclohexyloxy-7-fluoro-7-methyl-2-oxo-tetrahydro-2$\lambda^5$-furo[3,2-d][1,3,2]dioxaphosphinin-6-yl)-9H-purin-2-ylamine | $^1$H NMR (400 MHz, DMSO): δ 7.94 (s, 1H), 6.23 (d, J = 21.2 Hz, 1H), 5.80 (s, 2H), 4.55-4.75 (m, 2H), 4.35-4.45 (m, 2H), 4.00-4.35 (m, 5H), 2.30-2.40 (m, 2H), 1.85-2.00 (m, 2H), 1.65-1.80 (m, 2H), 1.50-1.65 (m, 2H), 1.40-1.50 (m, 1H), 1.10-1.40 (m, 6H). MS(ESI), m/z 483.13 (M + 1)$^+$. |
| 33b | 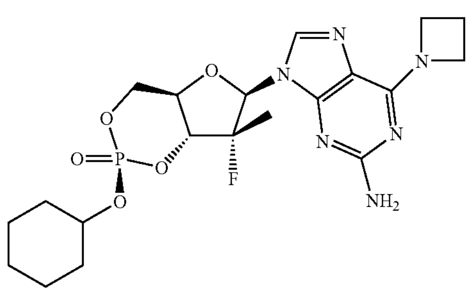 | 6-Azetidin-1-yl-9-((4aR,6R,7R,7aR)-2-cyclohexyloxy-7-fluoro-7-methyl-2-oxo-tetrahydro-2$\lambda^5$-furo[3,2-d][1,3,2]dioxaphosphinin-6-yl)-9H-purin-2-ylamine | $^1$H NMR (400 MHz, DMSO): δ 7.97 (s, 1H), 6.20 (d, J = 21.6 Hz, 1H), 6.05 (s, 2H), 4.65-4.75 (m, 1H), 4.50-4.65 (m, 1H), 4.30-4.45 (m, 3H), 4.10-4.30 (m, 4H), 2.30-2.40 (m, 2H), 1.80-1.90 (m, 2H), 1.60-1.70 (m, 2H), 1.40-1.60 (m, 3H), 1.15-1.40 (m, 6H). MS(ESI), m/z 483.13 (M + 1)$^+$. |

| Ex No | Structure | Chemical Name | Analytical Data |
|---|---|---|---|
| 34a | 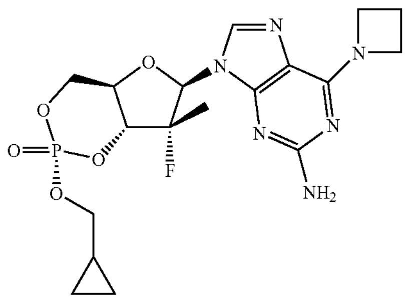 | 6-Azetidin-1-yl-9-((4aR,6R,7R,7aR)-2-cyclopropylmethoxy-7-fluoro-7-methyl-2-oxo-tetrahydro-2λ$^5$-furo[3,2-d][1,3,2]dioxaphosphinin-6-yl)-9H-purin-2-ylamine | $^1$H NMR (400 MHz, DMSO): δ 8.03 (s, 1H), 6.29 (d, J = 21.6 Hz, 1H), 6.16 (s, 2H), 5.10-5.25 (m, 1H), 4.60-4.85 (m, 2H), 4.15-4.50 (m, 5H), 2.30-2.45 (m, 4H), 2.10-2.25 (m, 2H), 1.70-1.80 (m, 1H), 1.50-1.60 (m, 1H), 1.28 (d, J = 22.8 Hz, 3H). MS(ESI), m/z 455.13 (M + 1)$^+$. |
| 34b | 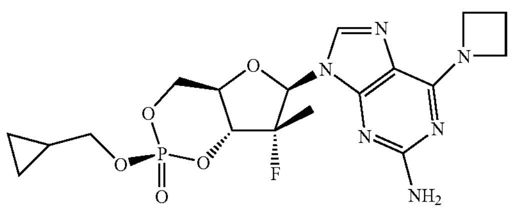 | 6-Azetidin-1-yl-9-((4aR,6R,7R,7aR)-2-cyclopropylmethoxy-7-fluoro-7-methyl-2-oxo-tetrahydro-2λ$^5$-furo[3,2-d][1,3,2]dioxaphosphinin-6-yl)-9H-purin-2-ylamine | $^1$H NMR (400 MHz, DMSO): δ = 7.95 (s, 1H), 6.23 (d, J = 20.8 Hz, 1H), 5.85 (s, 2H), 4.60-4.80 (m, 3H), 4.10-4.40 (m, 6H), 2.30-2.40 (m, 2H), 2.20-2.30 (m, 4H), 1.60-1.75 (m, 1H), 1.45-1.55 (m, 1H), 1.18 (d, J = 22.8 Hz, 3H). MS(ESI), m/z 455.13 (M + 1)$^+$. |
| 35 | 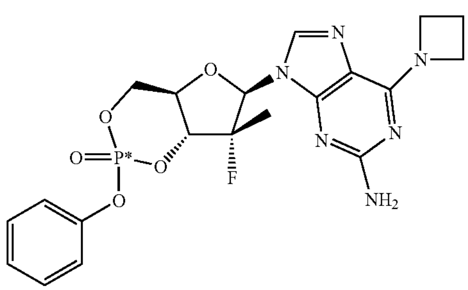 | 6-Azetidin-1-yl-9-((4aR,6R,7R,7aR)-7-fluoro-7-methyl-2-oxo-2-phenoxy-tetrahydro-2λ$^5$-furo[3,2-d][1,3,2]dioxaphosphinin-6-yl)-9H-purin-2-ylamine | $^{31}$P NMR (162 MHz, CDCl$_3$): δ −10.84; MS (ESI) m/z 477.3 (M + H)$^+$. |

| Ex No | Structure | Chemical Name | Analytical Data |
|---|---|---|---|
| 36a | 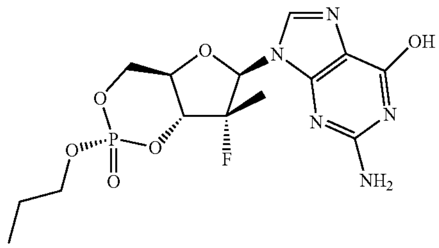 | 2-Amino-9-((2S,4aR,6R,7R,7aR)-7-fluoro-7-methyl-2-oxo-2-propoxy-tetrahydro-2$\lambda^5$-furo[3,2-d][1,3,2]dioxaphosphinin-6-yl)-9H-purin-6-ol | $^1$H NMR (400 MHz, DMSO-d6) δ 10.80 (s, 1H), 7.99 (s, 1H), 7.34 (s, 1H), 6.65 (s, 2H), 6.18 (d, J = 20.8 Hz, 1H), 4.78-4.57 (m, 2H), 4.41 (m, 1H), 4.03 (q, J = 8.0 Hz, 2H), 1.65 (sextet, J = 7.2 Hz, 2H), 1.24 (d, J = 22.8 Hz, 3H), 0.92 (t, J = 7.2 Hz, 3H); $^{31}$P NMR (162 MHz, DMSO-d6) δ −4.05; LRMS (ESI) calculated for $C_{14}H_{20}FN_5O_6P$ [(M + H)$^+$] 404.3, found 404.3. |
| 36b | 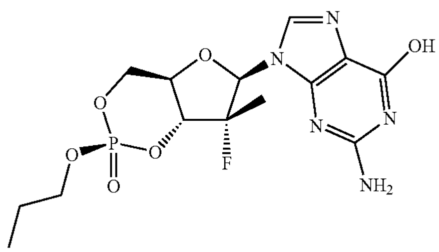 | 2-Amino-9-((2R,4aR,6R,7R,7aR)-7-fluoro-7-methyl-2-oxo-2-propoxy-tetrahydro-2$\lambda^5$-furo[3,2-d][1,3,2]dioxaphosphinin-6-yl)-9H-purin-6-ol | $^1$H NMR (400 MHz, DMSO-d6) δ 10.77 (s, 1H), 8.02 (s, 1H), 7.34 (s, 1H), 6.53 (bs, 2H), 6.19 (d, J = 20.8 Hz, 1H), 4.74-4.61 (m, 2H), 4.24 (m, 1H), 4.08 (q, J = 8.4 Hz, 2H), 1.72 (sextet, J = 7.2 Hz, 2H), 1.22 (d, J = 22.8 Hz, 3H), 0.95 (t, J = 7.2 Hz, 3H); $^{31}$P NMR (162 MHz, DMSO-d6) δ −5.36; LRMS (ESI) calculated for $C_{14}H_{20}FN_5O_6P$ [(M + H)$^+$] 404.3, found 404.3. |
| 37 | 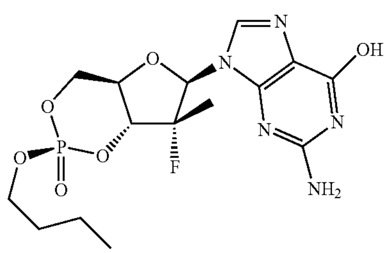 | 2-Amino-9-((2R,4aR,6R,7R,7aR)-2-butoxy-7-fluoro-7-methyl-2-oxo-tetrahydro-2$\lambda^5$-furo[3,2-d][1,3,2]dioxaphosphinin-6-yl)-9H-purin-6-ol | $^1$H NMR (400 MHz, DMSO): δ 10.76 (s, 1H), 7.98 (s, 1H), 6.51 (s, 2H), 6.17 (d, J = 21.6 Hz, 1H), 4.55-4.71 (m, 3H), 4.05-4.25 (m, 3H), 1.60-1.70 (m, 2H), 1.30-1.40 (m, 2H), 1.19 (d, J = 22.8 Hz, 3H), 0.88 (t, J = 7.2 Hz, 3H). MS(ESI) m/z 418.09 (M + 1)$^+$. |

| Ex No | Structure | Chemical Name | Analytical Data |
|---|---|---|---|
| 38a | 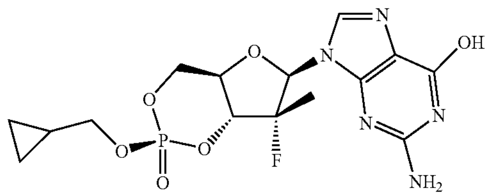 | 2-Amino-9-((4aR,6R,7R,7aR)-2-cyclopropylmethoxy-7-fluoro-7-methyl-2-oxo-tetrahydro-2λ$^5$-furo[3,2-d][1,3,2]dioxaphosphinin-6-yl)-9H-purin-6-ol | $^1$H NMR (400 MHz, DMSO): δ 10.76 (s, 1H), 7.99 (s, 1H), 6.48 (s, 2H), 6.16 (d, J = 21.2 Hz, 1H), 4.55-4.80 (m, 3H), 3.95-4.20 (m, 2H), 2.15-2.35 (m, 4H), 1.60-1.70 (m, 1H), 1.40-1.50 (m, 1H), 1.18 (d, J = 22.8 Hz, 3H). MS(ESI), m/z 416.05 (M + 1)$^+$. |
| 38b | 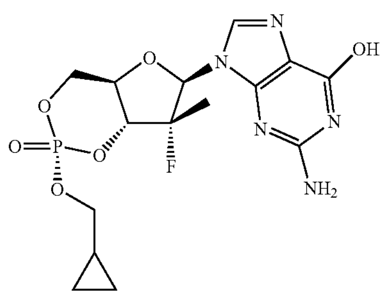 | 2-Amino-9-((4aR,6R,7R,7aR)-2-cyclopropylmethoxy-7-fluoro-7-methyl-2-oxo-tetrahydro-2λ$^5$-furo[3,2-d][1,3,2]dioxaphosphinin-6-yl)-9H-purin-6-ol | $^1$H NMR (400 MHz, DMSO): δ 10.76 (s, 1H), 7.91 (s, 1H), 6.65 (s, 2H), 6.12 (d, J = 21.6 Hz, 1H), 4.50-4.75 (m, 3H), 3.90-4.40 (m, 2H), 2.15-2.30 (m, 2H), 2.00-2.15 (m, 2H), 1.60-1.70 (m, 1H), 1.35-1.45 (m, 1H), 1.18 (d, J = 22.8 Hz, 3H). MS(ESI), m/z 416.07 (M + 1)$^+$. |
| 39 | 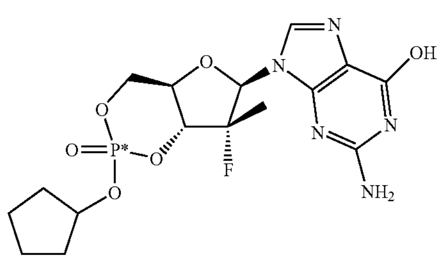 | 2-Amino-9-((4aR,6R,7R,7aR)-2-cyclopentyloxy-7-fluoro-7-methyl-2-oxo-tetrahydro-2λ$^5$-furo[3,2-d][1,3,2]dioxaphosphinin-6-yl)-9H-purin-6-ol | $^1$H NMR (400 MHz, DMSO): δ 10.79 (s, 1H), 8.01 (s, 1H), 6.50 (s, 2H), 6.19 (d, J = 20.8 Hz, 1H), 4.88-4.90 (m, 1H), 4.50-4.70 (m, 3H), 4.20-4.30 (m, 1H), 1.80-2.00 (m, 4H), 1.65-1.80 (m, 2H), 1.50-1.60 (m, 2H), 1.19 (d, J = 22.4 Hz, 6H). MS(ESI), m/z 430.03 (M + 1)$^+$. |

| Ex No | Structure | Chemical Name | Analytical Data |
|---|---|---|---|
| 40a | 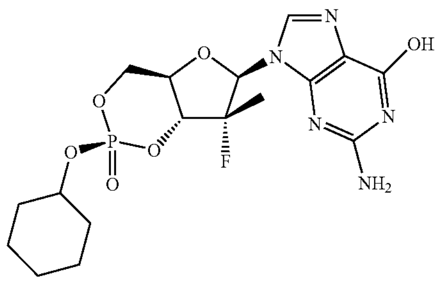 | 2-Amino-9-((2S,4aR,6R,7R,7aR)-2-cyclohexyloxy-7-fluoro-7-methyl-2-oxo-tetrahydro-2λ⁵-furo[3,2-d][1,3,2]dioxaphosphinin-6-yl)-9H-purin-6-ol | ¹H NMR (400 MHz, DMSO): δ 10.75 (s, 1H), 7.99 (s, 1H), 6.46 (s, 2H), 6.17 (d, J = 21.2 Hz, 1H), 4.50-4.90 (m, 3H), 4.30-4.40 (m, 1H), 4.15-4.25 (m, 1H), 1.80-2.00 (m, 2H), 1.60-1.75 (m, 2H), 1.40-1.60 (m, 3H), 1.10-1.35 (m, 6H). MS(ESI), m/e 444.08 (M + 1)⁺. |
| 40b | 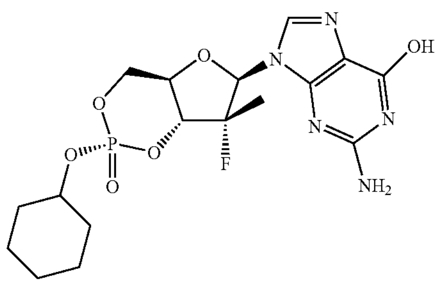 | 2-Amino-9-((2R,4aR,6R,7R,7aR)-2-cyclohexyloxy-7-fluoro-7-methyl-2-oxo-tetrahydro-2λ⁵-furo[3,2-d][1,3,2]dioxaphosphinin-6-yl)-9H-purin-6-ol | ¹H NMR (400 MHz, DMSO): δ 10.73 (s, 1H), 7.94 (s, 1H), 6.60 (s, 2H), 6.15 (d, J = 21.2 Hz, 1H), 4.50-5.30 (m, 3H), 4.20-4.45 (m, 2H), 1.80-1.95 (m, 2H), 1.60-1.70 (m, 2H), 1.38-1.55 (m, 3H), 1.10-1.35 (m, 6H). MS(ESI), m/z 444.11 (M + 1)⁺. |
| 41 | 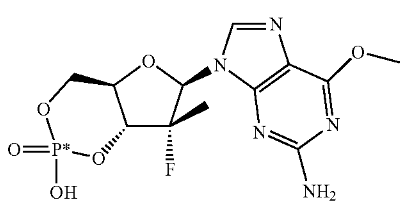 | (4aR,6R,7R,7aR)-6-(2-Amino-6-methoxy-purin-9-yl)-7-fluoro-7-methyl-2-oxo-tetrahydro-2λ⁵-furo[3,2-d][1,3,2]dioxaphosphinin-2-ol | ³¹P NMR (162 MHz, DMSO): δ −5.00; ¹H NMR (400 MHz, DMSO) δ: 8.14 (s, 1 H), 6.55 (bs, 2H), 6.24 (d, J = 21.2 Hz, 1H), 4.57-4.46 (m, 3 H), 4.19-4.16 (m, 1 H), 3.95 (s, 3H), 1.19 (d, J = 22.8 Hz, 3H); MS (ESI): m/z 374.4 [M + 1]⁺ |
| 42a | 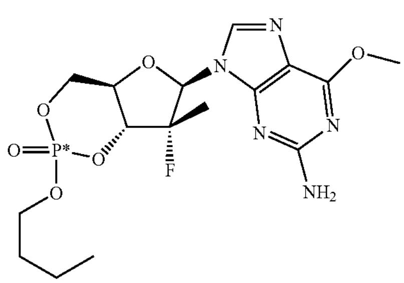 | 9-((4aR,6R,7R,7aR)-2-Butoxy-7-fluoro-7-methyl-2-oxo-tetrahydro-2λ⁵-furo[3,2-d][1,3,2]dioxaphosphinin-6-yl)-6-methoxy-9H-purin-2-ylamine | ¹H NMR (CDCl₃, 400 MHz) δ: 7.59 (s, 1 H), 6.03 (d, J = 19.6 Hz, 1 H), 4.87 (s, 2 H), 4.59-4.69 (m, 1 H), 4.38-4.51 (m, 2 H), 4.22-4.28 (m, 2 H), 4.08 (s, 3 H), 1.75-1.82 (m, 2 H), 1.44-1.52 (m, 2 H), 1.34 (d, J = 22 Hz, 3 H), 0.98 (t, J = 7.6 Hz, 3 H). |

| Ex No | Structure | Chemical Name | Analytical Data |
|---|---|---|---|
| 42b | 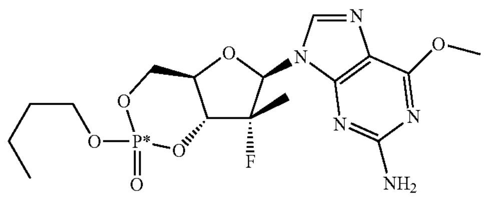 | 9-((4aR,6R,7R,7aR)-2-Butoxy-7-fluoro-7-methyl-2-oxo-tetrahydro-2λ⁵-furo[3,2-d][1,3,2]dioxaphosphinin-6-yl)-6-methoxy-9H-purin-2-ylamine | $^1$H NMR (CDCl$_3$, 400 MHz) δ: 7.58 (s, 1 H), 5.97 (d, J = 20 Hz, 1 H), 5.13 (s, 2 H), 4.60-4.66 (m, 2 H), 4.37-4.43 (m, 1 H), 4.18-4.24 (m, 2 H), 4.06 (s, 3 H), 1.68-1.76 (m, 2 H), 1.40-1.47 (m, 2 H), 1.32 (d, J = 29.2 Hz, 3 H), 0.95 (t, J = 14.8 Hz, 3 H). MS (ESI): m/z 432.1 [M + 1]$^+$. |
| 43a | 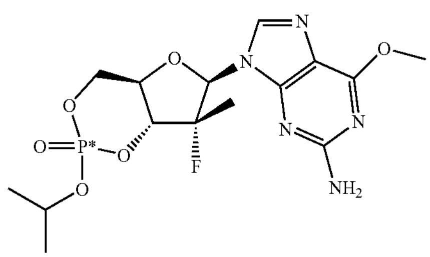 | 9-((4aR,6R,7R,7aR)-7-Fluoro-2-isopropoxy-7-methyl-2-oxo-tetrahydro-2λ⁵-furo[3,2-d][1,3,2]dioxaphosphinin-6-yl)-6-methoxy-9H-purin-2-ylamine | $^{31}$P NMR (162 MHz, CDCl$_3$): δ −5.99; $^1$H NMR (CDCl$_3$, 400 MHz) δ: 7.59 (s, 1 H), 6.02 (d, J = 18.8 Hz, 1 H), 4.86-4.91 (m, 2 H), 4.58-4.67 (m, 1 H), 4.50 (t, J = 9.8 Hz, 1H), 4.38-4.43 (m, 1 H), 4.08 (s, 3 H), 1.40-1.48 (m, 6 H), 1.39 (d, J = 16.4 Hz, 3 H). MS (ESI): m/z 418.4 [M + 1]$^+$. |
| 43b | 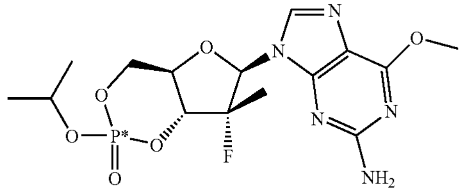 | 9-((2R,4aR,6R,7R,7aR)-7-Fluoro-2-isopropoxy-7-methyl-2-oxo-tetrahydro-2λ⁵-furo[3,2-d][1,3,2]dioxaphosphinin-6-yl)-6-methoxy-9H-purin-2-ylamine | $^{31}$P NMR (162 MHz, CDCl$_3$): δ −2.47; $^1$H NMR (CDCl$_3$, 400 MHz) δ: 7.57 (s, 1 H), 5.98 (d, J = 20 Hz, 1 H), 5.06 (s, 1 H), 4.79-4.85 (m, 1 H), 4.58-4.64 (m, 2 H), 4.41-4.45 (m, 1 H), 4.08 (s, 3 H), 1.34-1.47 (m, 9 H); MS (ESI): m/z 418.4 [M + 1]$^+$ |

| Ex No | Structure | Chemical Name | Analytical Data |
|---|---|---|---|
| 44 | 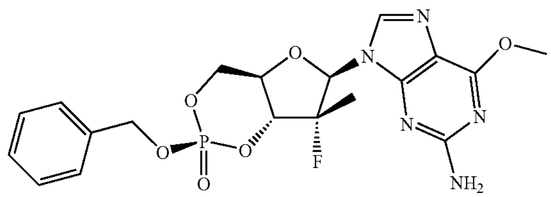 | 9-((2R,4aR,6R,7R,7aR)-2-Benzyloxy-7-fluoro-7-methyl-2-oxo-tetrahydro-2λ⁵-furo[3,2-d][1,3,2]dioxaphosphinin-6-yl)-6-methoxy-9H-purin-2-ylamine | ³¹P NMR (162 MHz, CDCl₃): δ −4.88; ¹H NMR (400 MHz, CDCl₃) δ: 7.51-7.49 (m, 3H), 7.44-7.37 (m, 3H), 5.93 (d, J = 19.6 Hz, 1H), 5.26-5.19 (m, 2H), 4.63 (dd, J = 8.8, 4.0 Hz, 1H), 4.57 (dd, J = 8.8, 4.4 Hz, 1H), 4.45-4.33 (m, 4H), 4.04 (s, 3H), 1.18 (d, J = 22.4 Hz, 3H); MS (ESI): m/z 466.4 [M + 1]⁺. |
| 45 | 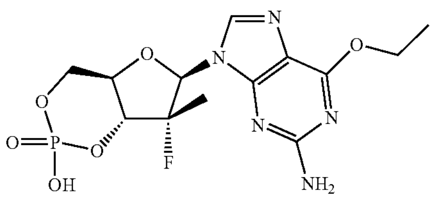 | (4aR,6R,7R,7aR)-6-(2-Amino-6-ethoxy-purin-9-yl)-7-fluoro-7-methyl-2-oxo-tetrahydro-2λ⁵-furo[3,2-d][1,3,2]dioxaphosphinin-2-ol | ³¹P NMR (162 MHz, DMSO): δ −4.97; ¹H NMR (400 MHz, DMSO) δ: 8.13 (s, 1H), 6.51 (bs, 2H), 6.23 (d, J = 21.2 Hz, 1H), 4.56-4.46 (m, 3H), 4.43 (q, J = 7.2 Hz, 2H), 4.18-4.12 (m, 1H), 1.34 (t, J = 7.2 Hz, 3H), 1.19 (d, J = 22.8 Hz, 3H); MS (ESI): m/z 390.3 [M + 1]⁺ |
| 46 | 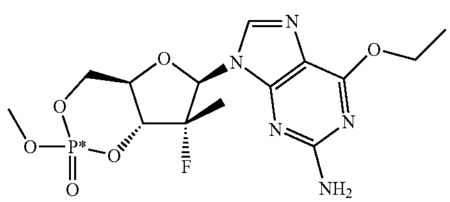 | 6-Ethoxy-9-((4aR,6R,7R,7aR)-7-fluoro-2-methoxy-7-methyl-2-oxo-tetrahydro-2λ⁵-furo[3,2-d][1,3,2]dioxaphosphinin-6-yl)-9H-purin-2-ylamine | Mixture of cis/trans isomers (ca. 1.5/1): ¹H NMR (400 MHz, DMSO-d6) δ 8.16 (s, 2.5H), 6.65 (s, 3H), 6.55 (s, 2H), 6.28 (d, J = 20.8 Hz, 2.5H), 4.78-4.60 (m, 7.5H), 4.45 (q, J = 6.8 Hz, 1H), 4.44 (q, J = 6.8 Hz, 1.5H), 4.25 (m, 2.5H), 3.83 (d, J = 11.6 Hz, 3H), 3.76 (d, J = 11.6 Hz, 4.5H), 1.36 (t, J = 7.2 Hz, 3H), 1.36 (t, J = 7.2 Hz, 4.5H), 1.23 (d, J = 22.4 Hz, 3H), 1.22 (d, J = 22.8 Hz, 4.5H); ³¹P NMR (162 MHz, DMSO-d6) δ −3.25, −4.16; LRMS (ESI) calculated for C14H20FN5O6P [(M + H)⁺] 404.3, found 404.3. |

| Ex No | Structure | Chemical Name | Analytical Data |
|---|---|---|---|
| 47a | 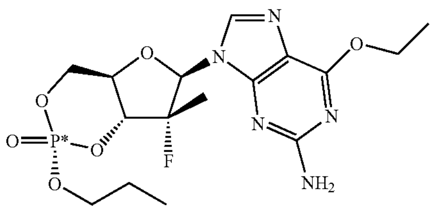 | 6-Ethoxy-9-((4aR,6R,7R,7aR)-7-fluoro-7-methyl-2-oxo-2-propoxy-tetrahydro-2$\lambda^5$-furo[3,2-d][1,3,2]dioxaphosphinin-6-yl)-9H-purin-2-ylamine | 1H NMR (400 MHz, DMSO-d6) δ 8.16 (s, 1H), 6.50 (bs, 2H), 6.29 (d, J = 20.8 Hz, 1H), 4.74-4.63 (m, 2H), 4.45 (q, J = 7.2 Hz, 2H), 4.25-4.22 (m, 1H), 4.09 (q, J = 7.6 Hz, 2H), 1.73 (quintet, J = 6.8 Hz, 2H), 1.37 (t, J = 7.2 Hz, 3H), 1.21 (d, J = 22.8 Hz, 3H), 0.94 (t, J = 7.2 Hz, 3H); $^{31}$P NMR (162 MHz, DMSO-d6) δ −5.29; LRMS (ESI) calculated for $C_{16}H_{24}FN_5O_6P$ [(M + H)$^+$] 432.4, found 432.3. |
| 47b | 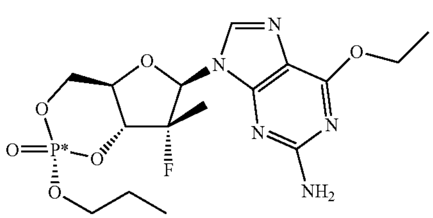 | 6-Ethoxy-9-((2S,4aR,6R,7R,7aR)-7-fluoro-7-methyl-2-oxo-2-propoxy-tetrahydro-2$\lambda^5$-furo[3,2-d][1,3,2]dioxaphosphinin-6-yl)-9H-purin-2-ylamine | $^1$H NMR (400 MHz, DMSO-d6) δ 8.15 (s, 1H), 6.64 (bs, 2H), 6.27 (d, J = 21.2 Hz, 1H), 4.76-4.63 (m, 2H), 4.44 (q, J = 7.2 Hz, 2H), 4.41 (m, 1H), 4.04 (q, J = 8.0 Hz, 2H), 1.66 (sextet, J = 7.2 Hz, 2H), 1.36 (t, J = 7.2 Hz, 3H), 1.23 (d, J = 23.2 Hz, 3H), 0.92 (t, J = 7.6 Hz, 3H); $^{31}$P NMR (162 MHz, DMSO-d6) δ −3.95; LRMS (ESI) calculated for $C_{16}H_{24}FN_5O_6P$ [(M + H)$^+$] 432.4, found 432.3. |

| Ex No | Structure | Chemical Name | Analytical Data |
|---|---|---|---|
| 48 | 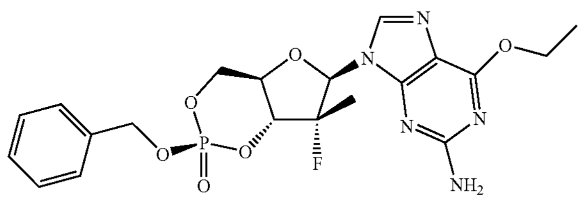 | 9-((4aR,6R,7R,7aR)-2-Benzyloxy-7-fluoro-7-methyl-2-oxo-tetrahydro-2λ5-furo[3,2-d][1,3,2]dioxaphosphinin-6-yl)-6-ethoxy-9H-purin-2-ylamine | $^{31}$P NMR (162 MHz, CDCl$_3$): δ −4.87; $^1$H NMR (400 MHz, CDCl$_3$) δ: 7.51-7.49 (m, 3H), 7.44-7.39 (m, 3H), 5.93 (d, J = 19.6 Hz, 1H), 5.27-5.19 (m, 2H), 4.63 (dd, J = 8.8, 4.4 Hz, 1H), 4.58 (dd, J = 8.8, 4.4 Hz, 1H), 4.51 (q, J = 7.0 Hz, 2H), 4.46-4.33 (m, 4H), 1.45 (t, J = 7.2 Hz, 3H), 1.20 (d, J = 22. Hz, 3H); MS (ESI): m/z 480.3 [M + 1]$^+$. |
| 49 | 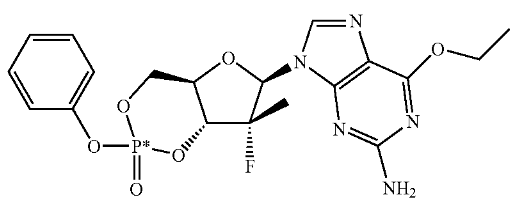 | 6-Ethoxy-9-((4aR,6R,7R,7aR)-7-fluoro-7-methyl-2-oxo-2-phenoxy-tetrahydro-2λ$^5$-furo[3,2-d][1,3,2]dioxaphosphinin-6-yl)-9H-purin-2-ylamine | Mixture of cis/trans isomers (ca. 1/0.5): $^1$H NMR (400 MHz, DMSO-d6) δ 8.22 (s, 1H), 8.12 (s, 0.5H), 7.49-7.27 (m, 7.5H), 6.70 (bs, 0.5H), 6.56 (bs, 1H), 6.33 (d, J = 20.8 Hz, 1H), 6.30 (d, J = 20.8 Hz, 0.5H), 4.95-4.78 (m, 3H), 4.60-4.32 (m, 6H), 1.36 (t, J = 7.2 Hz, 3H), 1.36 (t, J = 7.2 Hz, 1.5H), 1.21 (d, J = 22.4 Hz, 4.5H); $^{31}$P NMR (162 MHz, DMSO-d6) δ −10.16, −11.11; LRMS (ESI) calculated for C$_{19}$H$_{22}$FN$_5$O$_6$P [(M + H)$^+$] 466.4, found 466.3. |
| 50 | 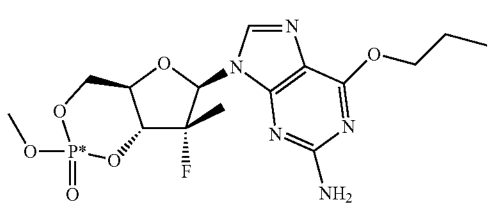 | 9-((4aR,6R,7R,7aR)-7-Fluoro-2-methoxy-7-methyl-2-oxo-tetrahydro-2λ$^5$-furo[3,2-d][1,3,2]dioxaphosphinin-6-yl)-6-propoxy-9H-purin-2-ylamine | $^{31}$P NMR (162 MHz, CDCl$_3$): δ −1.35, −3.90; MS (ESI) m/z 418.3 (M + H)$^+$. |
| 51 | 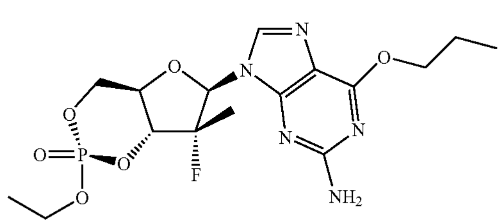 | 9-((2S,4aR,6R,7R,7aR)-2-Ethoxy-7-fluoro-7-methyl-2-oxo-tetrahydro-2λ$^5$-furo[3,2-d][1,3,2]dioxaphosphinin-6-yl)-6-propoxy-9H-purin-2-ylamine | $^{31}$P NMR (162 MHz, CDCl$_3$): δ −2.01, −4.98; MS (ESI) m/z 432.1 (M + H)$^+$. |

-continued

| Ex No | Structure | Chemical Name | Analytical Data |
|---|---|---|---|
| 52a | 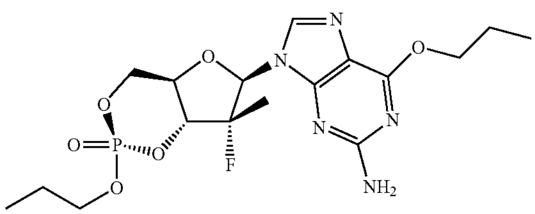 | 9-((2R,4aR,6R,7R,7aR)-7-Fluoro-7-methyl-2-oxo-2-propoxy-tetrahydro-2λ$^5$-furo[3,2-d][1,3,2]dioxaphosphinin-6-yl)-6-propoxy-9H-purin-2-ylamine | $^{31}$P NMR (162 MHz, CDCl$_3$): δ −4.945; MS (ESI) m/z 446.1 (M + H)$^+$. |
| 52b | 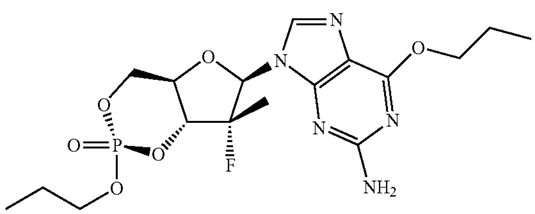 | 9-((2S,4aR,6R,7R,7aR)-7-Fluoro-7-methyl-2-oxo-2-propoxy-tetrahydro-2λ$^5$-furo[3,2-d][1,3,2]dioxaphosphinin-6-yl)-6-propoxy-9H-purin-2-ylamine | $^{31}$P NMR (162 MHz, CDCl$_3$): δ −1.90; MS (ESI) m/z 446.1 (M + H)$^+$. |
| 53a | 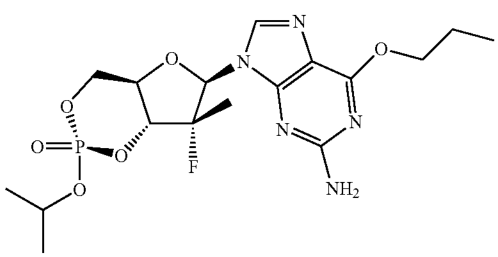 | 9-((2R,4aR,6R,7R,7aR)-7-Fluoro-2-isopropoxy-7-methyl-2-oxo-tetrahydro-2λ$^5$-furo[3,2-d][1,3,2]dioxaphosphinin-6-yl)-6-propoxy-9H-purin-2-ylamine | $^{31}$P NMR (162 MHz, CDCl$_3$): δ −5.97; MS (ESI) m/z 446.1 (M + H)$^+$. |
| 53b | 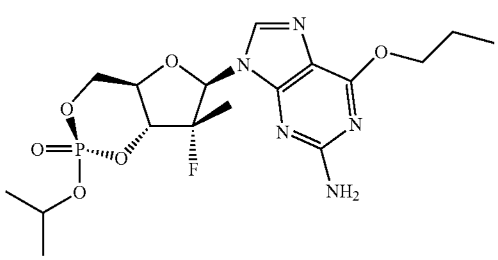 | 9-((2S,4aR,6R,7R,7aR)-7-Fluoro-2-isopropoxy-7-methyl-2-oxo-tetrahydro-2λ$^5$-furo[3,2-d][1,3,2]dioxaphosphinin-6-yl)-6-propoxy-9H-purin-2-ylamine | $^{31}$P NMR (162 MHz, CDCl$_3$): δ −2.51; MS (ESI) m/z 446.1 (M + H)$^+$. |
| 54 | 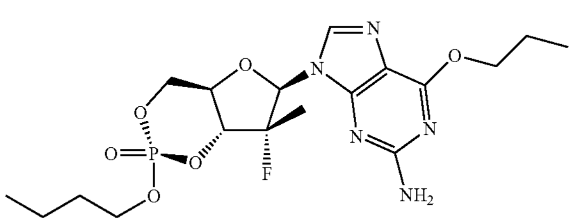 | 9-((2S,4aR,6R,7R,7aR)-2-Butoxy-7-fluoro-7-methyl-2-oxo-tetrahydro-2λ$^5$-furo[3,2-d][1,3,2]dioxaphosphinin-6-yl)-6-propoxy-9H-purin-2-ylamine | $^{31}$P NMR (162 MHz, CDCl$_3$): δ −4.92; MS (ESI) m/z 460.1 (M + H)$^+$. |
| 55 | 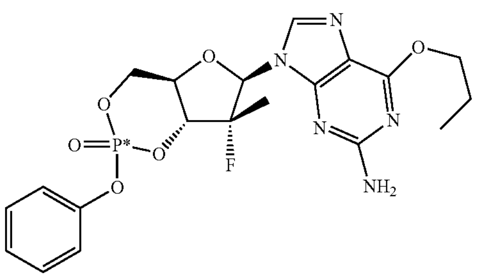 | 9-((4aR,6R,7R,7aR)-7-Fluoro-7-methyl-2-oxo-2-phenoxy-tetrahydro-2λ$^5$-furo[3,2-d][1,3,2]dioxaphosphinin-6-yl)-6-propoxy-9H-purin-2-ylamine | $^{31}$P NMR (162 MHz, CDCl$_3$): δ −11.05; MS (ESI) m/z 480.3 (M + H)$^+$. |

| Ex No | Structure | Chemical Name | Analytical Data |
|---|---|---|---|
| 56 | 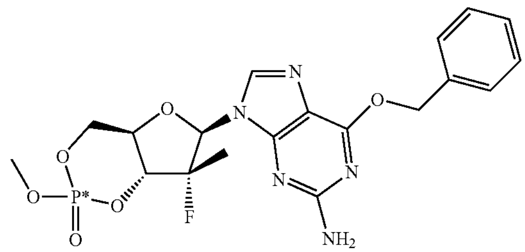 | 6-Benzyloxy-9-((4aR,6R,7R,7aR)-7-fluoro-2-methoxy-7-methyl-2-oxo-tetrahydro-2λ$^5$-furo[3,2-d][1,3,2]dioxaphosphinin-6-yl)-9H-purin-2-ylamine | Mixture of cis/trans isomers (ca. 1.5/1): $^1$H NMR (400 MHz, DMSO-d6) δ 8.16 (s, 2.5H), 7.53-7.34 (m, 12.5H), 6.74 (s, 3H), 6.64 (s, 2H), 6.18 (d, J = 21.2 Hz, 2.5H), 5.48 (s, 3H), 5.48 (s, 2H), 4.78-4.60 (m, 6H), 4.44 (m, 2.5H), 4.26 (m, 1.5H), 3.83 (d, J = 10.8 Hz, 3H), 3.76 (d, J = 11.6 Hz, 4.5H), 1.24 (d, J = 22.4 Hz, 3H), 1.23 (d, J = 22.8 Hz, 4.5H); $^{31}$P NMR (162 MHz, DMSO-d6) δ −3.25, −4.17; LRMS (ESI) calculated for $C_{19}H_{22}FN_5O_6P$ [(M + H)$^+$] 466.4, found 466.3. |
| 57 | 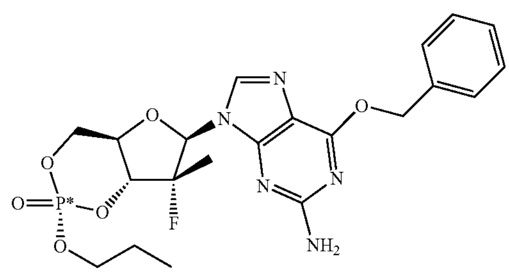 | 6-Benzyloxy-9-((2S,4aR,6R,7R,7aR)-7-fluoro-7-methyl-2-oxo-2-propoxy-tetrahydro-2λ$^5$-furo[3,2-d][1,3,2]dioxaphosphinin-6-yl)-9H-purin-2-ylamine | $^1$H NMR (400 MHz, DMSO-d6) δ 8.17 (s, 1H), 7.52-7.34 (m, 5H), 6.73 (bs, 2H), 6.28 (d, J = 21.2 Hz, 1H), 5.50 (d, J = 12.0 Hz, 1H), 5.46 (d, J = 12.0 Hz, 1H), 4.76-4.62 (m, 2H), 4.45-4.38 (m, 1H), 4.04 (q, J = 8.0 Hz, 2H), 1.66 (sextet, J = 7.2 Hz, 2H), 1.23 (d, J = 23.2 Hz, 3H), 0.92 (t, J = 7.6 Hz, 3H); $^{31}$P NMR (162 MHz, DMSO-d6) δ −3.96; LRMS (ESI) calculated for $C_{21}H_{26}FN_5O_6P$ [(M + H)$^+$] 494.4, found 494.3. |

HCV replicon assay. HCV replicon RNA-containing Huh7 cells (clone A cells; Apath, LLC, St. Louis, Mo.) were kept at exponential growth in Dulbecco's modified Eagle's medium (high glucose) containing 10% fetal bovine serum, 4 mM L-glutamine and 1 mM sodium pyruvate, 1× nonessential amino acids, and G418 (1,000 µg/ml). Antiviral assays were performed in the same medium without G418. Cells were seeded in a 96-well plate at 1,500 cells per well, and test compounds were added immediately after seeding. Incubation time 4 days. At the end of the incubation step, total cellular RNA was isolated (RNeasy 96 kit; Qiagen). Replicon RNA and an internal control (TaqMan rRNA control reagents; Applied Biosystems) were amplified in a single-step multiplex RT-PCR protocol as recommended by the manufacturer. The HCV primers and probe were designed with Primer Express software (Applied Biosystems) and covered highly conserved 5'-untranslated region (UTR) sequences (sense, 5'-AGCCATGGCGTTAGTA(T)GAGTGT-3' (SEQ ID NO: 1), and antisense, 5'-TTCCGCAGACCACTATGG-3' (SEQ ID NO: 2); probe, 5'-FAM - CCTCCAGGACCCCCCCTCCC-TAMRA-3' (SEQ ID NO: 3)).

To express the antiviral effectiveness of a compound, the threshold RT-PCR cycle of the test compound was subtracted from the average threshold RT-PCR cycle of the no-drug control ($\Delta Ct_{HCV}$). A $\Delta Ct$ of 3.3 equals a 1-log 10 reduction (equal to the 90% effective concentration [$EC_{90}$]) in replicon RNA levels. The cytotoxicity of the test compound could also be expressed by calculating the $\Delta Ct_{rRNA}$ values. The $\Delta\Delta Ct$ specificity parameter could then be introduced ($\Delta Ct_{HCV}$-$\Delta Ct_{rRNA}$), in which the levels of HCV RNA are normalized for the rRNA levels and calibrated against the no-drug control.

| No | CloneA $EC_{90}$ |
|---|---|
| 1a | 5.35 |
| 1b | 17.39 |
| 2a | 25.25 |
| 2b | 17.74 |
| 3 | 0.75 |
| 4 | 11.68 |
| 5 | 8.06 |
| 6 | 1.55 |
| 17 | 0.71 |
| 18 | 0.48 |
| 19 | 0.60 |

-continued

| No | CloneA $EC_{90}$ |
|---|---|
| 32a | 8.54 |
| 32b | 4.7 |
| 38b | 26.6 |
| 41 | 0.098 |
| 43a | 0.29 |
| 43b | 0.06 |
| 44 | 0.053 |
| 45 | 0.70 |
| 48 | 0.32 |

The contents of U.S. Pat. No. 7,964,580, filed Mar. 21, 2008 (see also WO 2008/121634), U.S. Provisional Patent Application No. 61/060,683, filed Jun. 11, 2008, and U.S. Provisional Patent Application Nos. 61/140,317 and 61/140,369, both being filed on Dec. 23, 2008 are hereby incorporated by reference in their entirety. Moreover, the patent and non-patent references disclosed herein are incorporated by reference. In the event that the incorporated subject matter contains a term that conflicts with a term disclosed in the present application text, the meaning of the term contained in the present application controls provided that the overall meaning of the incorporated subject matter is not lost.

We claim:
1. A compound or a salt thereof having the structure:

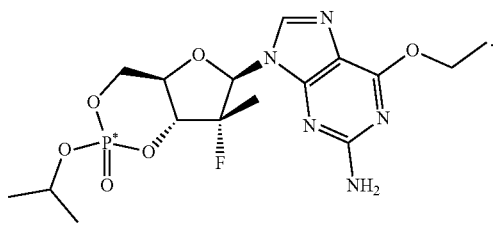

2. A composition comprising the compound or a salt thereof as claimed in claim 1 and optionally a pharmaceutically acceptable medium.
3. A composition for the treatment of hepatitis C virus comprising the compound or a salt thereof as claimed in claim 1 and a pharmaceutically acceptable medium.
4. A composition for the treatment of hepatitis C virus comprising an effective amount of the compound or a salt thereof as claimed in claim 1 and a pharmaceutically acceptable medium.
5. A method of treating a subject infected with a virus, which comprises:
    administering to the subject an effective amount of the compound or salt thereof as claimed in claim 1;
    wherein the virus is selected from among hepatitis C virus, West Nile virus, a yellow fever virus, a dengue virus, a rhinovirus, a polio virus, a hepatitis A virus, a bovine viral diarrhea virus, and a Japanese encephalitis virus.
6. A method of treating a hepatitis C virus infection in a subject, which comprises:
    administering to the subject an effective amount of the compound or salt thereof as claimed in claim 1.
7. The method as claimed in claim 6, wherein the subject is a human.
8. A composition for the treatment of hepatitis C virus comprising:
    an effective amount of the compound or a salt thereof as claimed in claim 1;
    an effective amount of at least one agent selected from among an HCV NS3 protease inhibitor, an HCV NS5B inhibitor, an HCV NS4 inhibitor, and an HCV NS5a inhibitor; and
    a pharmaceutically acceptable medium.
9. A method of treating a hepatitis C virus infection in a subject, which comprises:
    administering to the subject the composition as claimed in claim 8.
10. The method as claimed in claim 9, wherein the subject is a human.
11. A compound or a salt thereof having the structure:

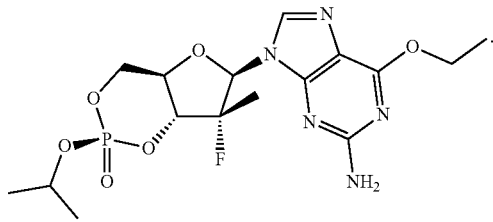

12. A composition comprising the compound or a salt thereof as claimed in claim 11 and optionally a pharmaceutically acceptable medium.
13. A composition for the treatment of hepatitis C virus comprising the compound or a salt thereof as claimed in claim 11 and a pharmaceutically acceptable medium.
14. A composition for the treatment of hepatitis C virus comprising an effective amount of the compound or a salt thereof as claimed in claim 11 and a pharmaceutically acceptable medium.
15. A method of treating a subject infected by a virus, which comprises:
    administering to the subject an effective amount of the compound or salt thereof as claimed in claim 11;
    wherein the virus is selected from among hepatitis C virus, West Nile virus, a yellow fever virus, a dengue virus, a rhinovirus, a polio virus, a hepatitis A virus, a bovine viral diarrhea virus, and a Japanese encephalitis virus.
16. A method of treating a hepatitis C virus infection in a subject, which comprises:
    administering to the subject an effective amount of the compound or salt thereof as claimed in claim 11.
17. The method as claimed in claim 16, wherein the subject is a human.
18. A composition for the treatment of hepatitis C virus comprising:
    an effective amount of the compound or a salt thereof as claimed in claim 11;
    an effective amount of at least one agent selected from among an HCV NS3 protease inhibitor, an HCV NS5B inhibitor, an HCV NS4A inhibitor, an HCV NS4B inhibitor, and an HCV NS5A inhibitor; and
    a pharmaceutically acceptable medium.
19. A composition for the treatment of hepatitis C virus comprising:
    an effective amount of the compound or a salt thereof as claimed in claim 11;
    an effective amount of at least one agent selected from among an HCV NS3 protease inhibitor, an HCV NS5B inhibitor, and an HCV NS5A inhibitor; and
    a pharmaceutically acceptable medium.
20. A composition for the treatment of hepatitis C virus comprising:
    an effective amount of the compound or a salt thereof as claimed in claim 11;
    an effective amount of at least one agent selected from among an HCV NS3 protease inhibitor and an HCV NS5B inhibitor; and
    a pharmaceutically acceptable medium.
21. A composition for the treatment of hepatitis C virus comprising:
    an effective amount of the compound or a salt thereof as claimed in claim 11;
    an effective amount of at least one agent selected from among an HCV NS3 protease inhibitor and an HCV NS5A inhibitor; and
    a pharmaceutically acceptable medium.
22. A method of treating a hepatitis C virus infection in a subject, which comprises: administering to the subject the composition as claimed in any one of claims 18-21.
23. The method as claimed in claim 22, wherein the subject is a human.

24. A compound having the structure:

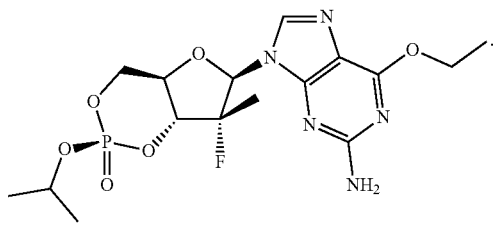

25. A composition comprising the compound as claimed in claim 24 and optionally a pharmaceutically acceptable medium.

26. A composition for the treatment of hepatitis C virus comprising the compound as claimed in claim 24 and a pharmaceutically acceptable medium.

27. A composition for the treatment of hepatitis C virus comprising an effective amount of the compound as claimed in claim 24 and a pharmaceutically acceptable medium.

28. A method of treating a subject infected by a virus, which comprises:
   administering to the subject an effective amount of the compound as claimed in claim 24;
   wherein the virus is selected from among hepatitis C virus, West Nile virus, a yellow fever virus, a dengue virus, a rhinovirus, a polio virus, a hepatitis A virus, a bovine viral diarrhea virus, and a Japanese encephalitis virus.

29. A method of treating a hepatitis C virus infection in a subject, which comprises:
   administering to the subject an effective amount of the compound as claimed in claim 24.

30. The method as claimed in claim 29, wherein the subject is a human.

31. A composition for the treatment of hepatitis C virus comprising:
   an effective amount of the compound as claimed in claim 24;
   an effective amount of at least one agent selected from among an HCV NS3 protease inhibitor, an HCV NS5B inhibitor, an HCV NS4A inhibitor, an HCV NS4B inhibitor, and an HCV NS5A inhibitor; and
   a pharmaceutically acceptable medium.

32. A composition for the treatment of hepatitis C virus comprising:
   an effective amount of the compound as claimed in claim 24;
   an effective amount of at least one agent selected from among an HCV NS3 protease inhibitor, an HCV NS5B inhibitor, and an HCV NS5A inhibitor; and
   a pharmaceutically acceptable medium.

33. A composition for the treatment of hepatitis C virus comprising:
   an effective amount of the compound as claimed in claim 24;
   an effective amount of at least one agent selected from among an HCV NS3 protease inhibitor and an HCV NS5B inhibitor; and
   a pharmaceutically acceptable medium.

34. A composition for the treatment of hepatitis C virus comprising:
   an effective amount of the compound as claimed in claim 24;
   an effective amount of at least one agent selected from among an HCV NS3 protease inhibitor and an HCV NS5A inhibitor; and
   a pharmaceutically acceptable medium.

35. A method of treating a hepatitis C virus infection in a subject, which comprises:
   administering to the subject the composition as claimed in claim in any one of claims 31-34.

36. The method as claimed in claim 34, wherein the subject is a human.

37. A compound or a salt thereof having the structure:

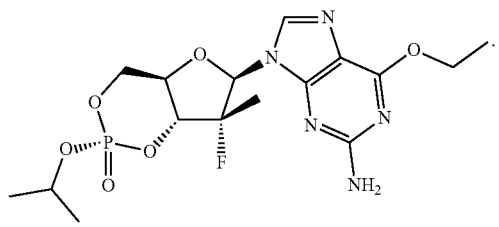

38. A composition comprising the compound or a salt thereof as claimed in claim 37 and optionally a pharmaceutically acceptable medium.

39. A composition for the treatment of hepatitis C virus comprising the compound or a salt thereof as claimed in claim 37 and a pharmaceutically acceptable medium.

40. A compound or a salt thereof having the structure:

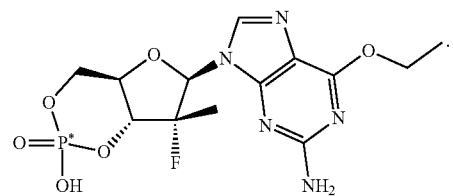

41. A composition comprising the compound or a salt thereof as claimed in claim 40 and optionally a pharmaceutically acceptable medium.

42. A composition for the treatment of hepatitis C virus comprising the compound or a salt thereof as claimed in claim 40 and a pharmaceutically acceptable medium.

43. A process for preparing the compound or a salt thereof as claimed in claim 1, said process comprising reacting compound 16 having the structure

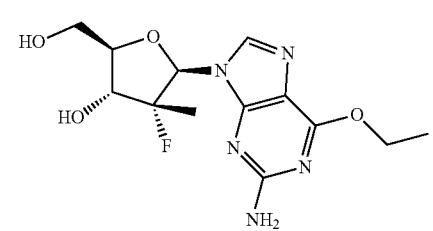

16 with $^iPrOP(N^iPr_2)_2$ in the presence of a base to obtain compound 16' having the structure,

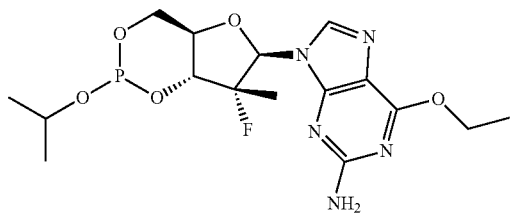

16' and
reacting compound 16' with an oxidant to obtain the compound or a salt thereof.

44. The process as claimed in claim 43, which further comprises separating the individual diastereomers of the compound or a salt thereof.

45. A composition comprising the compound or a salt thereof as obtained by the process as claimed in claim 43.

46. A composition comprising the compound or a salt thereof as obtained by the process as claimed in claim 44.

* * * * *

SEQUENCE LISTING

```
<160> NUMBER OF SEQ ID NOS: 3

<210> SEQ ID NO 1
<211> LENGTH: 23
<212> TYPE: DNA
<213> ORGANISM: Artificial Sequence
<220> FEATURE:
<223> OTHER INFORMATION: HCV Sense Primer

<400> SEQUENCE: 1
agccatggcg ttagtatgag tgt                                             23

<210> SEQ ID NO 2
<211> LENGTH: 18
<212> TYPE: DNA
<213> ORGANISM: Artificial Sequence
<220> FEATURE:
<223> OTHER INFORMATION: HCV Antisense Primer

<400> SEQUENCE: 2
ttccgcagac cactatgg                                                   18

<210> SEQ ID NO 3
<211> LENGTH: 20
<212> TYPE: DNA
<213> ORGANISM: Artificial Sequence
<220> FEATURE:
<223> OTHER INFORMATION: HCV Probe with 5'-FAM Label and 3'-TAMRA Label
<220> FEATURE:
<221> NAME/KEY: 5'-FAM-LABEL
<222> LOCATION: (1)..(1)
<220> FEATURE:
<221> NAME/KEY: 3'-TAMRA-LABEL
<222> LOCATION: (20)..(20)

<400> SEQUENCE: 3
cctccaggac cccccctccc                                                 20
```